United States Patent
Yamato et al.

(10) Patent No.: US 8,580,478 B2
(45) Date of Patent: Nov. 12, 2013

(54) LATENT ACIDS AND THEIR USE

(75) Inventors: Hitoshi Yamato, Takarazuka (JP);
Toshikage Asakura, Minoo (JP); Akira Matsumoto, Amagasaki (JP); Keita Tanaka, Hyogo (JP); Yuichi Nishimae, Osaka (JP)

(73) Assignee: BASF SE, Ludwigshafen (DE)

( * ) Notice: Subject to any disclaimer, the term of this patent is extended or adjusted under 35 U.S.C. 154(b) by 142 days.

(21) Appl. No.: 13/028,323

(22) Filed: Feb. 16, 2011

(65) Prior Publication Data

US 2011/0217654 A1      Sep. 8, 2011

Related U.S. Application Data

(60) Provisional application No. 61/307,480, filed on Feb. 24, 2010.

(51) Int. Cl.
| | | |
|---|---|---|
| G03F 7/004 | (2006.01) | |
| G03F 7/20 | (2006.01) | |
| C07C 69/753 | (2006.01) | |
| C07C 69/63 | (2006.01) | |
| C07D 311/74 | (2006.01) | |

(52) U.S. Cl.
USPC ......... 430/270.1; 430/913; 549/300; 548/543

(58) Field of Classification Search
USPC .................. 430/270.1, 913; 549/300; 548/543
See application file for complete search history.

(56) References Cited

U.S. PATENT DOCUMENTS

| 6,908,722 | B2 | 6/2005 | Ebata et al. | |
|---|---|---|---|---|
| 7,955,777 | B2 * | 6/2011 | Seshimo et al. | 430/270.1 |
| 8,012,669 | B2 * | 9/2011 | Shimizu et al. | 430/270.1 |
| 2006/0228648 | A1 | 10/2006 | Ohsawa et al. | |
| 2006/0276670 | A1 | 12/2006 | Junk et al. | |
| 2008/0032231 | A1 | 2/2008 | Hatakeyama et al. | |

FOREIGN PATENT DOCUMENTS

| EP | 1710230 | 11/2006 |
|---|---|---|
| JP | 2004004561 | 1/2004 |
| WO | 2008132966 | 11/2008 |
| WO | 2009037980 | 3/2009 |

OTHER PUBLICATIONS

Macromolecules 2007, 40, 8220-8224.

* cited by examiner

*Primary Examiner* — Amanda C. Walke
(74) *Attorney, Agent, or Firm* — Shiela A. Loggins

(57) ABSTRACT

The invention pertains to a compound generating an acid of the formula I or II, for instance corresponding sulfonium and iodonium salts, as well as corresponding sulfonyloximes

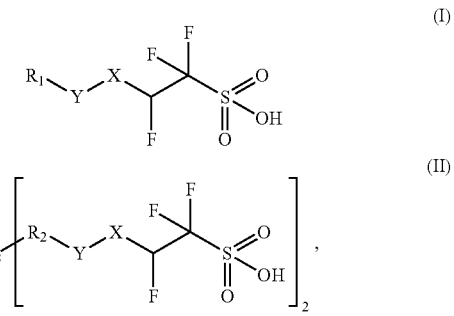

wherein
X is $CH_2$ or CO; Y is O, $NR_4$, S, O(CO), O(CO)O, O(CO)$NR_4$, $OSO_2$, O(CS), or O(CS)$NR_4$; $R_1$ is for example $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, $C_3$-$C_{30}$cycloalkyl, $C_3$-$C_{30}$cycloalkyl-$C_1$-$C_{18}$alkyl, interrupted $C_2$-$C_{18}$alkyl, interrupted $C_3$-$C_{30}$cycloalkyl, interrupted $C_3$-$C_{30}$cycloalkyl-$C_1$-$C_{18}$alkyl, interrupted $C_4$-$C_{30}$cycloalkenyl, phenyl, naphthyl, anthracyl, phenanthryl, biphenylyl, fluorenyl or heteroaryl, all unsubstituted or are substituted; or $R_1$ is $NR_{12}R_{13}$; $R_2$ and $R_3$ are for example $C_3$-$C_{30}$cycloalkylene, $C_3$-$C_{30}$cycloalkyl-$C_1$-$C_{18}$alkylene, $C_1$-$C_{18}$alkylene, $C_1$-$C_{10}$haloalkylene, $C_2$-$C_{12}$alkenylene, $C_4$-$C_{30}$cycloalkenylene, phenylene, naphthylene, anthracylene, phenanthrylene, biphenylene or heteroarylene; all unsubstituted or substituted; $R_4$ is for example $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl; $R_{12}$ and $R_{13}$ are for example $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, Ar, (CO)$R_{15}$, (CO)OR$_{15}$ or $SO_2R_{15}$; and Ar is phenyl, biphenylyl, fluorenyl, naphthyl, anthracyl, phenanthryl or heteroaryl, all unsubstituted or substituted.

17 Claims, No Drawings

LATENT ACIDS AND THEIR USE

This application claims the benefit of U.S. Provisional Application No. 61/307,480 filed Feb. 24, 2010 herein incorporated entirely by reference.

The invention relates to new latent acids releasing strong acid, chemically amplified photoresist compositions comprising said compounds and to the use of the compounds as latent acids, which can be activated by irradiation with actinic electromagnetic radiation and electron beams or heat treatment.

A chemically amplified resist comprising polymer bearing acid-labile groups and photoacid generator (PAG) as latent acid activated by light is employed for semiconductor manufacturing. For a good sensitivity and resolution performance PAG releasing strong acid such as perfluoroalkylsulfonic acid (PFAS) for instance nonafluorobutanesulfonic acid, is preferred.

However, resolution desired for further miniaturization of IC chips has not been obtained with these acids due to long diffusion length of such acids. In addition, there is a strong concern on PFAS from the environmental aspect. Thus, several PAG generating strong acid, which is not perfluorinated alkylsulfonic acid, have been reported as follows; triphenylsulfonium (adamantan-1-ylmethyl)oxycarbonyldifluoromethanesulfonate described in JP2004-004561, triphenylsulfonium 1,1,2,2-tetrafluoro-2-(norbornan-2-yl)ethanesulfonate described in U.S. Pat. No. 6,908,722, triphenylsulfonium 1,1,3,3,3-pentafluoro-2-benzoyloxypropane-1-sulfonate described in EP1710230, triphenylsulfonium 2-naphtylmethyloxytetrafluoroethanesulfonate described in WO2008/132966, triphenylsulfonium 2-(1'-adamantan)carbonyloxy-1,1-difluoroethanesulfonate described in WO2009/37980, triphenylsulfonium 2-pentafluoroethoxy-1,1,2-trifluoroethanesulfonate described in US2006/276670 and triphenylsulfonium 4-acetyloxy-1,1,2-trifluorobutanesulfonate described in Macromolecules (2007), 40(23), 8220-8224.

In the art exists a need for latent acids generating efficiently strong acid with short diffusion length and having high transparency for the actinic radiation. There is also a need for good solubility of such latent acids in common solvents like propylene glycol monomethyl ether acetate (PGMEA), ethyl lactate, cyclopentanone, and so on. Though alpha-,alpha-difluoroalkylsulfonic acid is known as a strong acid as described above, fluoroorganic compounds being available in a large scale are limited. Hence, alpha-,alpha-difluoroalkylsulfonic acids synthesized by simple processes from a fluoroorganic compound being available in a large scale and latent acids generating such strong acids are demanded.

Surprisingly, it has now been found that latent acids generating strong acids, as described below, are highly active and very soluble in common solvents, and the generated acids show the desired small diffusion length required for high resolution and high pattern fidelity, low mask edge error factor, wide exposure latitude and wide focur latitude in photoresist imaging. The strong acids in the present invention are prepared by simple processes from 2,2,3,3-tetrafluoropropanol, which is available on a large industrial scale and is employed for example as spin coating solvent for recording dyes in recordable DVD media manufacturing. The latent acids in the present invention are especially suitable as catalysts for acid catalyzed reactions in chemically amplified photoresist applications. Furthermore, chemically amplified photoresist compositions comprising the latent acid of the present invention provide high photospeed and high resolution.

Subject of the invention is a compound generating an acid of the formula I or II

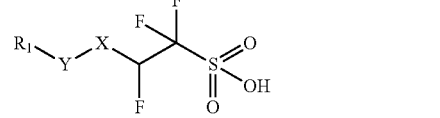

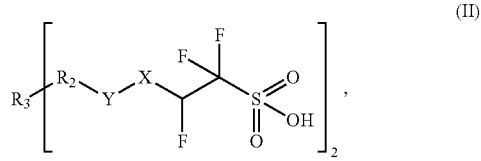

wherein
X is $CH_2$ or CO;
Y is O, O(CO), O(CO)O, O(CO)$NR_4$, O(CO)$NR_4$(CO), $OSO_2$, O(CS), or O(CS)$NR_4$;
in which for each of these the oxygen atom is directly bound to X;
or is $NR_4$, S, $NR_4$(CO)O, $NR_4$(CS)O, in which the N- or S-atom is directly bound to X;
$R_1$ is hydrogen, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, $C_3$-$C_{30}$cycloalkyl, $C_3$-$C_{30}$cycloalkyl-$C_1$-$C_{18}$alkyl;
or is $C_2$-$C_{18}$alkyl which is interrupted by one or more of O, S, $NR_{14}$, CO, O(CO) or $NR_{14}$(CO);
or is $C_2$-$C_{18}$alkenyl which is interrupted by one or more of O, S, $NR_{14}$, CO, O(CO), $NR_{14}$(CO), optionally substituted phenylene, naphthylene, anthracylene, phenanthrylene, biphenylene or heteroarylene;
or is $C_3$-$C_{30}$cycloalkyl which is interrupted by one or more of O, S, $NR_{14}$, CO, O(CO) or $NR_{14}$(CO);
or is $C_3$-$C_{30}$cycloalkyl-$C_1$-$C_{18}$alkyl which is interrupted by one or more of O, S, $NR_{14}$, CO, O(CO) or $NR_{14}$(CO);
or is $C_4$-$C_{30}$cycloalkenyl which is interrupted by one or more of O, S, $NR_{14}$, CO, O(CO) or $NR_{14}$(CO);
or $R_1$ is phenyl, naphthyl, anthracyl, phenanthryl, biphenylyl, fluorenyl or heteroaryl;
or $R_1$ is $NR_{12}R_{13}$;
or $R_1$ is a monovalent $C_{17}$-$C_{50}$ hydrocarbon group of steroid structure which may contain one or more heteroatoms;
where the $C_3$-$C_{30}$cycloalkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, $C_3$-$C_{30}$cycloalkyl-$C_1$-$C_{18}$alkyl, interrupted $C_2$-$C_{18}$alkyl, interrupted $C_3$-$C_{30}$cycloalkyl, interrupted $C_3$-$C_{30}$cycloalkyl-$C_1$-$C_{18}$alkyl, interrupted $C_4$-$C_{30}$cycloalkenyl, phenyl, naphthyl, anthracyl, phenanthryl, biphenylyl, fluorenyl or heteroaryl are unsubstituted or are substituted;
$R_2$ and $R_3$ independently of each other are $C_3$-$C_{30}$cycloalkylene, $C_3$-$C_{30}$cycloalkyl-$C_1$-$C_{18}$alkylene, $C_1$-$C_{18}$alkylene, $C_1$-$C_{10}$haloalkylene, $C_2$-$C_{12}$alkenylene, $C_4$-$C_{30}$cycloalkenylene;
or independently of each other are $C_2$-$C_{18}$alkylene which is interrupted by one or more of O, S, $NR_{14}$, CO, O(CO) or $NR_{14}$(CO);
or independently of each other are $C_3$-$C_{30}$cycloalkylene which is interrupted by one or more O, S, $NR_{14}$, CO, O(CO) or $NR_{14}$(CO);
or independently of each other are $C_3$-$C_{30}$cycloalkyl-$C_1$-$C_{18}$alkylene which is interrupted by one or more of O, S, $NR_{14}$, CO, O(CO) or $NR_{14}$(CO);

or independently of each other are $C_4$-$C_{30}$cycloalkenylene which is interrupted by one or more of O, S, $NR_{14}$, CO, O(CO) or $NR_{14}$(CO);

or $R_2$ and $R_3$ independently of each other are phenylene, naphthylene, anthracylene, phenanthrylene, biphenylene or heteroarylene;

wherein the $C_3$-$C_{30}$cycloalkylene, $C_3$-$C_{30}$cycloalkyl-$C_1$-$C_{18}$alkylene, $C_1$-$C_{18}$alkylene, $C_1$-$C_{10}$haloalkylene, $C_2$-$C_{12}$alkenylene, $C_4$-$C_{30}$cycloalkenylene, interrupted $C_2$-$C_{18}$alkylene, interrupted $C_3$-$C_{30}$cycloalkylene, interrupted $C_3$-$C_{30}$cycloalkyl-$C_1$-$C_{18}$alkylene, interrupted $C_4$-$C_{30}$cycloalkenylene, phenylene, naphthylene, anthracylene, phenanthrylene, biphenylene or heteroarylene are unsubstituted or substituted;

or $R_2$ and $R_3$ independently of each other are a direct bond, provided that $R_2$ and $R_3$ are not both simultaneously a direct bond;

$R_4$ is hydrogen, $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl;

or is $C_2$-$C_{18}$alkyl which is interrupted by one or more of O, S, $NR_{14}$, CO, O(CO) or $NR_{14}$(CO);

or is $C_3$-$C_{30}$cycloalkyl which is interrupted by one or more of O, S, $NR_{14}$, CO, O(CO) or $NR_{14}$(CO);

or is $C_3$-$C_{30}$cycloalkyl-$C_1$-$C_{18}$alkyl which is interrupted by one or more of O, S, $NR_{14}$, CO, O(CO) or $NR_{14}$(CO);

or is $C_4$-$C_{30}$cycloalkenyl which is interrupted by one or more of O, S, $NR_{14}$, CO, O(CO) or $NR_{14}$(CO);

or $R_4$ is phenyl, naphthyl, anthracyl, phenanthryl, biphenyl, heteroaryl, $C_1$-$C_{18}$alkanoyl, benzoyl, $C_2$-$C_{18}$alkoxycarbonyl, phenoxycarbonyl, $C_1$-$C_{18}$alkylsulfonyl or phenylsulfonyl;

wherein the $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, interrupted $C_2$-$C_{18}$alkyl, interrupted $C_3$-$C_{30}$cycloalkyl, interrupted $C_3$-$C_{30}$cycloalkyl-$C_1$-$C_{18}$alkyl, interrupted $C_4$-$C_{30}$cycloalkenyl, phenyl, naphthyl, anthracyl, phenanthryl, biphenyl, heteroaryl, $C_1$-$C_{18}$alkanoyl, benzoyl, $C_2$-$C_{18}$alkoxycarbonyl, phenoxycarbonyl, $C_1$-$C_{18}$alkylsulfonyl or phenylsulfonyl are unsubstituted or substituted;

or $R_1$ and $R_4$, together with the nitrogen atom to which $R_4$ is attached, form a 5-, 6- or 7-membered ring which optionally is interrupted by one or more O, $NR_{14}$ or CO;

$R_{12}$ and $R_{13}$ independently of each other are hydrogen, $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl;

or independently of each other are $C_2$-$C_{18}$alkyl which is interrupted by one or more of O, S, $NR_{14}$, CO, O(CO) or $NR_{14}$(CO);

or independently of each other are $C_3$-$C_{30}$cycloalkyl which is interrupted by one or more of O, S, $NR_{14}$, CO, O(CO) or $NR_{14}$(CO);

or independently of each other are $C_3$-$C_{30}$cycloalkyl-$C_1$-$C_{18}$alkyl which is interrupted by one or more of O, S, $NR_{14}$, CO, O(CO) or $NR_{14}$(CO);

or independently of each other are $C_4$-$C_{30}$cycloalkenyl which is interrupted by one or more of O, S, $NR_{14}$, CO, O(CO) or $NR_{14}$(CO);

or $R_{12}$ and $R_{13}$ independently of each other are Ar, (CO)$R_{15}$, (CO)O$R_{15}$ or SO$_2R_{15}$;

wherein the $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl;

interrupted $C_2$-$C_{18}$alkyl, interrupted $C_3$-$C_{30}$cycloalkyl, interrupted $C_3$-$C_{30}$cycloalkyl-$C_1$-$C_{18}$alkyl, interrupted $C_4$-$C_{30}$cycloalkenyl or Ar are unsubstituted or substituted;

or $R_{12}$ and $R_{13}$, together with the nitrogen atom to which they are attached, form a 5-, 6- or 7-membered ring which optionally is interrupted by one or more O, $NR_{14}$ or CO;

$R_{14}$ is hydrogen, $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl;

or is $C_2$-$C_{18}$alkyl which is interrupted by one or more of O, S, CO or O(CO);

or is $C_3$-$C_{30}$cycloalkyl which is interrupted by one or more of O, S, CO or O(CO);

or is $C_3$-$C_{30}$cycloalkyl-$C_1$-$C_{18}$alkyl which is interrupted by one or more of O, S, CO or O(CO);

or is $C_4$-$C_{30}$cycloalkenyl which is interrupted by one or more O, S, CO or O(CO); or $R_{14}$ is phenyl, naphthyl, anthracyl, phenanthryl, biphenylyl, heteroaryl, $C_1$-$C_{18}$alkanoyl, benzoyl, $C_2$-$C_{18}$alkoxycarbonyl, phenoxycarbonyl, $C_1$-$C_{18}$alkylsulfonyl or phenylsulfonyl;

wherein the $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, interrupted $C_2$-$C_{18}$alkyl, interrupted $C_3$-$C_{30}$cycloalkyl, interrupted $C_3$-$C_{30}$cycloalkyl-$C_1$-$C_{18}$alkyl, $C_4$-$C_{30}$cycloalkenyl, phenyl, naphthyl, anthracyl, phenanthryl, biphenylyl, heteroaryl, $C_1$-$C_{18}$alkanoyl, benzoyl, $C_2$-$C_{18}$alkoxycarbonyl, phenoxycarbonyl, $C_1$-$C_{18}$alkylsulfonyl or phenylsulfonyl are unsubstituted or substituted;

$R_{15}$ is hydrogen, Ar, $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl;

or is $C_2$-$C_{18}$alkyl which is interrupted by one or more of O, S, $NR_{14}$, CO, O(CO) or $NR_{14}$(CO);

or is $C_3$-$C_{30}$cycloalkyl which is interrupted by one or more of O, S, $NR_{14}$, CO, O(CO) or $NR_{14}$(CO);

or is $C_3$-$C_{30}$cycloalkyl-$C_1$-$C_{18}$alkyl which is interrupted by one or more of O, S, $NR_{14}$, CO, O(CO) or $NR_{14}$(CO);

or is $C_4$-$C_{30}$cycloalkenyl which is interrupted by one or more of O, S, $NR_{14}$, CO, O(CO) or $NR_{14}$(CO);

wherein the Ar, $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, interrupted $C_2$-$C_{18}$alkyl, interrupted $C_3$-$C_{30}$cycloalkyl, interrupted $C_3$-$C_{30}$cycloalkyl-$C_1$-$C_{18}$alkyl, or interrupted $C_4$-$C_{30}$cycloalkenyl are unsubstituted or substituted; and Ar is phenyl, biphenylyl, fluorenyl, naphthyl, anthracyl, phenanthryl or heteroaryl, wherein the phenyl, biphenylyl, fluorenyl, naphthyl, anthracyl, phenanthryl or heteroaryl are unsubstituted or substituted.

Subject of the invention are compounds of the formula I or II as defined above.

The acids of the formula I or II are characterized as substituted 1,1,2-trifluoroalkylsulfonic acids, in particular as 1,1,2-trifluoromethylsulfonic acids.

Especially subject of the invention pertains to a compound generating an acid of the formula I or II as described above, wherein $R_1$ is hydrogen, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, $C_3$-$C_{30}$cycloalkyl, $C_3$-$C_{30}$cycloalkyl-$C_1$-$C_{18}$alkyl, or is $C_2$-$C_{18}$alkyl which is interrupted by one or more of O, S, $NR_{14}$, CO, O(CO) or $NR_{14}$(CO);

or is $C_3$-$C_{30}$cycloalkyl which is interrupted by one or more of O, S, $NR_{14}$, CO, O(CO) or $NR_{14}$(CO);

or is $C_3$-$C_{30}$cycloalkyl-$C_1$-$C_{18}$alkyl which is interrupted by one or more of O, S, $NR_{14}$, CO, O(CO) or $NR_{14}$(CO);

or is $C_4$-$C_{30}$cycloalkenyl which is interrupted by one or more of O, S, $NR_{14}$, CO, O(CO) or $NR_{14}$(CO);

or $R_1$ is phenyl, naphthyl, anthracyl, phenanthryl, biphenylyl, fluorenyl or heteroaryl;

or $R_1$ is $NR_{12}R_{13}$;

or $R_1$ is a monovalent $C_{17}$-$C_{50}$hydrocarbon group of steroid structure which may contain one or more heteroatoms;

wherein the $C_3$-$C_{30}$cycloalkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, $C_3$-$C_{30}$cycloalkyl-$C_1$-$C_{18}$alkyl, interrupted $C_2$-$C_{18}$alkyl, interrupted $C_3$-$C_{30}$cycloalkyl, interrupted $C_3$-$C_{30}$cycloalkyl-$C_1$-$C_{18}$alkyl, interrupted $C_4$-$C_{30}$cycloalkenyl, phenyl, naphthyl, anthracyl, phenanthryl, biphenylyl, fluorenyl or heteroaryl are unsubstituted or are substituted by one or more Z;

Z is $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl;

or is $C_2$-$C_{18}$alkyl which is interrupted by one or more of O, S, $NR_{14}$, CO, O(CO) or $NR_{14}$(CO);

or is $C_3$-$C_{30}$cycloalkyl which is interrupted by one or more of O, S, $NR_{14}$, CO, O(CO) or $NR_{14}$(CO);

or is $C_3$-$C_{30}$cycloalkyl-$C_1$-$C_{18}$alkyl which is interrupted by one or more of O, S, $NR_{14}$, CO, O(CO) or $NR_{14}$(CO);

or is $C_4$-$C_{30}$cycloalkenyl which is interrupted by one or more of O, S, $NR_{14}$, O(CO) or $NR_{14}$(CO);

or is $C_5$-$C_{30}$cycloalkyl-$C_1$-$C_4$alkyl, which is substituted by one or more of $NR_{14}$(CO)$OR_{11}$ or $NR_{14}$(CO)$NR_{12}R_{13}$;

or is halogen, $NO_2$, CN, Ar, (CO)$R_{15}$, (CO)$OR_{11}$, (CO)$NR_{12}R_{13}$, O(CO)$R_{15}$, O(CO)$OR_{11}$, O(CO)$NR_{12}R_{13}$, $NR_{14}$(CO)$R_{15}$, $NR_{14}$(CO)$OR_{11}$, $NR_{14}$(CO)$NR_{12}R_{13}$, $OR_{11}$, $NR_{12}R_{13}$, $SR_{14}$, $SOR_{15}$, $SO_2R_{15}$ and/or $OSO_2R_{15}$;

optionally the radicals Z as $C_1$-$C_{18}$alkyl, $C_2$-$C_{12}$alkenyl, (CO)$R_{15}$, (CO)$OR_{11}$, (CO)$NR_{12}R_{13}$, O(CO)$R_{15}$, O(CO)$OR_{11}$, O(CO)$NR_{12}R_{13}$, $NR_{14}$(CO)$R_{15}$, $NR_{14}$(CO)$OR_{11}$, $NR_{14}$(CO)$NR_{12}R_{13}$, $OR_{11}$, $NR_{12}R_{13}$, $SR_{14}$, $SOR_{15}$, $SO_2R_{15}$ and/or $OSO_2R_{15}$ on the phenyl, naphthyl, anthracyl, phenanthryl, biphenylyl, fluorenyl or heteroaryl; form 5-, 6- or 7-membered rings, via the radicals $C_1$-$C_{18}$alkyl, $C_2$-$C_{12}$alkenyl, $R_{11}$, $R_{12}$, $R_{13}$, $R_{14}$ and/or $R_{15}$, with further substituents on the phenyl, naphthyl, anthracyl, phenanthryl, biphenylyl, fluorenyl or heteroaryl; or with one of the carbon atoms of the phenyl, naphthyl, anthracyl, phenanthryl, biphenylyl, fluorenyl or heteroaryl;

$R_2$ and $R_3$ independently of each other are $C_3$-$C_{30}$cycloalkylene, $C_3$-$C_{30}$cycloalkyl-$C_1$-$C_{18}$alkyl, $C_1$-$C_{18}$alkylene, $C_1$-$C_{10}$haloalkylene, $C_2$-$C_{12}$alkenylene, $C_4$-$C_{30}$cycloalkenylene;

or independently of each other are $C_2$-$C_{18}$alkylene which is interrupted by one or more of O, S, $NR_{14}$, CO, O(CO) or $NR_{14}$(CO);

or independently of each other are $C_3$-$C_{30}$cycloalkylene which is interrupted by one or more of O, S, $NR_{14}$, CO, O(CO) or $NR_{14}$(CO);

or independently of each other are $C_3$-$C_{30}$cycloalkyl-$C_1$-$C_{18}$alkyl which is interrupted by one or more of O, S, $NR_{14}$, CO, O(CO) or $NR_{14}$(CO);

or independently of each other are $C_4$-$C_{30}$cycloalkenylene which is interrupted by one or more of O, S, $NR_{14}$, CO, O(CO) or $NR_{14}$(CO);

or $R_2$ and $R_3$ independently of each other are phenylene, naphthylene, anthracylene, phenanthrylene, biphenylene or heteroarylene;

wherein the $C_3$-$C_{30}$cycloalkylene, $C_3$-$C_{30}$cycloalkyl-$C_1$-$C_{18}$alkyl, $C_1$-$C_{18}$alkylene, $C_1$-$C_{10}$haloalkylene, $C_2$-$C_{12}$alkenylene, $C_4$-$C_{30}$cycloalkenylene, interrupted $C_2$-$C_{18}$alkylene, interrupted $C_3$-$C_{30}$cycloalkylene, interrupted $C_3$-$C_{30}$cycloalkyl-$C_1$-$C_{18}$alkyl, interrupted $C_4$-$C_{30}$cycloalkenylene, phenylene, naphthylene, anthracylene, phenanthrylene, biphenylene or heteroarylene are unsubstituted or substituted by one or more Z;

optionally the radicals Z as $C_1$-$C_{18}$alkyl, $C_2$-$C_{12}$alkenyl, (CO)$R_{15}$, (CO)$OR_{11}$, (CO)$NR_{12}R_{13}$, O(CO)$R_{15}$, O(CO)$OR_{11}$, O(CO)$NR_{12}R_{13}$, $NR_{14}$(CO)$R_{15}$, $NR_{14}$(CO)$OR_{11}$, $NR_{14}$(CO)$NR_{12}R_{13}$, $OR_{11}$, $NR_{12}R_{13}$, $SR_{14}$, $SOR_{15}$, $SO_2R_{15}$ and/or $OSO_2R_{15}$ on the phenylene, naphthylene, anthracylene, phenanthrylene, biphenylene, fluorenylene or heteroarylene; form 5-, 6- or 7-membered rings, via the radicals $C_1$-$C_{18}$alkyl, $C_2$-$C_{12}$alkenyl, $R_{11}$, $R_{12}$, $R_{13}$, $R_{14}$ and/or $R_{15}$, with further substituents on the phenylene, naphthylene, anthracylene, phenanthrylene, biphenylene, fluorenylene or heteroarylene; or with one of the carbon atoms of the phenylene, naphthylene, anthracylene, phenanthrylene, biphenylene, fluorenylene or heteroarylene;

or $R_2$ and $R_3$ independently of each other are a direct bond;

$R_4$ is hydrogen, $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl;

or is $C_2$-$C_{18}$alkyl which is interrupted by one or more of O, S, $NR_{14}$, CO, O(CO) or $NR_{14}$(CO);

or is $C_3$-$C_{30}$cycloalkyl which is interrupted by one or more of O, S, $NR_{14}$, CO, O(CO) or $NR_{14}$(CO);

or is $C_3$-$C_{30}$cycloalkyl-$C_1$-$C_{18}$alkyl which is interrupted by one or more of O, S, $NR_{14}$, CO, O(CO) or $NR_{14}$(CO);

or is $C_4$-$C_{30}$cycloalkenyl which is interrupted by one or more of O, S, $NR_{14}$, CO, O(CO) or $NR_{14}$(CO);

or $R_4$ is phenyl, naphthyl, anthracyl, phenanthryl, biphenyl, heteroaryl, $C_1$-$C_{18}$alkanoyl, benzoyl, $C_2$-$C_{18}$alkoxycarbonyl, phenoxycarbonyl, $C_1$-$C_{18}$alkylsulfonyl or phenylsulfonyl;

wherein the $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, interrupted $C_2$-$C_{18}$alkyl, interrupted $C_3$-$C_{30}$cycloalkyl, interrupted $C_3$-$C_{30}$cycloalkyl-$C_1$-$C_{18}$alkyl, interrupted $C_4$-$C_{30}$cycloalkenyl, phenyl, naphthyl, anthracyl, phenanthryl, biphenyl, heteroaryl, $C_1$-$C_{18}$alkanoyl, benzoyl, $C_2$-$C_{18}$alkoxycarbonyl, phenoxycarbonyl, $C_1$-$C_{18}$alkylsulfonyl or phenylsulfonyl are unsubstituted or substituted by one or more Z;

or $R_1$ and $R_4$, together with the nitrogen atom to which $R_4$ is attached, form a 5-, 6- or 7-membered ring which optionally is interrupted by one or more O, $NR_{14}$ or CO;

$R_{11}$ is hydrogen, $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, or is $C_2$-$C_{18}$alkyl which is interrupted by one or more of O, S, $NR_{14}$, CO, O(CO) or $NR_{14}$(CO);

or is $C_3$-$C_{30}$cycloalkyl which is interrupted by one or more of O, S, $NR_{14}$, CO, O(CO) or $NR_{14}$(CO);

or is $C_3$-$C_{30}$cycloalkyl-$C_1$-$C_{18}$alkyl which is interrupted by one or more of O, S, $NR_{14}$, CO, O(CO) or $NR_{14}$(CO);

or is $C_4$-$C_{30}$cycloalkenyl which is interrupted by one or more of O, S, $NR_{14}$, CO, O(CO) or $NR_{14}$(CO);

or $R_{11}$ is Ar, (CO)$R_{15}$, (CO)$OR_{15}$, (CO)$NR_{12}R_{13}$ or $SO_2R_{15}$;

wherein the $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, interrupted $C_2$-$C_{18}$alkyl, interrupted $C_3$-$C_{30}$cycloalkyl, interrupted $C_3$-$C_{30}$cycloalkyl-$C_1$-$C_{18}$alkyl or interrupted $C_4$-$C_{30}$cycloalkenyl are unsubstituted or substituted by one or more $Z_1$;

$Z_1$ is Ar, OH, $C_1$-$C_{18}$alkyl, $C_1$-$C_{10}$haloalkyl, phenyl-$C_1$-$C_3$-alkyl, $C_3$-$C_{30}$cycloalkyl, halogen, $NO_2$, CN, $C_1$-$C_{18}$alkoxy, phenoxy, phenoxycarbonyl, phenylthio, phenylthiocarbonyl, $NR_{12}R_{13}$, $C_1$-$C_{12}$alkylthio, $C_2$-$C_{18}$alkoxycarbonyl, $C_2$-$C_{10}$haloalkanoyl, halobenzoyl, $C_1$-$C_{18}$alkylsulfonyl, phenylsulfonyl, (4-methylphenyl)sulfonyl, $C_1$-$C_{18}$alkylsulfonyloxy, phenylsulfonyloxy, (4-methylphenyl)sulfonyloxy, $C_1$-$C_{18}$alkanoyl, $C_1$-$C_{18}$alkanoyloxy, benzoyl and/or by benzoyloxy;

$R_{12}$ and $R_{13}$ independently of each other are hydrogen, $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl;

or independently of each other are $C_2$-$C_{18}$alkyl which is interrupted by one or more of O, S, $NR_{14}$, CO, O(CO) or $NR_{14}$(CO);

or independently of each other are $C_3$-$C_{30}$cycloalkyl which is interrupted by one or more of O, S, $NR_{14}$, CO, O(CO) or $NR_{14}$(CO);

or independently of each other are $C_3$-$C_{30}$cycloalkyl-$C_1$-$C_{18}$alkyl which is interrupted by one or more of O, S, $NR_{14}$, CO, O(CO) or $NR_{14}$(CO);

or independently of each other are $C_4$-$C_{30}$cycloalkenyl which is interrupted by one or more of O, S, $NR_{14}$, CO, O(CO) or $NR_{14}$(CO);

or $R_{12}$ and $R_{13}$ independently of each other are Ar, (CO)$R_{15}$, (CO)OR$_{15}$ or SO$_2R_{15}$;

wherein the $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, interrupted $C_2$-$C_{18}$alkyl, interrupted $C_3$-$C_{30}$cycloalkyl, interrupted $C_3$-$C_{30}$cycloalkyl-$C_1$-$C_{18}$alkyl or interrupted $C_4$-$C_{30}$cycloalkenyl are unsubstituted or substituted by one or more $Z_1$;

or $R_{12}$ and $R_{13}$, together with the nitrogen atom to which they are attached, form a 5-, 6- or 7-membered ring which optionally is interrupted by one or more O, $NR_{14}$ or CO;

$R_{14}$ is hydrogen, $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl;

or is $C_2$-$C_{18}$alkyl which is interrupted by one or more of O, S, CO or O(CO);

or is $C_3$-$C_{30}$cycloalkyl which is interrupted by one or more of O, S, CO or O(CO);

or is $C_3$-$C_{30}$cycloalkyl-$C_1$-$C_{18}$alkyl which is interrupted by one or more of O, S, CO or O(CO);

or is $C_4$-$C_{30}$cycloalkenyl which is interrupted by one or more O, S, CO or O(CO);

or $R_{14}$ is phenyl, naphthyl, anthracyl, phenanthryl, biphenylyl, heteroaryl, $C_1$-$C_{18}$alkanoyl, benzoyl, $C_2$-$C_{18}$alkoxycarbonyl, phenoxycarbonyl, $C_1$-$C_{18}$alkylsulfonyl or phenylsulfonyl;

wherein the $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, interrupted $C_2$-$C_{18}$alkyl, interrupted $C_3$-$C_{30}$cycloalkyl, interrupted $C_3$-$C_{30}$cycloalkyl-$C_1$-$C_{18}$alkyl, $C_4$-$C_{30}$cycloalkenyl, phenyl, naphthyl, anthracyl, phenanthryl, biphenylyl, heteroaryl, $C_1$-$C_{18}$alkanoyl, benzoyl, $C_2$-$C_{18}$alkoxycarbonyl, phenoxycarbonyl, $C_1$-$C_{18}$alkylsulfonyl or phenylsulfonyl are unsubstituted or substituted by one or more $Z_1$;

$R_{15}$ is hydrogen, Ar, $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl;

or is $C_2$-$C_{18}$alkyl which is interrupted by one or more of O, S, $NR_{14}$, CO, O(CO) or $NR_{14}$(CO);

or is $C_3$-$C_{30}$cycloalkyl which is interrupted by one or more of O, S, $NR_{14}$, CO, O(CO) or $NR_{14}$(CO);

or is $C_3$-$C_{30}$cycloalkyl-$C_1$-$C_{18}$alkyl which is interrupted by one or more of O, S, $NR_{14}$, CO, O(CO) or $NR_{14}$(CO);

or is $C_4$-$C_{30}$cycloalkenyl which is interrupted by one or more of O, S, $NR_{14}$, CO, O(CO) or $NR_{14}$(CO);

wherein the $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, interrupted $C_2$-$C_{18}$alkyl, interrupted $C_3$-$C_{30}$cycloalkyl, interrupted $C_3$-$C_{30}$cycloalkyl-$C_1$-$C_{18}$alkyl or interrupted $C_4$-$C_{30}$cycloalkenyl are unsubstituted or substituted by one or more $Z_1$;

Ar is phenyl, biphenylyl, fluorenyl, naphthyl, anthracyl, phenanthryl or heteroaryl, wherein the phenyl, biphenylyl, fluorenyl, naphthyl, anthracyl, phenanthryl or heteroaryl are unsubstituted or substituted by one or more $Z_2$, optionally the radicals $Z_2$ as $C_1$-$C_{18}$alkyl, $C_2$-$C_{12}$alkenyl, (CO)$R_{15}$, (CO)OR$_{11}$, (CO)NR$_{12}R_{13}$, O(CO)$R_{15}$, O(CO)OR$_{11}$, O(CO)NR$_{12}R_{13}$, $NR_{14}$(CO)$R_{15}$, $NR_{14}$(CO)OR$_{11}$, $NR_{14}$(CO)NR$_{12}R_{13}$, OR$_{11}$, $NR_{12}R_{13}$, SR$_{14}$, SOR$_{15}$, SO$_2R_{15}$ and/or OSO$_2R_{15}$, form 5-, 6- or 7-membered rings, via the radicals $C_1$-$C_{18}$alkyl, $C_2$-$C_{12}$alkenyl, $R_{11}$, $R_{12}$, $R_{13}$, $R_{14}$ and/or $R_{15}$, with further substituents on the phenyl, biphenylyl, fluorenyl, naphthyl, anthracyl, phenanthryl or heteroaryl ring or with one of the carbon atoms of the phenyl, biphenylyl, fluorenyl, naphthyl, anthracyl, phenanthryl or heteroaryl ring; and $Z_2$ is $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl;

or is $C_2$-$C_{18}$alkyl which is interrupted by one or more of O, S, $NR_{14}$, CO, O(CO) or $NR_{14}$(CO);

or is $C_3$-$C_{30}$cycloalkyl which is interrupted by one or more of O, S, $NR_{14}$, CO, O(CO) or $NR_{14}$(CO);

or is $C_3$-$C_{30}$cycloalkyl-$C_1$-$C_{18}$alkyl which is interrupted by one or more of O, S, $NR_{14}$, CO, O(CO) or $NR_{14}$(CO);

or is $C_4$-$C_{30}$cycloalkenyl which is interrupted by one or more of O, S, $NR_{14}$, O(CO) or $NR_{14}$(CO);

or is $C_5$-$C_{30}$cycloalkyl-$C_1$-$C_4$alkyl, which is substituted by one or more of $NR_{14}$(CO)OR$_{11}$ or $NR_{14}$(CO)NR$_{12}R_{13}$;

or is halogen, NO$_2$, CN, (CO)$R_{15}$, (CO)OR$_{11}$, (CO)NR$_{12}R_{13}$, O(CO)$R_{15}$, O(CO)OR$_{11}$, O(CO)NR$_{12}R_{13}$, $NR_{14}$(CO)$R_{15}$, $NR_{14}$(CO)OR$_{11}$, $NR_{14}$(CO)NR$_{12}R_{13}$, OR$_{11}$, $NR_{12}R_{13}$, SR$_{14}$, SOR$_{15}$, SO$_2R_{15}$, OSO$_2R_{15}$, phenyl, biphenylyl, fluorenyl, naphthyl, anthracyl, phenanthryl and/or heteroaryl;

optionally the radicals $Z_2$ as $C_1$-$C_{18}$alkyl, $C_2$-$C_{12}$alkenyl, (CO)$R_{15}$, (CO)OR$_{11}$, (CO)NR$_{12}R_{13}$, O(CO)$R_{15}$, O(CO)OR$_{11}$, O(CO)NR$_{12}R_{13}$, $NR_{14}$(CO)$R_{15}$, $NR_{14}$(CO)OR$_{11}$, $NR_{14}$(CO)NR$_{12}R_{13}$, OR$_{11}$, $NR_{12}R_{13}$, SR$_{14}$, SOR$_{15}$, SO$_2R_{15}$ and/or OSO$_2R_{15}$ on the phenyl, naphthyl, anthracyl, phenanthryl, biphenylyl, fluorenyl or heteroaryl; form 5-, 6- or 7-membered rings, via the radicals $C_1$-$C_{18}$alkyl, $C_2$-$C_{12}$alkenyl, $R_{11}$, $R_{12}$, $R_{13}$, $R_{14}$ and/or $R_{15}$, with further substituents on the phenyl, naphthyl, anthracyl, phenanthryl, biphenylyl, fluorenyl or heteroaryl; or with one of the carbon atoms of the phenyl, naphthyl, anthracyl, phenanthryl, biphenylyl, fluorenyl or heteroaryl.

A particular subject of the invention are compounds generating an acid of the formula I or II, which are of the formula IIIa, IIIb, IVa or IVb

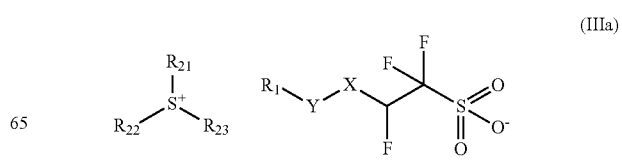

(IIIa)

-continued

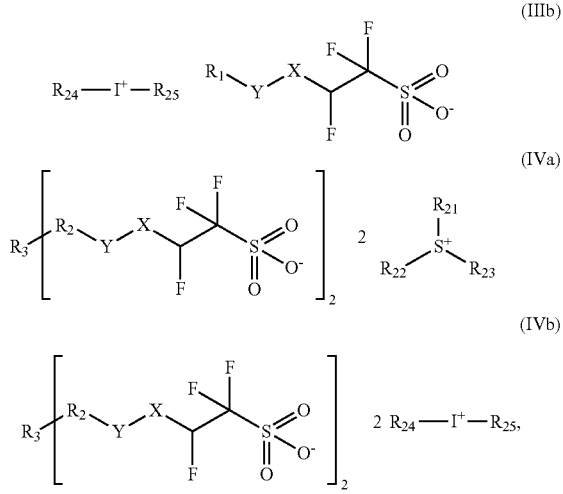

wherein
$R_{21}$, $R_{22}$ and $R_{23}$ independently of each other are $Ar_1$, $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl;
or independently of each other are $C_2$-$C_{18}$alkyl which is interrupted by one or more of O, S, $NR_{14}$, CO, O(CO) or $NR_{14}$(CO);
or independently of each other are $C_3$-$C_{30}$cycloalkyl which is interrupted by one or more of O, S, $NR_{14}$, CO, O(CO) or $NR_{14}$(CO);
or independently of each other are $C_3$-$C_{30}$cycloalkyl-$C_1$-$C_{18}$alkyl which is interrupted by one or more of O, S, $NR_{14}$, CO, O(CO) or $NR_{14}$(CO);
or independently of each other are $C_4$-$C_{30}$cycloalkenyl which is interrupted by one or more of O, S, $NR_{14}$, CO, O(CO) or $NR_{14}$(CO);
wherein the $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, interrupted $C_2$-$C_{18}$alkyl, interrupted $C_3$-$C_{30}$cycloalkyl, interrupted $C_3$-$C_{30}$cycloalkyl-$C_1$-$C_{18}$alkyl or $C_4$-$C_{30}$cycloalkenyl are unsubstituted or are substituted by one or more Z;
or $R_{21}$ and $R_{22}$, optionally together with a direct bond, O, S, $NR_{14}$ or (CO), form a fused ring system;
or $R_{21}$ and $R_{22}$, optionally together with direct bond, $C_1$-$C_6$alkylene, O, S, $NR_{14}$ or (CO), form a 5-, 6- or 7-membered ring;
wherein all $R_{21}$, $R_{22}$ and $R_{23}$ optionally additionally are substituted by a group having a —O—C-bond or a —O—Si-bond which cleaves upon the action of an acid;
Z is $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl;
or is $C_2$-$C_{18}$alkyl which is interrupted by one or more of O, S, $NR_{14}$, CO, O(CO) or $NR_{14}$(CO);
or is $C_3$-$C_{30}$cycloalkyl which is interrupted by one or more of O, S, $NR_{14}$, CO, O(CO) or $NR_{14}$(CO);
or is $C_3$-$C_{30}$cycloalkyl-$C_1$-$C_{18}$alkyl which is interrupted by one or more of O, S, $NR_{14}$, CO, O(CO) or $NR_{14}$(CO);
or is $C_4$-$C_{30}$cycloalkenyl which is interrupted by one or more of O, S, $NR_{14}$, CO, O(CO) or $NR_{14}$(CO);
or is $C_5$-$C_{30}$cycloalkyl-$C_1$-$C_4$alkyl, which is substituted by one or more of $NR_{14}$(CO)$OR_{11}$ or $NR_{14}$(CO)$NR_{12}R_{13}$;

or is halogen, $NO_2$, CN, Ar, (CO)$R_{15}$, (CO)$OR_{11}$, (CO)$NR_{12}R_{13}$, O(CO)$R_{15}$, O(CO)$OR_{11}$, O(CO)$NR_{12}R_{13}$, $NR_{14}$(CO)$R_{15}$, $NR_{14}$(CO)$OR_{11}$, $NR_{14}$(CO)$NR_{12}R_{13}$, $OR_{11}$, $NR_{12}R_{13}$, $SR_{14}$, $SOR_{15}$, $SO_2R_{15}$ and/or $OSO_2R_{15}$;
$R_{24}$ and $R_{25}$ independently of each other are $Ar_1$;
or $R_{24}$ and $R_{25}$, optionally together with a direct bond, O, S, $NR_{14}$ or (CO) form a fused ring;
or $R_{24}$ and $R_{25}$, optionally together with $C_1$-$C_2$alkylene, O, S, $NR_{14}$ or (CO), form a 5-, 6- or 7-membered ring;
wherein all $R_{24}$ and $R_{25}$ optionally additionally are substituted by a group having a —O—O-bond or a —O—Si-bond which cleaves upon the action of an acid;
Ar is phenyl, biphenylyl, fluorenyl, naphthyl, anthracyl, phenanthryl or heteroaryl, wherein the phenyl, biphenylyl, fluorenyl, naphthyl, anthracyl, phenanthryl or heteroaryl are unsubstituted or substituted by one or more $Z_2$;
$Ar_1$ is phenyl, biphenylyl, fluorenyl, naphthyl, anthracyl, phenanthryl or heteroaryl, wherein said phenyl, biphenylyl, fluorenyl, naphthyl, anthracyl, phenanthryl or heteroaryl are unsubstituted or are substituted by one or more Z, or are substituted by

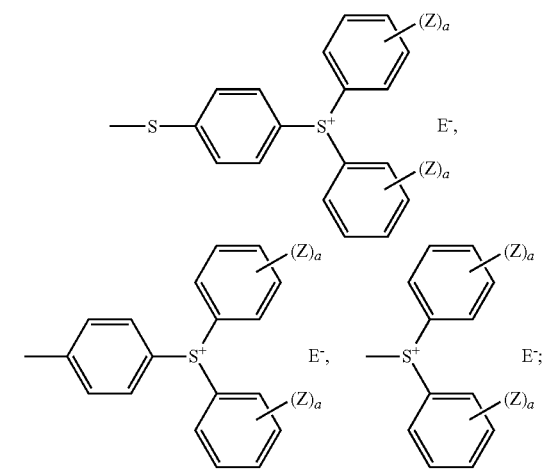

optionally the radicals Z as $C_1$-$C_{18}$alkyl, $C_2$-$C_{12}$alkenyl, (CO)$R_{15}$, (CO)$OR_{11}$, (CO)$NR_{12}R_{13}$, O(CO)$R_{15}$, O(CO)$OR_{11}$, O(CO)$NR_{12}R_{13}$, $NR_{14}$(CO)$R_{15}$, $NR_{14}$(CO)$OR_{11}$, $NR_{14}$(CO)$NR_{12}R_{13}$, $OR_{11}$, $NR_{12}R_{13}$, $SR_{14}$, $SOR_{15}$, $SO_2R_{15}$ and/or —$OSO_2R_{15}$, form 5-, 6- or 7-membered rings, via the radicals $C_1$-$C_{18}$alkyl, $C_2$-$C_{12}$alkenyl, $R_{11}$, $R_{12}$, $R_{13}$, $R_{14}$ and/or $R_{15}$, with further substituents on the phenyl, biphenylyl, fluorenyl, naphthyl, anthracyl, phenanthryl, or heteroaryl ring or with one of the carbon atoms of the phenyl, biphenylyl, fluorenyl, naphthyl, anthracyl, phenanthryl, or heteroaryl ring;
$Z_2$ is $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl;
or is $C_2$-$C_{18}$alkyl which is interrupted by one or more of O, S, $NR_{14}$, CO, O(CO) or $NR_{14}$(CO);
or is $C_3$-$C_{30}$cycloalkyl which is interrupted by one or more of O, S, $NR_{14}$, CO, O(CO) or $NR_{14}$(CO);
or is $C_3$-$C_{30}$cycloalkyl-$C_1$-$C_{18}$alkyl which is interrupted by one or more of O, S, $NR_{14}$, CO, O(CO) or $NR_{14}$(CO);
or is $C_4$-$C_{30}$cycloalkenyl which is interrupted by one or more of O, S, $NR_{14}$, CO, O(CO) or $NR_{14}$(CO);
or is $C_5$-$C_{30}$cycloalkyl-$C_1$-$C_4$alkyl, which is substituted by one or more of $NR_{14}$(CO)$OR_{11}$ or $NR_{14}$(CO)$NR_{12}R_{13}$;

or is halogen, $NO_2$, CN, $(CO)R_{15}$, $(CO)OR_{11}$, $(CO)NR_{12}R_{13}$, $O(CO)R_{15}$, $O(CO)OR_{11}$, $O(CO)NR_{12}R_{13}$, $NR_{14}(CO)R_{15}$, $NR_{14}(CO)OR_{11}$, $NR_{14}(CO)NR_{12}R_{13}$, $OR_{11}$, $NR_{12}R_{13}$, $SR_{14}$, $SOR_{15}$, $SO_2R_{15}$, $OSO_2R_{15}$, phenyl, biphenylyl, fluorenyl, naphthyl, anthracyl, phenanthryl and/or heteroaryl;

optionally the radicals $Z_2$ as $C_1$-$C_{18}$alkyl, $C_2$-$C_{12}$alkenyl, $(CO)R_{15}$, $(CO)OR_{11}$, $(CO)NR_{12}R_{13}$, $O(CO)R_{15}$, $O(CO)OR_{11}$, $O(CO)NR_{12}R_{13}$, $NR_{14}(CO)R_{15}$, $NR_{14}(CO)OR_{11}$, $NR_{14}(CO)NR_{12}R_{13}$, $OR_{11}$, $NR_{12}R_{13}$, $SR_{14}$, $SOR_{15}$, $SO_2R_{15}$ and/or $OSO_2R_{15}$ on the phenyl, naphthyl, anthracyl, phenanthryl, biphenylyl, fluorenyl or heteroaryl; form 5-, 6- or 7-membered rings, via the radicals $C_1$-$C_{18}$alkyl, $C_2$-$C_{12}$alkenyl, $R_{11}$, $R_{12}$, $R_{13}$, $R_{14}$ and/or $R_{15}$, with further substituents on the phenyl, naphthyl, anthracyl, phenanthryl, biphenylyl, fluorenyl or heteroaryl; or with one of the carbon atoms of the phenyl, naphthyl, anthracyl, phenanthryl, biphenylyl, fluorenyl or heteroaryl;

a is 0 or 1;

E is

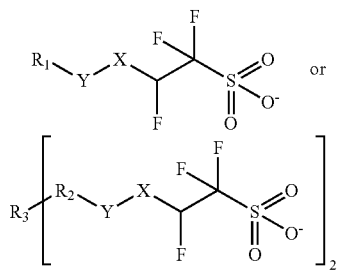

$R_{11}$ is hydrogen, $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, or is $C_2$-$C_{18}$alkyl which is interrupted by one or more of O, S, $NR_{14}$, CO, O(CO) or $NR_{14}$(CO);

or is $C_3$-$C_{30}$cycloalkyl which is interrupted by one or more of O, S, $NR_{14}$, CO, O(CO) or $NR_{14}$(CO);

or is $C_3$-$C_{30}$cycloalkyl-$C_1$-$C_{18}$alkyl which is interrupted by one or more of O, S, $NR_{14}$, CO, O(CO) or $NR_{14}$(CO);

or is $C_4$-$C_{30}$cycloalkenyl which is interrupted by one or more of O, S, $NR_{14}$, CO, O(CO) or $NR_{14}$(CO);

or $R_{11}$ is Ar, $(CO)R_{15}$, $(CO)OR_{15}$, $(CO)NR_{12}R_{13}$ or $SO_2R_{15}$;

wherein the $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, interrupted $C_2$-$C_{18}$alkyl, interrupted $C_3$-$C_{30}$cycloalkyl, interrupted $C_3$-$C_{30}$cycloalkyl-$C_1$-$C_{18}$alkyl or interrupted $C_4$-$C_{30}$cycloalkenyl are unsubstituted or substituted by one or more $Z_1$;

$Z_1$ is Ar, OH, $C_1$-$C_{18}$alkyl, $C_1$-$C_{10}$haloalkyl, phenyl-$C_1$-$C_3$-alkyl, $C_3$-$C_{30}$cycloalkyl, halogen, $NO_2$, CN, $C_1$-$C_{18}$alkoxy, phenoxy, phenoxycarbonyl, phenylthio, phenylthiocarbonyl, $NR_{12}R_{13}$, $C_1$-$C_{12}$alkylthio, $C_2$-$C_{18}$alkoxycarbonyl, $C_2$-$C_{10}$haloalkanoyl, halobenzoyl, $C_1$-$C_{18}$alkylsulfonyl, phenylsulfonyl, (4-methylphenyl)sulfonyl, $C_1$-$C_{18}$alkylsulfonyloxy, phenylsulfonyloxy, (4-methylphenyl)sulfonyloxy, $C_1$-$C_{18}$alkanoyl, $C_1$-$C_{18}$alkanoyloxy, benzoyl and/or by benzoyloxy; and $R_1$, $R_2$, $R_3$, X, Y, $R_{12}$, $R_{13}$, $R_{14}$ and $R_{15}$ are as defined above.

Another particular subject of the invention are compounds generating an acid of the formula I or II, which are of the formula IIIc, IIId, IIIe, IVc or IVe

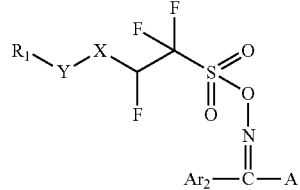

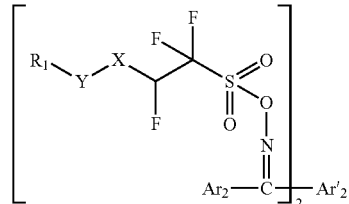

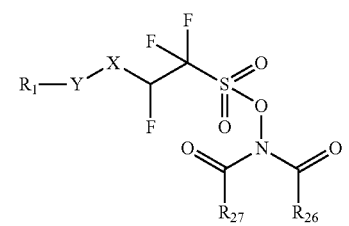

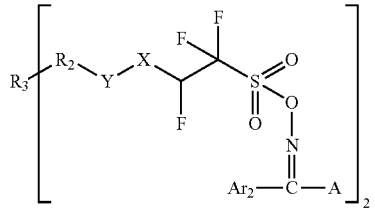

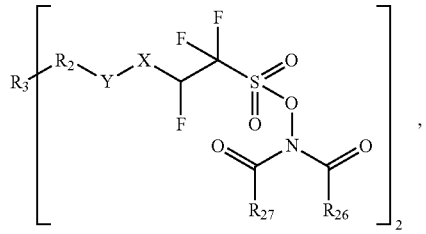

wherein

A is $C_1$-$C_{10}$haloalkyl, CN, $(CO)OR_{11}$ or $SO_2R_{15}$;

$Ar_2$ is $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl;

or is $C_2$-$C_{18}$alkyl which is interrupted by one or more of O, S, $NR_{14}$, CO, O(CO) or $NR_{14}$(CO);

or is $C_3$-$C_{30}$cycloalkyl which is interrupted by one or more of O, S, $NR_{14}$, CO, O(CO) or $NR_{14}$(CO);

or is $C_3$-$C_{30}$cycloalkyl-$C_1$-$C_{18}$alkyl which is interrupted by one or more of O, S, $NR_{14}$, CO, O(CO) or $NR_{14}$(CO);

or is $C_4$-$C_{30}$cycloalkenyl which is interrupted by one or more of O, S, $NR_{14}$, CO, O(CO) or $NR_{14}$(CO);

or $Ar_2$ is phenyl, naphthyl, anthracyl, phenanthryl, biphenylyl, fluorenyl or heteroaryl; wherein the phenyl, naphthyl, anthracyl, phenanthryl, biphenylyl, fluorenyl or heteroaryl are unsubstituted or are substituted by one or more Z;

optionally the radicals Z as $C_1$-$C_{18}$alkyl, $C_2$-$C_{12}$alkenyl, $(CO)R_{15}$, $(CO)OR_{11}$, $(CO)NR_{12}R_{13}$, $O(CO)R_{15}$, $O(CO)OR_{11}$, $O(CO)NR_{12}R_{13}$, $NR_{14}(CO)R_{15}$, $NR_{14}(CO)OR_{11}$, $NR_{14}(CO)NR_{12}R_{13}$, $OR_{11}$, $NR_{12}R_{13}$, $SR_{14}$, $SOR_{15}$, $SO_2R_{15}$ and/or $OSO_2R_{15}$ on the phenyl, naphthyl, anthracyl, phenanthryl, biphenylyl, fluorenyl or heteroaryl form 5-, 6- or 7-membered rings, via the radicals $C_1$-$C_{18}$alkyl, $C_2$-$C_{12}$alkenyl, $R_{11}$, $R_{12}$, $R_{13}$, $R_{14}$ and/or $R_{15}$, with further substituents on the phenyl, naphthyl, anthracyl, phenanthryl, biphenyl, fluorenyl or heteroaryl; or with one of the carbon atoms of the phenyl, naphthyl, anthracyl, phenanthryl, biphenylyl, fluorenyl or heteroaryl;

wherein all $Ar_2$ optionally additionally are substituted by a group having a —O—C-bond or a —O—Si-bond which cleaves upon the action of an acid;

$Ar'_2$ is $C_3$-$C_{30}$cycloalkylene, $C_3$-$C_{30}$cycloalkyl-$C_1$-$C_{18}$alkylene, $C_1$-$C_{18}$alkylene, $C_1$-$C_{10}$haloalkylene, $C_2$-$C_{12}$alkenylene, $C_4$-$C_{30}$cycloalkenylene;

or is $C_2$-$C_{18}$alkylene which is interrupted by one or more of O, S, $NR_{14}$, CO, O(CO) or $NR_{14}$(CO);

or is $C_3$-$C_{30}$cycloalkylene which is interrupted by one or more of O, S, $NR_{14}$, CO, O(CO) or $NR_{14}$(CO);

or is $C_3$-$C_{30}$cycloalkyl-$C_1$-$C_{18}$alkylene which is interrupted by one or more of O, S, $NR_{14}$, CO, O(CO) or $NR_{14}$(CO);

or is $C_4$-$C_{30}$cycloalkenylene which is interrupted by one or more of O, S, $NR_{14}$, CO, O(CO) or $NR_{14}$(CO);

or $Ar'_2$ is a direct bond, phenylene, naphthylene,

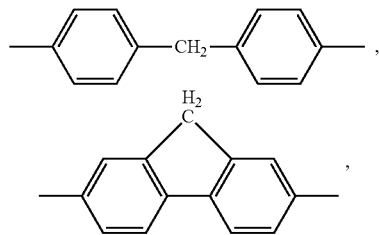

diphenylene, heteroarylene, oxydiphenylene or

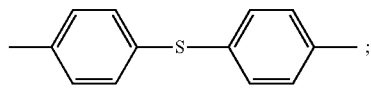

wherein the phenylene, naphthylene,

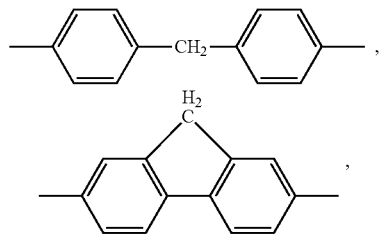

diphenylene, heteroarylene, oxydiphenylene or

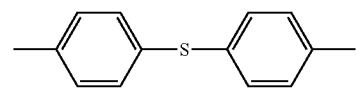

are unsubstituted or are substituted by one or more Z: optionally the radicals Z as $C_1$-$C_{18}$alkyl, $C_2$-$C_{12}$alkenyl, $(CO)R_{15}$, $(CO)OR_{11}$, $(CO)NR_{12}R_{13}$, $O(CO)R_{15}$, $O(CO)$ $OR_{11}$, $O(CO)NR_{12}R_{13}$, $NR_{14}(CO)R_{15}$, $NR_{14}(CO)OR_{11}$, $NR_{14}(CO)NR_{12}R_{13}$, $OR_{11}$, $NR_{12}R_{13}$, $SR_{14}$, $SOR_{15}$, $SO_2R_{15}$ and/or $OSO_2R_{15}$ on the phenylene, naphthylene,

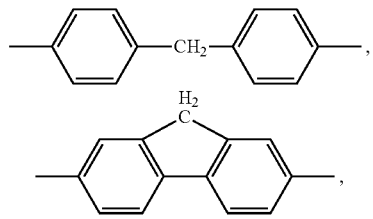

diphenylene, heteroarylene, oxydiphenylene or

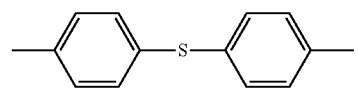

form 5-, 6- or 7-membered rings, via the radicals $C_1$-$C_{18}$, $C_2$-$C_{12}$alkenyl, $R_{11}$, $R_{12}$, $R_{13}$, $R_{14}$ and/or $R_{15}$, with further substituents on the phenylene, naphthylene,

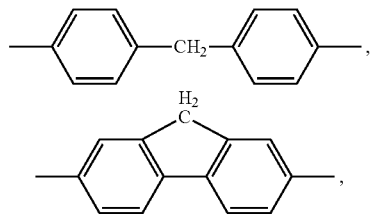

diphenylene, heteroarylene, oxydiphenylene or

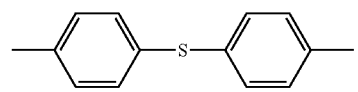

or with one of the carbon atoms of the phenylene, naphthylene,

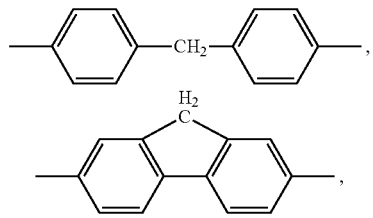

diphenylene, heteroarylene, oxydiphenylene or

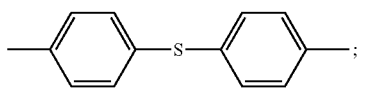

wherein all Ar'$_2$ with the exception of direct bond optionally additionally are substituted by a group having a —O—C-bond or a —O—Si-bond which cleaves upon the action of an acid;

or Ar'$_2$ is a group —Ar"$_2$-A$_1$-Y$_1$-A$_1$-Ar"$_2$—;

Ar"$_2$ is phenylene, naphthylene, anthracylene, phenanthrylene or heteroarylene, wherein the phenylene, naphthylene, anthracylene, phenanthrylene or heteroarylene are unsubstituted or are substituted by one or more Z;

optionally the radicals Z as C$_1$-C$_{18}$alkyl, C$_2$-C$_{12}$alkenyl, (CO)R$_{15}$, (CO)OR$_{11}$, (CO)NR$_{12}$R$_{13}$, O(CO)R$_{15}$, O(CO)OR$_{11}$, O(CO)NR$_{12}$R$_{13}$, NR$_{14}$(CO)R$_{15}$, NR$_{14}$(CO)OR$_{11}$, NR$_{14}$(CO)NR$_{12}$R$_{13}$, OR$_{11}$, NR$_{12}$R$_{13}$, SR$_{14}$, SOR$_{15}$, SO$_2$R$_{15}$ and/or OSO$_2$R$_{15}$ on the phenylene, naphthylene, anthracylene, phenanthrylene, or heteroarylene form 5-, 6- or 7-membered rings, via the radicals C$_1$-C$_{18}$alkyl, C$_2$-C$_{12}$alkenyl, R$_{11}$, R$_{12}$, R$_{13}$, R$_{14}$ and/or R$_{15}$, with further substituents on the phenylene, naphthylene, anthracylene, phenanthrylene, or heteroarylene or with one of the carbon atoms of the phenylene, naphthylene, anthracylene, phenanthrylene, or heteroarylene;

wherein all radicals Ar"$_2$ optionally additionally are substituted by a group having a —O—C-bond or a —O—Si-bond which cleaves upon the action of an acid;

A$_1$ is a direct bond, O, S, NR$_{14}$, CO, O(CO), S(CO), NR$_{14}$(CO), SO, SO$_2$, or OSO$_2$; or A$_1$ is C$_1$-C$_{18}$alkylene which is unsubstituted or substituted by one or more C$_1$-C$_4$haloalkyl, halogen, OR$_{11}$ and/or SR$_{14}$, or is phenylene which is unsubstituted or substituted by one or more C$_1$-C$_{12}$alkyl, C$_1$-C$_4$haloalkyl, halogen, OR$_{11}$ and/or SR$_{14}$;

Y$_1$ is C$_1$-C$_{18}$alkylene which is unsubstituted or substituted by one or more OR$_{11}$, SR$_{14}$, halogen or phenyl; or Y$_1$ is C$_2$-C$_{18}$alkylene, which is interrupted by one or more of O, S, NR$_{14}$, CO, O(CO), S(CO), NR$_{14}$(CO), SO, SO$_2$ or OSO$_2$, and wherein the interrupted C$_2$-C$_{18}$alkylene is unsubstituted or substituted by one or more OR$_{11}$, SR$_{14}$, halogen or phenyl;

R$_{26}$ and R$_{27}$ independently of each other are C$_3$-C$_{30}$cycloalkyl, C$_3$-C$_{30}$cycloalkyl-C$_1$-C$_{18}$alkyl, C$_1$-C$_{18}$alkyl, C$_1$-C$_{10}$haloalkyl, C$_2$-C$_{12}$alkenyl, C$_4$-C$_{30}$cycloalkenyl, phenyl-C$_1$-C$_3$-alkyl;

or independently of each other are C$_2$-C$_{18}$alkyl which is interrupted by one or more of O, S, NR$_{14}$, CO, O(CO) or NR$_{14}$(CO);

or independently of each other are C$_3$-C$_{30}$cycloalkyl which is interrupted by one or more of O, S, NR$_{14}$, CO, O(CO) or NR$_{14}$(CO);

or independently of each other are C$_3$-C$_{30}$cycloalkyl-C$_1$-C$_{18}$alkyl which is interrupted by one or more of O, S, NR$_{14}$, CO, O(CO) or NR$_{14}$(CO);

or independently of each other are C$_4$-C$_{30}$cycloalkenyl which is interrupted by one or more of O, S, NR$_{14}$, CO, O(CO) or NR$_{14}$(CO);

or R$_{26}$ and R$_{27}$ independently of each other are phenyl, naphthyl, anthracyl, phenanthryl, biphenylyl, fluorenyl or heteroaryl;

wherein the C$_3$-C$_{30}$cycloalkyl, C$_3$-C$_{30}$cycloalkyl-C$_1$-C$_{18}$alkyl, C$_1$-C$_{18}$alkyl, C$_1$-C$_{10}$haloalkyl, C$_2$-C$_{12}$alkenyl, C$_4$-C$_{30}$cycloalkenyl, phenyl-C$_1$-C$_3$-alkyl; interrupted C$_2$-C$_{18}$alkyl, interrupted C$_3$-C$_{30}$cycloalkyl, interrupted C$_3$-C$_{30}$cycloalkyl-C$_1$-C$_{18}$alkyl, interrupted C$_4$-C$_{30}$cycloalkenyl, phenyl, naphthyl, anthracyl, phenanthryl, biphenylyl, fluorenyl or heteroaryl are unsubstituted or are substituted by one or more Z;

or R$_{26}$ and R$_{27}$ together are 1,2-phenylene or 1,2- or 2,3- or 1,8-naphthylene or R$_{26}$ and R$_{27}$, optionally together with a direct bond, C$_1$-C$_4$alkylene, C$_3$-C$_{30}$cycloalkylene, C$_3$-C$_{30}$cycloalkyl-C$_1$-C$_{18}$alkylene, C$_1$-C$_4$haloalkylene, C$_2$-C$_4$alkenylene, C$_4$-C$_{30}$cycloalkenylene, O, S, NR$_{14}$, (CO), form a 5-, 6-, or 7-membered ring;

optionally the radicals Z as C$_1$-C$_{18}$alkyl, C$_2$-C$_{12}$alkenyl, (CO)R$_{15}$, (CO)OR$_{11}$, (CO)NR$_{12}$R$_{13}$, O(CO)R$_{15}$, O(CO)OR$_{11}$, O(CO)NR$_{12}$R$_{13}$, NR$_{14}$(CO)R$_{15}$, NR$_{14}$(CO)OR$_{11}$, NR$_{14}$(CO)NR$_{12}$R$_{13}$, OR$_{11}$, NR$_{12}$R$_{13}$, SR$_{14}$, SOR$_{15}$, SO$_2$R$_{15}$ and/or OSO$_2$R$_{15}$ on the phenyl, naphthyl, anthracyl, phenanthryl, biphenylyl, fluorenyl or heteroaryl form 5-, 6- or 7-membered rings, via the radicals C$_1$-C$_{18}$alkyl, C$_2$-C$_{12}$alkenyl, R$_{11}$, R$_{12}$, R$_{13}$, R$_{14}$ and/or R$_{15}$, with further substituents on the phenyl, naphthyl, anthracyl, phenanthryl, biphenylyl, fluorenyl or heteroaryl; or with one of the carbon atoms of the phenyl, naphthyl, anthracyl, phenanthryl, biphenylyl, fluorenyl or heteroaryl;

wherein all R$_{26}$ and R$_{27}$ optionally additionally are substituted by a group having a —O—O-bond or a —O—Si-bond which cleaves upon the action of an acid; and R$_1$, R$_2$, R$_3$, X, Y, R$_{11}$, R$_{12}$, R$_{13}$, R$_{14}$, R$_{15}$ and Z is are defined above.

If R$_1$ in the compounds of the formulas IIIa, IIIb, IIIc and IIIe is C$_2$-C$_{12}$alkenyl or interrupted C$_2$-C$_{18}$alkenyl, such latent acid compounds comprising a polymerizable double bond can be co-polymerized, for example, with monomers containing an acid dissociable, dissolution inhibiting group, and/or other monomers which comprise a polymerizable double bond.

Compounds (Vc and Vd) are particular examples of such new polymerizable latent acids according to this invention:

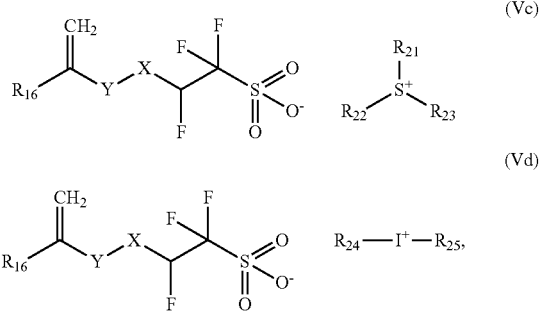

wherein Y, X, R$_{21}$, R$_{22}$, R$_{23}$, R$_{24}$ and R$_{25}$ are as defined above and R$_{16}$ is hydrogen or C$_1$-C$_{10}$alkyl.

The compounds of the formulas (Ve) and (Vf) show the monomer units derived from compounds Vc and Vd, respectively, after polymerization as part of a polymer backbone:

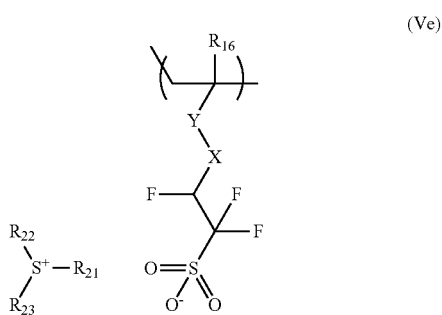

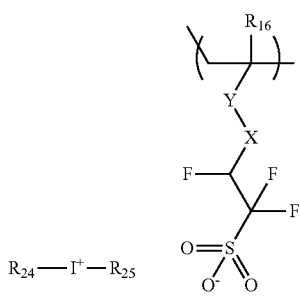

Of particular interest as polymerizable latent acids are for example:

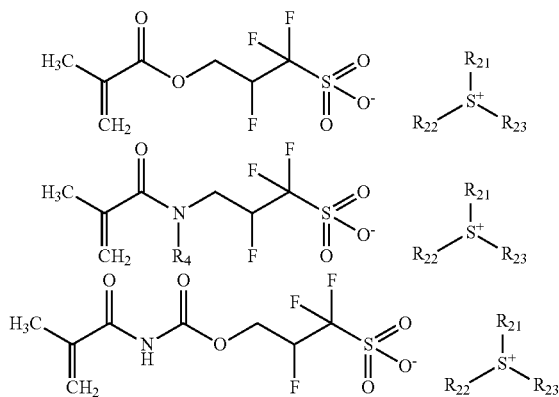

These can be prepared according to known methods, for example from methacrylic acid, methacrylic acid anhydride, methacryloyl chloride, or methacryloyl isocyanate, respectively with the corresponding alcohol intermediate compound B

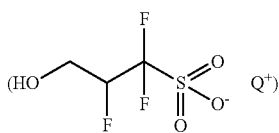

wherein $Q^+$ is proton or any cation species, or the corresponding alcoholate salt anion.

Accordingly, another subject of the invention is the use of the compounds of the formula IIIa, IIIb, IIIc and IIIe as defined above, wherein $R_1$ as $C_2$-$C_{12}$alkenyl or interrupted $C_2$-$C_{18}$alkenyl is a polymerizable group containing at least one double bond, for the preparation of polymers by polymerizing said compounds of the formula IIIa, IIIb, IIIc and IIIe comprising a polymerizable group with at least one other polymerizable monomer which comprises a polymerizable double bond.

Suitable co-monomers for said reaction are described below. For use in positive photoresist compositions at least one of the co-monomers preferably comprises an acid-labile group.

Therefore, another area of interest is the method of polymerizing a compounds of the formula IIIa, IIIb, IIIc and IIIe as defined above, wherein $R_1$ as $C_2$-$C_{12}$alkenyl or interrupted $C_2$-$C_{18}$alkenyl is a polymerizable group containing at least one double bond, with at least one monomer which comprises a polymerizable double bond and an acid labile group which increases the solubility in aqueous alkaline developer upon action of acid and—optionally—further monomers which comprise a polymerizable double bond.

Interesting is a compound generating an acid of the formula I or II which is of the formula IIIa, IIIb, IVa or IVb as described above, wherein X is $CH_2$;
Y is O, O(CO), O(CO)O, O(CO)$NR_4$, O(CO)$NR_4$(CO), $OSO_2$, O(CS), or O(CS)$NR_4$;
in which for each of these the oxygen atom is directly bound to X;
or is $NR_4$, S, $NR_4$(CO)O, $NR_4$(CS)O, in which the N- or S-atom is directly bound to X;
$R_1$ is hydrogen, $C_1$-$C_{18}$alkyl, $C_2$-$C_{12}$alkenyl, $C_4$-$C_{30}$cycloalkenyl, $C_3$-$C_{30}$cycloalkyl, $C_3$-$C_{30}$cycloalkyl-$C_1$-$C_{18}$alkyl;
or is $C_2$-$C_{18}$alkyl which is interrupted by one or more O, S, $NR_{14}$ or CO;
or is $C_2$-$C_{18}$alkenyl which is interrupted by one or more O, S, $NR_{14}$, or CO;
or is $C_3$-$C_{30}$cycloalkyl which is interrupted by one or more O, S, $NR_{14}$, CO, O(CO) or $NR_{14}$(CO);
or is $C_3$-$C_{30}$cycloalkyl-$C_1$-$C_{18}$alkyl which is interrupted by one or more O, S, $NR_{14}$, CO or O(CO);
or $R_1$ is $NR_{12}R_{13}$;
where the $C_3$-$C_{30}$cycloalkyl, $C_1$-$C_{18}$alkyl, $C_2$-$C_{12}$alkenyl, $C_4$-$C_{30}$cycloalkenyl, $C_3$-$C_{30}$cycloalkyl-$C_1$-$C_{18}$alkyl, interrupted $C_2$-$C_{18}$alkyl, interrupted $C_3$-$C_{30}$cycloalkyl, interrupted $C_3$-$C_{30}$cycloalkyl-$C_1$-$C_{18}$alkyl, are unsubstituted or are substituted by one or more Z;
$R_2$ and $R_3$ independently of each other are $C_3$-$C_{30}$cycloalkylene, $C_1$-$C_{18}$alkylene, $C_2$-$C_{12}$alkenylene, $C_4$-$C_{30}$cycloalkenylene;
$R_4$ is hydrogen, $C_3$-$C_{30}$cycloalkyl, $C_3$-$C_{30}$cycloalkyl-$C_1$-$C_{18}$alkyl, $C_1$-$C_{18}$alkyl,
$R_{11}$ is hydrogen, $C_3$-$C_{30}$cycloalkyl, $C_3$-$C_{30}$cycloalkyl-$C_1$-$C_{18}$alkyl, $C_1$-$C_{18}$alkyl, or $R_{11}$ is Ar,
$R_{12}$ and $R_{13}$ independently of each other are hydrogen, $C_3$-$C_{30}$cycloalkyl, $C_3$-$C_{30}$cycloalkyl-$C_1$-$C_{18}$alkyl, $C_1$-$C_{18}$alkyl;
or $R_{12}$ and $R_{13}$ independently of each other are (CO)$R_{15}$, (CO)O$R_{15}$ or $SO_2R_{15}$;
or $R_{12}$ and $R_{13}$, together with the nitrogen atom to which they are attached, form a 5-, 6- or 7-membered ring which optionally is interrupted by one or more O, $NR_{14}$ or CO;
$R_{14}$ is hydrogen, $C_3$-$C_{30}$cycloalkyl, $C_3$-$C_{30}$cycloalkyl-$C_1$-$C_{18}$alkyl, $C_1$-$C_{18}$alkyl, phenyl-$C_1$-$C_3$-alkyl;
or $R_{14}$ is phenyl, naphthyl, $C_1$-$C_{18}$alkylsulfonyl or phenylsulfonyl;
wherein the $C_3$-$C_{30}$cycloalkyl, $C_3$-$C_{30}$cycloalkyl-$C_1$-$C_{18}$alkyl, $C_1$-$C_{18}$alkyl, phenyl, naphthyl, $C_1$-$C_{18}$alkylsulfonyl are unsubstituted or substituted by one or more $Z_1$;
$R_{15}$ is hydrogen Ar, —$C_{30}$cycloalkyl, $C_3$-$C_{30}$cycloalkyl-$C_1$-$C_{18}$alkyl, $C_1$-$C_{18}$alkyl, wherein the Ar, $C_3$-$C_{30}$cycloalkyl, $C_3$-$C_{30}$cycloalkyl-$C_1$-$C_{18}$alkyl, $C_1$-$C_{18}$alkyl are unsubstituted or substituted by one or more $Z_2$; Ar is phenyl, biphenylyl or naphthyl, wherein the phenyl, biphenylyl or naphthyl are unsubstituted or substituted by one or more $Z_2$;
$R_{21}$, $R_{22}$ and $R_{23}$ independently of each other are $Ar_1$, $C_3$-$C_{30}$cycloalkyl, $C_3$-$C_{30}$cycloalkyl-$C_1$-$C_{18}$alkyl, $C_1$-$C_{18}$alkyl,
wherein the $Ar_1$, $C_3$-$C_{30}$cycloalkyl, $C_3$-$C_{30}$cycloalkyl-$C_1$-$C_{18}$alkyl, $C_1$-$C_{18}$alkyl are unsubstituted or are substituted by one or more Z;

or $R_{21}$ and $R_{22}$, optionally together with a direct bond, O, S, $NR_{14}$ or (CO), form a fused ring system;

or $R_{21}$ and $R_{22}$, optionally together with $C_1$-$C_6$alkylene O, S, $NR_{14}$ or (CO), form a 5-, 6- or 7-membered ring;

Z is $C_3$-$C_{30}$cycloalkyl, $C_3$-$C_{30}$cycloalkyl-$C_1$-$C_{18}$alkyl, $C_1$-$C_{18}$alkyl;

or is $C_5$-$C_{30}$cycloalkyl-$C_1$-$C_4$alkyl, which is substituted by one or more of $NR_{14}(CO)OR_{11}$ or $NR_{14}(CO)NR_{12}R_{13}$;

or is $(CO)R_{15}$, $(CO)OR_{11}$, $O(CO)OR_{11}$, $NR_{14}(CO)OR_{11}$, $OR_{11}$, $NR_{12}R_{13}$, and/or $SR_{14}$;

$R_{24}$ and $R_{25}$ independently of each other are $Ar_1$;

$Ar_1$ is phenyl, biphenylyl, naphthyl, in particular phenyl or naphthyl, wherein the phenyl, biphenylyl or naphthyl are unsubstituted or are substituted by one or more Z, optionally the radicals Z as $C_1$-$C_{18}$alkyl$(CO)R_{15}$, $(CO)OR_{11}$, $OR_{11}$, $NR_{12}R_{13}$, form 5-, 6- or 7-membered rings, via the radicals $C_1$-$C_{18}$alkyl $R_{11}$, $R_{12}$, $R_{13}$ and/or $R_{15}$ with one of the carbon atoms of the phenyl, biphenylyl or naphthyl ring;

$Z_2$ is $C_3$-$C_{30}$cycloalkyl, $C_3$-$C_{30}$cycloalkyl-$C_1$-$C_{18}$alkyl, $C_1$-$C_{18}$alkyl, or $(CO)R_{15}$, $(CO)OR_{11}$, $(CO)NR_{12}R_{13}$, $O(CO)R_{15}$, $O(CO)OR_{11}$;

$R_{11}$ is hydrogen, $C_3$-$C_{30}$cycloalkyl, $C_3$-$C_{30}$cycloalkyl-$C_1$-$C_{18}$alkyl, $C_1$-$C_{18}$alkyl, or $R_{11}$ is Ar; and $Z_1$ is Ar.

Especially interesting are compounds generating an acid of the formula I or II described above, wherein X is $CH_2$;

Y is O, O(CO), O(CO)O, O(CO)$NR_4$, O(CO)$NR_4$(CO), $OSO_2$ or O(CS)$NR_4$; in which for each of these the oxygen atom is directly bound to X;

$R_1$ is hydrogen, $C_3$-$C_{30}$cycloalkyl, $C_3$-$C_{30}$cycloalkyl-$C_1$-$C_{18}$alkyl, $C_1$-$C_{18}$alkyl, $C_2$-$C_{12}$alkenyl or $C_4$-$C_{30}$cycloalkenyl;

or is $C_2$-$C_{18}$alkyl which is interrupted by one or more O;

or is $C_2$-$C_{18}$alkenyl which is interrupted by one or more O;

or is $C_3$-$C_{30}$cycloalkyl which is interrupted by one or more O, CO, O(CO) or $NR_{14}$(CO);

or $R_1$ is $NR_{12}R_{13}$;

or is $C_3$-$C_{30}$cycloalkyl-$C_1$-$C_{18}$alkyl which is interrupted by one or more O, CO or O(CO);

wherein the $C_1$-$C_{18}$alkyl, $C_3$-$C_{30}$cycloalkyl, $C_4$-$C_{30}$cycloalkenyl, interrupted $C_2$-$C_{18}$alkyl, interrupted $C_3$-$C_{30}$cycloalkyl, interrupted $C_3$-$C_{30}$cycloalkyl-$C_1$-$C_{18}$alkyl are unsubstituted or are substituted by one or more Z;

Z is $C_1$-$C_{18}$alkyl, $C_3$-$C_{30}$cycloalkyl, $C_3$-$C_{30}$cycloalkyl-$C_1$-$C_{18}$alkyl, halogen, $(CO)OR_{11}$, $O(CO)R_{11}$, $OR_{11}$, $SR_{14}$ or $NR_{14}(CO)OR_{11}$, or is $C_5$-$C_{30}$cycloalkyl-$C_1$-$C_4$alkyl, which is substituted by one or more of $NR_{14}(CO)OR_{11}$ or $NR_{14}(CO)NR_{12}R_{13}$;

$R_2$ and $R_3$ independently of each other are $C_3$-$C_{30}$cycloalkylene or $C_1$-$C_{18}$alkylene;

$R_4$ is hydrogen;

$R_{11}$ is hydrogen, $C_1$-$C_{18}$alkyl or Ar;

$R_{12}$ and $R_{13}$ independently of each other are hydrogen, $C_3$-$C_{30}$cycloalkyl or $C_1$-$C_{18}$alkyl;

or $R_{12}$ and $R_{13}$ independently of each other are $(CO)R_{15}$ or $SO_2R_{15}$;

or $R_{12}$ and $R_{13}$, together with the nitrogen atom to which they are attached, form a 5-, 6- or 7-membered ring which optionally is interrupted by one or more O, $NR_{14}$ or CO;

$R_{14}$ is hydrogen, $C_1$-$C_{18}$alkyl, $C_1$-$C_{18}$alkanoyl, $C_1$-$C_{18}$alkylsulfonyl, phenyl, phenylsulfonyl, wherein the phenyl or $C_1$-$C_8$alkylsulfonyl are unsubstituted or substituted by one or more $Z_1$;

$R_{15}$ is hydrogen or Ar;

Ar is phenyl, which is unsubstituted or is substituted by one or more $Z_2$;

$Z_2$ is $C_1$-$C_{18}$alkyl or $(CO)R_{15}$; and $Z_1$ is Ar.

Further of interest are compounds generating an acid of the formula I or II described above, wherein X is $CH_2$;

Y is O, O(CO), O(CO)O, O(CO)$NR_4$, O(CO)$NR_4$(CO), $OSO_2$ or O(CS)$NR_4$; in which for each of these the oxygen atom is directly bound to X;

$R_1$ is hydrogen, $C_3$-$C_{30}$cycloalkyl, $C_3$-$C_{30}$cycloalkyl-$C_1$-$C_{18}$alkyl, $C_1$-$C_{18}$alkyl or $C_4$-$C_{30}$cycloalkenyl;

or is $C_2$-$C_{18}$alkyl which is interrupted by one or more O;

or is $C_3$-$C_{30}$cycloalkyl which is interrupted by one or more O, CO, O(CO) or $NR_{14}$(CO);

or $R_1$ is $NR_{12}R_{13}$;

or is $C_3$-$C_{30}$cycloalkyl-$C_1$-$C_{18}$alkyl which is interrupted by one or more CO;

wherein the $C_1$-$C_{18}$alkyl, $C_4$-$C_{30}$cycloalkenyl, interrupted $C_2$-$C_{18}$alkyl, interrupted $C_3$-$C_{30}$cycloalkyl-$C_1$-$C_{18}$alkyl are unsubstituted or are substituted by one or more Z;

Z is $C_1$-$C_{18}$alkyl, $(CO)OR_{11}$ or $NR_{14}(CO)OR_{11}$, or is $C_5$-$C_{30}$cycloalkyl-$C_1$-$C_4$alkyl, which is substituted by one or more of $NR_{14}(CO)OR_{11}$ or $NR_{14}(CO)NR_{12}R_{13}$;

$R_2$ and $R_3$ independently of each other are $C_3$-$C_{30}$cycloalkylene or $C_1$-$C_{18}$alkylene;

$R_4$ is hydrogen;

$R_{11}$ is hydrogen or $C_1$-$C_{18}$alkyl;

$R_{12}$ and $R_{13}$ independently of each other are hydrogen, $C_3$-$C_{30}$cycloalkyl or $C_1$-$C_{18}$alkyl;

or $R_{12}$ and $R_{13}$ independently of each other are $(CO)R_{15}$ or $SO_2R_{15}$;

or $R_{12}$ and $R_{13}$, together with the nitrogen atom to which they are attached, form a 5-, 6- or 7-membered ring which optionally is interrupted by one or more O, $NR_{14}$ or CO;

$R_{14}$ is hydrogen, $C_1$-$C_{18}$alkyl, $C_1$-$C_{18}$alkanoyl or $C_1$-$C_{18}$alkylsulfonyl;

$R_{15}$ is hydrogen or Ar; and

Ar is phenyl, which is unsubstituted or is substituted by one or more Z.

Y is for example O, O(CO), O(CO)O, O(CO)$NR_4$, O(CO)$NR_4$(CO), $OSO_2$ or O(CS)$NR_4$;

in which for each of these radicals the oxygen atom is directly bound to X; or Y is for example, O(CO), O(CO)O, O(CO)$NR_4$, $OSO_2$ or O(CS)$NR_4$.

$R_1$ is for example hydrogen, $C_3$-$C_{30}$cycloalkyl, $C_3$-$C_{30}$cycloalkyl-$C_1$-$C_{18}$alkyl, $C_1$-$C_{18}$alkyl, $C_4$-$C_{30}$cycloalkenyl, or is $C_2$-$C_{18}$alkyl which is interrupted by one or more O, CO, O(CO) or $NR_{14}$(CO), or is $C_3$-$C_{30}$cycloalkyl which is interrupted by one or more O, CO, O(CO) or $NR_{14}$(CO), or $R_1$ is $NR_{12}R_{13}$, or is $C_3$-$C_{30}$cycloalkyl-$C_1$-$C_{18}$alkyl which is interrupted by one or more O, CO, O(CO) or $NR_{14}$(CO), wherein the $C_1$-$C_{18}$alkyl, $C_4$-$C_{30}$cycloalkenyl, interrupted $C_2$-$C_{18}$alkyl, interrupted $C_3$-$C_{30}$cycloalkyl-$C_1$-$C_{18}$alkyl are unsubstituted or are substituted by one or more Z.

Z is for example is $C_1$-$C_{18}$alkyl, $(CO)OR_{11}$, $O(CO)R_{15}$, $NR_{14}(CO)OR_{11}$, $OR_{11}$, $OSO_2R_{15}$, or is $C_5$-$C_{30}$cycloalkyl-$C_1$-$C_4$alkyl, which is substituted by one or more of $NR_{14}(CO)OR_{11}$ or $NR_{14}(CO)NR_{12}R_{13}$.

Z as substituent for $C_1$-$C_{18}$alkyl preferably is methyl, ethyl, propyl, butyl or hexyl.

Z as substituent for $C_4$-$C_{30}$cycloalkenyl preferably is cyclopentenyl, cyclohexenyl,

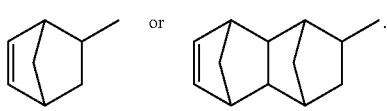

Z as substituent for $C_3$-$C_{30}$cycloalkyl-$C_1$-$C_{18}$alkyl preferably is

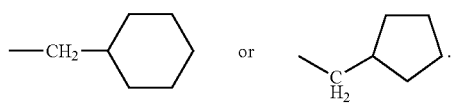

$R_2$ and $R_3$ for example independently of each other are $C_3$-$C_{30}$cycloalkylene, $C_1$-$C_{18}$alkylene, $C_4$-$C_{30}$cycloalkenylene or a direct bond, provided that $R_2$ and $R_3$ are not both simultaneously a direct bond.

$R_4$ for example is hydrogen or $C_1$-$C_{18}$alkyl.

$R_{11}$ for example is hydrogen, $C_1$-$C_{18}$alkyl, (CO)$R_{15}$, (CO)N$R_{12}R_{13}$ or SO$_2R_{15}$.

$R_{12}$ and $R_{13}$ for example independently of each other are hydrogen, $C_3$-$C_{30}$cycloalkyl or $C_1$-$C_{18}$alkyl, or independently of each other are (CO)$R_{15}$ or SO$_2R_{15}$, or $R_{12}$ and $R_{13}$, together with the nitrogen atom to which they are attached, form a 5-, 6- or 7-membered ring which optionally is interrupted by one or more O, N$R_{14}$ or CO.

$R_{14}$ for example is hydrogen, $C_1$-$C_{18}$alkyl, $C_1$-$C_{18}$alkanoyl or $C_1$-$C_{18}$alkylsulfonyl.

$R_{15}$ for example is hydrogen, Ar or $C_1$-$C_{18}$alkyl.

Ar for example is phenyl, which is unsubstituted or is substituted by one or more $Z_2$, where Z is $C_1$-$C_{18}$alkyl, O(CO)$R_{15}$, O$R_{11}$ or OSO$_2R_{15}$.

If any radical defined for $R_{12}$, $R_{13}$, $R_{14}$, $R_{15}$ is substituted, it is substituted by one or more $Z_1$ as defined above.

If any radical defined for $R_1$, $R_2$, $R_3$, $R_4$ Ar$_1$, Ar$_2$, Ar'$_2$, Ar"$_2$ is substituted, it is substituted by one or more Z as defined above.

If any radical defined for Ar is substituted it is substituted by one or more $Z_2$ as defined above.

Of particular interest are the compounds of formula (I) as given in the example 1-54, as well as the compounds of the following formulas (a)-(m):

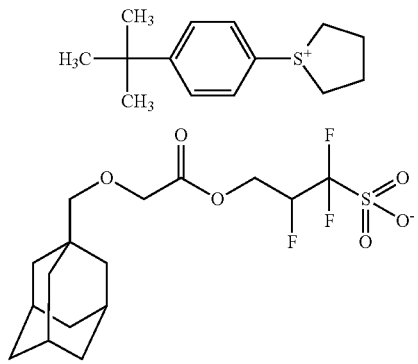
(a)

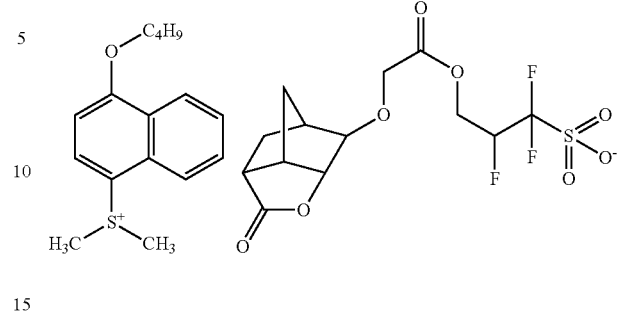
(b)

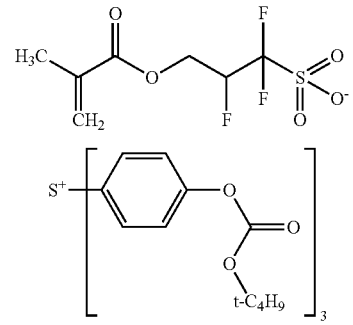
(c)

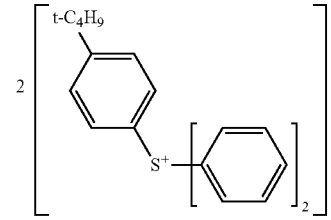
(d)

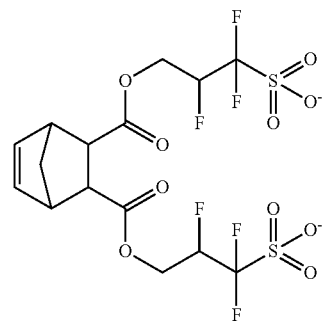

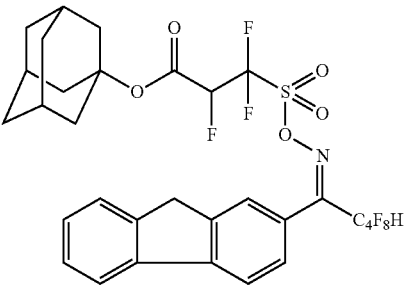
(e)

-continued (f)
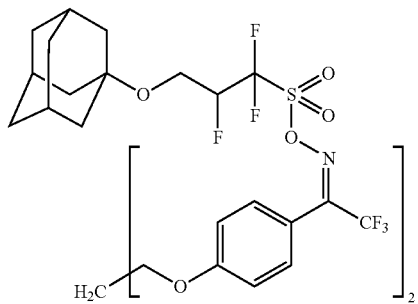

(g)
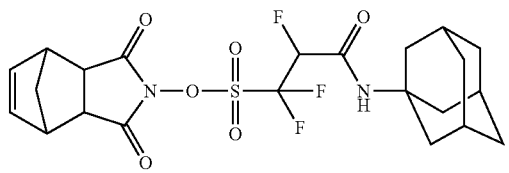

(h)
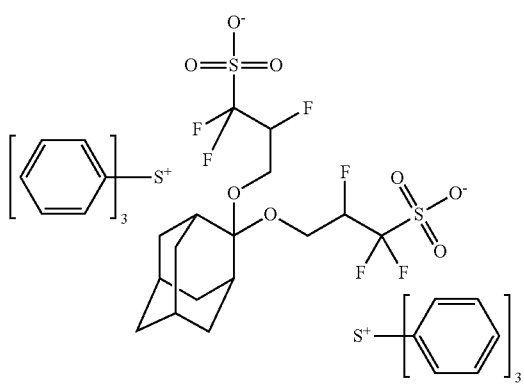

(i)
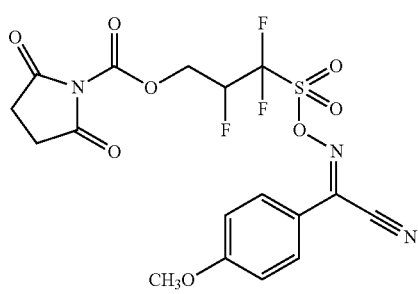

(k)
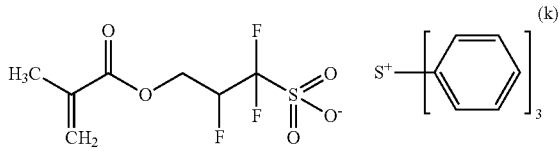

-continued (l)
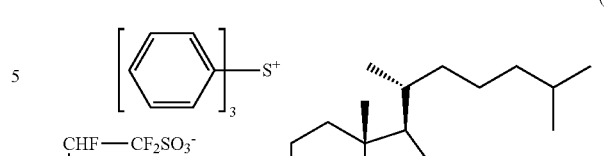

(m)
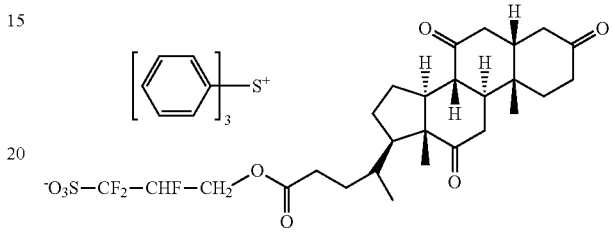

Suitable sulfonium cations, which besides the ones present in the formulas above, also can be used as cations in the sulfonyl compounds of the present invention are for example disclosed in WO 2008/056795 pages: 13-23; U.S. Pat. No. 6,855,476 cols: 11-14, 19-20; US 2007/0122750 pages: 9-16; US 2008/0182203 page 1, chemical formula 1, page 2, chemical formulas 2-4; US 2009/0068591 the cation part of the formulas that are shown on page 44: formula 54, Page 45: formula 56 and 57, page 47: formula 62, page 48: formula 67, page 52: formula 73, page 53: formula 76, page 54: formula 80; US 2006/0194982 pages 5-11; WO 2007/118794 pages 60 ff: cation part of formulas of examples: 1-6, 13, 15, 17, 19; EP 1036789 generic formula (1), formula on page 12: [0115], formulas on page 14: [0127] and [0129], formulas on Page 15: compounds VII and VIII; and U.S. Pat. No. 7,611,817 cols: 7-11.

Particularly suitable are the sulfonium cations, wherein $R_{21}$ and $R_{22}$ as defined above are identical and $R_{23}$ differs from $R_{21}$ and $R_{22}$.

The compounds of the invention with such unsymmetrical sulfonium cations exhibit good solubility properties.

In particular suitable are compounds wherein $R_{21}$ and $R_{22}$ are unsubstituted phenyl and $R_{23}$ is substituted $Ar_1$ or naphthyl. Preferably $Ar_1$ is substituted by Z, which denotes halogen or $SR_{14}$. Special interest is laid on compounds wherein $R_{21}$ and $R_{22}$ are unsubstituted phenyl and $R_{23}$ is naphthyl or $Ar_1$ substituted by $SR_{14}$. $Ar_1$ in this case preferably is phenyl.

Compounds with these preferred definitions of $R_{21}$, $R_{22}$ and $R_{23}$, which exhibit good solubility, in the anion part of the molecule (of the formula IIIa and IVa) preferably have a cycloalkyl (or cycloalkylene) substituent. That is in the compounds of the formula IIIa and IVa, wherein $R_{21}$, $R_{22}$ and $R_{23}$ are as defined in the previous paragraph, X in particular denotes $CH_2$, Y preferably is O(CO) and $R_1$ is for example $C_3$-$C_{30}$cycloalkyl-$C_1$-$C_{18}$alkyl which is interrupted by one or more O, S, $NR_{14}$, CO, O(CO) or $NR_{14}$(CO); especially $R_1$ in these cases is $C_3$-$C_{30}$cycloalkyl-$C_1$-$C_{18}$alkyl which is interrupted by one or more O, CO or O(CO); in particular preferred $R_1$ in these cases is camphoryl. Preferred compounds are the compounds of examples 55, 56 and 57; in particular the compounds of example 55 and 57.

Interesting as the cations in the compounds of the present invention are for example sulfonium ions shown in the below formulas s1-s54.

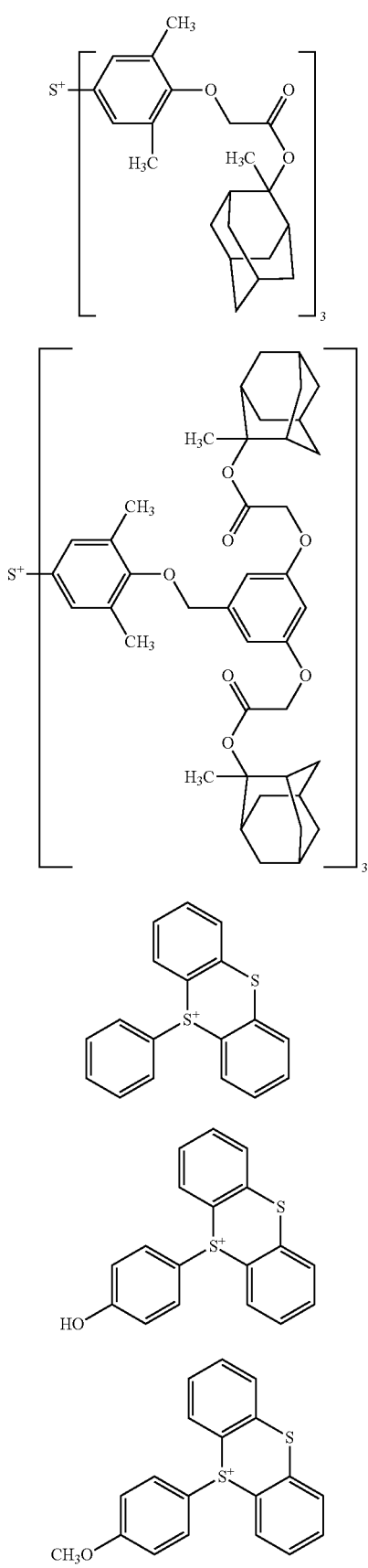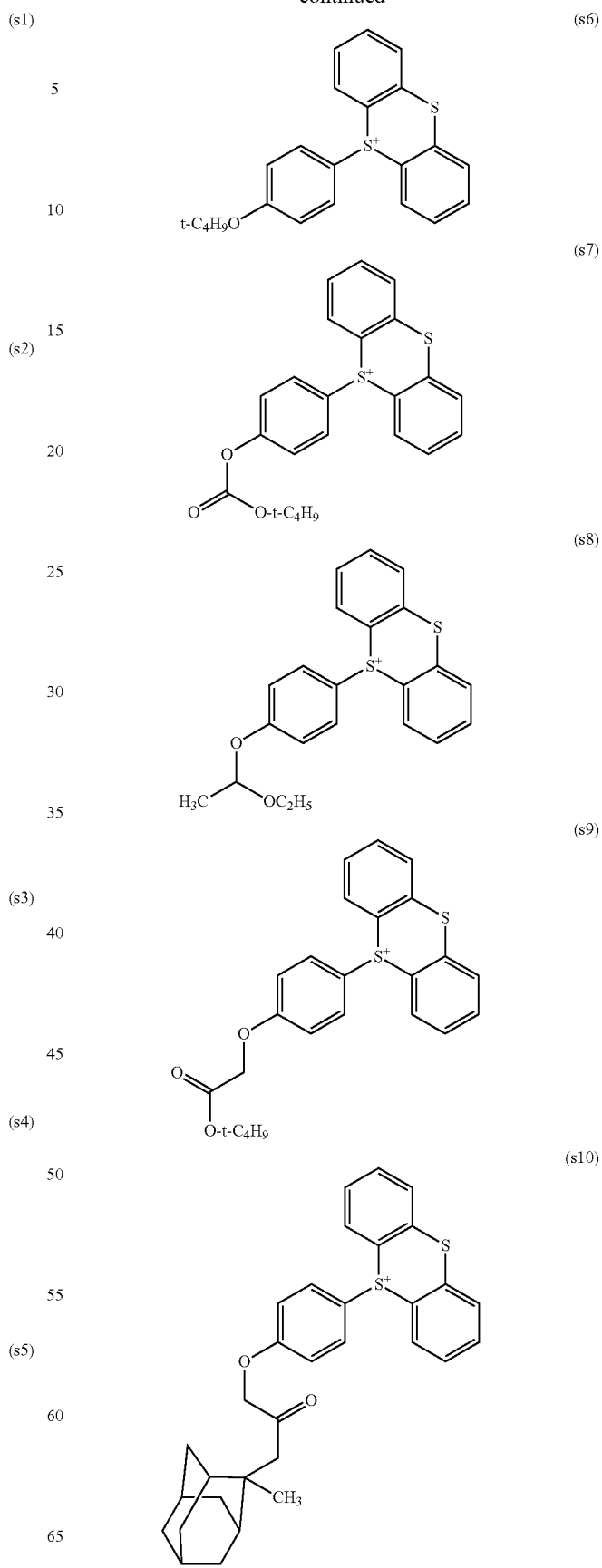

(s11)
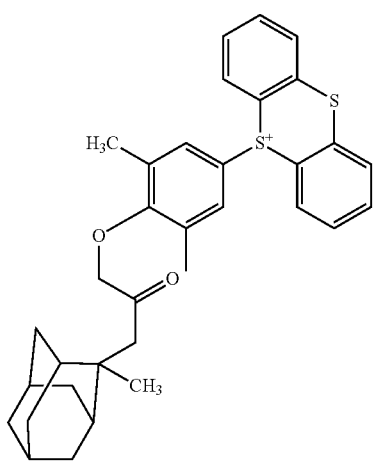
(s12)
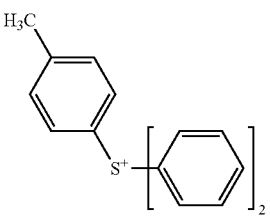
(s13)
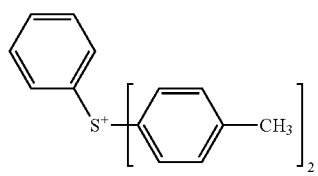
(s14)
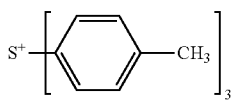
(s15)
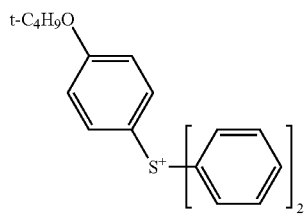
(s16)
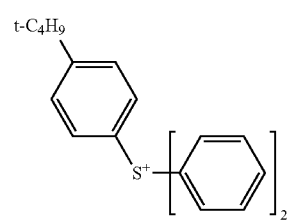
(s17)
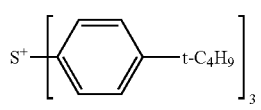
(s18)
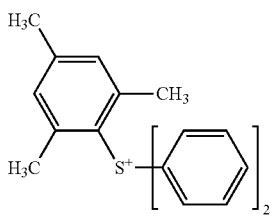
(s19)
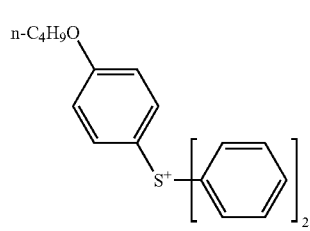
(s20)
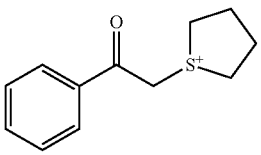
(s21)
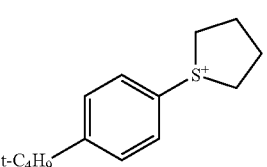
(s22)
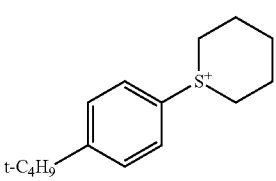
(s23)
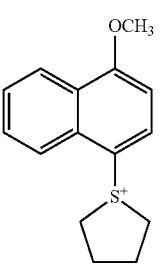
(s24)
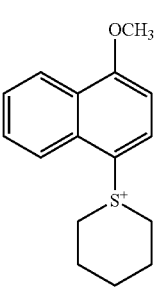

-continued
(s25)
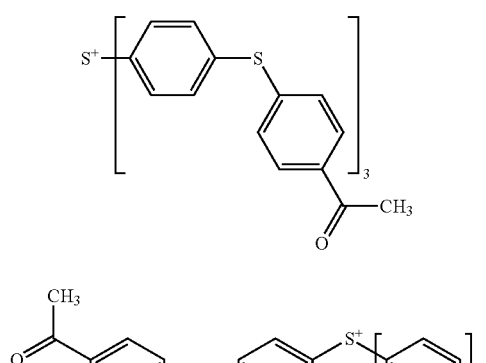
(s26)
(s27)
(s28)
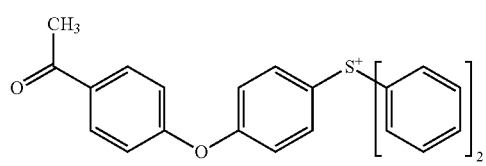
(s29)
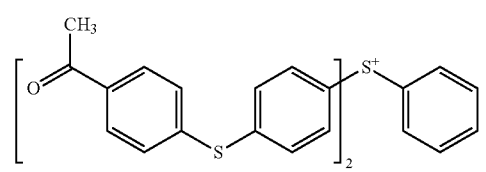
(s30)
(s31)
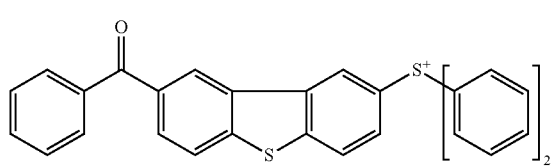
-continued
(s32)
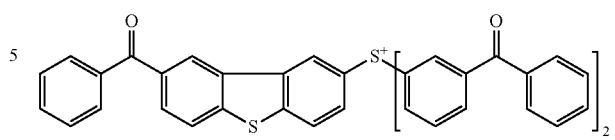
(s33)
(s34)
(s35)
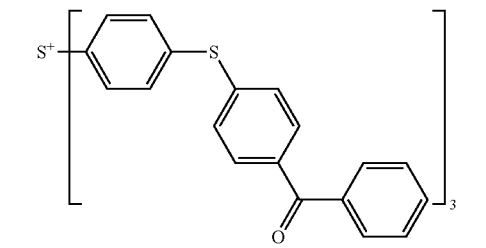
(s36)
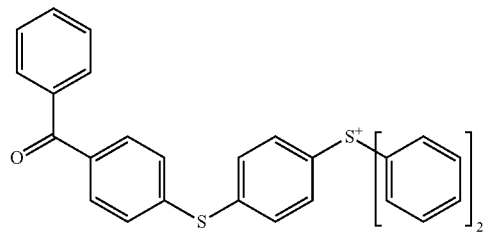
(s37)
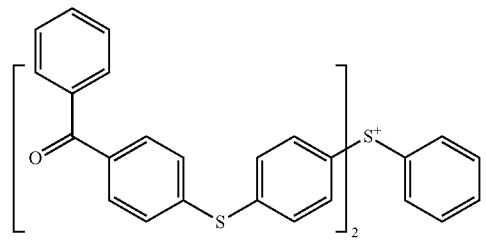
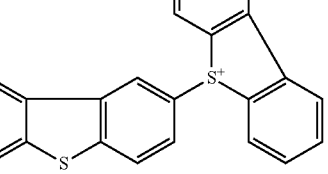

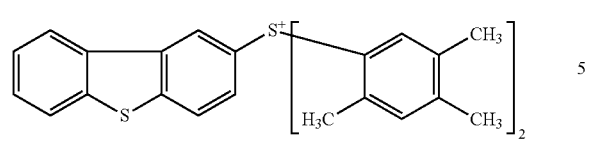
(s38)
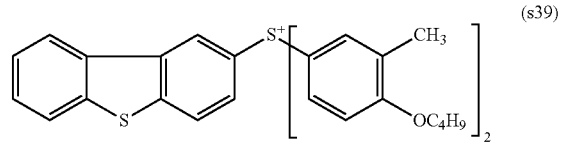
(s39)
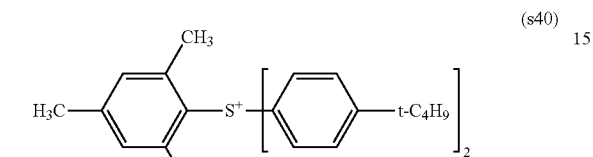
(s40)
(s41)
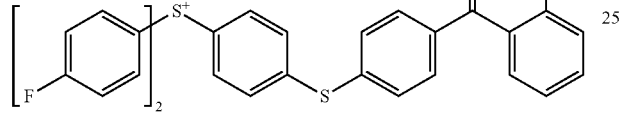
(s42)
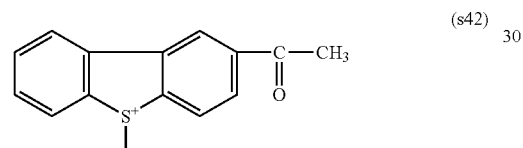
(s43)
(s44)
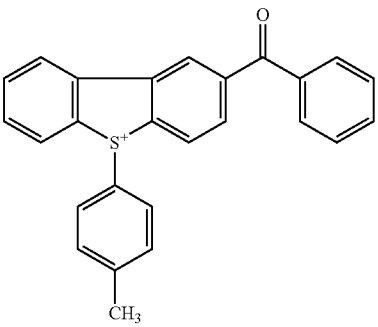
(s45)
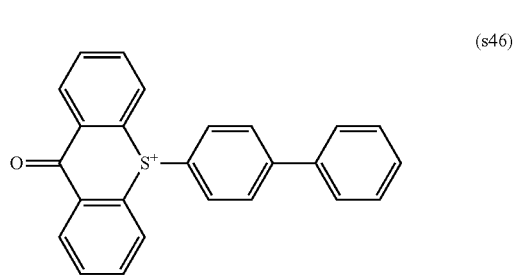
(s46)
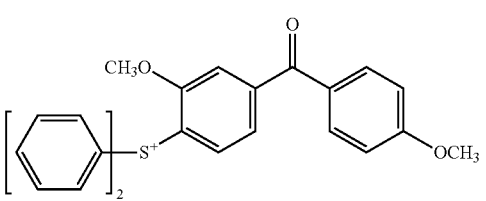
(s47)
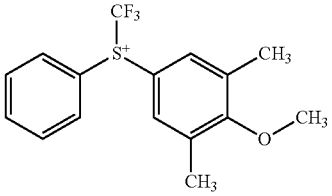
(s48)
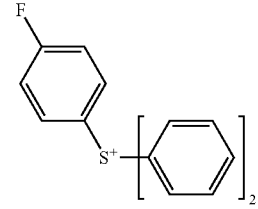
(s49)
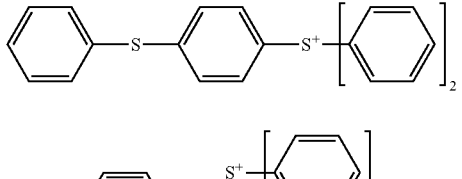
(s50)
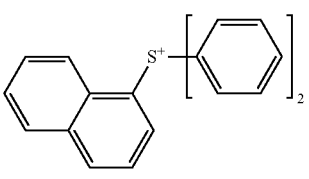
(s51)

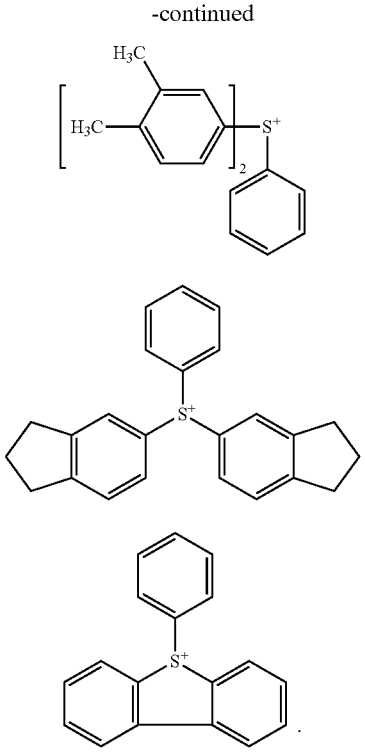

(s52)

(s53)

(s54)

In particular preferred are compounds of the invention with sulfonium cations s12, s15, s16, s18, s19, s42, s43, s45, s47, s48, s49, s50, s51, s52, s53, s54 especially s49, s50, s51, s52, s53, s54.

Furthermore, the iodonium cations shown in formulas i1-i5 are particularly useful.

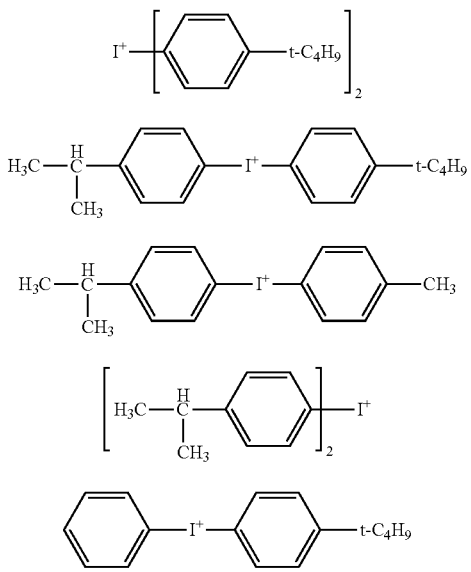

(i1)

(i2)

(i3)

(i4)

(i5)

The preferences referring to the compounds generating an acid of the formula I or II (as well as the compounds of the formula IIIa, IIIb, Iva, IVb, IIIc, IIId, IIIe, IVc, IVe, Ia, IIa etc.) as given hereinbefore and in the context of the whole text are intended not to refer to the compounds as such only, but to all categories of the claims. That is to the compositions, comprising the compounds generating an acid of the formula I or II II (as well as the compounds of the formula IIIa, IIIb, Iva, IVb, IIIc, IIId, IIIe, IVc, IVe, Ia, IIa etc.), to the photo-initiator and/or photoacid generator mixtures comprising said compounds, as well as the use or process claims in which said compounds are employed.

Any defined radical $R_1$, $R_2$, $R_3$, X, Y, $Y_1$, $R_4$, $R_{11}$, $R_{12}$, $R_{13}$, $R_{14}$, $R_{15}$, Ar, $Ar_1$, $Ar_2$, Z, $Z_1$, $Z_2$, $R_{21}$, $R_{22}$, $R_{23}$, $R_{24}$, $R_{25}$, $R_{26}$, $R_{27}$, E, A, $A_1$, $Ar'_2$, $Ar''_2$ in the context of the present application is meant to have an identical meaning, regardless in which formula it is present.

$NR_4$ in the context of the definitions in the present text is not intended to define an ammonium group, but a N-atom which is substituted by one radical $R_4$, namely $N(R_4)$.

$C_1$-$C_{18}$alkyl is linear or branched and is, for example, $C_1$-$C_{16}$—, $C_1$-$C_{12}$—, $C_1$-$C_8$—, $C_1$-$C_6$- or $C_1$-$C_4$-alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, undecyl, dodecyl, tetradecyl, pentadecyl, hexadecyl, heptadecyl and octadecyl, preferably $C_1$-$C_4$alkyl, such as methyl, isopropyl or butyl.

$C_2$-$C_{18}$alkyl which is interrupted by one or more O, S, $NR_{14}$, CO, O(CO) or $NR_{14}$(CO) is, for example, interrupted from one to five times, for example from one to three times or once or twice, by non-successive O, S, $NR_{14}$, CO, O(CO) or $NR_{14}$(CO). Accordingly, resulting structural units are for example: $O(CH_2)_2OH$, $O(CH_2)_2OCH_3$, $O(CH_2CH_2O)_2CH_2CH_3$, $CH_2$—O—$CH_3$, $CH_2CH_2$—O—$CH_2CH_3$, $[CH_2CH_2O]_y$—$CH_3$, wherein y=1-5, $(CH_2CH_2O)_5CH_2CH_3$, $CH_2$—$CH(CH_3)$—O—$CH_2$—$CH_2CH_3$, $CH_2$—$CH(CH_3)$—O—$CH_2$—$CH_3$, $S(CH_2)_2SCH_3$, $(CH_2)_2NR_{14}CH_3$, $(CH_2)_2O(CO)CH_3$, $(CH_2)_2(CO)CH_3$ or $(CH_2)_2NR_{14}(CO)CH_3$, wherein $R_{14}$ is defined as given hereinbefore.

If, in the context of the present invention a group, e.g. alkyl or alkylene, is interrupted by one or more defined radicals, e.g. O, S, $NR_{14}$, CO, O(CO) or $NR_{14}$(CO), the "interrupting" radicals not only are meant to be situated in between the interrupted group, for example the alkyl or alkylene, but also are meant to be terminal.

$C_3$-$C_{30}$cycloalkyl is a mono- or polycyclic aliphatic ring, for example a mono-, bi- or tricyclic aliphatic ring, e.g. $C_3$-$C_{20}$—, $C_3$-$C_{18}$—, $C_3$-$C_{12}$—, $C_3$-$C_{10}$cycloalkyl.

Examples of monocyclic rings are cyclopropyl, cyclobutyl, cyclopentyl, cyclohexyl, or cycloheptyl, especially cyclopentyl and cyclohexyl.

Examples of polycyclic rings are perhydroanthracyl, perhydrophenyathryl, perhydronaphthyl, perhydrofluorenyl, perhydrochrysenyl, perhydropicenyl, adamantyl, bicyclo[1.1.1]pentyl, bicyclo[4.2.2]decyl, bicyclo[2.2.2]octyl, bicyclo[3.3.2]decyl, bicyclo[4.3.2]undecyl, bicyclo[4.3.3]dodecyl, bicyclo[3.3.3]undecyl, bicyclo[4.3.1]decyl, bicyclo[4.2.1]nonyl, bicyclo[3.3.1]nonyl, bicyclo[3.2.1]octyl,

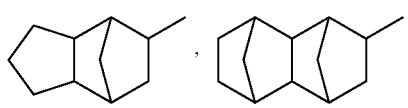

and the like.

Also "spiro"-cycloalkyl compounds are covered by the definition $C_3$-$C_{30}$cycloalkyl in the present context, e.g. spiro[5.2]octyl, spiro[5.4]decyl, spiro[5.5]undecyl. More examples of polycyclic cycloalkyl groups, which are subject of the respective definition in the compounds of the present invention are listed in EP 878738, page 11 and 12, wherein to the formulae (1)-(46) a bond to achieve the "yl" has to be added. The person skilled in the art is aware of this fact. In general, the cycloaliphatic rings may form repeating structural units.

Said $C_3$-$C_{30}$cycloalkyl further optionally is substituted by $C_1$-$C_{18}$alkyl, which refers to structures like for example

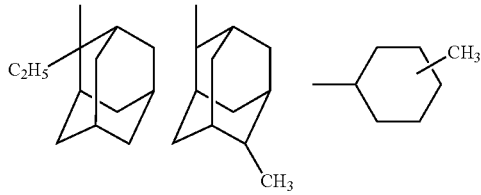

etc.

$C_3$-$C_{30}$cycloalkyl-$C_1$-$C_{18}$alkyl refers to any cycloalkyl as defined above, which is linked via an alkyl group. Examples are structures like

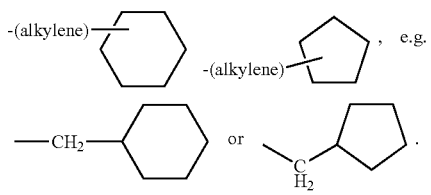

Said $C_3$-$C_{30}$cycloalkyl-$C_1$-$C_{18}$alkyl further optionally is substituted by $C_1$-$C_{18}$alkyl, which refers to structures like for example

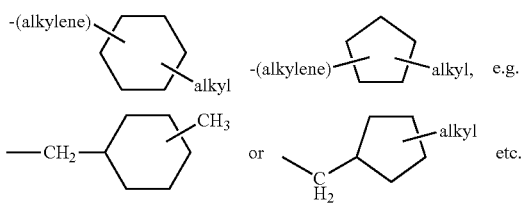

$C_3$-$C_{30}$cycloalkyl or $C_3$-$C_{30}$cycloalkyl-$C_1$-$C_{18}$alkyl which is interrupted by one or more O, S, $NR_{14}$, CO, O(CO) or $NR_{14}$(CO) is a mono- or polycyclic aliphatic ring which is interrupted by one or more O, S, $NR_{14}$, CO, O(CO) or $NR_{14}$(CO), for example,

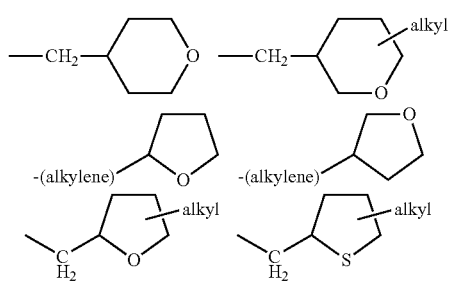

$C_2$-$C_{12}$alkenyl radicals are for example mono- or polyunsaturated, linear or branched and are for example $C_2$-$C_8$—, $C_2$-$C_6$- or $C_2$-$C_4$alkenyl. Examples are allyl, methallyl, vinyl, 1,1-dimethylallyl, 1-butenyl, 3-butenyl, 2-butenyl, 1,3-pentadienyl, 5-hexenyl or 7-octenyl, especially allyl or vinyl.

$C_2$-$C_{12}$alkenyl as a polymerizable group has the unsaturated bond(s) in a position of the molecule that the double bond is free to undergo a polymerization reaction.—Examples are allyl, methallyl or vinyl.

$C_2$-$C_{18}$alkenyl which is interrupted by one or more of O, S, $NR_{14}$, CO, O(CO), $NR_{14}$(CO), optionally substituted phenylene, naphthylene, anthracylene, phenanthrylene, biphenylene or heteroarylene is a linear or branched alkenyl group interrupted by one or more of the above mentioned divalent groups. Examples are

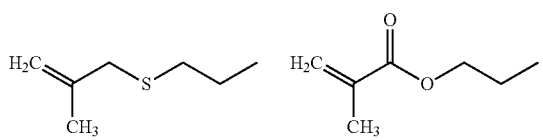

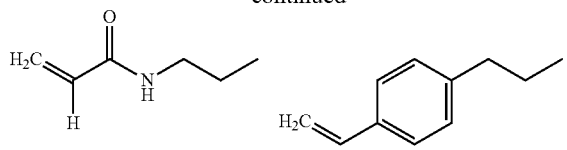

$C_4$-$C_{30}$cycloalkenyl is a mono- or polycyclic and mono- or polyunsaturated ring, for example a mono-, bi-, tri- or tetracyclic mono- or polyunsaturated ring, e.g. $C_4$-$C_{20}$—, $C_4$-$C_{18}$—, $C_4$-$C_{12}$—, $C_4$-$C_{10}$cycloalkenyl. Examples of cycloalkenyl are cyclobutenyl, cyclopentenyl, cyclohexenyl, cycloheptenyl. Also bridged alkenyl groups are covered by the above definition, for example

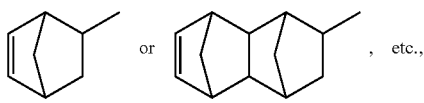

especially cyclopentenyl, cyclohexenyl,

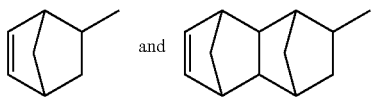

$C_4$-$C_{30}$cycloalkenyl which is interrupted by one or more O, S, $NR_{14}$, CO, O(CO) or $NR_{14}$(CO) is a mono- or polycyclic and mono- or polyunsaturated ring, which is interrupted by one or more O, S, $NR_{14}$, CO, O(CO) or $NR_{14}$(CO), for example,

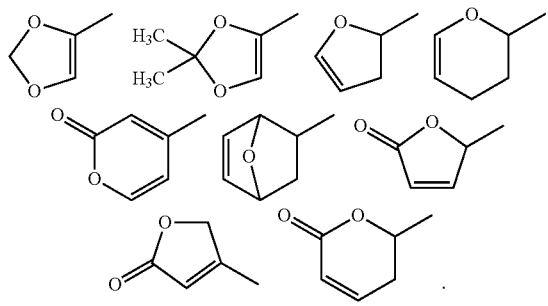

$C_1$-$C_{18}$alkylene is linear or branched alkylene, e.g. $C_1$-$C_2$-$C_2$-$C_5$alkylene. Examples are methylene, ethylene, propylene, butylene, pentylene, hexylene.

$C_2$-$C_{18}$alkylene which is interrupted by one or more O, S, $NR_{14}$, CO, O(CO) or $NR_{14}$(CO), is interrupted, for example, from one to five times, for example from one to three times or once or twice, by "non-successive O", by, S, $NR_{14}$, CO, O(CO) or $NR_{14}$(CO).

"Interrupted" in this definition in the context of the present application is also meant to comprise $C_2$-$C_{18}$alkylene having one or more of said defined groups attached at one end or both ends of the corresponding interrupted chain. Accordingly, resulting structural units are for example: —O(CH$_2$)$_2$—, —O(CH$_2$)$_2$OCH$_2$—, —O(CH$_2$CH$_2$O)$_2$— —S(CH$_2$)$_2$— —(CH$_2$)$_2$NH—, —(CH$_2$)$_2$O(CO)CH$_2$—, —CH$_2$CH$_2$NHCO—.

$C_3$-$C_{30}$cycloalkylene is a mono- or polycyclic aliphatic ring, for example a mono-, bi- or tricyclic aliphatic ring, e.g. $C_3$-$C_{20}$—, $C_3$-$C_{18}$—, $C_3$-$C_{12}$—, $C_3$-$C_{10}$cycloalkylene. Examples of monocyclic rings are cyclopropylene, cyclobutylene, cyclopentylene, cyclohexylene, or cycloheptylene. Examples of polycyclic rings are perhydroanthracylene, perhydrophenyathrylene, perhydronaphthylene, perhydrofluorenylene, perhydrochrysenylene, perhydropicenylene, adamantylene, bicyclo[1.1.1]pentylene, bicyclo[4.2.2]decylene, bicyclo[2.2.2]octylene, bicycle[3.3.2]decylene, bicyclo[4.3.2]undecylene, bicyclo[4.3.3]-dodecylene, bicyclo[3.3.3]undecylene, bicyclo[4.3.1]decylene, bicyclo[4.2.1]nonylene, bicyclo[3.3.1]nonylene, bicyclo[3.2.1]octylene,

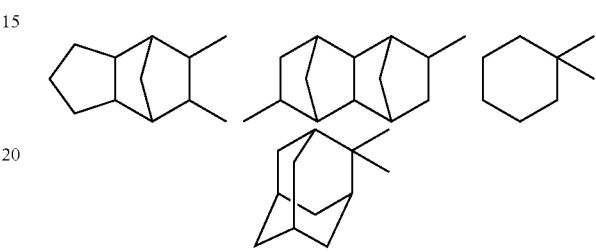

and the like. Also "spiro"-cycloalkylene compounds are covered by the definition $C_3$-$C_{30}$cycloalkylene in the present context, e.g. spiro[5.2]octylene, spiro[5.4]decylene, spiro[5.5]undecylene. More examples of polycyclic cycloalkylene groups, which are subject of the respective definition in the compounds of the present invention are listed in EP878738, page 11 and 12, wherein to the formulae (1)-(46) two bonds to achieve the "ylene" has to be added. The person skilled in the art is aware of this fact.

$C_3$-$C_{30}$cycloalkylene which is interrupted by one or more O, S, $NR_{14}$, CO, O(CO) or $NR_{14}$(CO), is a mono- or polycyclic aliphatic ring which is interrupted by one or more O, S, $NR_{14}$, CO, O(CO) or $NR_{14}$(CO), for example,

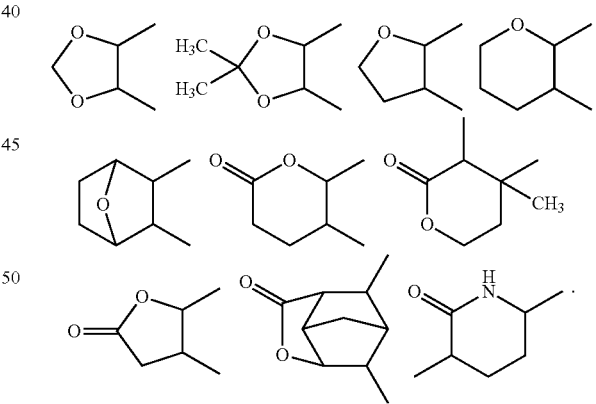

$C_2$-$C_{12}$alkenylene radicals are for example mono- or polyunsaturated, linear or branched and are for example $C_2$-$C_8$—, $C_2$-$C_6$- or $C_2$-$C_4$alkenylene. Examples are —CH=CHCH$_2$—, —CH=C(CH$_3$)CH$_2$—, —CH=C(CH$_3$)—,

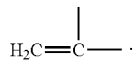

$C_4$-$C_{30}$cycloalkenylene is a mono- or polycyclic and mono- or polyunsaturated ring, for example a mono-, bi-, tri- or tetracyclic mono- or polyunsaturated ring, e.g. $C_4$-$C_{20}$—, $C_4$-$C_{18}$—, $C_4$-$C_{12}$—, $C_4$-$C_{10}$cycloalkenylene;

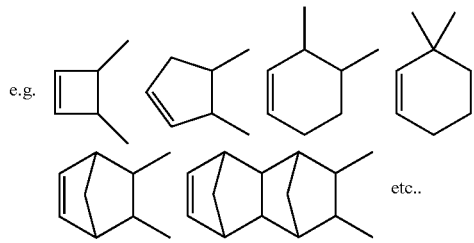

$C_4$-$C_{30}$cycloalkenylene which is interrupted by one or more O, S, $NR_{14}$, CO, O(CO) or $NR_{14}$(CO), is a mono- or polycyclic and mono- or polyunsaturated ring, which is interrupted by one or more O, S, $NR_{14}$, CO, O(CO) or $NR_{14}$(CO), for example

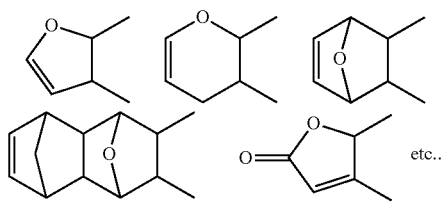

Substituted phenyl carries from one to five, for example one, two or three, especially one or two, substituents on the phenyl ring. The substitution is preferably in the 4-, 3,4-, 3,5- or 3,4,5-position of the phenyl ring.

When the radicals phenyl, naphthyl, anthracyl, phenanthryl, biphenylyl, fluorenyl or heteroaryl are substituted by one or more radicals, they are, for example, mono- to penta-substituted, for example mono-, di- or tri-substituted, especially mono- or di-substituted.

When the radicals Z as $C_1$-$C_{18}$alkyl, $C_2$-$C_{12}$alkenyl, (CO)$R_{15}$, (CO)$OR_{11}$, (CO)$NR_{12}R_{13}$, O(CO)$R_{15}$, O(CO)$OR_{11}$, O(CO)$NR_{12}R_{13}$, $NR_{14}$(CO)$R_{15}$, $NR_{14}$(CO)$OR_{11}$, $NR_{14}$(CO)$NR_{12}R_{13}$, $OR_{11}$, $NR_{12}R_{13}$, $SR_{14}$, $SOR_{15}$, $SO_2R_{15}$ and/or —$OSO_2R_{15}$, on the phenyl, naphthyl, anthracyl, phenanthryl, biphenyl, fluorenyl or heteroaryl; form 5-, 6- or 7-membered rings, via the radicals $C_1$-$C_{18}$alkyl, $C_2$-$C_{12}$alkenyl, $R_{11}$, $R_{12}$, $R_{13}$, $R_{14}$ and/or $R_{15}$, with further substituents on the phenyl, naphthyl, anthracyl, phenanthryl, biphenyl, fluorenyl or heteroaryl; or with one of the carbon atoms of the phenyl, naphthyl, anthracyl, phenanthryl, biphenyl, fluorenyl or heteroaryl, for example the following structural units are obtained

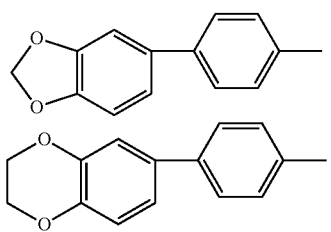

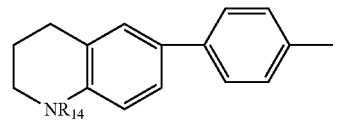
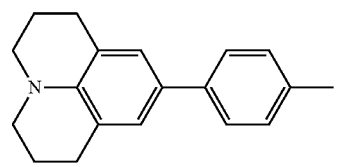
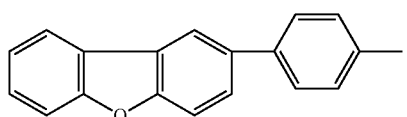
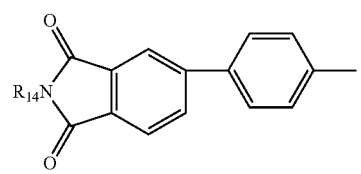
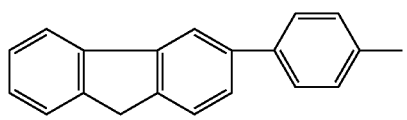
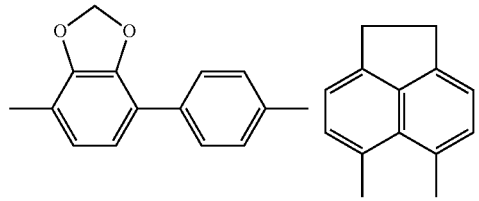
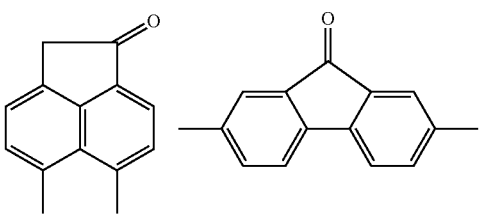
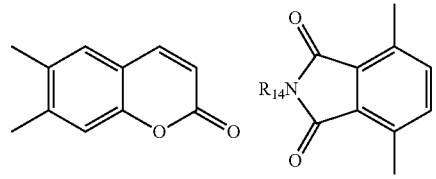
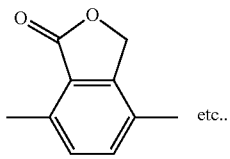

If the substituents $C_1$-$C_{18}$alkyl form alkylene bridges from one carbon atom of the biphenyl, naphthyl, or fluorenyl ring to another carbon atom of said ring, in particular ethylene, propylene and butylene bridges are formed and for example the following structures are obtained

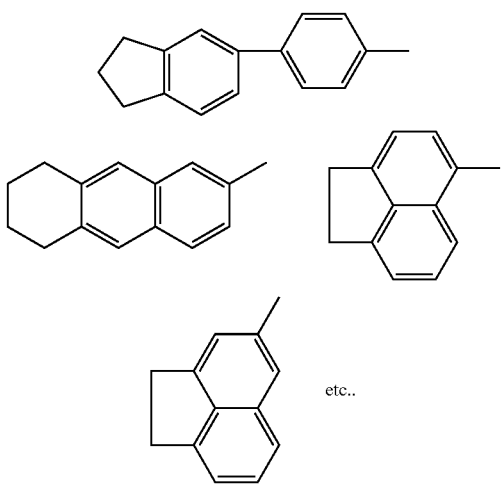

The definition according to the present application in this connection also is intended to cover branched alkylene bridges:

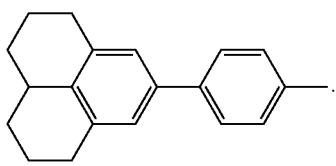 [SMILES: Cc1ccc(-c2cc3c4c(c2)CCCC4CCC3)cc1]

In case said alkylene bridges are condensed with further phenyl rings for example structures like the following are given

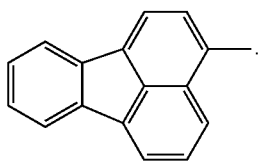 [SMILES: Cc1ccc2c3c(cccc13)-c1ccccc1-2]

If $R_{21}$ and $R_{22}$ together with a direct bond, $C_1$-$C_4$alkylene, O, S, $NR_{14}$ or (CO), form a fused ring system, for example the structural units like the following are obtained,

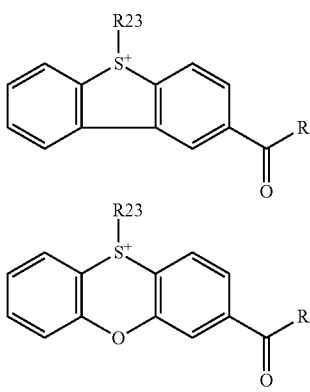

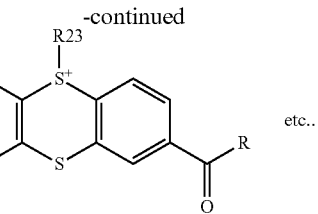

etc..

If $R_{21}$ and $R_{22}$ together with a direct bond, $C_1$-$C_4$alkylene, O, S, $NR_{14}$ or (CO), form a 5-, 6-, or 7-membered ring, for example structural units like the following are obtained

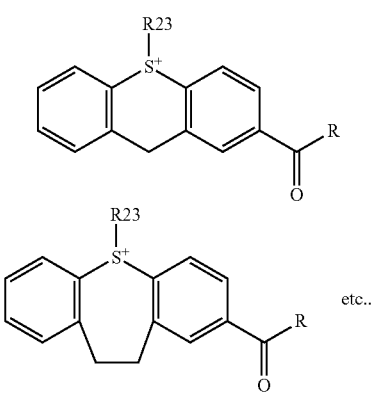

etc..

$C_1$-$C_{18}$alkanoyl is e.g. $C_1$-$C_{12}$, $C_1$-$C_8$—, $C_1$-$C_6$—, $C_1$-$C_4$—, $C_2$-$C_{12}$, $C_2$-$C_8$—, $C_2$-$C_6$- or $C_2$-$C_4$alkanoyl, wherein the alkyl moiety is linear or branched. Examples are formyl, acetyl, propionyl, butanoyl or hexanoyl, especially acetyl.

$C_1$-$C_{18}$alkoxy is e.g. $C_1$-$C_{12}$—, $C_1$-$C_8$—, $C_1$-$C_6$—, $C_1$-$C_4$alkoxy, and is linear or branched. Examples are methoxy, ethoxy, propoxy, n-butoxy, t-butoxy, octyloxy and dodecyloxy.

$C_2$-$C_{18}$alkoxycarbonyl is ($C_1$-$C_{17}$alkyl)-O—C(O)—, wherein $C_1$-$C_{17}$alkyl is linear or branched and is as defined above up to the appropriate number of carbon atoms. Examples are $C_2$-$C_{10}$—, $C_2$-$C_8$—, $C_2$-$C_6$- or $C_2$-$C_4$alkoxycarbonyl, such as methoxycarbonyl, ethoxycarbonyl, propoxycarbonyl, butoxycarbonyl or pentoxycarbonyl.

$C_1$-$C_{10}$haloalkyl are for example $C_1$-$C_8$—, $C_1$-$C_6$- or $C_1$-$C_4$-alkyl mono- or poly-substituted by halogen, the alkyl moieties being, for example, as defined above. There are, for example, from 1 to 23 halogen substituents at the alkyl radical. Examples are chloromethyl, trichloromethyl, trifluoromethyl, nonafluorobutyl or 2-bromopropyl, especially trifluoromethyl or trichloromethyl. Preferred is $C_1$-$C_{10}$fluoroalkyl.

$C_2$-$C_{10}$haloalkanoyl is ($C_1$-$C_9$haloalkyl)-C(O)—, wherein $C_1$-$C_9$haloalkyl is as defined above up to the appropriate number of carbon atoms. Examples are chloroacetyl, trichloroacetyl, trifluoroacetyl, pentafluoropropionyl, perfluorooctanoyl, or 2-bromopropionyl, especially trifluoroacetyl or trichloroacetyl.

Halobenzoyl is benzoyl which is mono- or poly-substituted by halogen and/or $C_1$-$C_4$haloalkyl, $C_1$-$C_4$-haloalkyl being as defined above. Examples are pentafluorobenzoyl, trichlorobenzoyl, trifluoromethylbenzoyl, especially pentafluorobenzoyl.

Halogen is fluorine, chlorine, bromine or iodine, especially chlorine or fluorine, preferably fluorine.

Phenyl-$C_1$-$C_3$alkyl is, for example, benzyl, 2-phenylethyl, 3-phenylpropyl, -methylbenzyl or, -dimethylbenzyl, especially benzyl.

If $R_{12}$ and $R_{13}$ together with the nitrogen atom to which they are bonded form a 5-, 6- or 7-membered ring that optionally is interrupted by O, $NR_{14}$ or CO, for example structures like the following are obtained

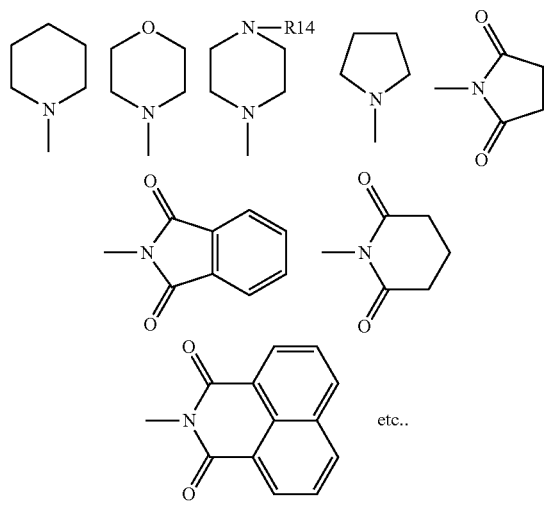

The monovalent $C_{17}$-$C_{50}$ hydrocarbon group of steroid structure which may contain one or more heteroatoms is a mono-valent group having a tetracyclic ring system such as

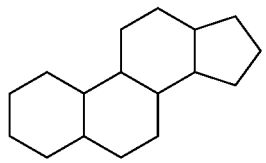 [SMILES: C1CCC2C(C1)CCC1C3CCCC3CCC21]

which may contain one or more heteroatoms (e.g. O, S or N) in the group. It may also have one or more unsaturated bonds and one or more functional groups; for example

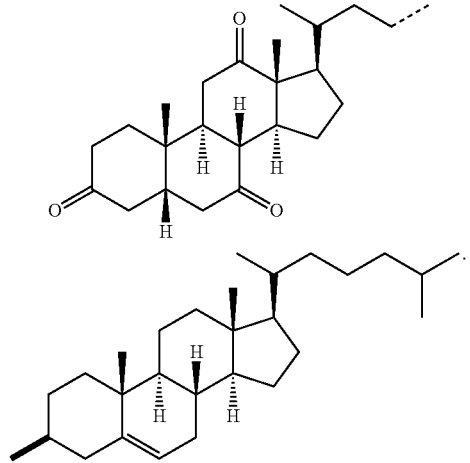

The definition $C_1$-$C_{18}$alkylsulfonyl, refers to the corresponding radical $C_1$-$C_{18}$alkyl, as described in detail above, being linked to a sulfonyl group (—$SO_2$—). Accordingly, also phenylsulfonyl and (4-methylphenyl)sulfonyl refer to the corresponding radicals linked to a sulfonyl group.

$C_2$-$C_{18}$alkanoyloxy is ($C_1$-$C_{17}$alkyl)-C(O)—O—, wherein $C_1$-$C_{17}$alkyl is linear or branched and is as defined above up to the appropriate number of carbon atoms. Examples are $C_2$-$C_{10}$—, $C_2$-$C_8$—, $C_2$-$C_6$- or $C_2$-$C_4$alkanoyloxy, such as acetyloxy, ethanoyloxy, propanoyloxy, butanoyloxy or hexanoyloxy.

$C_1$-$C_{18}$alkylsulfonyloxy is ($C_1$-$C_{18}$alkyl)-S(O)$_2$—O—, wherein $C_1$-$C_{18}$alkyl is linear or branched and is as defined above up to the appropriate number of carbon atoms. Examples are $C_1$-$C_{10}$—, $C_1$-$C_8$—, $C_1$-$C_6$- or $C_1$-$C_4$alkylsulfonyloxy, such as methanesulfonyloxy, propanesulfonyloxy or hexanesulfonyloxy. Accordingly, also phenylsulfonyloxy refers to the corresponding radicals linked to a —S(O)$_2$—O— group.

In the present application, the term "heteroaryl" is meant to comprise either one ring or a multiple ring system, e.g. a fused ring-system, wherein one or more of the rings optionally are substituted, in particular by one or more $C_1$-$C_{20}$alkyl and/or $C_1$-$C_{20}$alkoxy. $C_5$-$C_{20}$heteroaryl as heteroatom comprises one or more, e.g. 1-3 or 1 or, especially 1 heteroatom(s), selected from the group consisting of O, S or N. Heteroaryl is for example $C_5$-$C_{20}$heteroaryl, $C_5$-$C_{18}$heteroaryl, $C_5$-$C_{12}$heteroaryl and denotes unsubstituted and substituted radicals, for example 3-thienyl, 2-thienyl

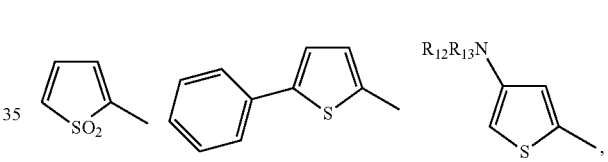

wherein $R_{12}$ and $R_{13}$ are as defined above, thianthrenyl, isobenzofuranyl, xanthenyl, phenoxanthiinyl

wherein E is S, O or $NR_{14}$ and $R_{14}$ is as defined above. Examples thereof are pyrazolyl, thiazolyl, oxazolyl, isothiazolyl or isoxazolyl. Also included are, for example, furyl, pyrrolyl, 1,2,4-triazolyl,

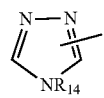

or b-membered ring heterocycles having a fused-on aromatic group, for example benzimidazolyl, benzothienyl, benzofuranyl, benzoxazolyl and benzothiazolyl.

Other examples of "heteroaryls" are imidazolyl, pyridyl, especially 3-pyridyl,

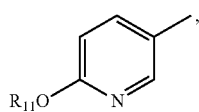

wherein $R_{11}$ is as defined above, pyrimidinyl, pyrazinyl, 1,3,5-triazinyl, 2,4-, 2,2- or 2,3-diazinyl, indolizinyl, isoindolyl, indolyl, indazolyl, purinyl, isoquinolyl, quinolyl, phenoxazinyl or phenazinyl. In this Application, the term "heteroaryl" also denotes the radicals thioxanthyl, xanthyl,

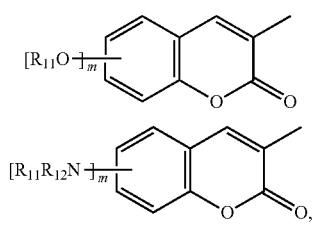

wherein m is 0 or 1 and $R_{11}$, $R_{12}$, $R_{13}$ are as defined above,

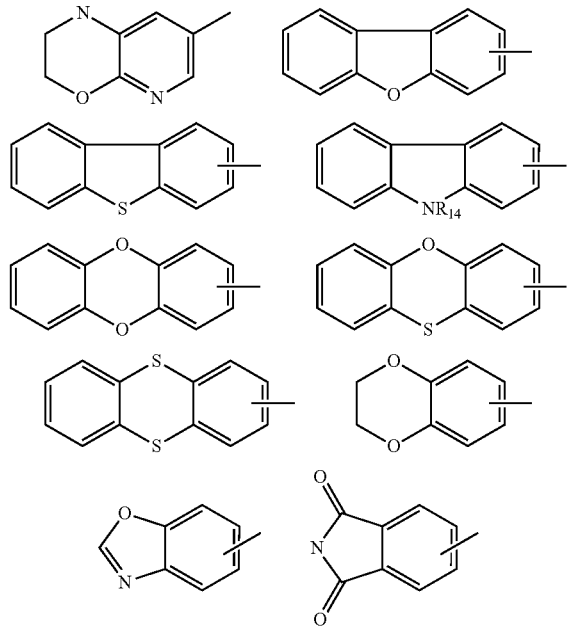

anthraquinonyl. Each of the heteroaryls may carry the substituents indicated above or in claim 1. Naphthylene is

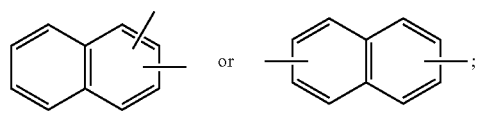

biphenylene is

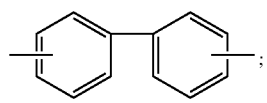

anthracylene is

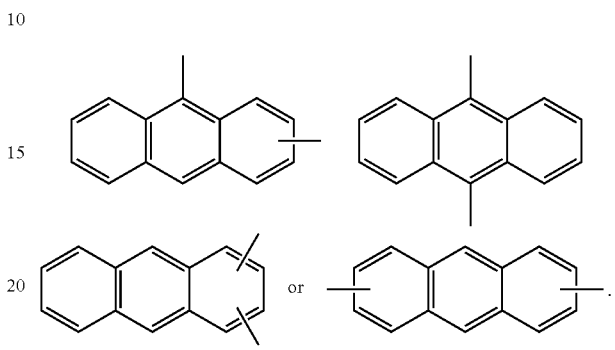

Similarly the bondings are placed at the different rings of the phenanthrylene. Heteroarylene is a divalent radical of the heteroaryl rings as described above, for example

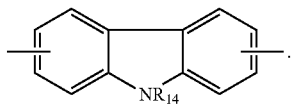

Groups having a —O—C-bond or a —O—Si-bond which cleaves upon the action of an acid, and being substituents of the radicals R21, R22, R23, R24 and R25 are acid cleavable groups which increase the solubility of the compounds in the present invention in the alkaline developer after reaction with an acid. This effect is for example described in U.S. Pat. No. 4,883,740.

Examples of groups suitable as such substitutents are for example known orthoesters, trityl and benzyl groups, tert.-butyl esters of carboxylic acids, tert.-butyl carbonates of phenols or silyl ethers of phenols, e.g. $OSi(CH_3)_3$, $CH_2(CO)OC(CH_3)_3$, $(CO)OC(CH_3)_3$, $O(CO)OC(CH_3)_3$ or —O—C($E_1$)($E_3$)($OE_2$), wherein $E_1$ and $E_2$ independently of one another are hydrogen, $C_1$-$C_5$alkyl, $C_3$-$C_8$-cycloalkyl, phenyl-$C_1$-$C_3$-alkyl, or $E_1$ and $E_2$ together are $C_2$-$C_5$alkylene, and $E_3$ is unsubstituted or halogen-substituted $C_1$-$C_5$alkyl, unsubstituted or halogen-substituted $C_3$-$C_8$cycloalkyl, or phenyl-$C_1$-$C_3$-alkyl, or, if $E_1$ and $E_2$ together are no $C_2$-$C_5$alkylene, $E_3$ and $E_2$ together may be $C_2$-$C_5$alkylene, which may be interrupted by O or S.

The terms "and/or" or "or/and" in the claims and throughout the specification are meant to express that not only one of the defined alternatives (substituents) may be present, but also several of the defined alternatives (substituents) together, namely mixtures of different alternatives (substituents). The term "optionally" is intended to cover both corresponding options which are defined. The term "at least" is meant to define one or more than one, for example one or two or three, preferably one or two.

Compounds generating an acid of the formula I or II in this invention are classified into ionic compounds and non-ionic compounds. The ionic compounds expressed by, for example, formula IIIa, IIIb, IVa, IVb are synthesized by ion exchange reaction from the compounds represented by formula Ia or IIa. One of the preparation methods of the non-ionic compounds expressed by, for example, formula IIIc, IIId, IIIe, IVc, IVe is reaction with the corresponding sulfonyl halides, which are synthesized from the compounds represented by formula Ia or IIa in the presence of halogenating reagents. The person skilled in the art is well aware of the appropriate reactions as well as of the reaction conditions which have to be taken.

The compounds of the formula Ia and IIa as defined below, for instance, are prepared from compound B

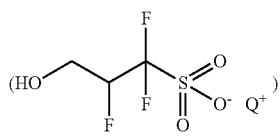

wherein $Q^+$ is proton, metal cation such as lithium, sodium, potassium, (un)substituted ammonium and pyridinium salt such as triethylammonium, or any other cation species.

For example, the hydroxyl group at the end of the chain undergoes esterification with carboxylic acid or sulfonic acid derivatives as in an example described below:

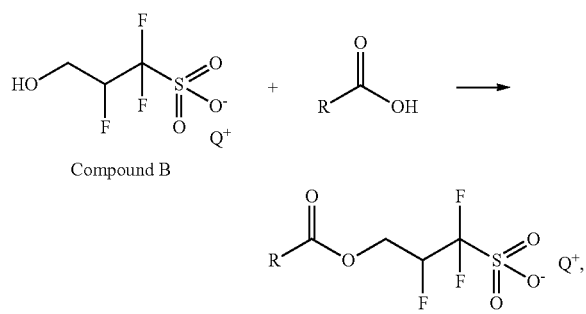

Compound B wherein the group

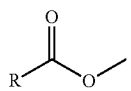

represents $R_1$—Y— as defined above in the compounds of the formula I; or

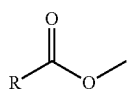

represents $R_3$-$R_2$—Y— as defined above in the compounds of the formula II.

The esterification is carried out, for example, using carboxylic or sulfonic acid, acid halide (i.e. carboxylic acid halide or i.e. sulfonic acid halide) or acid anhydride. The acid halide can be prepared by known methods, for example by reacting carboxylic acid with sulfonyl chloride, oxalyl chloride, phosphoryl chloride, etc. The person skilled in the art is well aware of the appropriate reactions as well as of the reaction conditions which have to be taken.

For example, compound (I) is obtained by esterification of Compound B with cholesteryl chloroformate in presence of a base, such as triethylamine and N,N-dimethylaminopyridine, and succeeding cation exchange.

In another example, compound (m) is obtained by esterification of Compound B with dehydrocholic acid chloride in presence of a base, such as triethylamine and N,N-diethylaminopyridine, and succeeding cation exchange.

In yet another example, Compound C

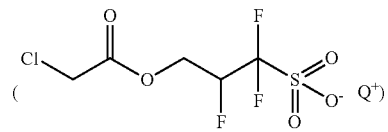

is obtained by esterification of Compound B with chloroacetyl chloride in presence of a base, such as pyridine.

Compound (IIIf) is obtained from reaction of Compound C with sodium dehydrocholate and replacement (cation exchange) of $Q^+$ with the triphenyl sulfonium cation.

(IIIf)

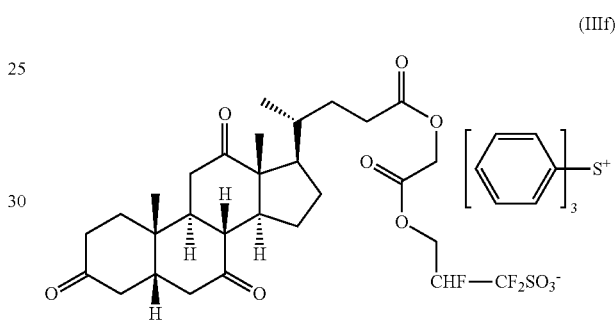

As another example of derivatization, the hydroxyl group of the Compound B further reacts with isocyanate compounds to form an —O(CO)NR$_4$— (i.e. $R_4$=H) group as defined above for Y.

As another example, the hydroxyl group of the Compound B can be converted to leaving groups such as iodide, bromide, chloride, tosylate, mesylate, trifluoroacetate etc. These compounds undergo substitution reaction with nucleophiles such as alcohol, thiol, amine, amide etc to form O, NR$_4$, S, as Y defined above. The person skilled in the art is well aware of the appropriate reactions as well as of the reaction conditions which have to be taken.

The hydroxyl group of the Compound B can also be converted to carboxylic acid by oxidation with oxidizing agents such as chromic acid, permanganate, and nitric acid. The resultant carboxylic acid further reacts with alcohol or amine to yield ester and amide as an example shown below:

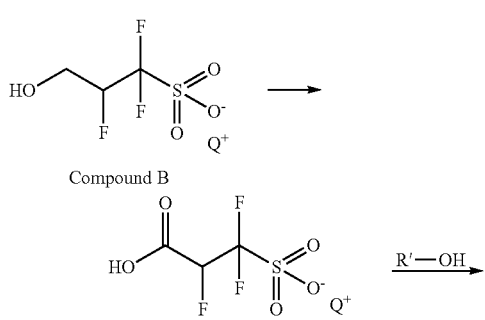

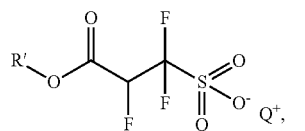

wherein CO and the group

respectively represents X and $R_1$—Y— as defined above in the compounds of the formula I, IIIa, IIIb; IIIc, IIId and IIIe; or $R_3$-$R_2$—Y— as defined above in the compounds of the formula II, IVa, IVb, IVc and IVe.

The person skilled in the art is well aware of the appropriate reactions as well as of the reaction conditions which have to be taken.

The intermediate Compound B is obtained from 2,2,3,3-tetrafluoropropanol (TFP) according to the following reaction scheme and according to known methods:

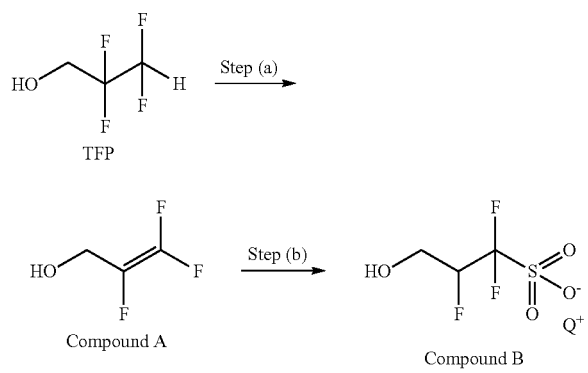

In the step (a) TFP undergoes elimination by a base, yielding 2,3,3-trifluoro-2-propen-1-ol (Compound A) as described in J. Org. Chem. 5640 (1989). In the step (b) Compound A undergoes sulfonation with sulfite, yielding 1,1,2-trifluoro-3-hydroxypropane-1-sulfonic acid or its salt (Compound B) according to similar reactions, known from literature e.g. in J. Am. Chem. Soc., 75, 4595 (1953) and Green Chem., 9, 30 (2007).

While in the examples of this invention presented herein the cation $Q^+$ is replaced (exchanged) after the reaction(s) has (have) been completed that yield the final anion structure, it is obvious to the person skilled in the art that the cation $Q^+$ can be exchanged with a sulfonium or iodonium ion, or any other cation desired, at the stage of the compound B or, optionally at any salt intermediate stage in the reaction sequence later on. Thus, the scope and working of the invention is not limited to any particular process or sequence of any cation exchange.

The acid of the formula I and II, and the compounds generating an acid of the formula I and II are novel. Its salts expressed, for example, by the formula Ia and IIa are also novel compounds. The invention accordingly pertains to a compound of the formula Ia or IIa,

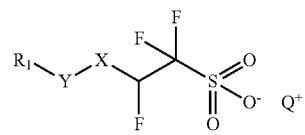

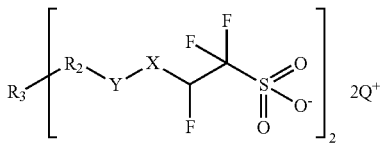

wherein
$Q^+$ is a cation, in particular a proton, lithium, sodium, potassium, cesium, magnesium, calcium, heteroaryl having one or more nitrogen atom with plus charge which is unsubstituted or substituted by one or more $(NR_{28}R_{29}R_{30}R_{31})^+$;
$R_{28}$, $R_{29}$, $R_{30}$ and $R_{31}$ independently of each other have one of the meanings of $R_{12}$ and $R_{13}$ as defined in claim 1;
or $R_{28}$, $R_{29}$, $R_{30}$, together are with a nitrogen atom to which they are attached, form a polycyclic ring which optionally is interrupted by one or more O, $NR_{14}$, CO, and/or optionally interrupted by $CR_{15}$ or N at the bridgehead; and
X, Y, $R_1$, $R_2$, and $R_3$, $R_{14}$ and $R_{15}$ are as defined above.

Examples of $(NR_{25}R_{29}R_{30}R_{31})^+$ are pyridinium which optionally is substituted by one or more $C_1$-$C_{10}$alkyl, ammonium, tetra($C_1$-$C_{10}$alkyl)ammonium, tri($C_1$-$C_{10}$alkyl)ammonium, di($C_1$-$C_{10}$alkyl)ammonium or mono($C_1$-$C_{10}$alkyl)ammonium.

Example of suitable cations are protons, alkali metals, especially lithium or sodium, onium compounds, e.g. sulfonium, iodonium, phosphonium cations, quaternary ammonium compounds, dye cations, cationic transition metal coordination complex compounds. Example of tetraalkylammonium is tetra($C_1$-$C_4$alkyl)ammonium. This refers to compounds of the following formula: $N(C_1$-$C_4$ alkyl)$_4^+$, in which $C_1$-$C_4$alkyl can have the definitions indicated above up to the corresponding number of C atoms. Examples of appropriate ammonium compounds are tetramethylammonium, tetraethylammonium, tetrapropylammonium and tetrabutylammonium, especially tetramethylammonium and tetrabutylammonium. Benzyltri($C_1$-$C_4$alkyl) ammonium is also suitable. This is $C_6H_5$—$CH_2$—$N(C_1$-$C_4$alkyl)$_3^+$, where $C_1$-$C_4$alkyl can have the definitions indicated above up to the corresponding number of C atoms. Examples of such radicals are benzyltrimethylammonium, benzyltriethylammonium, benzyltripropylammonium and benzyltributylammonium, especially benzyltrimethylammonium and benyzltributylammonium. However, trisalkylammonium ions are also suitable, for example trimethylammonium. Phosphonium and ammonium counterions of the formulae $^+PR_wR_xR_yR_z$ and $^+NR_wR_xR_yR_z$ are suitable, where $R_w$, $R_x$, $R_y$ and $R_z$ independently of one another are hydrogen, unsubstituted or substituted alkyl, cycloalkyl, alkenyl, phenyl or arylalkyl. Examples of substituents of these alkyl, cycloalkyl, alkenyl, phenyl and aralkyl radicals are halides, hydroxyl, heterocycloalkyl (e.g. epoxy, aziridyl, oxetanyl, furanyl, pyrrolidinyl, pyrrolyl, thiophenyl, tetrahydrofuranyl, etc.), dialkylamino, amino, carboxyl, alkyl- and arylcarbonyl and aryloxy- and alkoxycarbonyl.

The tetravalent nitrogen may also be part of a 5- or 6-membered ring, which may in turn be fused onto other ring systems. These systems may also include additional heteroatoms, for example S, N, O. The tetravalent nitrogen may also be part of a polycyclic ring system, for example azoniapropellane. These systems may also contain further heteroatoms, for example S, N, O.

Suitable ammonium salts and phosphonium salts can for example be substituted by colourless electron acceptors (e.g. benzophenones), such as

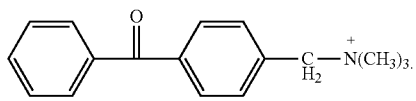

Other quaternary ammonium compounds which are of interest are, for example, trimethylcetylammonium or cetylpyridinium compounds.

Other examples of positive counterions $Q^+$ to be used in the compound of the formula Ia and IIa include the following:

Aryl-$CH_2$—$Z(R)_3$, in which Z is P, S or N and R is an alkyl or aryl radical. Also suitable are compounds such as

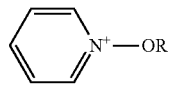

(described by Yagci et al. in J. Polym. Sci. Part A: Polymer Chem. 1992, 30, 1987 and Polymer 1993, 34(6), 1130), or compounds such as

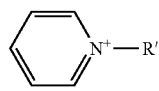

where R'=unsubstituted or substituted benzyl or phenacyl (described in JP-A-07 70221). In these compounds, the aromatic rings in the pyridinium may also be substituted.

The compounds generating an acid of the formula I or II, that includes the compounds of the formula IIIa, IIIb, IVa, IVb, IIIc, IIId, IIIe, IVc and IVe as described above can be used as radiation-sensitive acid donors.

Also the polymers, prepared by copolymerizing compounds of the formula IIIa, IIIb, IIIc and IIIe as defined above, wherein $R_1$ as $C_2$-$C_{12}$alkenyl or interrupted $C_2$-$C_{18}$alkenyl is a polymerizable group containing at least one double bond, with a monomer can be used as radiation-sensitive acid donors.

Subject of the invention therefore is a composition comprising (a) at least one compound of the formula IIIa, IIIb, IIIe, IVa, IVb, IIIc, IIId, IVc and IVe as a latent acid donor as described above; and
(b) a compound which cures or crosslinks or decreases the solubility of the composition in a developer upon the action of an acid.

Another subject of the invention is a composition comprising as component (a), or (a) and (b) a polymer prepared by copolymerizing compounds of the formula IIIa, IIIb, IIIc and IIIe as defined above, wherein $R_1$ as $C_2$-$C_{12}$alkenyl or interrupted $C_2$-$C_{18}$alkenyl is a polymerizable group containing at least one double bond, with at least one other comonomer.

Yet another subject of the invention is a composition comprising
(a) at least one compound of the formula IIIa, IIIb, IIIe, IVa, IVb, IIIc, IIId, IVc and IVe as a latent acid donor as described above; and
(c) a compound that upon reaction with an acid enhances the solubility of the composition in a developer.

Yet another subject of the invention is a composition comprising as component (a), or (a) and (c) a polymer prepared by copolymerizing compounds of the formula IIIa, IIIb, IIIc and IIIe as defined above, wherein $R_1$ as $C_2$-$C_{12}$alkenyl or interrupted $C_2$-$C_{18}$alkenyl is a polymerizable group containing at least one double bond, with at least one other co-monomer.

The invention accordingly relates to a chemically amplified (negative and positive) photoresist composition comprising
(a) as photosensitive acid donor, at least one compound generating an acid of the formula I or II as defined above; and
(b) a compound which crosslinks upon the action of an acid; or
(c) a compound whose solubility in a developer is increased upon the action of an acid.

A subject of the invention is a chemically amplified positive resist composition comprising as radiation sensitive acid donor (a) at least one compound generating an acid of the formula I or II as defined above; and a compound (c) which is insoluble or essentially insoluble in a developer and becomes soluble upon the action of the acid.

Said at least one compound generating an acid of the formula I or II as defined above includes a compound of the formula IIIa, IIIb, IIIe, IVa, IVb, IIIc, IIId, IVc and IVe as described above and a polymer, prepared by copolymerizing a compound of the formula IIIa, IIIb, IIIc and IIIe as defined above, wherein $R_1$ as $C_2$-$C_{12}$alkenyl or interrupted $C_2$-$C_{18}$alkenyl is a polymerizable group containing at least one double bond, with a monomer.

Thus, subject of the invention also is a chemically amplified photoresist composition as described above which is a positive photoresist composition, comprising as component (a) and (c) a polymer obtained by polymerizing a compound of the formula IIIa, IIIb, IIIc or IIIe as defined above, wherein $R_1$ as $C_2$-$C_{12}$alkenyl or interrupted $C_2$-$C_{18}$alkenyl is a polymerizable group containing at least one double bond, with at least one further monomer which comprises a polymerizable double bond and an acid labile group, enhancing the dissolution rate of the polymer in an aqueous alkaline developer upon action of an acid.

The invention pertains to a chemically amplified resist composition comprising as radiation sensitive acid donor a polymer obtained by polymerizing a compound of the formula IIIa, IIIb, IIIc or IIIe as defined above, wherein $R_1$ as $C_2$-$C_{12}$alkenyl or interrupted $C_2$-$C_{18}$alkenyl is a polymerizable group containing at least one double bond, with at least one further monomer which comprises a polymerizable double bond.

Subject of the invention also is a chemically amplified negative resist composition comprising as photosensitive acid donor (a), at least one compound generating an acid of the formula I or II as defined above; and a compound (b) which crosslinks or polymerizes upon action of the acid, wherein the coated and dried resist composition is soluble in a developer and becomes insoluble or essentially insoluble upon action of the acid.

The chemically amplified positive resist composition as described above, which comprise additionally other additives (d) are a further subject of the invention.

A chemically amplified photoresist is understood to be a resist composition wherein the radiation sensitive component provides a catalytic amount of acid which subsequently catalyses a chemical reaction of at least one acid-sensitive component of the resist. A solubility difference between the irradiated and non-irradiated areas of the resist results from this reaction. Because of the catalytic nature of this process one acid molecule can trigger reactions at multiple sites as it diffuses through the reactive polymer matrix, from one reaction site to the next, as long as it is not trapped or destroyed by any secondary reaction. Therefore, a small acid concentration is sufficient to induce a high difference in the solubility between exposed and unexposed areas in the resist. Thus, only a small concentration of the latent acid compound is necessary. As a result, resists with high contrast and high transparency at the exposure wavelength in optical imaging can be formulated, which in turn produce steep, vertical image profiles at high photosensitivity. However, as a result of this catalytic process, it is required that the latent acid catalysts are chemically and thermally sufficiently stable (as long as not irradiated) in order not to generate acid during resist storage or during processing, which—in most cases—requires a bake step after generation of the acid to start or to complete the catalytic reaction which leads to the solubility differential. It is also required to have good solubility of the latent catalysts in the liquid resist formulation and the solid resist film to avoid any particle generation which would interfere with the application of these resists in microelectronic manufacturing processes.

In contrast, positive resist materials which are not based on the chemical amplification mechanism must contain a high concentration of the latent acid, because it is only the acid concentration which is generated from the latent acid under exposure which contributes to the increased solubility of the exposed areas in alkaline developer. Because small acid concentration has only a little effect on the change of the dissolution rate of such resist and the reaction proceeds typically without a post exposure bake here, the requirements regarding chemical and thermal stability of the latent acid are less demanding than for chemically amplified positive resists. These resists require also a much higher exposure dose to generate enough acid for achieving sufficient solubility in the alkaline developer in the exposed areas and also suffer from the relatively low optical transparency (due to the high concentration of latent acid necessary) and thus also lower resolution and sloped images. Resist compositions based on non-chemically amplified technology are therefore inferior in photosensitivity, resolution and image quality compared to chemically amplified resists.

From the above it becomes clear that chemical and thermal stability of a latent catalyst is vital for a chemically amplified resist and that latent acids which can work in a non-chemically amplified resist are not necessarily applicable to chemically amplified resists because of the different acid diffusion requirements, acid strength requirements and thermal and chemical stability requirements.

Subject of the invention is the use of compounds generating an acid of the formula I or II as defined above or of a polymer obtained by polymerizing a compounds of the formula IIIa, IIIb, IIIc or IIIe as defined above, wherein $R_1$ as $C_2$-$C_{12}$alkenyl or interrupted $C_2$-$C_{18}$alkenyl is a polymerizable group containing at least one double bond, with a monomer which comprises a polymerizable double bond, in the preparation of chemically amplified resists or colour filters.

Said monomer which comprises a polymerizable double bond is for example a monomer comprising an acid-labile group as described above.

The difference in resist solubility between irradiated and non-irradiated sections that occurs as a result of the acid-catalysed reaction of the resist material during or after irradiation of the resist may be of two types depending upon which further constituents are present in the resist. If the compositions according to the invention comprise components that increase the solubility of the composition in the developer after irradiation, the resist is positive.

The invention accordingly relates to a chemically amplified photoresist composition, which is a positive resist.

If, on the other hand, the components of the formulation reduce the solubility of the composition after irradiation, the resist is negative.

The invention accordingly relates also to a chemically amplified composition, which is a negative photoresist.

Preferred are chemically amplified positive photoresist compositions.

A monomeric or polymeric compound which—in the unexposed areas—reduces the dissolution rate of an additionally present alkaline soluble binder resin in the resist formulation and which is essentially alkali-insoluble in the unexposed areas so that the resist film remains in the unexposed area after development in alkaline solution, but which is cleaved in the presence of acid, or is capable of being rearranged, in such a manner that its reaction product becomes soluble in the alkaline developer is referred to hereinafter as dissolution inhibitor.

The invention includes, as a special embodiment a chemically amplified positive alkaline-developable photoresist composition, comprising
(a) at least one compound generating an acid of the formula I or II;
such compounds generating an acid of the formula I or II are, as already mentioned above, include the compounds of the formula IIIa, IIIb, IIIe, IVa, IVb, IIIc, IIId, IVc and IVe as defined above; and
(c1) at least one polymer having acid-labile groups which decompose in the presence of an acid and increase the solubility of the resist film in an aqueous alkaline developer solution in the irradiated area.

A further embodiment of the invention is a chemically amplified positive alkaline-developable photoresist composition, comprising
(a) at least one compound generating an acid of the formula I or II; and
(c2) at least one monomeric or oligomeric dissolution inhibitor having at least one acid-labile group which decomposes in the presence of acid and as a result increases the solubility of the composition in an aqueous alkaline developer solution, and at least one alkali-soluble polymer.

Another specific embodiment of the invention resides in a chemically amplified positive alkaline-developable photoresist composition, comprising
(a) at least one compound generating an acid of the formula I or II; and
(c1) at least one polymer having acid labile groups which decompose in the presence of an acid and increase the solubility in an alkaline developer in the exposed area;
(c2) a monomeric or oligomeric dissolution inhibitor, having at least one acid labile group, which decomposes in the presence of an acid and increase the alkaline solubility in the exposed area; and/or
(c3) an alkali-soluble monomeric, oligomeric or polymeric compound at a concentration which still keeps the resist film in the unexposed area essentially insoluble in the alkaline developer.

The invention therefore pertains to a chemically amplified photoresist composition, comprising
(a) as photosensitive acid donor, at least one compound generating an acid of the formula I or II as defined above, or a polymer obtained by polymerizing compounds of the formula IIIa, IIIb, IIIc or IIIe as defined above, wherein $R_1$ as $C_2$-$C_{12}$alkenyl or interrupted $C_2$-$C_{18}$alkenyl is a polymerizable group containing at least one double bond, with at least one further monomer comprising a polymerizable double bond and optionally with a monomer comprising an acid-labile group; and (c1) at least one polymer having an acid-labile group which decomposes in the presence of an acid to increase the solubility in aqueous alkaline developer solution and/or (c2) at least one monomeric or oligomeric dissolution inhibitor having an acid-labile group which decomposes in the presence of an acid to increase the solubility in aqueous alkaline developer solution; and/or (c3) at least one alkali-soluble monomeric, oligomeric or polymeric compound.

The compositions may comprise additionally to the component (a) other photosensitive acid donors and/or (d) other additives.

Such chemically amplified positive resist systems are described, for example, in E. Reichmanis, F. M. Houlihan, O. Nalamasu, T. X. Neenan, Chem. Mater. 1991, 3, 394; or in C. G. Willson, "Introduction to Microlithography, 2nd. Ed.; L. S. Thompson, C. G. Willson, M. J. Bowden, Eds., Amer. Chem. Soc., Washington D.C., 1994, p. 139. Suitable examples of acid-labile groups which decompose in the presence of an acid to produce aromatic hydroxy groups, carboxylic groups, keto groups and aldehyde groups and increase the solubility in aqueous alkaline developer solution are, for example, alkoxyalkyl ether groups, tetrahydrofuranyl ether groups, tetrahydropyranyl ether groups, tert.-alkyl ester groups, trityl ether groups, silyl ether groups, alkyl carbonate groups as for example tert.-butyloxycarbonyloxy-, trityl ester groups, silyl ester groups, alkoxymethyl ester groups, cumyl ester groups, acetal groups, ketal groups, tetrahydropyranyl ester groups, tetrafuranyl ester groups, tertiary alkyl ether groups, tertiary alkyl ester groups, and the like. Examples of such group include alkyl esters such as methyl ester and tert-butyl ester, acetal type esters such as methoxymethyl ester, ethoxymethyl enter, 1-ethoxyethyl ester, 1-isobutoxyethyl ester, 1-isopropoxyethyl ester, 1-ethoxypropyl ester, 1-(2-methoxyethoxy) ethyl ester, 1-(2-acetoxyethoxy)ethyl ester, 1-[2-(1-adamantyloxy)ethoxy]ethyl ester, 1-[2-(1-adamantylcarbonyloxy) ethoxy]ethyl ester, tetrahydro-2-furyl ester and tetrahydro-2-pyranyl ester, and alicyclic ester such as isobornyl ester.

The polymer having functional groups capable of decomposing by the action of an acid to enhance solubility of the resist film comprising this polymer in an alkaline developing solution, which can be incorporated in the positive resist according to the present invention, may have the acid-labile groups in the backbone and/or side chains thereof, preferably in side chains thereof.

The polymer having acid-labile groups suitable for the use in the present invention can be obtained with a polymer analogous reaction where the alkaline soluble groups are partially or completely converted into the respective acid labile groups or directly by (co)-polymerization of monomers which have the acid labile groups already attached, as is for instance disclosed in EP 254853, EP 878738, EP 877293, JP-A-2-25850, JP-A-3-223860, and JP-A-4-251259.

Monomers which have the acid-labile groups already attached are suitable for the copolymerization with the compounds of the formula IIIa, IIIb, IIIc and IIIe as defined above, wherein $R_1$ as $C_2$-$C_{12}$alkenyl or interrupted $C_2$-$C_{18}$alkenyl is a polymerizable group containing at least one double bond, for the preparation of polymers. Other comonomers without acid labile groups can be used additionally for co-polymerization to improve adhesion, mechanical properties, dry etch stability and other properties important in the application, such as described in detail below. Said polymers, comprising acid-labile groups as well as photolatent acid moieties are suitable as component (a)+(c) in the compositions as described above.

Specific examples of suitable monomers having acid-labile groups already attached are given below.

The polymers which have acid labile groups pendant to the polymer backbone, in the present invention preferably are polymers which have, for example silylether, acetal, ketal and alkoxyalkylester groups (called "low-activation energy blocking groups") which cleave completely at relatively low post exposure bake temperatures (typically between room temperature and 110° C.) and polymers which have, for example, tert-butylester groups or tert.-butyloxycarbonyl (TBOC) groups or other ester groups which contain a secondary or tertiary carbon atom next to the oxygen atom of the ester bond (called "high-activation energy blocking groups") which need higher bake temperatures (typically >90° C.) in order to complete the deblocking reaction in the presence of acid. Hybrid systems can also be applied, wherein, both, high activation energy blocking groups as well as low activation energy blocking groups are present within one polymer. Alternatively, polymer blends of polymers, each utilizing a different blocking group chemistry, can be used in the photosensitive positive resist compositions according to the invention.

Preferred polymers which have acid labile groups are polymers and co-polymers comprising the following distinct monomer types:

1) monomers that contain acid-labile groups which decompose in the presence of an acid to increase the solubility in aqueous alkaline developer solution and 2) monomers that are free of acid labile groups and free of groups that contribute to the alkaline solubility and/or adhesion to the substrate;

3) monomers that contribute to aqueous alkaline solubility of the polymer. Examples of monomers of type 1) are: non-cyclic or cyclic secondary and tertiary-alkyl(meth)acrylates such as butyl acrylate, including t-butyl acrylate, butyl methacrylate, including t-butyl methacrylate, 3-oxocyclohexyl (meth)acrylate, tetrahydropyranyl(meth)acrylate, 2-methyl-adamantyl(meth)acrylate, 2-ethyl-2-adamantyl (meth)acrylate, cyclohexyl(meth)acrylate, norbornyl(meth)-acrylate, (2-tetrahydropyranyl)oxynorbonylalcohol acrylates, (2-tetrahydropyranyl) oxymethyltricyclododecanemethanol methacrylates, trimethylsilylmethyl(meth)acrylate, (2-tetrahydropyranyl) oxynorbonylalcohol acrylates, (2-tetrahydropyranyl)oxymethyltricyclododecanemethanol methacrylates, trimethylsilylmethyl(meth)acrylate o-/m-/p-(3-oxocyclohexyloxy) styrene, o-/m-/p-(1-methyl-1-phenylethoxy)styrene, o-/m-/p-tetrahydropyranyloxystyrene, o-/m-/p-adamantyloxystyrene, o-/m-/p-cyclohexyloxystyrene, o-/m-/p-norbornyloxystyrene, non-cyclic or cyclic alkoxycarbonylstyrenes such as o-/m-/p-butoxycarbonylstyrene, including p-t-butoxycarbonylstyrene, o-/m-/p-(3-oxocyclohexyloxycarbonyl)styrene, o-/m-/p-(1-methyl-1-phenylethoxycarbonyl)styrene, o-/m-/p-tetrahydropyranyloxycarbonylstyrene, o-/m-/p-adamantyloxycarbonylstyrene, o-/m-/p-cyclohexyloxycarbonylstyrene, o-/m-/p-norbornyloxycarbonylstyrene, non-cyclic or cyclic alkoxycarbonyloxystyrenes such as o-/m-/p-butoxycarbonyloxystyrene, including p-t-butoxycarbonyloxystyrene, o-/m-/p-(3-oxocyclohexyloxycarbonyloxy)styrene, o-/m-/p-(1-methyl-1-phenylethoxycarbonyloxy)styrene, o-/m-/p-tetrahydropyranyloxycarbonyloxystyrene, o-/m-/p-adamantyloxycarbonyloxystyrene, o-/m-/p- cyclohexyloxycarbonyloxystyrene, o-/m-/p-norbornyloxycarbonyloxystyrene, non-cyclic or cyclic alkoxycarbonylalkoxystyrenes such as o/m/p-butoxycarbonylmethoxystyrene, p-t-butoxycarbonylmethoxystyrene, o-/m-/p-(3-oxocyclohexyloxycarbonylmethoxy)styrene, o-/m-/p-(1-methyl-1-phenylethoxycarbonylmethoxy)styrene, o-/m-/p-tetrahydropyranyloxycarbonylmethoxystyrene, o-/m-/p-adamantyloxycarbonylmethoxystyrene, o-/m-/p-cyclohexyloxycarbonylmethoxystyrene, o-/m-/p-norbornyloxycarbonylmethoxystyrene, trimethylsiloxystyrene, dimethyl(butyl)siloxystyrene, unsaturated alkyl acetates such as isopropenyl acetate and the derivatives of thereof.

Monomers of type 1) bearing low activation energy acid labile groups include, for example, p- or m-(1-methoxy-1-methylethoxy)-styrene, p- or m-(1-methoxy-1-methylethoxy)-methylstyrene, p- or m-(1-methoxy-1-methylpropoxy)styrene, p- or m-(1-methoxy-1-methylpropoxy)methylstyrene, p- or m-(1-methoxyethoxy)-styrene, p- or m-(1-methoxyethoxy)-methylstyrene, p- or m-(1-ethoxy-1-methylethoxy)styrene, p- or m-(1-ethoxy-1-methylethoxy)-methylstyrene, p- or m-(1-ethoxy-1-methylpropoxy)styrene, p- or m-(1-ethoxy-1-methylpropoxy)-methylstyrene, p- or m-(1-ethoxyethoxy)styrene, p- or m-(1-ethoxyethoxy)-methylstyrene, p-(1-ethoxyphenyl-ethoxy)styrene, p- or m-(1-n-propoxy-1-methylethoxy)styrene, p- or m-(1-n-propoxy-1-methylethoxy)-methylstyrene, p- or m-(1-n-propoxyethoxy)styrene, p- or m-(1-n-propoxyethoxy)-methylstyrene, p- or m-(1-isopropoxy-1-methylethoxy)styrene, p- or m-(1-isopropoxy-1-methylethoxy)-methylstyrene, p- or m-(1-isopropoxyethoxy)styrene, p- or m-(1-isopropoxyethoxy)-methylstyrene, p- or m-(1-isopropoxy-1-methylpropoxy)styrene, p- or m-(1-isopropoxy-1-methylpropoxy)-methylstyrene, p- or m-(1-isopropoxypropoxy)styrene, p- or m-(1-isopropoxypropoxy)-methylstyrene, p- or m-(1-n-butoxy-1-methylethoxy)styrene, p- or m-(1-n-butoxyethoxy)styrene, p- or m-(1-isobutoxy-1-methylethoxy)styrene, p- or m-(1-tert-butoxy-1-methylethoxy)styrene, p- or m-(1-n-pentoxy-1-methylethoxy)styrene, p- or m-(1-isoamyloxy-1-methylethoxy)styrene, p- or m-(1-n-hexyloxy-1-methylethoxy)styrene, p- or m-(1-cyclohexyloxy-1-methylethoxy)styrene, p- or m-(1-trimethylsilyloxy-1-methylethoxy)styrene, p- or m-(1-trimethylsilyloxy-1-methylethoxy)-methylstyrene, p- or m-(1-benzyloxy-1-methylethoxy)styrene, p- or m-(1-benzyloxy-1-methylethoxy)-methylstyrene, p- or m-(1-methoxy-1-methylethoxy)styrene, p- or m-(1-methoxy-1-methylethoxy)-methylstyrene, p- or m-(1-trimethylsilyloxy-1-methylethoxy)styrene p- or m-(1-trimethylsilyloxy-1-methylethoxy)-methylstyrene. Other examples of polymers having alkoxyalkylester acid labile groups are given in U.S. Pat. No. 5,225,316 and EP 829766. Examples of polymers with acetal blocking groups are given in U.S. Pat. No. 5,670, 299, EP 780732, U.S. Pat. No. 5,627,006, U.S. Pat. No. 5,558, 976, U.S. Pat. No. 5,558,971, U.S. Pat. No. 5,468,589, EP 704762, EP 762206, EP 342498, EP 553737 and described in ACS Symp. Ser. 614, Microelectronics Technology, pp. 35-55 (1995) and J. Photopolymer Sci. Technol. Vol. 10, No. 4 (1997), pp. 571-578. The polymer used in the present invention is not limited thereto.

With respect to polymers having acetal groups as acid-labile groups, it is possible to incorporate acid labile crosslinks as for example described in H.-T. Schacht, P. Falcigno, N. Muenzel, R. Schulz, and A. Medina, ACS Symp. Ser. 706 (Micro- and Nanopatterning Polymers), p. 78-94, 1997; H.-T. Schacht, N. Muenzel, P. Falcigno, H. Holzwarth, and J. Schneider, J. Photopolymer Science and Technology, Vol. 9, (1996), 573-586. This crosslinked system is preferred from the standpoint of heat resistance of the resist patterns.

Monomers with high activation energy acid labile groups are, for example, p-tert.-butoxycarbonyloxystyrene, tert.-butyl-acrylate, tert.-butyl-methacrylate, 2-methyl-2-adamantyl-methacrylate, isobornyl-methacrylate.

Monomers of type 1) suitable for ArF resist technology in particular include, for example, 2-methyl-2-adamantyl acrylate, 2-ethyl-2-adamantyl acrylate, 2-n-butyl-2-adamantyl acrylate, 2-n-butyl-2-adamantyl methacrylate, 2-methyl-2-adamantyl methacrylate, 2-ethyl-2-adamantyl methacrylate, 2-(1-adamantyl)isopropyl methacrylate, 2-(1-adamantyl)isopropyl acrylate, 2-(1-adamantyl)isobutyl methacrylate, 2-(1-adamantyl)isobutyl acrylate, 2-(1-adamantyl)isohexyl methacrylate, 2-(1-adamantyl)isohexyl acrylate, t-butyl methacrylate, t-butyl acrylate, 1-methylcyclohexyl methacrylate, 1-methylcyclohexyl acrylate, 1-ethylcyclohexyl methacrylate, 1-ethylcyclohexyl acrylate, 1-(n-propyl)cyclohexyl methacrylate, 1-(n-propyl)cyclohexyl acrylate, mevalonic lactone methacrylate (MLMA), tetrahydro-2-methacryloyloxy-2H-pyran and tetrahydro-2-acryloyloxy-2H-pyran. Other monomers comprising acid-labile adamantyl moieties are disclosed in JP-A-2009-269953, JP-A-2010-008912, JP-A-2010-001461 and WO2008/132966A1.

Particular olefins with acid labile-group are also suitable for ArF resist technology as shown in, for example, JP-A-2009-280799, JP-A-2009-301020, JP-A-2010-002599, JP-A-2010-002762, JP-A-2010-013627, JP-A-2010-013627, JP-A-2010-020256.

Examples of comonomers according to type 2) are:
aromatic vinyl monomers, such as styrene, -methylstyrene, acetoxystyrene, -methylnaphthylene, acenaphthylene, vinyl alicyclic compounds such as vinyl norbornane, vinyl adamantane. vinyl cyclohexane, alkyl(meth)acrylates such as methyl methacrylate, (meth)acrylonitrile, vinylcyclohexane, vinylcyclohexanol, itaconic anhydride, as well as maleic anhydride.

Comonomers according to type 2) suitable for ArF resist technology in particular include, for example, alpha-acryloyloxy-gamma-butyrolactone, alpha-methacryloyloxy-gamma-butyrolactone, alpha-acryloyloxy-beta,beta-dimethyl-gamma-butyro-lactone, alpha-methacryloyloxy-beta, beta-dimethyl-gamma-butyrolactone, alpha-acryloyloxy-alpha-methyl-gamma-butyrolactone, alpha-methacryloyloxy-alpha-methyl-gamma-butyrolactone, beta-acryloyloxy-gamma,beta-methacryloyloxy-alpha-methyl-gamma-butyrolactone, 5-acryloyloxy-2,6-norbornanecarbolactone, 5-methacryloyloxy-2,6-norbonanecarbolactone, 2-norbornene, methyl 5-norbornene-2-carboxylate, tert-butyl 5-norbornene-2-carboxylate, 1-cyclohexyl-1-methylethyl 5-norbornene-2-carboxylate, 1-(4-methylcyclohexyl)-1-methylethyl 5-norbornene-2-carboxylate, 1-methyl-1-(4-oxocyclohexyl)ethyl 5-norbornene-2-carboxylate, 1-(1-adamantyl)-1methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2carboxylate, 5-norbornene-2,3-dicarboxylic acid anhydrate, 2(5H)-furanone, 3-vinyl-gamma-butyrolactone, 3-methacryloyloxybicyclo[4,3,0]nonane, 3-acryloyloxybicyclo[4,3,0]nonane, 1-adamantyl methacrylate, 1-adamantyl acrylate, 3-methacryloyloxymethyltetracyclo$[4,4,0,1^{2,5}1^{7,10}]$dodecane, 3-acryloyloxymethyltetracyclo$[4,4,0,1^{2,5}1^{7,10}]$dodecane, 2-methacryloyloxynorbornane, 2-acryloyloxynorbornane, 2-methacryloyloxyisobornane, 2-acryloyloxyisobornane, 2-methacryloyloxymethylnorbornane, 2-acryloyloxymethylnorbornane.

Other monomers comprising lactone moieties suitable for ArF technology are disclosed in, for example, JP-A-2009-221111, JP-A-2010-002910, JP-A-2009-269953, JP-A-2010-008912. Other olefins suitable for ArF technology are published in, for example, JP-A-2009-235176, JP-A-2010-002593, JP-A-2009-235176, WO 2008/035640.

Examples of comonomers according to type 3) are: vinyl aromatic compounds such as hydroxystyrene, acrylic acid compounds such as methacrylic acid, ethylcarbonyloxystyrene and derivatives of thereof. These polymers are described, for example, in U.S. Pat. No. 5,827,634, U.S. Pat. No. 5,625,020, U.S. Pat. No. 5,492,793, U.S. Pat. No. 5,372,912, EP 660187, U.S. Pat. No. 5,679,495, EP 813113 and EP 831369. Further examples are crotonic acid, isocrotonic acid, 3-butenoic acid, acrylic acid, 4-pentenoic acid, propiolic acid, 2-butynoic acid, maleic acid, fumaric acid, and acetylenecarboxylic acid. The polymer used in the present invention is not limited thereto.

Comonomers according to type 3) suitable for ArF resist technology in particular include, for example, 3-hydroxy-1-adamantyl acrylate, 3-hydroxy-1-adamantyl methacrylate, 3,5-dihydroxy-1-adamantyl acrylate, 3,5-dihydroxy-1-adamantyl methacrylate, 2-hydroxy-5-norbornene, 5-norbornene-2-carboxylic acid, 1-(4-hydroxycyclohexyl)-1-methylethyl 5-norbornene-2-carboxylate, 2-hydroxy-1-ethyl 5-norbornene-2-carboxylate, 5-norbornene-2methanol, 8-hydroxymethyl-4-methacryloyloxymethyltricyclo-[5.2.1.0$^{2.6}$]decane, 8-hydroxymethyl-4-acryloyloxymethyl-tricyclo[5.2.1.0$^{2.6}$]decane, 4-hydroxymethyl-8-methacryloyloxymethyltricyclo[5.2.1.0$^{2.6}$]decane, 4-hydroxymethyl-8-acryloyloxymethyltricyclo[5.2.1.0$^{2.6}$]decane.

Other monomers comprising hydrophilic moieties suitable for ArF resist technology are disclosed in, for example JP-A-2009-269953, JP-A-2010-008912, JP-A-2009-221394, JP-A-2009-237559, JP-A-2009-269845, JP-A-2009-276363, JP-A-2009-276363, JP-A-2009-301017, WO-A-2008-035640. Further suitable monomers and polymers for ArF positive resists are described in U.S. Pat. No. 6,746,818; US 2006/0194982-A, U.S. Pat. No. 7,569,324; US 2009/0068591-A; US 2008/0182203-A; US 2008/0160448-A; US 2007/0122750-A; US 2008/0085469-A; US 2009/0274978-A and EP1710230.

The content of acid labile monomers in the polymer may vary over a wide range and depends on the amount of the other comonomers and the alkaline solubility of the de-protected polymer. Typically, the content of monomers with acid labile groups in the polymer is between 5 and 60 mol %. If the content is too small, too low development rates and residues of the resist in the exposed areas result. If the content of acid labile monomers is too high, resist patterns are poorly defined (eroded) after development and narrow features cannot be resolved anymore and/or the resist looses its adhesion to the substrate during development.

Preferably the copolymers which have acid labile groups have a $M_w$ of from about 3'000 to about 200'000, more preferably from about 5'000 to about 50'000 with a molecular weight distribution of about 3 or less, more preferably a molecular weight distribution of about 2 or less. Non-phenolic polymers, e.g. a copolymer of an alkyl acrylate such as t-butyl acrylate or t-butyl-methacrylate and a vinyl alicyclic compound, such as a vinyl norbonanyl or vinyl cyclohexanol compound, also may be prepared by such free radical polymerization or other known procedures and suitably will have a $M_w$ of from about 8'000 to about 50'000, and a molecular weight distribution of about 3 or less. Other comonomers may suitably be added in an appropriate amount for the purpose of controlling the glass transition point of the polymer and the like.

In the present invention a mixture of two or more polymers having acid-labile groups may be used. For example, use may be made of a mixture of a polymer having acid-labile groups, which are cleaved very easily, such as acetal groups or tetrahydropyranyloxy-groups and a polymer having acid-cleavable groups, that are less easily cleaved, such as for example tertiary alkyl ester groups. Also, acid cleavable groups of different size can be combined by blending two or more polymers having different acid cleavable groups, such as a tert-butylester group and 2-methyl-adamantyl group or an 1-ethoxy-ethoxy group and a tetrahydropyranyloxy group. A mixture of a non-cross-linked resin and a crosslinked resin may also be used. The amount of these polymers in the present invention is preferably from 30 to 99% by weight, more preferably from 50 to 98% by weight, based on the total amount of all solid components. An alkali-soluble resin or monomeric or oligomeric compound having no acid-labile groups may be further incorporated into the composition in order to control the alkali solubility. Examples of polymer blends with polymers having different acid-labile groups are given in EP 780732, EP 679951 and U.S. Pat. No. 5,817,444.

Preferably monomeric and oligomeric dissolution inhibitors (c2) are used in the present invention. The monomeric or oligomeric dissolution inhibitor having the acid-labile group for use in the present invention is a compound which has at least one acid-labile group in the molecular structure, which decomposes in the presence of acid to increase the solubility in aqueous alkaline developer solution. Examples are alkoxymethyl ether groups, tetrahydrofuranyl ether groups, tetrahydropyranyl ether groups, alkoxyethyl ether groups, trityl ether groups, silyl ether groups, alkyl carbonate groups, trityl ester groups, silyl ester groups, alkoxymethyl ester groups, vinyl carbamate groups, tertiary alkyl carbamate groups, trityl amino groups, cumyl ester groups, acetal groups, ketal groups, tetrahydropyranyl ester groups, tetrafuranyl ester groups, tertiary alkyl ether groups, tertiary alkyl ester groups, and the like. The molecular weight of the acid-decomposable dissolution inhibitive compound for use in the present invention is 3'000 or lower, preferably from 100 to 3'000, more preferably from 200 to 2'500.

Examples of monomeric and oligomeric dissolution inhibitors having acid-labile groups are described as formulas (I) to (XVI) in EP0831369. Other suitable dissolution inhibitors having acid-labile groups are shown in U.S. Pat. No. 5,356,752, U.S. Pat. No. 5,037,721, U.S. Pat. No. 5,015,554, JP-A-05-045869, JP-A-05-158233, JP-A-06-080913, JP-A-05-257275, JP-A-05-297583, JP-A-05-303197, JP-A-05-303200, JP-A-05-341510, JP-A-06-080913, JP-A-05-297581, JP-A-05-297583, JP-A-05-303197, JP-A-05-303200, and JP-A-05-341510. The composition can also contain polymeric dissolution inhibitors, for example, polyacetals as described for example in U.S. Pat. No. 5,354,643 or poly-N,O-acetals for example those described in U.S. Pat. No. 5,498,506, either in combination with an alkaline soluble polymer, or in combination with a polymer containing acid labile groups which increase the solubility of the resist film in the developer after exposure, or with a combination of both types of polymers.

In the case where the dissolution inhibitor having acid-labile groups is used in the present invention in combination with the compounds generating an acid of the formula I or II, the alkali-soluble polymer and/or the polymer having acid-labile groups, the amount of the dissolution inhibitor is from 3 to 55% by weight, preferably from 5 to 45% by weight, most preferably from 10 to 35% by weight, based on the total amount of all solid components of the photosensitive composition.

A polymer soluble in an aqueous alkali solution (c3) can be used in the present invention. Examples of these polymers include novolak resins, hydrogenated novolak resins, acetone-pyrogallol resins, poly(o-hydroxystyrene), poly(m-hydroxystyrene), poly(p-hydroxystyrene), hydrogenated poly(hydroxystyrene)s, halogen- or alkyl-substituted poly (hydroxystyrene)s, hydroxystyrene/N-substituted maleimide copolymers, o/p- and m/p-hydroxystyrene copolymers, partially o-alkylated poly(hydroxystyrene)s, [e.g., o-methylated, o-(1-methoxy)ethylated, o-(1-ethoxy)ethylated, o-2-tetrahydropyranylated, and o-(t-butoxycarbonyl)methylated poly (hydroxystyrene)s having a degree of substitution of from 5 to 30 mol % of the hydroxyl groups], o-acylated poly(hydroxystyrene)s [e.g., o-acetylated and o-(t-butoxy)carbonylated poly(hydroxystyrene)s having a degree of substitution of from 5 to 30 mol % of the hydroxyl groups], styrene/maleic anhydride copolymers, styrene/hydroxystyrene copolymers, α-methylstyrene/hydroxystyrene copolymers, carboxylated methacrylic resins, and derivatives thereof. Further suitable are poly(meth)acrylic acid [e.g. poly(acrylic acid)], (meth) acrylic acid/(meth)acrylate copolymers [e.g. acrylic acid/methyl acrylate copolymers, methacrylic acid/methyl methacrylate copolymers or methacrylic acid/methyl methacrylate/t-butyl methacrylate copolymers], (meth)acrylic acid/alkene copolymers [e.g. acrylic acid/ethylene copolymers], (meth) acrylic acid/(meth)acrylamide copolymers [e.g. acrylic acid/acrylamide copolymers], (meth)acrylic acid/vinyl chloride copolymers [e.g. acrylic acid/vinyl chloride copolymers], (meth)acrylic acid/vinyl acetate copolymer [e.g. acrylic acid/vinyl acetate copolymers], maleic acid/vinyl ether copolymers [e.g. maleic acid/methyl vinyl ether copolymers], maleic acid mono ester/methyl vinyl ester copolymers [e.g. maleic acid mono methyl ester/methyl vinyl ether copolymers], maleic acid/(meth)acrylic acid copolymers [e.g. maleic acid/acrylic acid copolymers or maleic acid/methacrylic acid copolymers], maleic acid/(meth)acrylate copolymers [e.g. maleic acid/methyl acrylate copolymers], maleic acid/vinyl chloride copolymers, maleic acid/vinyl acetate copolymers and maleic acid/alkene copolymers [e.g. maleic acid/ethylene copolymers and maleic acid/1-chloropropene copolymers]. However, the alkali-soluble polymer for use in the present invention should not be construed as being limited to these examples.

Preferred alkali-soluble polymers (c3) are novolak resins, poly(o-hydroxystyrene), poly(m-hydroxystyrene), poly(p-hydroxystyrene), copolymers of the respective hydroxystyrene monomers, for example with p-vinylcyclohexanol, alkyl-substituted poly(hydroxystyrene)s, partially o- or m-alkylated and o- or m-acylated poly(hydroxystyrene)s, styrene/hydroxystyrene copolymer, and α-methylstyrene/hydroxystyrene copolymers. The novolak resins are obtained by addition-condensing one or more given monomers as the main ingredient with one or more aldehydes in the presence of an acid catalyst. Examples of monomers useful in preparing alkaline soluble resins include hydroxylated aromatic compounds such as phenol, cresols, i.e., m-cresol, p-cresol, and o-cresol, xylenols, e.g., 2,5-xylenol, 3,5-xylenol, 3,4-xylenol, and 2,3-xylenol, alkoxyphenols, e.g., p-methoxyphenol, m-methoxyphenol, 3,5-dimethoxyphenol, 2-methoxy-4-methylphenol, m-ethoxyphenol, p-ethoxyphenol, m-propoxyphenol, p-propoxyphenol, m-butoxyphenol, and p-butoxyphenol, dialkylphenols, e.g., 2-methyl-4-isopropylphenol, and other hydroxylated aromatics including m-chlorophenol, p-chlorophenol, o-chlorophenol, dihydroxybiphenyl, bisphenol A, phenylphenol, resorcinol, and naphthol. These compounds may be used alone or as a mixture of two or more thereof. The main monomers for novolak resins should not be construed as being limited to the above examples.

Examples of the aldehydes for polycondensation with phenolic compounds to obtain novolaks include formaldehyde, p-formaldehyde, acetaldehyde, propionaldehyde, benzaldehyde, phenylacetaldehyde, α-phenylpropionaldehyde, β-phenylpropionaldehyde, o-hydroxybenzaldehyde, m-hydroxybenzaldehyde, p-hydroxybenzaldehyde, o-chlorobenzaldehyde, m-chlorobenzaldehyde, p-chlorobenzaldehyde, o-nitrobenzaldehyde, m-nitrobenzaldehyde, o-methylbenzaldehyde, m-methylbenzaldehyde, p-methylbenzaldehyde, p-ethylbenzaldehyde, p-n-butylbenzaldehyde, furfural, chloroacetaldehyde, and acetals derived from these, such as chloroacetaldehyde diethyl acetal. Preferred of these is formaldehyde.

These aldehydes may be used alone or in combination of two or more thereof. Examples of the acid catalyst include hydrochloric acid, sulfuric acid, formic acid, acetic acid, and oxalic acid.

The weight-average molecular weight of the thus-obtained novolak resin suitably is from 1'000 to 30'000. If the weight-average molecular weight thereof is lower than 1'000, the film reduction at unexposed parts during development is liable to be large. If the weight-average molecular weight there of exceeds 50'000, the developing rate may be too low. The especially preferred range of the molecular weight of the novolak resin is from 2'000 to 20'000.

The poly(hydroxystyrene)s and derivatives and copolymers thereof shown above as alkali-soluble polymers other than novolak resins each have a weight-average molecular weight of 2'000 or higher, preferably from 4'000 to 200'000, more preferably from 5'000 to 50'000. From the standpoint of obtaining a polymer film having improved heat resistance, the weight-average molecular weight thereof is desirably at least 5'000 or higher.

Weight-average molecular weight in the context of the present invention is meant to be the one determined by gel permeation chromatography and calibrated for with polystyrene standard.

In the present invention the alkali-soluble polymers may be used as a mixture of two or more thereof. In the case where a mixture of an alkali-soluble polymer and the polymer having groups which decompose by the action of an acid to enhance solubility in an alkaline developing solution is used, the addition amount of the alkali-soluble polymer is preferably up to 80% by weight, more preferably up to 60% by weight, most preferably up to 40% by weight, based on the total amount of the photosensitive composition (excluding the solvent). The amount exceeding 80% by weight is undesirable because the resist pattern suffers a considerable decrease in thickness, resulting in poor images and low resolution.

In the case where an alkali-soluble polymer is used together with a dissolution inhibitor, without the polymer having groups which decompose by the action of an acid, to enhance solubility in an alkaline developing solution, the amount of the alkali-soluble polymer is preferably from 40% to 90% by weight, more preferably from 50 to 85% by weight, most preferably 60 to 80% by weight. If the amount thereof is smaller than 40% by weight, undesirable results such as reduced sensitivity are caused. On the other hand, if it exceeds 90% by weight, the resist pattern suffers a considerable decrease in film thickness, resulting in poor resolution and image reproduction.

The use of the compounds generating an acid of the formula I or II (including the compounds of the formula IIIa, IIIb, IIIe, IVa, IVb, IIIc, IIId, IVc and IVe as defined above, as well as the co-polymers obtained from the compounds of the formula IIIa, IIIb, IIIc and IIIe as defined above, wherein $R_1$ as $C_2$-$C_{12}$alkenyl or interrupted $C_2$-$C_{18}$alkenyl is a polymerizable group containing at least one double bond) according to the invention in chemically amplified systems, which operates on the principle of the removal of a protecting group from a polymer, generally produces a positive resist. Positive resists are preferred over negative resists in many applications, especially because of their higher resolution. There is, however, also interest in producing a negative image using the positive resist mechanism, in order to combine the advantages of the high degree of resolution of the positive resist with the properties of the negative resist. This can be achieved by introducing a so-called image-reversal step as described, for example, in EP361906. For this purpose, the image-wise irradiated resist material is before the developing step treated with, for example, a gaseous base, thereby image-wise neutralizing the acid which has been produced. Then, a second irradiation, over the whole area, and thermal aftertreatment are carried out and the negative image is then developed in the customary manner.

The compounds generating an acid of the formula I or II (including the compounds of the formula IIIa, IIIb, IIIe, IVa, IVb, IIIc, IIId, IVc and IVe as defined above, as well as the co-polymers obtained from the compounds of the formula IIIa, IIIb, IIIc and IIIe as defined above, wherein $R_1$ as $C_2$-$C_{12}$alkenyl or interrupted $C_2$-$C_{18}$alkenyl is a polymerizable group containing at least one double bond) according to the present invention are in particular suitable as photolatent acids in the ArF resist technology, i.e. a technology using ArF excimer lasers (193 nm) for the imaging step. This technology requests the use of specific polymers/copolymers. Suitable formulations and the preparation of suitable polymer/copolymers are for example published in *Proceedings of SPIE* 2438, 474 (1995); *Proceedings of SPIE* 3049, 44 (1997); *Proceedings of SPIE* 3333, 144 (1998); *J. Photopolym. Sci. Technol.* 14, 631 (2001); *Proceedings of SPIE* 3333, 546 (1998); *J. Photopolym. Sci. Technol.* 13, 601 (2000); JP2001-242627A; JP2001-290274A; JP2001-235863A; JP2001-228612A; *Proceedings of SPIE* 3333, 144 (1998); JP2001-5184A, commercially available as Lithomax alpha-7K from Mitsubishi Rayon; JP2001-272783A; U.S. patent application Ser. No. 09/413,763 (filed 1999 Oct. 7); EP 1091249; JP2000-292917A; JP2003-241385A; *J. Photopolym. Sci. Technol.* 14, 631 (2001); *Proceedings of SPIE* 3333, 11 (1998); ACS 1998 (University of Texas); JP2001-290274A; JP2001-235863A; JP2001-228612A; *Proceedings of SPIE* 3999, 13 (2000); JP2001-296663A; U.S. patent application Ser. No. 09/567,814 (filed 2000.5.9); EP 1128213; *Proceedings of SPIE* 3049, 104 (1997); *J. Photopolym. Sci. Technol.* 10, 521 (1997); JP2001-290274A; JP2001-235863A; JP2001-228612A; *Proceedings of SPIE* 4345, 680 (2001); *J. Vac. Sci. Technol.* B 16(6), p. 3716, 1998; *Proceedings of SPIE* 2724, 356 (1996); *Proceedings of SPIE* 4345, 67 (2001); *Proceedings of SPIE* 3333, 546 (1998); *Proceedings of SPIE* 4345, 87 (2001); *Proceedings of SPIE* 4345, 159 (2001); *Proceedings of SPIE* 3049, 92 (1997); *Proceedings of SPIE* 3049, 92 (1997); *Proceedings of SPIE* 3049, 92 (1997); *Proceedings of SPIE* 3999, 2 (2000); *Proceedings of SPIE* 3999, 23 (2000); *Proceedings of SPIE* 3999, 54 (2000); *Proceedings of SPIE* 4345, 119 (2001).

The formulations disclosed in the aforementioned publications are incorporated herein by reference. It is understood, that the compounds of the present invention are in particular suitable for use as photolatent acid in all the polymers/copolymers and compositions described in these cited publications.

The compounds generating an acid of the formula I or II (including the compounds of the formula IIIa, IIIb, IIIe, IVa, IVb, IIIc, IIId, IVc and IVe as defined above, as well as the co-polymers obtained from the compounds of the formula IIIa, IIIb, IIIc and IIIe as defined above, wherein $R_1$ as $C_2$-$C_{12}$alkenyl or interrupted $C_2$-$C_{18}$alkenyl is a polymerizable group containing at least one double bond) according to the present invention are suitable as photolatent acids in the bi-layer resist. This technology requests the use of specific polymers/copolymers. Suitable formulations and the preparation of suitable polymer/copolymers are for example published in Proc. SPIE 4345, 361-370 (2001), Proc. SPIE 4345, 406-416 (2001), JP-A-2002-278073, JP-A-2002-30116, JP-A-2002-30118, JP-A-2002-72477, JP-A-2002-348332, JP-A-2003-207896, JP-A-2002-82437, US2003/65101, US2003/64321.

The compounds generating an acid of the formula I or II (including the compounds of the formula IIIa, IIIb, IIIe, IVa, IVb, IIIc, IIId, IVc and IVe as defined above, as well as the co-polymers obtained from the compounds of the formula IIIa, IIIb, IIIc and IIIe as defined above, wherein $R_1$ as $C_2$-$C_{12}$alkenyl or interrupted $C_2$-$C_{18}$alkenyl is a polymerizable group containing at least one double bond) according to the present invention are suitable as photolatent acids in the multi-layer resist. This technology requests the use of specific polymers/copolymers. Suitable formulations and the preparation of suitable polymer/copolymers are for example published in JP-A-2003-177540, JP-A-2003-280207, JP-A-2003-149822, JP-A-2003-177544.

In order to make fine hole pattern, thermal flow process or chemical shrink technology, so-called RELACS (resolution enhancement lithography assisted by chemical shrink) process, are applied for chemically amplified resist. The compounds generating an acid of the formula I or II (including the compounds of the formula IIIa, IIIb, IIIe, IVa, IVb, IIIc, IIId, IVc and IVe as defined above, as well as the co-polymers obtained from the compounds of the formula IIIa, IIIb, IIIc and IIIe as defined above, wherein $R_1$ as $C_2$-$C_{12}$alkenyl or interrupted $C_2$-$C_{18}$alkenyl is a polymerizable group containing at least one double bond) according to the present invention are suitable as photolatent acids in the resists for thermal flow process or RELACS process. These technologies request the use of specific polymers/copolymers. Suitable formulations and the preparation of suitable polymer/copolymers are for example published in JP-A-2003-167357, JP-A-2001-337457, JP-A-2003-66626, US2001/53496, *Proceedings of SPIE* 5039, 789 (2003), *IEDM98, Dig.*, 333 (1998), *Proceedings Silicon Technology* 11, 12 (1999), The compounds generating an acid of the formula I or II (including the compounds of the formula IIIa, IIIb, IIIe, IVa, IVb, IIIc, IIId, IVc and IVe as defined above, as well as the co-polymers obtained from the compounds of the formula IIIa, IIIb, IIIc and IIIe as defined above, wherein $R_1$ as $C_2$-$C_{12}$alkenyl or interrupted $C_2$-$C_{18}$alkenyl is a polymerizable group containing at least one double bond) according to the present invention are suitable as photolatent acids in the EUV resist, i.e. a technology using light source of extreme ultra violet (13 nm) for the imaging step. This technology requests the use of specific polymers/copolymers. Suitable formulations and the preparation of suitable polymer/copolymers are for example published in JP-A-2009221194, JP-A-2009221195, JP-A-2010002593.

The compounds generating an acid of the formula I or II (including the compounds of the formula IIIa, IIIb, IIIe, IVa, IVb, IIIc, IIId, IVc and IVe as defined above, as well as the co-polymers obtained of the compounds from the formula IIIa, IIIb, IIIc and IIIe as defined above, wherein $R_1$ as $C_2$-$C_{12}$alkenyl or interrupted $C_2$-$C_{18}$alkenyl is a polymerizable group containing at least one double bond) according to the present invention are suitable as photolatent acids in the EB (electron beam) or X-ray resist, i.e. a technology using EB or X-ray for the imaging step. These technologies request the use of specific polymers/copolymers. Suitable formulations and the preparation of suitable polymer/copolymers are for example published in JP-A-2002-99088, JP-A-2002-99089, JP-A-2002-99090, JP-A-2002-244297, JP-A-2003-5355, JP-A-2003-5356, JP-A-2003-162051, JP-A-2002-278068, JP-A-2002-333713, JP-A-2002-31892.

The compounds generating an acid of the formula I or II (including the compounds of the formula IIIa, IIIb, IIIe, IVa, IVb, IIIc, IIId, IVc and IVe as defined above, as well as the co-polymers obtained from the compounds of the formula IIIa, IIIb, IIIc and IIIe as defined above, wherein $R_1$ as $C_2$-$C_{12}$alkenyl or interrupted $C_2$-$C_{18}$alkenyl is a polymerizable group containing at least one double bond) according to the present invention are suitable as photolatent acids in the chemically amplified resist for immersion lithography. This technology reduces minimum feature size of resist pattern using a liquid medium between the lens and the resist as described in Advanced Process for 193-nm Immersion Lithography" by Y. Wei and L. Brainard published from SPIE (2008), *Proceedings of SPIE* 5040, 667 (2003), *Proceedings of SPIE* 5040, 679 (2003), *Proceedings of SPIE* 5040, 690 (2003), *Proceedings of SPIE* 5040, 724 (2003).

The compounds generating an acid of the formula I or II (including the compounds of the formula IIIa, IIIb, IIIe, IVa, IVb, IIIc, IIId, IVc and IVe as defined above, as well as the co-polymers obtained from the compounds of the formula IIIa, IIIb, IIIc and IIIe as defined above, wherein $R_1$ as $C_2$-$C_{12}$alkenyl or interrupted $C_2$-$C_{18}$alkenyl is a polymerizable group containing at least one double bond) according to the present invention are suitable as photolatent acids in the chemically amplified resist for immersion lithography with so called Double Patterning Technique. This technology is employed to achieve minimum feature density using exposure process twice as described in Chapter 9 of "Advanced Process for 193-nm Immersion Lithography" by Y. Wei and L. Brainard published from SPIE (2008), Proc. SPIE, Vol. 6349, 22 (2006), JP-A-2009-223294, JP-A-2009-251216, JP-A-2009-300978, JP-A-2009-301007, JP-A-2010-014886, JP-A-2010-020109.

The compounds generating an acid of the formula I or II (including the compounds of the formula IIIa, IIIb, IIIe, IVa, IVb, IIIc, IIId, IVc and IVe as defined above, as well as the co-polymers obtained from the compounds of the formula IIIa, IIIb, IIIc and IIIe as defined above, wherein $R_1$ as $C_2$-$C_{12}$alkenyl or interrupted $C_2$-$C_{18}$alkenyl is a polymerizable group containing at least one double bond) according to the present invention are suitable as photolatent acids in the positive and negative photosensitive polyimide. This technology requests the use of specific polymers/copolymers. Suitable formulations and the preparation of suitable polymer/copolymers are for example published in JP-A-2002-356555, JP-A-2002-356554, JP-A-2002-303977, JP-A-2002-284875, JP-A-2002-268221, JP-A-2002-162743, JP-A-2002-122993, JP-A-2002-99084, JP-A-2002-40658, JP-A-2002-37885, JP-A-2003-26919.

The formulations disclosed in the aforementioned publications are incorporated herein by reference. It is understood, that the compounds of the present invention are in particular suitable for use as photolatent acid in all the polymers/copolymers and compositions described in these cited publications.

Acid-sensitive components (b) that produce a negative resist characteristically are especially compounds which are capable of undergoing a cationic or acid-catalytic polymerization or cross-linking reaction with themselves and/or with one or more further components of the composition by an acid (e.g. the acid formed during irradiation of the compounds of formulae I). Examples thereof include cyclic ethers, especially epoxides and oxetanes, and also vinyl ethers and hydroxy-containing compounds. Lactone compounds and cyclic thioethers as well as vinyl thioethers can also be used. Further examples include aminoplastics or phenolic resole resins. These are especially melamine, urea, epoxy, phenolic, acrylic, polyester and alkyd resins, or mixtures thereof. Amino resins, phenolic resins and epoxy resins are very suitable. Acid-curable resins are generally known and are described, for example, in Wagner, Sarx/Lackkunstharze (Munich, 1971), pages 86 to 123 and 229 to 238, or in Ullmann/Encyclopädie der techn. Chemie, $4^{th}$ edition, volume 15 (1978), pages 613 to 628, or Ullmann's Encyclopedia of Industrial Chemistry, Verlag Chemie, 1991, Vol. 18, 360 ff., Vol. A19, 371 ff.

It is possible, for example, to use all customary epoxides, such as aromatic, aliphatic or cycloaliphatic epoxy resins. These are compounds having at least one, preferably at least two, epoxy group(s) in the molecule. Examples thereof are the glycidyl ethers and -methyl glycidyl ethers of aliphatic or cycloaliphatic diols or polyols, e.g. those of ethylene glycol, propane-1,2-diol, propane-1,3-diol, butane-1,4-diol, diethylene glycol, polyethylene glycol, polypropylene glycol, glycerol, trimethylolpropane or 1,4-dimethylolcyclohexane or of 2,2-bis(4-hydroxycyclohexyl)propane and N,N-bis(2-hydroxyethyl)aniline; the glycidyl ethers of di- and poly-phenols, for example of resorcinol, of 4,4'-dihydroxyphenyl-2,2-propane, of novolaks or of 1,1,2,2-tetrakis(4-hydroxyphenyl) ethane. Examples thereof include phenyl glycidyl ether, p-tert-butyl glycidyl ether, o-cresyl glycidyl ether, polytetrahydrofuran glycidyl ether, n-butyl glycidyl ether, 2-ethylhexylglycidylether, $C_{12/15}$alkyl glycidyl ether and cyclohexanedimethanol diglycidyl ether. Further examples include N-glycidyl compounds, for example the glycidyl compounds of ethyleneurea, 1,3-propyleneurea or 5-dimethyl-hydantoin or of 4,4'-methylene-5,5'-tetramethyldihydantoin, or compounds such as triglycidyl isocyanurate.

Further examples of glycidyl ether components that are used in the formulations according to the invention are, for example, glycidyl ethers of polyhydric phenols obtained by the reaction of polyhydric phenols with an excess of chlorohydrin, such as, for example, epichlorohydrin (e.g. glycidyl ethers of 2,2-bis(2,3-epoxypropoxyphenol)-propane. Further examples of glycidyl ether epoxides that can be used in connection with the present invention are described, for example, in U.S. Pat. No. 3,018,262 and in "Handbook of Epoxy Resins" by Lee and Neville, McGraw-Hill Book Co., New York (1967). There is also a large number of commercially available glycidyl ether epoxides that are suitable as component (b), such as, for example, glycidyl methacrylate, diglycidyl ethers of bisphenol A, for example those obtainable under the trade names EPON 828, EPON 825, EPON 1004 and EPON 1010 (Shell); DER-331, DER-332 and DER-334 (Dow Chemical); 1,4-butanediol diglycidyl ethers of phenolformaldehyde novolak, e.g. DEN-431, DEN-438 (Dow Chemical); and resorcinol diglycidyl ethers; alkyl glycidyl ethers, such as, for example, $C_8$-$C_{10}$glycidyl ethers, e.g. HELOXY Modifier 7, $C_{12}$-$C_{14}$glycidyl ethers, e.g. HELOXY Modifier 8, butyl glycidyl ethers, e.g. HELOXY Modifier 61, cresyl glycidyl ethers, e.g. HELOXY Modifier 62, p-tert-butylphenyl glycidyl ethers, e.g. HELOXY Modifier 65, polyfunctional glycidyl ethers, such as diglycidyl ethers of 1,4-butanediol, e.g. HELOXY Modifier 67, diglycidyl ethers of neopentyl glycol, e.g. HELOXY Modifier 68, diglycidyl ethers of cyclohexanedimethanol, e.g. HELOXY Modifier 107, trimethylolethane triglycidyl ethers, e.g. HELOXY Modifier 44, trimethylolpropane triglycidyl ethers, e.g. HELOXY Modifier 48, polyglycidyl ethers of aliphatic polyols, e.g. HELOXY Modifier 84 (all HELOXY glycidyl ethers are obtainable from Shell).

Also suitable are glycidyl ethers that comprise copolymers of acrylic esters, such as, for example, styrene-glycidyl methacrylate or methyl methacrylate-glycidyl acrylate. Examples thereof include 1:1 styrene/glycidyl methacrylate, 1:1 methyl methacrylate/glycidyl acrylate, 62.5:24:13.5 methyl methacrylate/ethyl acrylate/glycidyl methacrylate.

The polymers of the glycidyl ether compounds can, for example, also comprise other functionalities provided that these do not impair the cationic curing.

Other suitable glycidyl ether compounds that are commercially available are polyfunctional liquid and solid novolak glycidyl ether resins, e.g. PY 307, EPN 1179, EPN 1180, EPN 1182 and ECN 9699.

It will be understood that mixtures of different glycidyl ether compounds may also be used as component (b).

The glycidyl ethers (a5) are, for example, compounds of formula XX

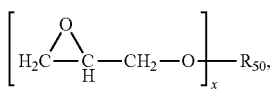
(XX)

wherein x is a number from 1 to 6; and $R_{50}$ is a mono- to hexavalent alkyl or aryl radical.

Preference is given, for example, to glycidyl ether compounds of formula XX, wherein X is the number 1, 2 or 3; and $R_{50}$ when x=1, is unsubstituted or $C_1$-$C_{12}$alkyl-substituted phenyl, naphthyl, anthracyl, biphenylyl, $C_1$-$C_{20}$alkyl, or $C_2$-$C_{20}$alkyl interrupted by one or more oxygen atoms, or $R_{50}$ when x=2, is 1,3-phenylene, 1,4-phenylene, $C_6$-$C_{10}$cycloalkylene, unsubstituted or halo-substituted $C_1$-$C_{40}$alkylene, $C_2$-$C_{40}$alkylene interrupted by one or more oxygen atoms, or a group

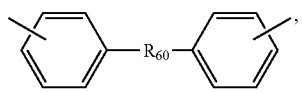

or $R_{50}$ when x=3, is a radical

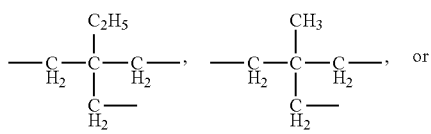

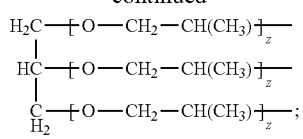

$z$ is a number from 1 to 10; and $R_{60}$ is $C_1$-$C_{20}$alkylene, oxygen or

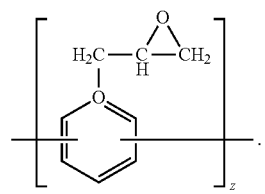

The glycidyl ethers (a5) are, for example, compounds of formula

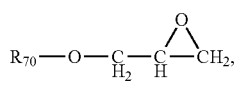
(XXa)

wherein $R_{70}$ is unsubstituted or $C_1$-$C_{12}$alkyl-substituted phenyl; naphthyl; anthracyl; biphenylyl; $C_1$-$C_{20}$alkyl, $C_2$-$C_{20}$alkyl interrupted by one or more oxygen atoms; or a group of formula

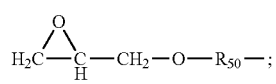

$R_{50}$ is phenylene, $_1$-$C_{20}$alkylene, $C_2$-$C_{20}$alkylene interrupted by one or more oxygen atoms, or a group

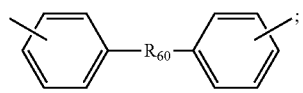

and $H_{60}$ is $C_1$-$C_{20}$alkylene or oxygen.

Preference is given to the glycidyl ether compounds of formula XXb

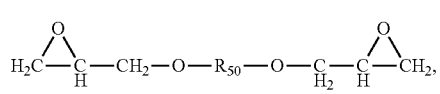
(XXb)

wherein $R_{50}$ is phenylene, $C_1$-$C_{20}$alkylene, $C_2$-$C_{20}$alkylene interrupted by one or more oxygen atoms, or a group

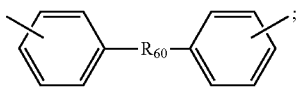

and $R_{60}$ is $C_1$-$C_{20}$alkylene or oxygen.

Further examples are polyglycidyl ethers and poly(-methylglycidyl)ethers obtainable by the reaction of a compound containing at least two free alcoholic and/or phenolic hydroxy groups per molecule with the appropriate epichlorohydrin under alkaline conditions, or alternatively in the presence of an acid catalyst with subsequent alkali treatment. Mixtures of different polyols may also be used.

Such ethers can be prepared with poly(epichlorohydrin) from acyclic alcohols, such as ethylene glycol, diethylene glycol and higher poly(oxyethylene)glycols, propane-1,2-diol and poly(oxypropylene)glycols, propane-1,3-diol, butane-1,4-diol, poly(oxytetramethylene)glycols, pentane-1,5-diol, hexane-1,6-diol, hexane-2,4,6-triol, glycerol, 1,1,1-trimethylol-propane, pentaerythritol and sorbitol, from cycloaliphatic alcohols, such as resorcitol, quinitol, bis(4-hydroxycyclohexyl)methane, 2,2-bis(4-hydroxycyclohexyl) propane and 1,1-bis-(hydroxymethyl)cyclohex-3-ene, and from alcohols having aromatic nuclei, such as N,N-bis(2-hydroxyethyl)aniline and p,p'-bis(2-hydroxyethylamino) diphenylmethane. They can also be prepared from mononuclear phenols, such as resorcinol and hydroquinone, and polynuclear phenols, such as bis(4-hydroxyphenyl)methane, 4,4-dihydroxydiphenyl, bis(4-hydroxyphenyl)sulphone, 1,1,2,-2-tetrakis(4-hydroxyphenyl)ethane, 2,2-bis(4-hydroxyphenyl)-propane (bisphenol A) and 2,2-bis(3,5-dibromo-4-hydroxyphenyl)propane.

Further hydroxy compounds suitable for the preparation of polyglycidyl ethers and poly(-methylglycidyl)ethers are the novolaks obtainable by the condensation of aldehydes, such as formaldehyde, acetaldehyde, chloral and furfural, with phenols, such as, for example, phenol, o-cresol, m-cresol, p-cresol, 3,5-dimethylphenol, 4-chlorophenol and 4-tert-butylphenol.

Poly(N-glycidyl) compounds can be obtained, for example, by dehydrochlorination of the reaction products of epichlorohydrin with amines containing at least two amino-hydrogen atoms, such as aniline, n-butylamine, bis(4-aminophenyl)methane, bis(4-aminophenyl)-propane, bis(4-methylaminophenyl)methane and bis(4-aminophenyl)ether, sulphone and sulphoxide. Further suitable poly(N-glycidyl) compounds include triglycidyl isocyanurate, and N,N'-diglycidyl derivatives of cyclic alkyleneureas, such as ethyleneurea and 1,3-propyleneurea, and hydantoins, such as, for example, 5,5-dimethylhydantoin.

Poly(S-glycidyl) compounds are also suitable. Examples thereof include the di-S-glycidyl derivatives of dithiols, such as ethane-1,2-dithiol and bis(4-mercaptomethylphenyl)ether.

There also come into consideration as component (b) epoxy resins in which the glycidyl groups or -methyl glycidyl groups are bonded to hetero atoms of different types, for example the N,N,O-triglycidyl derivative of 4-aminophenol, the glycidyl ether/glycidyl ester of salicylic acid or p-hydroxybenzoic acid, N-glycidyl-N'-(2-glycidyloxypropyl)-5,5-dimethyl-hydantoin and 2-glycidyloxy-1,3-bis(5,5-dimethyl-1-glycidylhydantoin-3-yl)propane. Preference is given to diglycidyl ethers of bisphenols. Examples thereof include diglycidyl ethers of bisphenol A, e.g. ARALDIT GY 250, diglycidyl ethers of bisphenol F and diglycidyl ethers of bisphenol S. Special preference is given to diglycidyl ethers of bisphenol A.

Further glycidyl compounds of technical importance are the glycidyl esters of carboxylic acids, especially di- and poly-carboxylic acids. Examples thereof are the glycidyl esters of succinic acid, adipic acid, azelaic acid, sebacic acid, phthalic acid, terephthalic acid, tetra- and hexa-hydrophthalic acid, isophthalic acid or trimellitic acid, or of dimerised fatty acids.

Examples of polyepoxides that are not glycidyl compounds are the epoxides of vinylcyclohexane and dicyclopentadiene, 3-(3',4'-epoxycyclohexyl)-8,9-epoxy-2,4-dioxaspiro[5.5]undecane, the 3',4'-epoxycyclohexylmethyl esters of 3,4-epoxycyclohexanecarboxylic acid, (3,4-epoxycyclohexyl-methyl 3,4-epoxycyclohexanecarboxylate), butadiene diepoxide or isoprene diepoxide, epoxidised linoleic acid derivatives or epoxidised polybutadiene.

Further suitable epoxy compounds are, for example, limonene monoxide, epoxidised soybean oil, bisphenol-A and bisphenol-F epoxy resins, such as, for example, Araldit GY 250 (A), ARALDIT GY 282 (F), ARALDIT GY 285 (F)), and photocurable siloxanes that contain epoxy groups.

Further suitable cationically polymerisable or crosslinkable components (b) can be found, for example, also in U.S. Pat. No. 3,117,099, U.S. Pat. No. 4,299,938 and U.S. Pat. No. 4,339,567.

From the group of aliphatic epoxides there are suitable especially the monofunctional symbol-olefin epoxides having an unbranched chain consisting of 10, 12, 14 or 16 carbon atoms.

Because nowadays a large number of different epoxy compounds are commercially available, the properties of the binder can vary widely. One possible variation, for example depending upon the intended use of the composition, is the use of mixtures of different epoxy compounds and the addition of flexibilisers and reactive diluents.

The epoxy resins can be diluted with a solvent to facilitate application, for example when application is effected by spraying, but the epoxy compound is preferably used in the solvent-less state. Resins that are viscous to solid at room temperature can be applied hot.

The compounds generating an acid of the formula I or II can also be used as acid generators, which can be activated photochemically, for the acid-catalysed crosslinking of, for example, poly(glycidyl)methacrylates in negative resist systems. Such crosslinking reactions are described, for example, by Chae et al. in Pollimo 1993, 17(3), 292.

Also suitable as component (b) are all customary vinyl ethers, such as aromatic, aliphatic or cycloaliphatic vinyl ethers and also silicon-containing vinyl ethers. These are compounds having at least one, preferably at least two, vinyl ether groups in the molecule. Examples of vinyl ethers suitable for use in the compositions according to the invention include triethylene glycol divinyl ether, 1,4-cyclohexanedimethanol divinyl ether, 4-hydroxybutyl vinyl ether, the propenyl ether of propylene carbonate, dodecyl vinyl ether, tert-butyl vinyl ether, tert-amyl vinyl ether, cyclohexyl vinyl ether, 2-ethylhexyl vinyl ether, ethylene glycol monovinyl ether, butanediol monovinyl ether, hexanediol monovinyl ether, 1,4-cyclohexanedimethanol monovinyl ether, diethylene glycol monovinyl ether, ethylene glycol divinyl ether, ethylene glycol butylvinyl ether, butane-1,4-diol divinyl ether, hexanediol divinyl ether, diethylene glycol divinyl ether, triethylene glycol divinyl ether, triethylene glycol methylvinyl ether, tetra-ethylene glycol divinyl ether, pluriol- E-200 divinyl ether, polytetrahydrofuran divinyl ether-290, trimethylolpropane trivinyl ether, dipropylene glycol divinyl ether, octadecyl vinyl ether, (4-cyclohexyl-methyleneoxyethene)-glutaric acid methyl ester and (4-butoxyethene)-isophthalic acid ester.

Examples of hydroxy-containing compounds include polyester polyols, such as, for example, polycaprolactones or polyester adipate polyols, glycols and polyether polyols, castor oil, hydroxy-functional vinyl and acrylic resins, cellulose esters, such as cellulose acetate butyrate, and phenoxy resins.

Further cationically curable formulations can be found, for example, in EP 119425.

As component (b), preference is given to cycloaliphatic epoxides, or epoxides based on bisphenol A.

The compounds generating an acid of the formula I or II (including the compounds of the formula IIIa, IIIb, IIIe, IVa, IVb, IIIc, IIId, IVc and IVe as defined above, as well as the co-polymers obtained from the compounds of the formula IIIa, IIIb, IIIc and IIIe as defined above, wherein $R_1$ as $C_2$-$C_{12}$alkenyl or interrupted $C_2$-$C_{18}$alkenyl is a polymerizable group containing at least one double bond) can also be used, for example, as photo-activatable hardeners for siloxane-group-containing resins. Those resins can, for example, either undergo self-condensation by way of acid-catalysed hydrolysis or can be crosslinked with a second resin component, such as, for example, a polyfunctional alcohol, a hydroxygroup-containing acrylic or polyester resin, a partially hydrolysed polyvinylacetal or a poly-vinyl alcohol. That type of polycondensation of polysiloxanes is described, for example, in J. J. Lebrun, H. Pode, Comprehensive Polymer Science Vol. 5, page 593, Pergamon Press, Oxford, 1989.

Especially preferred as acid-curable resins (b) are amino resins, such as non-etherified or etherified melamine, urea, guanidine or biuret resins, especially methylated melamine resins or butylated melamine resins, corresponding glycolurils and urones. By "resins" in this context, there are to be understood both customary technical mixtures, which generally also comprise oligomers, and pure and high purity compounds. N-hexa(methoxymethyl)melamine and tetramethoxymethyl glucoril and N,N'-dimethoxymethylurone are the acid-curable resins given the greatest preference.

The crosslinker components should generally be present in a concentration of from 2 to 40, preferably from 5 to 30, percent by weight, based on the total solids content of the negative resist composition.

The concentration of the compound generating an acid of the formula I or II in negative resists in general is from 0.1 to 30, preferably up to 20, percent by weight, based on the total solids content of the compositions. From 1 to 15 percent by weight is especially preferred.

Binders may also be added to the compositions according to the invention, this being especially advantageous when the photopolymerisable compounds are liquid or viscous substances. The amount of binder may be, for example, from 5 to 95% by weight, preferably from 10 to 90% by weight and especially from 40 to 90% by weight, based on total solids. The binder will be selected according to the field of use and the properties required therefor, such as developability in aqueous and organic solvent systems, adhesion to substrates and sensitivity to oxygen. Suitable binders are, for example, polymers having a molecular weight of approximately from 2000 to 2 000 000, preferably from 5000 to 1 000 000. Examples thereof are: homo- and co-polymers of acrylates and methacrylates, for example copolymers of methyl methacrylate/ethyl acrylate/methacrylic acid, poly(methacrylic acid alkyl esters), poly(acrylic acid alkyl esters); phenolic resins, cellulose derivatives, such as cellulose esters and ethers, for example cellulose acetate, cellulose acetate butyrate, methyl cellulose, ethyl cellulose; polyvinyl butyral, polyvinylformal, polyolefins, cyclised rubber, polyethers, such as polyethylene oxide, polypropylene oxide, polytetrahydrofuran; polystyrene, polycarbonate, poly-urethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylene/vinyl acetate), polymers such as polycaprolactam and poly(hexamethyleneadipamide), polyesters such as poly(ethylene glycol terephthalate) and poly(hexamethylene glycol succinate); and polyamides.

Where appropriate, the negative compositions may comprise a film-forming polymeric binder. This binder is preferably an alkali-soluble phenolic resin. Well suited for this purpose are, for example, novolaks, derived from an aldehyde, for example acetaldehyde or furfuraldehyde, but especially from formaldehyde, and a phenol, for example unsubstituted phenol, mono- or di-chlorosubstituted phenol, such as p-chlorophenol, phenol mono- or di-substituted by $C_1$-$C_9$alkyl, such as o-, m- or p-cresol, the various xylenols, p-tert-butylphenol, p-nonylphenol, p-phenylphenol, resorcinol, bis(4-hydroxyphenyl)methane or 2,2-bis(4-hydroxyphenyl)propane. Also suitable are homo- and copolymers based on ethylenically unsaturated phenols, for example homopolymers of vinyl- and 1-propenyl-substituted phenols, such as p-vinylphenol or p-(1-propenyl)-phenol or copolymers of these phenols with one or more ethylenically unsaturated materials, for example styrenes. The amount of binder should generally be from 30 to 95 percent by weight or, preferably, from 40 to 80 percent by weight.

Suitable formulations and the preparation of suitable polymer/copolymers for the negative resist using the compounds generating an acid of the formula I or II according to the present invention (including the compounds of the formula IIIa, IIIb, IIIe, IVa, IVb, IIIc, IIId, IVc and IVe as defined above, as well as the co-polymers obtained from the compounds of the formula IIIa, IIIb, IIIc and IIIe as defined above, wherein $R_1$ as $C_2$-$C_{12}$alkenyl or interrupted $C_2$-$C_{18}$alkenyl is a polymerizable group containing at least one double bond) are for example published in JP-A-2010-015089, JP-A-2003-43688, JP-A-2003-114531, JP-A-2003-233185, JP-A-2003-186195, U.S. Pat. No. 6,576,394.

The chemically amplified negative, solvent-developable photoresists request the use of a specific component that when catalysed by an acid undergoes a crosslinking reaction or a polymerization with itself and/or with other components in the formulation. Suitable formulations are for example published in U.S. Pat. No. 4,882,245, U.S. Pat. No. 5,026,624, U.S. Pat. No. 6,391,523.

A suitable component (b) that when catalysed by an acid undergoes a crosslinking reaction or a polymerization with itself and/or with other components includes, for example, an epoxidized bisphenol A formaldehyde novolak resin and an epoxidized tetrabromo bisphenol A formaldehyde novolak resin. The preferred epoxy resin contains an average of eight epoxy groups, consisting of the glycidyl ether of the novolak condensation product of bisphenol A and formaldehyde, with an average molecular weight of about 1400 gram/mole, with an epoxy equivalent weight of about 215 gram/mole. Such a resin is, for example, commercially available from Shell Chemical under the trade name EPON® Resin SU-8.

Various kinds of polymers can be used as the binder resin in the chemically amplified negative solvent-developable photoresist. Suitable examples include a phenoxy polyol resin which is a condensation product between epichlorohydrin and bisphenol A. A resin of this type is, for example, sold by Union Carbide Corporation under the Trade Mark PKHC.

The positive and the negative resist compositions may comprise in addition to the photosensitive acid donor component (a), further photosensitive acid donor compounds (a1), further additives (d), other photoinitiators (e), and/or sensitizers (f).

Therefore, subject of the invention also are chemically amplified resist compositions as described above, in addition to components (a) and (b), or components (a) and (c1), (c2), (c3), or components (a) and (c), comprising further additives (d), further photosensitive acid donor compounds (a1), other photoinitiators (e), and/or sensitizers (f).

The compounds generating an acid of the formula I or II (including the compounds of the formula IIIa, IIIb, IIIe, IVa, IVb, IIIc, IIId, IVc and IVe as defined above, as well as the co-polymers obtained from the compounds of the formula IIIa, IIIb, IIIc and IIIe as defined above, wherein $R_1$ as $C_2$-$C_{12}$alkenyl or interrupted $C_2$-$C_{18}$alkenyl is a polymerizable group containing at least one double bond) of the present invention in the positive and negative resist can also be used together with other, known photolatent acids (a1), for example, onium salts, 6-nitrobenzylsulfonates, bis-sulfonyl diazomethane compounds, cyano group-containing oxime sulfonate compounds, etc. Examples of known photolatent acids for chemically amplified resists are described in U.S. Pat. No. 5,731,364, U.S. Pat. No. 5,800,964, EP 704762, U.S. Pat. No. 5,468,589, U.S. Pat. No. 5,558,971, U.S. Pat. No. 5,558,976, U.S. Pat. No. 6,004,724, GB 2348644 and particularly in EP 794457 and EP 795786.

If a mixture of photolatent acids is used in the resist compositions according to the invention, the weight ratio of the compounds generating an acid of the formula I or II to the other photolatent acid (a1) in the mixture is preferably from 1:99 to 99:1.

Examples of photolatent acids (a1) which are suitable to be used in admixture with the compounds generating an acid of the formula I or II (including the compounds of the formula IIIa, IIIb, IIIe, IVa, IVb, IIIc, IIId, IVc and IVe as defined above, as well as the co-polymers obtained from the compounds of the formula IIIa, IIIb, IIIc and IIIe as defined above, wherein $R_1$ as $C_2$-$C_{12}$alkenyl or interrupted $C_2$-$C_{18}$alkenyl is a polymerizable group containing at least one double bond) are (1) onium salt compounds, for example, iodonium salts, sulfonium salts, phosphonium salts, diazonium salts, pyridinium salts. Preferred are diphenyliodonium triflate, diphenyliodonium pyrenesulfonate, diphenyliodonium dodecylbenzenesulfonate, triphenylsulfonium triflate, triphenylsulfonium nonafluorobutanesulfonate, triphenylsulfonium hexafluoroantimonate, diphenyliodonium hexafluoroantimonate, triphenylsulfonium naphthalenesulfonate, (hydroxyphenyl)benzylmethylsulfonium toluenesulfonate, bis(4-tert-butylphenyl)iodonium bis(nonafluorobutanesulfonyl)imide, bis(4-tert-butylphenyl)-iodonium tris(trifluoromethanesulfonyl)methide, triphenylsulfonium bis(trifluoromethanesulfonyl)imide, triphenylsulfonium (octafluorobutane-1,4-disulfonyl)imide, triphenylsulfonium tris(trifluoromethanesulfonyl)methide, tert-butyldiphenylsulfonium tris(trifluoromethanesulfonyl) methide, triphenylsulfonium 1,3-disulfonylhexafluoropropyleneimide, triarylsulfonium tetrakis-(pentafluorophenyl)borates, e.g. triphenylsulfonium tetrakis-(pentafluorophenyl)borate, diaryliodonium tetrakis (pentafluorophenyl)borates, e.g. diphenyliodonium tetrakis (pentafluorophenyl)borate, diphenyl[4-(phenylthio)phenyl]-sulfonium trifluorotris(pentafluoroethyl)phosphate and the like; the iodonium cation may also be 4-methylphenyl-4'-isobutylphenyliodonium or 4-methylphenyl-4'-isopropylphenyliodonium. Particularly preferred are triphenylsulfonium triflate, diphenyliodonium hexafluoroantimonate. Other examples are described in JP-A-2002-229192, JP-A-2003-140332, JP-A-2002-128755, JP-A-2003-35948, JP-A-2003-149800, JP-A-2002-6480, JP-A-2002-116546, JP-A-2002-156750, U.S. Pat. No. 6,458,506, US2003/27061, U.S. Pat. No. 5,554,664, WO2007/118794.

(2) halogen-containing compounds haloalkyl group-containing heterocyclic compounds, haloalkyl group-containing hydrocarbon compounds and the like. Preferred are (trichloromethyl)-s-triazine derivatives such as phenyl-bis(trichloromethyl)-s-triazine, methoxyphenyl-bis(trichloromethyl)-s-triazine, naphthyl-bis(trichloromethyl)-s-triazine and the like; 1.1-bis(4-chlorophenyl)-2,2,2-trichloroethane; and the like.

(3) sulfone compounds, for example of the formula

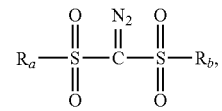

wherein $R_a$ and $R_b$ independently of one another are alkyl, cycloalkyl or aryl, each of which may have at least one substituent, e.g.

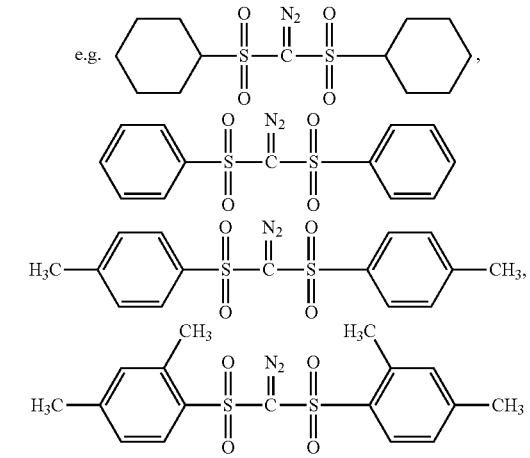

Such compounds are disclosed for example in US2002/0172886-A, JP-A-2003-192665, US2002/9663-A. More examples are β-ketosulfones, β-sulfonylsulfones and their α-diazo derivatives and the like. Preferred are phenacylphenylsulfone, mesitylphenacylsulfone, bis(phenylsulfonyl)-methane, bis(phenylsulfonyl)diazomethane.

(4) sulfonate compounds, for example alkylsulfonic acid esters, haloalkylsulfonic acid esters, arylsulfonic acid esters, iminosulfonates, imidosulfonates and the like. Preferred imidosulfonate compounds are, for example, N-(trifluoromethlsulfonyloxy)succinimide, N-(trifluoromethylsulfonyloxy)phthalimide, N-(trifluoromethylsulfonyloxy)naphthylimide, N-(trifluoromethylsulfonyloxy) diphenylmaleimide, N-(trifluoromethylsulfonyloxy)-bicyclo-[2,2,1]-hept-5-ene-2,3-dicarboximide, N-(trifluoromethylsulfonyloxy)-7-oxabicyclo-[2,2,1]-hept-5-ene-2,3-dicarboximide, N-(trifluoromethylsulfonyloxy)-7-oxabicyclo-[2,2,1]-hept-5-ene-2,3-dicarboximide, N-(trifluoromethylsulfonyloxy)-bicyclo-[2,2,1]-heptan-5,6-oxy-2,3-dicarboximide, N-(camphanylsulfonyloxy)succinimide, N-(camphanylsulfonyloxy)phthalimide, N-(camphanylsulfonyloxy)naphthylimide, N-(camphanylsulfonyloxy)diphenylmaleimide, N-(camphanylsulfonyloxy)-bicyclo-[2,2,1]-hept-5-ene-2,3dicarboximide, N-(camphanylsulfonyloxy)-7-oxabicyclo-[2,2,1]-hept-5-ene-2,3-dicarboximide, N-(camphanylsulfonyloxy)-7-oxabicyclo-[2,2,1]hept-5-ene-2,3-dicarboximide, N-(camphanylsulfonyloxy)-bicyclo-[2,2,1]-heptan-5,6-oxy-2,3-dicarboximide, N-(4-methylphenylsulfonyloxy)succinimide, N-(4-methylphenylsulfonyloxy)phthalimide, N-(4-methylphenylsulfonyloxy)naphthylimide, N-(4-methylphenylsulfonyloxy)naphthylimide, N-(4-methylphenylsulfonlyoxy)diphenylmaleimide, N-(4-methylphenylsulfonyloxy)-bicyclo-[2,2,1]-hept-5-ene2,3-dicarboximide, N-(4-methylphenylsulfonyloxy)-7-oxabicyclo-[2,2,1]-hept-5-ene-2,3-dicarboximide, N-(4-methylphenylsulfonyloxy)-bicyclo-[2,2,1]-heptan-5,6-oxy-2,3-dicarboximide, N-(2-trifluoromethylphenylsulfonyloxy) succinimide, N-(2-trifluoromethylphenylsulfonyloxy) naphthylimide, N-(2-trifluoromethylphenylsulfonyloxy) diphenylmaleimide, N-(2-trifluoromethylphenylsulfonyloxy)-bicyclo-[2,2,1]-hept-5-ene-2,3-dicarboximide, N-(2-trifluoromethylphenylsulfonyloxy)-7-oxabicyclo-[2,2,1]-hept-5-ene-2,3-dicarboximide, N-(2-trifluoromethylphenylsulfonyloxy)-bicyclo-[2,2,1]-heptan-5,6-oxy-2,3-dicarboximide and the like. Other suitable sulfonate compounds preferably are, for example, benzoin tosylate, pyrogallol tristriflate, pyrogallolomethanesulfonic acid triester, nitorobenzyl-9,10-diethoxyanthracene-2-sulfonate, -(4-toluene-sulfonyloxyimino)-benzyl cyanide, -(4-toluene-sulfonyloxyimino)-4-methoxybenzyl cyanide, -(4-toluene-sulfonyloxyimino)-2-thienylmethyl cyanide, -(methanesulfonyloxyimino)-1-cyclohexenylacetonitrile, -(butylsulfonyloxyimino)-1-cyclopentenylacetonitrile, (4-methylsulfonyloxyimino-cyclohexa-2,5-dienylidene)-phenylacetonitrile, (5-methylsulfonyloxyimino-5H-thiophen-2-ylidene)-phenyl-acetonitrile, (5-methylsulfonyloxyimino-5H-thiophen-2-ylidene)-(2-methylphenyl)-acetonitrile, (5-propylsulfonyloxyimino5H-thiophen-2-ylidene)-(2-methylphenyl)-acetonitrile, (5-(p-toluenesulfonyloxyimino)-5H-thiophen2-ylidene)-(2-methylphenyl)-acetonitrile, (5-(10-camphorsulfonyloxyimino)-5H-thiophen2-ylidene)-(2-methylphenyl)-acetonitrile, (5-methylsulfonyloxyimino-5H-thiophen-2-ylidene)(2-chlorophenyl)-acetonitrile, 2,2,2-trifluoro-1-{4-(3-[4-{2,2,2-trifluoro-1-(1-propanesulfonyloxyimino)-ethyl]-phenoxy]-propoxy)-phenyl}-ethanone oxime 1-propanesulfonate, 2,2,2-trifluoro-1-{4-(3-[4-{2,2,2-trifluoro-1-(1-p-toluenesulfonyloxyimino)-ethyl}-phenoxy]-propoxy)-phenyl}-ethanone oxime 1-p-toluenesulfonate, 2-[2,2,3,3,4,4,5,5,6,6,7,7-dodecafluoro-1(nonafluorobutylsulfonyloxyimino)-heptyl]-fluorene, 2-[2,2,3,3,4,4,4-heptafluoro-1-(nonafluorobutylsulfonyloxyimino)-butyl]-fluorene, 2-[2,2,3,3,4,4,5,5-octafluoro-1-(nonafluorobutylsulfonyloxyimino)-pentyl]-fluorene, 8-[2,2,3,3,4,4,5,5-octafluoro-1-(nonafluorobutylsulfonlyoxyimino)-pentyl]-fluoranthene and the like.

In the radiation sensitive resin composition of this invention, particularly preferred sulfonate compounds include pyrogallolmethanesulfonic acid triester, N-(trifluoromethylsulfonyloxy)bicyclo-[2,2,1]-hept-5-ene-2,3-dicarboximide, N-(camphanylsulfonyloxy)naphthylimide, N-(2-trifluoromethylphenylsulfonyloxy)phthalimide, N-(trifluoromethylsulfonyloxy)-bicyclo-[2,2,1]hept-5-ene-2,3-dicarboximide, N-(camphanylsulfonyloxy)-naphthylimide, N-(2-trifluoromethylphenylsulfonyloxy)phthalimide and the like.

(5) Quinonediazide compounds, for example 1,2-quinonediazidesulfonic acid ester compounds of polyhydroxy compounds. Preferred are compounds having a 1,2-quinonediazidesulfonyl group, e.g. a 1,2-benzoquinonediazide-4-sulfonyl group, a 1,2-naphthoquinonediazide-4-sulfonyl group, a 1,2-naphthoquinonediazide-5-sulfonyl group, a 1,2-naphthoquinonediazide-6-sulfonyl group or the like. Particularly preferred are compounds having a 1,2-naphthoquinonediazide-4-sulfonyl group or a 1,2-naphthoquinonediazide-5-sulfonyl group. In particular suitable are 1,2-quinonediazidesulfonic acid esters of (poly)hydroxyphenyl aryl ketones such as 2,3,4-trihydroxybenzophenone, 2,4,6-trihydroxybenzophenone, 2,3,4,4'-tetrahydroxybenzophenone, 2,2',3,4-tetrahydroxybenzophenone, 2,3,4,4'-tetrahydroxybenzophenone, 2,2',4,4'tetrahydroxybenzophenone 2,2',3,4,4'-pentahydroxybenzophenone, 2,2'3,2,6'-pentahydroxybenzophenone, 2,3,3',4,4'5'-hexahydroxybenzophenone, 2,3',4,4',5'6-hexahydroxybenzophenone and the like; 1,2-quinonediazidesulfonic acid esters of bis-[(poly)hydroxylphenyl]alkanes such as bis(4-hydroxyphenyl)ethane, bis(2,4-dihydroxyphenyl)ethane, 2,2-bis(4-hydroxyphenyl)propane, 2,2-bis(2,4-dihydroxyphenyl)propane, 2,2-bis-(2,3,4-trihydroxyphenyl)propane and the like; 1,2-quinonediazidesulfonic acid esters of (poly)hydroxylphenylalkanes such as 4,4'-dihydroxytriphenylmethane, 4,4'4"-trihydroxytriphenylmethane, 4,4'5,5'-tetramethyl-2,2'2"-trihydroxytriphenylmethane, 2,2,5,5'-tetramethyl-4,4',4"-trihydroxytriphenylmethane, 1,1,1-tris(4-hydroxyphenyl)ethane, 1,1-bis(4-hydroxyphenyl)-1-phenylethane, 1,1-bis(4-hydroxyphenyl)-1-(4-[1-(hydroxyphenyl)-1-methylethyl]phenyl)ethane and the like; 1,2-quinonediazidesulfonic acid esters of (poly)hydroxylphenylflavans such as 2,4,4-trimethyl-2',4',7-trihydroxy-2-phenylflavan, 2,4,4-trimethyl-2',4',5',6,7-pentahydroxy-2-phenylflavan and the like. Other examples of photolatent acids which are suitable to be used in admixture with the compounds according to the present invention are described in JP-A-2003-43678, JP-A-2003-5372, JP-A-2003-43677, JP-A-2002-357904, JP-A-2002-229192, JP-A-2009-269953, JP-A-2010-008912.

The positive and negative photoresist composition of the present invention may optionally contain one or more additives (d) customarily used in photoresists in the customary amounts known to a person skilled in the art, for example, dyes, pigments, plasticizers, surfactants, flow improvers, wetting agents, adhesion promoters, thixotropic agents, colourants, fillers, solubility accelerators, acid-amplifier, photosensitizers, organic acidic compound and/or fluorinated alcohol, and organic basic compounds. Especially in ArF immersion lithography, control of hydrophobicity/hydrophilicity of resist surface becomes crucial. Additive for this purpose is available and known to the person skilled in the art (examples are given below).

Examples for organic acidic derivatives and fluorinated alcohols that may be comprised in the resist formulations in an amount of up to 5 parts, and especially up to 1 part by weight, per 100 parts per weight of the total solids of the resist composition, are for example given in U.S. Pat. No. 7,569,324. The organic acidic compounds and fluorinated alcohols are not restricted to the examples given therein.

Examples for organic basic compounds which can be used in the resist composition of the present invention, for example to quench the acid in unexposed or partially exposed areas and/or capable of suppressing the rate of diffusion when the acid generated by the photolatent acid diffuses within the resist film (so called quenchers), are compounds which are stronger bases than phenol, in particular, nitrogen-containing basic compounds. These compounds may be ionic, like, for example, tetraalkylammonium salts or non-ionic. Preferred organic basic compounds are nitrogen-containing basic compounds having, per molecule, two or more nitrogen atoms having different chemical environments. Especially preferred are compounds containing both at least one substituted or unsubstituted amino group and at least one nitrogen-containing ring structure, and compounds having at least one alkylamino group. Examples of such preferred compounds include guanidine, aminopyridine, amino alkylpyridines, aminopyrrolidine, indazole, imidazole, pyrazole, pyrazine, pyrimidine, purine, imidazoline, pyrazoline, piperazine, aminomorpholine, and aminoalkylmorpholines. Suitable are both, the unsubstituted compounds or substituted derivatives thereof. Preferred substituents include amino, aminoalkyl groups, alkylamino groups, aminoaryl groups, arylamino groups, alkyl groups, alkoxy groups, acyl groups, acyloxy groups aryl groups, aryloxy groups, nitro, hydroxy, and cyano. Specific examples of especially preferred organic basic compounds include guanidine, 1,1-dimethylguanidine, 1,1,3,3-tetramethylguanidine, 2-aminopyridine, 3-aminopyridine, 4-aminopyridine, 2-dimethylaminopyridine, 4-dimethylaminopyridine, 2-diethylaminopyridine, 2-(aminomethyl)pyridine, 2-amino-3-methylpyridine, 2-amino-4-methylpyridine, 2-amino-5-methylpyridine, 2-amino-6-methylpyridine, 3-aminoethylpyridine, 4-aminoethylpyridine, 3-aminopyrrolidine, piperazine, N-(2-aminoethyl)piperazine, N-(2-aminoethyl)piperidine, 4-amino-2,2,6,6-tetramethylpiperidine, 4-piperidinopiperidine, 2-imimopiperidine, 1-(2-aminoethyl)pyrrolidine, pyrazole, 3-amino-5-methylpyrazole, 5-amino-3-methyl-1-p-tolylpyrazole, pyrazine, 2-(aminomethyl)-5-methylpyrazine, pyrimidine, 2,4-diaminopyrimidine, 4,6-dihydroxypyrimidine, 2-pyrazoline, 3-pyrazoline, N-aminomorpholine, and N-(2-aminoethyl)morpholine.

Other examples of suitable organic basic compounds are described in DE 4408318, U.S. Pat. No. 5,609,989, U.S. Pat. No. 5,556,734, EP 762207, DE 4306069, EP 611998, EP 813113, EP 611998, and U.S. Pat. No. 5,498,506, JP-A-2003-43677, JP-A-2003-43678, JP-A-2002-226470, JP-A-2002-363146, JP-A-2002-363148, JP-A-2002-363152, JP-A-2003-98672, JP-A-2003-122013, JP-A-2002-341522 and in U.S. Pat. No. 7,569,324, which are, for example, particularly suitable as quenchers for chemically amplified resists. However, the organic basic compounds suitable in the present invention are not limited to these examples.

The nitrogen-containing basic compounds may be used alone or in combination of two or more thereof. The added amount of the nitrogen-containing basic compounds is usually from 0.001 to 10 parts by weight, preferably from 0.01 to 5 parts by weight, per 100 parts by weight of the photosensitive resin composition (excluding the solvent). If the amount thereof is smaller than 0.001 part by weight, the effects of the present invention cannot be obtained. On the other hand, if it exceeds 10 parts by weight, reduced sensitivity and impaired developability at unexposed parts are likely to be caused.

The composition can further contain a basic organic compound which decomposes under actinic radiation ("suicide base") such as for example described in EP 710885, U.S. Pat. No. 5,663,035, U.S. Pat. No. 5,595,855, U.S. Pat. No. 5,525,453, and EP 611998.

Examples of dyes (d) suitable for the compositions of the present invention are oil-soluble dyes and basic dyes, e.g. Oil Yellow #101, Oil Yellow #103, Oil Pink #312, Oil Green BG, Oil Blue BOS, Oil Blue #603, Oil Black BY, Oil Black BS, Oil Black T-505 (all manufactured by Orient Chemical Industries Ltd., Japan), crystal violet (C142555), methyl violet (CI 42535), rhodamine B (CI 45170B), malachite green (CI 42000), and methylene blue (CI52015).

Spectral sensitizers (f) may be further added to sensitize the photo latent acid to exhibit absorption in a region of longer wavelengths than far ultraviolet, whereby the photosensitive composition of the present invention can, for example, be rendered sensitive to an i-line or g-line radiation. Examples of suitable spectral sensitizers include benzophenones, p,p'-tetramethyldiaminobenzophenone, p, p'-tetraethylethylaminobenzophenone, thioxanthone, 2-chlorothioxanthone, anthrone, pyrene, perylene, phenothiazine, benzil, acridine orange, benzoflavin, cetoflavin T, 9,10-diphenylanthracene, 9-fluorenone, acetophenone, phenanthrene, 2-nitrofluorene, 5-nitroacenaphthene, benzoquinone, 2-chloro-4-nitroaniline, N-acetyl-p-nitroaniline, p-nitroaniline, N-acetyl-4-nitro-1-naphthylamine, picramide, anthraquinone, 2-ethylanthraquinone, 2-tert-butylanthraquinone, 1,2-benzanthraquinone, 3-methyl-1,3-diaza-1,9-benzanthrone, dibenzalacetone, 1,2-naphthoquinone, 3-acylcoumarin derivatives, 3,3'-carbonyl-bis(5,7-dimethoxycarbonylcoumarin), 3-(aroylmethylene)thiazolines, eosin, rhodamine, erythrosine, and coronene. However, the suitable spectral sensitizers are not limited to these examples. These spectral sensitizers can be used also as light absorbers for absorbing the far ultraviolet emitted by a light source. In this case, the light absorber reduces light reflection from the substrate and lessens the influence of multiple reflection within the resist film, thereby diminishing the effect of standing waves. Specific examples of such sensitizer compounds are disclosed in WO 06/008251, page 36, line 30 to page 38, line 8, the disclosure of which is hereby incorporated by reference.

Further suitable additives (d) are "acid-amplifiers", compounds that accelerate the acid formation or enhance the acid concentration. Such compounds may also be used in combination with the compounds generating an acid of the formula I or II (including the compounds of the formula IIIa, IIIb, IIIe, IVa, IVb, IIIc, IIId, IVc and IVe as defined above, as well as the co-polymers obtained from the compounds of the formula IIIa, IIIb, IIIc and IIIe as defined above, wherein $R_1$ as $C_2$-$C_{12}$alkenyl or interrupted $C_2$-$C_{18}$alkenyl is a polymerizable group containing at least one double bond) according to the invention in positive or negative resists, or in imaging systems as well as in all coating applications. Such acid amplifiers are described e.g. in Arimitsu, K. et al. J. Photopolym. Sci. Technol. 1995, 8, pp 43; Kudo, K. et al. J. Photopolym. Sci. Technol. 1995, 8, pp 45; Ichimura, K. et al. Chem: Letters 1995, pp 551.

If desired, the composition according to the invention can also contain free-radically polymerisable components, such as ethylenically unsaturated monomers, oligomers or polymers. These radically polymerizable components may be added to the component (a) or (b). Said radically curable components may, however, also be part of (b1), (b2), (b3), (a4), (a5) or (a6). Suitable materials contain at least one ethylenically unsaturated double bond and are capable of undergoing addition polymerisation. Such compounds are also the subject of component (ax), accordingly, the description below also refers to component (ax).

Examples of suitable monomers include those described for example in WO2008/138724, page 34, line 25 to page 38, line 19. This disclosure is herein incorporated by reference.

It is also possible to use compounds that can be crosslinked equally both free-radically and cationically. Such compounds contain, for example, both a vinyl group and a cycloaliphatic epoxy group. Examples thereof are described in JP 2-289611-A and U.S. Pat. No. 6,048,953.

Mixtures of two or more such free-radically polymerisable materials can also be used.

The formulations can also comprise dyes and/or white or coloured pigments as additional additives (d). Depending upon the intended use, it is possible to use both inorganic and organic pigments. Such additives are known to the person skilled in the art; some examples thereof are titanium dioxide pigments, for example of the rutile or anatase type, carbon black, zinc oxide, such as zinc white, iron oxides, such as iron oxide yellow, iron oxide red, chromium yellow, chromium green, nickel titanium yellow, ultra-marine blue, cobalt blue, bismuth vanadate, cadmium yellow and cadmium red. Examples of organic pigments are mono- or bis-azo pigments, and metal complexes thereof, phthalocyanine pigments, polycyclic pigments, such as, for example, perylene, anthraquinone, thioindigo, quinacridone and triphenylmethane pigments, and diketopyrrolo-pyrrole, isoindolinone, e.g. tetrachloro-isoindolinone, isoindoline, dioxazine, benzimidazolone and quinophthalone pigments. The pigments can be used individually or in admixture in the formulations. Depending upon the intended use, the pigments are added to the formulations in amounts customary in the art, for example in an amount of from 1 to 60% by weight, or from 10 to 30% by weight, based on the total weight.

The formulations may, for example, also comprise organic dyes of a wide variety of classes. Examples thereof include azo dyes, methine dyes, anthraquinone dyes and metal complex dyes. Customary concentrations are, for example, from 0.1 to 20%, especially from 1 to 5%, based on the total weight.

The pigments, latent pigments or dyes or differently coloured precursors of such pigments and dyes that are added may be so selected that they undergo a colour change in the presence of the acid formed from the iodonium salt as a result of irradiation. Such compositions then show, by the colour change, that they have been irradiated and can be used, for example, as irradiation dose indicators, e.g. for UV radiation, electron beams, X-rays, etc.

In ArF Immersion lithography, control of surface hydrophobicity is important to achieve high through-put and low defects. Additive for this purpose can also be employed in the formulations as additional additives (c). Typical examples are described in JP-A-2009-270086, JP-A-2009-282508, JP-A-2010-002870, and JP-A-2010-020284.

Other additives (d) to improve the resist performance such as resolution, pattern profile, process latitude, line edge roughness, stability are described in JP-A-2002-122992, JP-A-2002-303986, JP-A-2002-278071, JP-A-2003-57827, JP-A-2003-140348, JP-A-2002-6495, JP-A-2002-23374, JP-A-2002-90987, JP-A-2002-91004, JP-A-2002-131913, JP-A-2002-131916, JP-A-2002-214768, JP-A-2001-318464, JP-A-2001-330947, JP-A-2003-57815, JP-A-2003-280200, JP-A-2002-287362, JP-A-2001-343750. Such compounds may also be used in combination with the compounds generating an acid of the formula I or II according to the invention (including the compounds of the formula IIIa, IIIb, IIIe, IVa, IVb, IIIc, IIId, IVc and IVe as defined above, as well as the co-polymers obtained from the compounds of the formula IIIa, IIIb, IIIc and IIIe as defined above, wherein $R_1$ as $C_2$-$C_{12}$alkenyl or interrupted $C_2$-$C_{18}$alkenyl is a polymerizable group containing at least one double bond) in positive or negative resists.

Usually, for the application to a substrate of the photosensitive composition of the present invention, the composition is dissolved in an appropriate solvent. Preferred examples of these solvents include ethylene dichloride, cyclohexanone, cyclopentanone, 2-heptanone, γ-butyrolactone, methyl ethyl ketone, ethylene glycol monomethyl ether, ethylene glycol monoethyl ether, 2-methoxyethyl acetate, 2-ethoxyethyl acetate, 2-ethoxyethanol, diethyl glycol dimethyl ether, ethylene glycol monoethyl ether acetate, propylene glycol monomethyl ether, propylene glycol monomethyl ether acetate, toluene, ethyl acetate, butyl acetate, methyl lactate, ethyl lactate, methyl methoxypropionate, ethyl ethoxypropionate, methyl pyruvate, ethyl pyruvate, propyl pyruvate, N,N-dimethylformamide, dimethyl sulfoxide, N-methylpyrrolidone, and tetrahydrofuran. These solvents may be used alone or as mixtures. Preferred examples of the solvents are esters, such as 2-methoxyethyl acetate, ethylene glycolmonoethyl ether acetate, propylene glycol monomethyl ether acetate, methyl methoxypropionate, ethyl ethoxypropionate, and ethyl lactate. Use of such solvents is advantageous because the compounds generating an acid of the formula I or II according to the present invention have good compatibility therewith and better solubility therein.

A surfactant can be added to the solvent. Examples of suitable surfactants include nonionic surfactants, such as polyoxyethylene alkyl ethers, e.g. polyoxyethylene lauryl ether, polyoxyethylene stearyl ether, polyoxyethylene acetyl ether, and polyoxyethylene oleyl ether; polyoxyethylene alkylaryl ethers, e.g. polyoxyethylene, octylphenol ether and polyoxyethylene nonylphenol ether; polyoxyethylene/polyoxypropylene block copolymers, sorbitan/fatty acid esters, e.g. sorbitan monolaurate, sorbitan monopalmitate, sorbitan monostearate, sorbitan monooleate, sorbitan trioleate; fluorochemical surfactants such as F-top EF301, EF303, and EF352 (manufactured by New Akita Chemical Company, Japan). Megafac F171 and F17.3 (manufactured by Dainippon Ink & Chemicals, Inc, Japan), Fluorad FC 430 and FC431 (manufactured by Sumitomo 3M Ltd., Japan), Asahi Guard AG710 and Surflon S-382, SC101, SC102, SC103, SC104, SC105, and SC106 (manufactured by Asahi Glass Co., Ltd., Japan); organosiloxane polymer KP341 (manufactured by Shin-Etsu Chemical Co., Ltd., Japan); and acrylic or methacrylic (co)polymers Poly-flow Now.75 and NO.95 (manufactured by Kyoeisha Chemical Co., Ltd., Japan). Other examples are described in JP-A-2001-318459, JP-A-2002-6483. The added amount of the surfactant usually is 2 parts by weight or lower, desirably 0.5 part by weight or lower, per 100 parts by weight of the solid components of the composition of the present invention. The surfactants may be added alone or in combination of two or more thereof.

The solution is uniformly applied to a substrate by means of known coating methods, for example by spin-coating, immersion, knife coating, curtain pouring techniques, brush application, spraying and roller coating. It is also possible to apply the photosensitive layer to a temporary, flexible support and then to coat the final substrate by coating transfer (laminating).

The amount applied (coating thickness) and the nature of the substrate (coating substrate) are dependent on the desired field of application. The range of coating thicknesses can in principle include values from approximately 0.01 m to more than 100 m.

After the coating operation generally the solvent is removed by heating, resulting in a layer of the photoresist on the substrate. The drying temperature must of course be lower than the temperature at which certain components of the resist might react or decompose. In general, drying temperatures are in the range from 60 to 160° C.

The resist layer may optionally be coated with a protective top-coat that may be used to protect the resist layer from the immersion fluid that is used in case of immersion lithography.

The resist coating is then irradiated image-wise. The expression "image-wise irradiation" includes irradiation in a predetermined pattern using actinic radiation, i.e. both irradiation through a mask containing a predetermined pattern, for example a transparency, a chrome mask or a reticle, and irradiation using a laser beam or electron beam that writes directly onto the resist surface, for example under the control of a computer, and thus produces an image. Another way to produce a pattern is by interference of two beams or images as used for example in holographic applications. It is also possible to use masks made of liquid crystals that can be addressed pixel by pixel to generate digital images, as is, for example described by A. Bertsch; J. Y. Jezequel; J. C. Andre in Journal of Photochemistry and Photobiology A: Chemistry 1997, 107 pp. 275-281 and by K. P. Nicolay in Offset Printing 1997, 6, pp. 34-37.

After the irradiation and, if necessary, thermal treatment, the irradiated sites (in the case of positive resists) or the non-irradiated sites (in the case of negative resists) of the composition are removed in a manner known per se using a developer.

In order to accelerate the catalytic reaction and hence the development of a sufficient difference in solubility between the irradiated and unirradiated sections of the resist coating in the developer, the coating is preferably heated before being developed. The heating can also be carried out or begun during the irradiation. Temperatures from 60 to 160° C. are preferably used. The period of time depends on the heating method and, if necessary, the optimum period can be determined easily by a person skilled in the art by means of a few routine experiments. It is generally from a few seconds to several minutes. For example, a period of from 10 to 300 seconds is very suitable when a hot-plate is used and from 1 to 30 minutes when a convection oven is used. It is important for the latent acid donors according to the invention in the unirradiated sites on the resist to be stable under those processing conditions.

The coating is then developed, the portions of the coating that, after irradiation, are more soluble in the developer being removed. If necessary, slight agitation of the workpiece, gentle brushing of the coating in the developer bath or spray developing can accelerate that process step. The aqueous-alkaline developers customary in resist technology may, for example, be used for the development. Such developers comprise, for example, sodium or potassium hydroxide, the corresponding carbonates, hydrogen carbonates, silicates or metasilicates, but preferably metal-free bases, such as ammonia or amines, for example ethylamine, n-propylamine, diethylamine, di-n-propylamine, triethylamine, methyl diethylamine, alkanolamines, for example dimethyl ethanolamine, triethanolamine, quaternary ammonium hydroxides, for example tetramethylammonium hydroxide or tetraethylammonium hydroxide. The developer solutions are generally up to 0.5 N, but are usually diluted in suitable manner before use. For example solutions having a normality of approximately 0.1-0.3 are well suited. The choice of developer depends on the nature of the photocurable surface coating, especially on the nature of the binder used or of the resulting photolysis products. The aqueous developer solutions may, if necessary, also comprise relatively small amounts of wetting agents and/or organic solvents. Typical organic solvents that can be added to the developer fluids are, for example, cyclohexanone, 2-ethoxyethanol, toluene, acetone, isopropanol and also mixtures of two or more of these solvents. A typical aqueous/organic developer system is based on Butylcellosolve®/water.

Subject of the invention also is a photoresist application process comprising the steps:
(1) applying to a substrate a composition as defined above
(2) post apply baking the composition at temperatures between 60° C. and 160° C.;
(3) image-wise irradiating with electromagnetic radiation in the wavelength range of 10 nm to 1500 nm, or with an electron beam;
(4) optionally post exposure baking the composition at temperatures between 60° C. and 160° C.; and
(5) developing with a solvent or with an aqueous alkaline developer.

Preferred is a process, wherein the image-wise irradiation is carried out with monochromatic or polychromatic radiation in the wavelength range from 10 to 450 nm, in particular in the range from 10 to 260 nm.

The photoresist compositions can be used on all substrates and with all exposure techniques known to the person skilled in the art. For example, semiconductor substrates can be used, such as silicon, gallium arsenide, germanium, indium antimonide; furthermore substrate covered by oxide or nitride layers, such as silicon dioxide, silicon nitride, titanium nitride, siloxanes, as well as metal substrates and metal coated substrates with metals such as aluminium, copper, tungsten, etc. The substrate can also be coated with polymeric materials, for example with organic antireflective coatings, insulation layers and dielectric coatings from polymeric materials prior to coating with the photoresist.

The photoresist layer can be exposed by all common techniques, such as direct writing, i.e. with a laser beam or electron beam or projection lithography in step- and repeat mode or scanning mode, or by contact printing through a mask.

In case of projection lithography a wide range of optical conditions can be used such as coherent, partial coherent or incoherent irradiation. This includes off-axis illumination techniques, for example annular illumination and quadrupol illumination where the radiation is allowed to pass only certain regions of the lens, excluding the lens center.

The mask used to replicate the pattern can be a hard mask or a flexible mask. The mask can include transparent, semitransparent and opaque patterns. The pattern size can include also patterns which are at or below the resolution limit of the projection optics and placed on the mask in a certain way in order to modify the aerial image, intensity and phase modulation of the irradiation after having passed the mask. This includes phase shift masks and half-tone phase shift masks.

The patterning process of the photoresist composition can be used to generate patterns of any desired geometry and shape, for example dense and isolated lines, contact holes, trenches, dots, etc.

The photoresists according to the invention have excellent lithographic properties, in particular a high sensitivity, and high resist transparency for the imaging radiation.

Possible areas of use of the composition according to the invention are as follows: use as photoresists for electronics, such as etching resists, ion-implantation resist, electroplating resists or solder resists, the manufacture of integrated circuits or thin film transistor-resist (TFT); the manufacture of printing plates, such as offset printing plates or screen printing stencils, use in the etching of mouldings or in stereolithography or holography techniques, which are employed for various applications, for example, 3D optical information storage described in J. Photochem. Photobio. A, 158, 163 (2003), Chem. Mater. 14, 3656 (2002).

The composition according to the invention is also suitable for making inter-metal dielectrics layer, buffer layer, passivation coat of semiconductor devices and suitable for making waveguide for optoelectronics. For MEMS (micro electro mechanical systems) application, the composition according to the invention can be used as etching resist, mold for material deposition, and three dimensional objects of device itself. The coating substrates and processing conditions vary accordingly. Such example is described in U.S. Pat. No. 6,391,523.

The compounds generating an acid of the formula I or II (including the compounds of the formula IIIa, IIIb, IIIe, IVa, IVb, IIIc, IIId, IVc and IVe as defined above, as well as the co-polymers obtained from the compounds of the formula IIIa, IIIb, IIIc and IIIe as defined above, wherein $R_1$ as $C_2$-$C_{12}$alkenyl or interrupted $C_2$-$C_{18}$alkenyl is a polymerizable group containing at least one double bond) according to the present invention, in combination with a sensitizer compound as described above, can also be used in holographic data storage (HDS) systems as for example described in WO 03/021358.

The compositions according to the invention include also adhesives, as used, for example, for adhesive bonding (DVD bonding) in the manufacture of digital versatile disks (DVD) and as described, for example, in: WO 99/66506, WO 99/63017, JP 11241055 A2 Heisei, JP 11181391 A2 Heisei, WO 98/31765, and also as radiation-curable laminating adhesives for flexible packaging (see, e.g., U.S. Pat. No. 5,328, 940), optical adhesives (e.g. German Patent Application DD 225985) and pressure-sensitive adhesives (e.g. U.S. Pat. No. 4,988,741 and EP 115870).

The compositions according to the invention are advantageously used where there is a need for hard coatings, adhesive bonds or photopolymerised dimensionally stable three-dimensional mouldings (e.g. for rapid prototyping) having good adhesion to paper, glass, metal, silicon, polycarbonate, acrylate polymers and other polymer substrates, and that exhibit only slight shrinkage during curing.

The compositions according to the invention are also outstandingly suitable as coating compositions for substrates of all types, including wood, textiles, paper, ceramics, glass, plastics, such as polyesters, polyethylene terephthalate, polyolefins or cellulose acetate, especially in the form of films, but especially for coating metals, such as Ni, Fe, Zn, Mg, Co or especially Cu and Al, and also Si, silicon oxides or nitrides, to which an image is to be applied by means of image-wise irradiation.

The invention relates also to the use of compounds generating an acid of the formula I or II (including the compounds of the formula IIIa, IIIb, IIIe, IVa, IVb, IIIc, IIId, IVc and IVe as defined above); or a polymer obtained by polymerizing a compound of the formula IIIa, IIIc or IIIe as defined above, wherein $R_1$ as $C_2$-$C_{12}$alkenyl or interrupted $C_2$-$C_{18}$alkenyl is a polymerizable group containing at least one double bond, with at least one further monomer which comprises a polymerizable double bond and which may further comprise an acid labile group, as acid donor in a composition which increases its solubility in a developer upon action of an acid; as well as the use of a compound generating an acid of the formula I or II according to anyone of claims 1-4 or a polymer obtained by polymerizing a compound of the formula IIIa or IIIb as defined in claim 2 or a compound of the formula IIIc or IIIe as defined in claim 3, wherein $R_1$ as $C_2$-$C_{12}$alkenyl or interrupted $C_2$-$C_{18}$alkenyl is a polymerizable group containing at least one double bond, with at least one further monomer which comprises a polymerizable double bond and which may further comprise an acid labile group, as acid donor in a composition which increases its solubility in a developer upon action of the acid.

Subject of the invention further is a process of crosslinking and/or polymerization of compounds that can be crosslinked and/or polymerized under the action of an acid, which method comprises adding compounds generating an acid of the formula I or II (including the compounds of the formula IIIa, IIIb, IIIe, IVa, IVb, IIIc, IIId, IVc and IVe as defined above) to the above-mentioned compositions and irradiating image-wise or over the whole area with light having a wavelength of 10-1500 nm.

The invention relates also to the use of compounds generating an acid of the formula I or II; or a co-polymer obtained by copolymerizing compounds of the formula IIIa, IIIb, IIIc or IIIe as defined above, $R_1$ as $C_2$-$C_{12}$alkenyl or interrupted $C_2$-$C_{18}$alkenyl is a polymerizable group containing at least one double bond, with a monomer with at least one further monomer which comprises a polymerizable double bond, as photosensitive acid donor in the preparation of pigmented and non-pigmented surface coatings, adhesives, laminating adhesives, structural adhesives, pressure-sensitive adhesives, printing inks, printing plates, relief printing plates, planographic printing plates, intaglio printing plates, processless printing plates, screen printing stencils, dental compositions, colour filters, spacers, electroluminescence displays and liquid crystal displays (LCD), waveguides, optical switches, color proofing systems, resists, photoresists for electronics, sacrificial coatings, electroplating resists, etch resists both for liquid and dry films, solder resist, photoresist materials for a UV and visible laser direct imaging system, photoresist materials for forming dielectric layers in a sequential build-up layer of a printed circuit board, image-recording materials, image-recording materials for recording holographic images, optical information storage or holographic data storage, decolorizing materials, decolorizing materials for image recording materials, image recording materials using microcapsules, magnetic recording materials, micromechanical parts (MEMS) and microfluidic devices, plating masks, etch masks, glass fibre cable coatings, microelectronic circuits; in particular to the use of compounds generating an acid of the formula I or II, as photosensitive acid donors in the preparation of surface coatings, printing inks, printing plates, dental compositions, colour filters, resists or image-recording materials, or image-recording materials for recording holographic images; as well as to a process for the preparation for the preparation of pigmented and non-pigmented surface coatings, adhesives, laminating adhesives, structural adhesives, pressure-sensitive adhesives, printing inks, printing plates, relief printing plates, planographic printing plates, intaglio printing plates, processless printing plates, screen printing stencils, dental compositions, colour filters, spacers, electroluminescence displays and liquid crystal displays (LCD), waveguides, optical switches, color proofing systems, resists, photoresists for electronics, sacrificial coatings electroplating resists, etch resists both for liquid and dry films, solder resist, photoresist materials for a UV and visible laser direct imaging system, e-beam resist materials, photoresist materials for forming dielectric layers in a sequential build-up layer of a printed circuit board, image-recording materials, image-recording materials for recording holographic images, optical information storage or holographic data storage, decolorizing materials, decolorizing materials for image recording materials, image recording materials using microcapsules, magnetic recording materials, micromechanical parts, micromechanical parts (MEMS) and microfluidic devices, plating masks, etch masks, glass fibre cable coatings, microelectronic circuits; in particular to a process for the preparation of surface coatings, printing inks, printing plates, dental compositions, colour filters, resists, or image-recording materials, or image-recording materials for recording holographic images.

Subject of the invention is also the use of compounds generating an acid of the formula I or II (including the compounds of the formula IIIa, IIIb, IIIe, IVa, IVb, IIIc, IIId, IVc and IVe as defined above, as well as the co-polymers obtained from the compounds of the formula IIIa, IIIb, IIIc and IIIe as defined above, wherein $R_1$ as $C_2$-$C_{12}$alkenyl or interrupted $C_2$-$C_{18}$alkenyl is a polymerizable group containing at least one double bond) as photosensitive acid donors in the preparation of colour filters or chemically amplified resist materials; as well as to a process for the preparation of colour filters or chemically amplified resist materials.

The invention further pertains to a color filter manufactured by providing on a transparent substrate red, green and blue (sub)pixel elements and optionally a black matrix from photosensitive compositions comprising acid crosslinkable or acid curable resin or acid solubilizing resin and at least a pigment and/or dye and providing a transparent electrode either on the surface of the substrate or on the surface of the color filter layer, wherein said photosensitive composition comprises a compounds generating an acid of the formula I or II as defined above or a polymer obtained by polymerizing a compound of the formula IIIa, IIIb, IIIc or IIIe as defined above, wherein $R_1$ as $C_2$-$C_{12}$alkenyl or interrupted $C_2$-$C_{18}$alkenyl is a polymerizable group containing at least one double bond, with a monomer comprising a polymerizable double bond, as acid donor.

The person skilled in the art is aware of suitable pigments or dyes to provide the color elements, as well as the black matrix and corresponding suitable resins as shown in, for examples, JP-A-9-203806, JP-A-10-282650, JP-A-10-333334, JP-A-11-194494, JP-A-10-203037, JP-A-2003-5371.

As already mentioned above, in photocrosslinkable compositions, compounds generating an acid of the formula I or II (including the compounds of the formula IIIa, IIIb, IIIe, IVa, IVb, IIIc, IIId, IVc and IVe as defined above, as well as the co-polymers obtained from the compounds of the formula IIIa, IIIb, IIIc and IIIe as defined above, wherein $R_1$ as $C_2$-$C_{12}$alkenyl or interrupted $C_2$-$C_{18}$alkenyl is a polymerizable group containing at least one double bond) act as latent curing catalysts: when irradiated with light they release acid which catalyses the crosslinking or polymerization reaction. In addition, the acid released by the radiation can, for example, catalyse the removal of suitable acid-sensitive protecting groups from a polymer structure, or the cleavage of polymers containing acid-sensitive groups in the polymer backbone. Other applications are, for example, colour-change systems based on a change in the pH or in the solubility of, for example, a pigment protected by acid-sensitive protecting groups.

Compounds generating an acid of the formula I or II according to the present invention can also be used to produce so-called "print-out" images when the compound is used together with a colourant that changes colour when the pH changes, as described e.g. in JP Hei 4 328552-A or in U.S. Pat. No. 5,237,059. Such color-change systems can be used according to EP 199672 also to monitor goods that are sensitive to heat or radiation.

In addition to a colour change, it is possible during the acid-catalysed deprotection of soluble pigment molecules (as described e.g. in EP 648770, EP 648817 and EP 742255) for the pigment crystals to be precipitated; this can be used in the production of colour filters as described e.g. in EP 654711 or print out images and indicator applications, when the colour of the latent pigment precursor differs from that of the precipitated pigment crystal.

Compositions using pH sensitive dyes or latent pigments in combination with compounds generating an acid of the formula I or II can be used as indicators for electromagnetic radiation, such as gamma radiation, electron beams, UV- or visible light, or simple throw away dosimeters. Especially for light, that is invisible to the human eye, like UV- or IR-light, such dosimeters are of interest.

Finally, compounds generating an acid of the formula I or II that are sparingly soluble in an aqueous-alkaline developer can be rendered soluble in the developer by means of light-induced conversion into the free acid, with the result that they can be used as solubility enhancers in combination with suitable film-forming resins.

Resins which can be crosslinked by acid catalysis and accordingly by the photolatent acid compounds generating an acid of the formula I or II according to the invention, are, for example, mixtures of polyfunctional alcohols or hydroxy-group-containing acrylic and polyester resins, or partially hydrolysed polyvinylacetals or polyvinyl alcohols with polyfunctional acetal derivatives. Under certain conditions, for example the acid-catalysed self-condensation of acetal-functionalised resins is also possible. Suitable acid-curable resins in general are all resins whose curing can be accelerated by acid catalysts, such as aminoplasts or phenolic resole resins. These resins are for example melamine, urea, epoxy, phenolic, acrylic, polyester and alkyd resins, but especially mixtures of acrylic, polyester or alkyd resins with a melamine resin. Also included are modified surface-coating resins, such as acrylic-modified polyester and alkyd resins. Examples of individual types of resins that are covered by the expression acrylic, polyester and alkyd resins are described, for example, in Wagner, Sarx, Lackkunstharze (Munich, 1971), pp. 86-123 and pp. 229-238, or in Ullmann, Encyclopädie der techn. Chemie, 4th Ed., Vol. 15 (1978), pp. 613-628, or Ullmann's Encyclopedia of Industrial Chemistry, Verlag Chemie, 1991, Vol. 18, p. 360 ff., Vol. A19, p. 371 ff.

In coating applications the surface coating preferably comprises an amino resin. Examples thereof are etherified or non-etherified melamine, urea, guanidine or biuret resins. Acid catalysis is especially important in the curing of surface coatings comprising etherified amino resins, such as methylated or butylated melamine resins (N-methoxymethyl- or N-butoxymethyl-melamine) or methylated/butylated glycolurils. Examples of other resin compositions are mixtures of polyfunctional alcohols or hydroxy-group-containing acrylic and polyester resins, or partially hydrolysed polyvinyl acetate or polyvinyl alcohol with polyfunctional dihydropropanyl derivatives, such as derivatives of 3,4-dihydro-2H-pyran-2-carboxylic acid. Polysiloxanes can also be crosslinked using acid catalysis. These siloxane group-containing resins can, for example, either undergo self-condensation by means of acid-catalysed hydrolysis or be crosslinked with a second component of the resin, such as a polyfunctional alcohol, a hydroxy-group-containing acrylic or polyester resin, a partially hydrolysed polyvinyl acetal or a polyvinyl alcohol. This type of polycondensation of polysiloxanes is described, for example, in J. J. Lebrun, H. Pode, Comprehensive Polymer Science, Vol. 5, p. 593, Pergamon Press, Oxford, 1989. Other cationically polymerisable materials that are suitable for the preparation of surface coatings are ethylenically unsaturated compounds polymerisable by a cationic mechanism, such as vinyl ethers, for example methyl vinyl ether, isobutyl vinyl ether, trimethylolpropane trivinyl ether, ethylene glycol divinyl ether; cyclic vinyl ethers, for example 3,4-dihydro-2- formyl-2H-pyran (dimeric acrolein) or the 3,4-dihydro-2H-pyran-2-carboxylic acid ester of 2-hydroxymethyl-3,4-dihydro-2H-pyran; vinyl esters, such as vinyl acetate and vinyl stearate, mono- and di-olefins, such as a-methylstyrene, N-vinylpyrrolidone or N-vinylcarbazole.

For certain purposes, resin mixtures having monomeric or oligomeric constituents containing polymerisable unsaturated groups are used. Such surface coatings can also be cured using compounds generating an acid of the formula I or II (including the compounds of the formula IIIa, IIIb, IIIe, IVa, IVb, IIIc, IIId, IVc and IVe as defined above). In that process, radical polymerisation initiators or photoinitiators can additionally be used. The former initiate polymerisation of the unsaturated groups during heat treatment, the latter during UV irradiation.

The invention further pertains to a composition comprising
(a) as photosensitive acid donor at least one of the compounds generating an acid of the formula I or II.

As already mentioned above a compound generating an acid of the formula I or II is for example a compound of the formula IIIa, IIIb, IIIe, IVa, IVb, IIIc, IIId, IVc and IVe as defined above, as well as a polymer obtained from any of the compounds of the formula IIIa, IIIb, IIIc and IIIe as defined above, wherein $R_1$ as $C_2$-$C_{12}$alkenyl or interrupted $C_2$-$C_{18}$alkenyl contains at least one double bond as a polymerizable group, with any other polymerizable monomer.
(b) a compound which cures upon the action of an acid or
(c) a compound whose solubility is increased upon the action of an acid.

In particular the invention pertains to a composition comprising
(a) as acid donor, at least one compound of the formula Ia, IIa, IIIa, IIIb, IIIe, IVa, IVb, IIIc, IIId, IVc and IVe as defined above; and
(b) a compound which cures or crosslinks upon the action of the acid; as well as to a composition comprising
as acid donor, at least one compound of the formula Ia, IIa, IIIa, IIIb, IIIe, IVa, IVb, IIIc, IIId, IVc and IVe as defined above; and
a compound which decomposes upon the action of an acid.

According to the invention, the compounds generating an acid of the formula I or II can be used together with further photosensitive acid donor compounds (a1), further photoinitiators (e), sensitisers (f) and/or additives (d).

Suitable photosensitive acid donor compounds (a1), sensitizers (f) and additives (d) are described above.

Examples of additional photoinitiators (e) are radical photoinitiators as for example disclosed in WO2008/138724, page 40, line 15 to page 41, line 26. Hereby this disclosure is incorporated by reference.

The compositions can also comprise a thermally curable component as additional additives (d). Examples are disclosed in WO2008/040648, page 30, line 24 to page 34, line 5, which disclosure is hereby incorporated by reference.

It is also possible to add to the resin, for example, photosensitisers which shift or increase the spectral sensitivity so that the irradiation period can be reduced and/or other light sources can be used. Examples of photosensitisers are aromatic ketones or aromatic aldehydes (as described, for example, in U.S. Pat. No. 4,017,652), 3-acyl-coumarins (as described, for example, in U.S. Pat. No. 4,366,228, EP 738928, EP 22188), keto-coumarines (as described e.g. in U.S. Pat. No. 5,534,633, EP 538997, JP 8272095-A), styryl-coumarines (as described e.g. in EP 624580), 3-(aroylmethylene)-thiazolines, thioxanthones, condensed aromatic compounds, such as perylene, aromatic amines (as described, for example, in U.S. Pat. No. 4,069,954 or WO 96/41237) or cationic and basic colourants (as described, for example, in U.S. Pat. No. 4,026,705), for example eosine, rhodanine and erythrosine colourants, as well as dyes and pigments as described for example in JP 8320551-A, EP 747771, JP 7036179-A, EP 619520, JP 6161109-A, JP 6043641, JP 6035198-A, WO 93/15440, EP 568993, JP 5005005-A, JP 5027432-A, JP 5301910-A, JP 4014083-A, JP 4294148-A, EP 359431, EP 103294, U.S. Pat. No. 4,282,309, EP 39025, EP 5274, EP 727713, EP 726497 or DE 2027467.

Other customary additives are—depending on the intended use—optical brighteners, fillers, pigments, colourants, wetting agents or flow improvers and adhesion promoters.

Compounds generating an acid of the formula I or II can also be used, for example, in hybrid systems. These systems are based on formulations that are fully cured by two different reaction mechanisms. Examples thereof are systems that comprise components that are capable of undergoing an acid-catalysed crosslinking reaction or polymerisation reaction, but that also comprise further components that crosslink by a second mechanism. Examples of the second mechanism are radical full cure, oxidative crosslinking or humidity-initiated crosslinking. The second curing mechanism may be initiated purely thermally, if necessary with a suitable catalyst, or also by means of light using a second photoinitiator. Suitable additional photoinitiators are described above. If the composition comprises a radically crosslinkable component, the curing process, especially of compositions that are pigmented (for example with titanium dioxide), can also be assisted by the addition of a component that is radical-forming under thermal conditions, such as an azo compound, for example 2, 2'-azobis(4-methoxy-2,4-dimethylvaleronitrile), a triazene, a diazosulfide, a pentazadiene or a peroxy compound, such as, for example, a hydroperoxide or peroxycarbonate, for example tert-butyl hydroperoxide, as described, for example, in EP 245639. The addition of redox initiators, such as cobalt salts, enables the curing to be assisted by oxidative crosslinking with oxygen from the air.

The surface coating can be applied by one of the methods customary in the art, for example by spraying, painting or immersion. When suitable surface coatings are used, electrical application, for example by anodic electrophoretic deposition, is also possible. After drying, the surface coating film is irradiated. If necessary, the surface coating film is then fully cured by means of heat treatment.

The compounds generating an acid of the formula I or II according to the present invention can also be used for curing mouldings made from composites. A composite consists of a self-supporting matrix material, for example a glass fibre fabric, impregnated with the photocuring formulation.

It is known from EP 592139 that sulfonate derivatives can be used as acid generators, which can be activated by light in compositions that are suitable for the surface treatment and cleaning of glass, aluminium and steel surfaces. The use of such compounds in organosilane systems results in compositions that have significantly better storage stability than those obtained when the free acid is used. The compounds generating an acid of the formula I or II according to the present invention are also suitable for this application.

The compounds generating an acid of the formula I or II of the present invention can also be used to shape polymers that undergo an acid induced transition into a state where they have the required properties using photolithography. For instance the compounds generating an acid of the formula I or II can be used to pattern conjugated emissive polymers as described, for example, in M. L. Renak; C. Bazan; D. Roitman; Advanced materials 1997, 9, 392. Such patterned emissive polymers can be used to manufacture microscalar patterned Light Emitting Diodes (LED) which can be used to manufacture displays and data storage media. In a similar way precursors for polyimides (e.g. polyimid precursors with acid labile protecting groups that change solubility in the developer) can be irradiated to form patterned polyimide layers which can serve as protective coatings, insulating layers and buffer layers in the production of microchips and printed circuit boards.

The formulations of the invention may also be used as conformal coatings, photoimagable insulating layers and dielectrics as they are used in sequential build up systems for printed circuit boards, stress buffer layers in the manufacturing of integrated circuits. It is known that conjugated polymers like, e.g. polyanilines can be converted from semiconductive to conductive state by means of proton doping. The compounds generating an acid of the formula I or II of the present invention can also be used to imagewise irradiate compositions comprising such conjugated polymers in order to form conducting structures (exposed areas) embedded in insulating material (non exposed areas). These materials can be used as wiring and connecting parts for the production of electric and electronic devices.

As already mentioned above a compound generating an acid of the formula I or II is for example a compound of the formula IIIa, IIIb, IIIe, IVa, IVb, IIIc, IIId, IVc and IVe as defined above, as well as a polymer obtained from any of the compounds of the formula IIIa, IIIb, IIIc and IIIe as defined above, wherein $R_1$ as $C_2$-$C_{12}$alkenyl or interrupted $C_2$-$C_{18}$alkenyl contains at least one double bond as a polymerizable group, with any other polymerizable monomer.

Suitable radiation sources for the compositions comprising compounds generating an acid of the formula I or II are radiation sources that emit radiation of a wavelength of approximately from 10 to 1500, for example from 10 to 1000, or preferably from 10 to 700 nanometers as well as e-beam radiation and high-energy electromagnetic radiation such as X-rays. Both, point sources and planiform projectors (lamp carpets) are suitable. Examples are: carbon arc lamps, xenon arc lamps, medium pressure, high pressure and low pressure mercury lamps, optionally doped with metal halides (metal halide lamps), microwave-excited metal vapour lamps, excimer lamps, superactinic fluorescent tubes, fluorescent lamps, argon filament lamps, electronic flash lamps, photographic flood lights, electron beams and X-ray beams generated by means of synchrotrons or laser plasma. The distance between the radiation source and the substrate according to the invention to be irradiated can vary, for example, from 2 cm to 150 cm, according to the intended use and the type and/or strength of the radiation source. Suitable radiation sources are mercury vapour lamps, especially medium and high pressure mercury lamps, from the radiation of which emission lines at other wavelengths can, if desired, be filtered out. That is especially the case for relatively short wavelength radiation. It is, however, also possible to use low energy lamps (for example fluorescent tubes) that are capable of emitting in the appropriate wavelength range. An example thereof is the Philips TL03 lamp. Another type of radiation source that can be used are the light emitting diodes (LED) that emit at different wavelengths throughout the whole spectrum either as small band emitting source or as broad band (white light) source. Especially suitable are laser radiation sources, for example excimer lasers, such as KrF lasers for irradiation at 248 nm, ArF lasers at 193 nm, or $F_2$ laser at 157 nm and EUV (extreme ultraviolet) sources. Lasers in the visible range and in the infrared range can also be used. As a light source EUV (Extreme Ultra Violet) source at 13 nm wavelength is also suitable. Especially suitable is radiation of the mercury i, h and g lines at wavelengths of 365, 405 and 436 nanometers, KrF laser radiation of 248 nm wavelength and ArF laser radiation of 193 nanometers and EUV radiation of 13 nm wavelength. The radiation exposure can rely dry or on immersion lithography. Particularly preferred is immersion lithography comprising radiation from an ArF excimer laser having a wavelength of 193 nm through a projection lens, with a liquid such as water, glycerol or ethylene glycol as an immersion fluid between the coated substrate and the projection lens. Other suitable laser-beam source is, for example, the argon-ion laser, which emits radiation at wavelengths of 454, 458, 466, 472, 478, 488 and 514 nanometers. Nd-YAG-lasers emitting light at 1064 nm and its second and third harmonic (532 nm and 355 nm respectively) can also be used. Also suitable is, for example, a helium/cadmium laser having an emission at 442 nm or lasers that emit in the UV range. With that type of irradiation, it is not absolutely essential to use a photomask in contact with the photopolymeric coating to produce a positive or negative resist; the controlled laser beam is capable of writing directly onto the coating. For that purpose the high sensitivity of the materials according to the invention is very advantageous, allowing high writing speeds at relatively low intensities. On irradiation, the compounds of the invention in the composition in the irradiated sections of the surface coating decompose to form the acids.

In contrast to customary UV curing with high-intensity radiation, with the compounds according to the invention activation is achieved under the action of radiation of relatively low intensity. Such radiation includes, for example, daylight (sunlight), and radiation sources equivalent to daylight. Sunlight differs in spectral composition and intensity from the light of the artificial radiation sources customarily used in UV curing. The absorption characteristics of the compounds according to the invention are as well suitable for exploiting sunlight as a natural source of radiation for curing. Daylight-equivalent artificial light sources that can be used to activate the compounds according to the invention are to be understood as being projectors of low intensity, such as certain fluorescent lamps, for example the Philips TL05 special fluorescent lamp or the Philips TL09 special fluorescent lamp. Lamps having a high daylight content and daylight itself are especially capable of curing the surface of a surface-coating layer satisfactorily in a tack-free manner. In that case expensive curing apparatus is superfluous and the compositions can be used especially for exterior finishes. Curing with daylight or daylight-equivalent light sources is an energy-saving method and prevents emissions of volatile organic components in exterior applications. In contrast to the conveyor belt method, which is suitable for flat components, daylight curing can also be used for exterior finishes on static or fixed articles and structures.

The surface coating to be cured can be exposed directly to sunlight or daylight-equivalent light sources. The curing can, however, also take place behind a transparent layer (e.g. a pane of glass or a sheet of plastics).

The examples, which follow, illustrate the invention in more detail. Parts and percentages are, as in the remainder of the description and in the claims, by weight, unless stated otherwise. Where alkyl radicals having more than three carbon atoms are referred to without any mention of specific isomers, the n-isomers are meant in each case.

PREPARATION EXAMPLES

Example 1

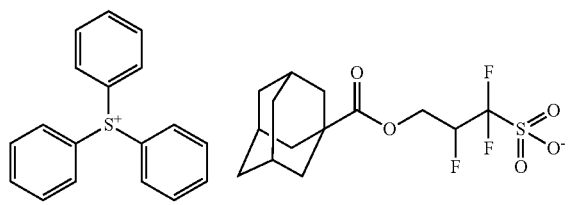 [SMILES: c1ccc([S+](c2ccccc2)c2ccccc2)cc1 ; O=C(OCC(F)C(F)(F)S(=O)(=O)[O-])C12CC3CC(CC(C3)C1)C2]

1.1: 2,3,3-Trifluoro-2-propen-1-ol 6.6 g (50 mmol) of 2,2,3,3-tetrafluoro-1-propanol are added to 10 ml of THF and cooled by ice bath. To the solution are added 2.0 g (50 mmol) of 60% NaH by portions. After the suspension is stirred at room temperature (r.t.) for 2 hours, 31 ml of 1.6M n-butyllithium in hexane is added to the reaction mixture with cooling by ice-salt bath. The reaction mixture is stirred at r.t. overnight, poured into ice water, and acidified with HCl. The product is extracted with tert-butylmethylether (TBME). The organic phase is washed with brine, water, dried over $MgSO_4$, and concentrated. The crude product is used in the next step without further purification. The structure is confirmed by the $^1$H-NMR and $^{19}$F-NMR spectrum ($CDCl_3$). [ppm]: 4.28 (d, 2H), −180.6 (m, 1 F), −120.0 (m, 1 F), −102.6 (m, 1 F).

1.2: Sodium 1,1,2-trifluoro-3-hydroxypropane-1-sulfonate

A mixture of sodium sulfite (0.80 g; 6.0 mmol) and the compound of example 1.1 (6.0 mmol) in water (6 mL) is stirred at 90° C. for 2.5 hours. After cooled to r.t., water is distilled off under reduced pressure to give 1,1,2-trifluoro-3-hydroxypropane-1-sulfonic acid disodium salt as a solid. The crude product is used in the next step without further purification after neutralization with acid. The structure is confirmed as a form of sodium 1,1,2-trifluoro-3-hydroxypropane-1-sulfonate by the $^1$H-NMR and $^{19}$F-NMR spectrum (DMSO-$d_6$). [ppm]: 3.48-3.61 (m, 1H), 4.04 (dd, 1H), 4.69-4.92 (m, 1H), 5.08 (bs, 1H), −206.0 (m, 1 F), −120.3 (d, 1 F), −110.9 (d, 1 F).

1.3

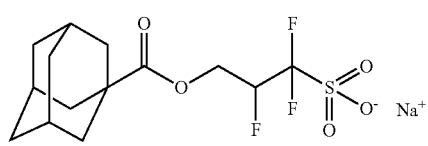 [SMILES: O=C(OCC(F)C(F)(F)S(=O)(=O)[O-])C12CC3CC(CC(C3)C1)C2 ; [Na+]]

1.58 g (7.3 mmol) of the compound of example 1.2, 1.32 g (7.3 mmol) of 1-adamanthanecarboxylic acid and 72 mg (0.73 mmol) of sulfuric acid are added to 10 ml of toluene, and stirred at 130° C. overnight. To the reaction mixture 5 ml of water is added, and organic products are extracted with ethyl acetate. The organic phase is concentrated by a rotary evaporator, and 5 ml of water is added to the residue and neutralized with 1N NaOH. TBME is added and separated, which includes unnecessary organic by-products. The compound of example 1.3 is obtained as aqueous solution form. The aqueous solution is used in the next step without further purification. The solution is partially concentrated and the structure of the compound of example 1.3 is confirmed by the $^1$H-NMR and $^{19}$F-NMR spectrum (DMSO-$d_6$). [ppm]: 1.60-2.00 (m, 15H), 4.20-4.32 (m, 1H), 4.60 (dd, 1H), 4.96-5.18 (m, 1H), −206.7 (m, 1 F), −119.6 (d, 1 F), −111.6 (d, 1 F).

1.4

To 57.5 ml of 4.4% aqueous solution containing the compound of example 1.3 (2.53 g: 6.7 mmol) 2.3 g (6.7 mmol) of triphenylsulfonium bromide and 30 ml of $CH_2Cl_2$ are added, and the reaction mixture is stirred at r.t. overnight, poured into water, and extracted with $CH_2Cl_2$. The organic phase is washed with water, dried over $MgSO_4$, and concentrated. The residue is purified by flash chromatography on silica gel with $CH_2Cl_2$ and methanol (20:1) as eluent, yielding 3.26 g (5.3 mmol; 78%) of the title compound of example 1.4 as a pale yellow solid. The structure is confirmed by the $^1$H-NMR and $^{19}$F-NMR spectrum (DMSO-$d_6$). [ppm]: 1.60-2.00 (m, 15H), 4.20-4.32 (m, 1H), 4.60 (dd, 1H), 4.96-5.18 (m, 1H), 7.74-7.90 (m, 15H), −206.7 (m, 1 F), −119.6 (d, 1 F), −111.5 (d, 1 F).

Examples 2-37

The compounds of examples 2 to 37 are obtained according to the method described in examples 1.1-1.4 or *Bull. Chem. Soc. Jpn.*, 1988, 61, 707-714, using the corresponding educts. The structures and physical data of intermediates and products are listed in table 1.

TABLE 1

| Ex. | Structures | Intermediate Physical properties | Final product Physical properties |
|---|---|---|---|
| 2 | 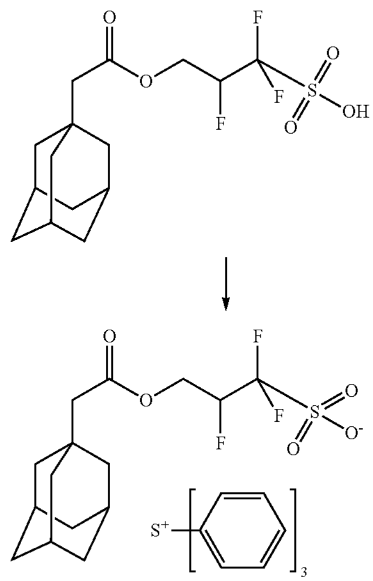 | ¹H-NMR and ¹⁹F-NMR (DMSO-d₆). [ppm]: 1.5-1.7 (m, 12H), 1.8-2.0 (m, 5H), 2.09 (s, 2H), 4.18-4.28 (m, 1H), 4.57-4.69 (m, 1H), 4.98-5.14 (m, 1H), −205.9 (m, 1F), −119.4 (d, 1F), −111.4 (d, 1F). | ¹H-NMR and ¹⁹F-NMR (DMSO-d₆). [ppm]:1.55-1.65 (m, 12H), 1.91 (s, 3H), 2.08 (s, 2H), 4.18-4.28 (m, 1H), 4.57-4.69 (m, 1H), 4.98-5.14 (m, 1H), 7.75-7.87 (m, 15H), −205.8 (m, 1F), −119.8 (d, 1F), −111.5 (d, 1F). |
| 3 | 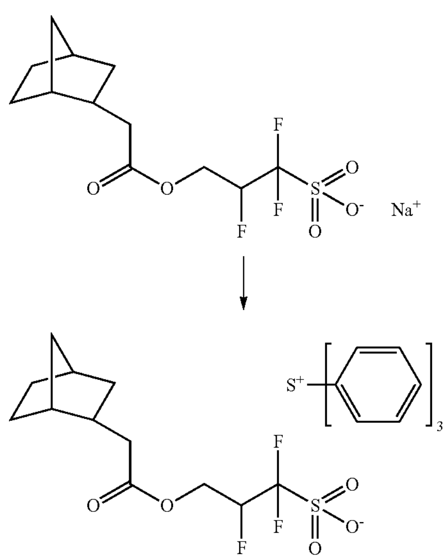 | ¹H-NMR and ¹⁹F-NMR (DMSO-d₆). [ppm]: 0.90-1.50 (m, 8H), 1.74-2.18 (m, 4H), 2.31 (q, 1H), 4.18-4.28 (m, 1H), 4.58-4.70 (m, 1H), 4.97-5.10 (m, 1H), −206.0 (m, 1F), −119.7 (d, 1F), −111.6 (d, 1F). | ¹H-NMR and ¹⁹F-NMR (DMSO-d₆). [ppm]: 1.01-1.20 (m, 4H), 1.28-1.45 (m, 4H), 1.73-1.83 (m, 1H), 1.93 (s, 1H), 2.10-2.20 (m, 2H), 2.28 (q, 1H), 4.18-4.28 (m, 1H), 4.58-4.68 (m, 1H), 4.98-5.15 (m, 1H), −206.1 (m, 1F), −119.8 (d, 1F), −111.6 (d, 1F). |

TABLE 1-continued

| Ex. | Structures | Intermediate Physical properties | Final product Physical properties |
|---|---|---|---|
| 4 | 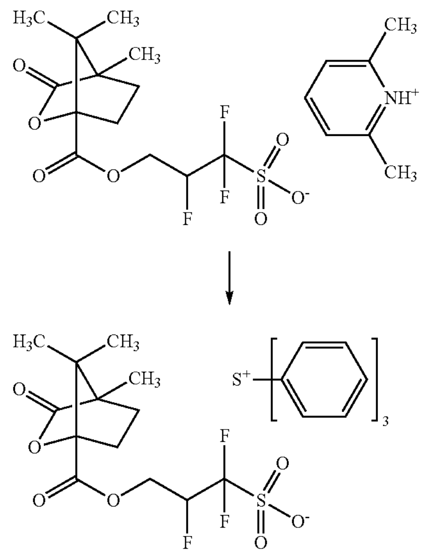 | $^1$H-NMR and $^{19}$F-NMR (CDCl$_3$). [ppm]: 0.96 (s, 3H), 1.07 (s, 3H), 1.12 (s, 3H), 1.69 (m, 1H), 1.96 (m, 1H), 2.05 (m, 1H), 2.46 (m, 1H), 2.87 (s, 6H), 4.72-4.93 (m, 2H), 5.31 (m, 1H), 7.52 (d, 2H), 8.18 (t, 1H), −206.4 (m, 1F), −117.5 (dd, 1F), −113.5 (d, 1F). | $^1$H-NMR and $^{19}$F-NMR (DMSO-d$_6$). [ppm]: 0.83 (s, 3H), 1.00 (s, 6H), 1.50-1.59 (m, 1H), 1.88-2.03 (m, 2H), 2.34-2.44 (m, 1H), 4.43-4.59 (m, 1H), 4.69-4.88 (m, 1H), 5.07-5.28 (m, 1H), 7.74-7.90 (m, 15H), −206.9 (m, 1F), −119.4 (d, 1F), −111.3 (d, 1F). |
| 5 | 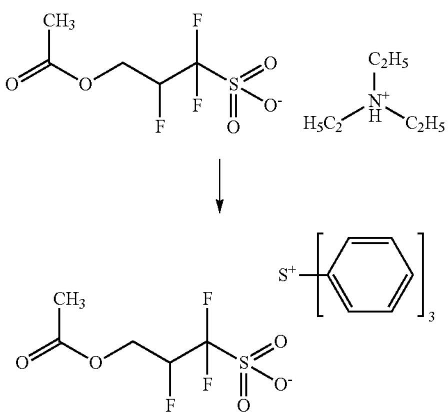 | $^1$H-NMR and $^{19}$F-NMR (DMSO-d$_6$). [ppm]: 1.16 (t, 9H), 2.03 (s, 3H), 2.98 (q, 6H), 4.20 (ddd, 1H), 4.65 (dd, 1H), 5.08 (m, 1H), −205.8 (m, 1F), −119.8 (d, 1F), −111.4 (d, 1F). | $^1$H-NMR and $^{19}$F-NMR (DMSO-d$_6$). [ppm]: 2.03 (s, 3H), 4.20 (ddd, 1H), 4.67 (dd, 1H), 5.08 (m, 1H), 7.74-7.87 (m, 15H), −205.8 (m, 1F), −119.9 (d, 1F), −111.5 (d, 1F). |
| 6 | 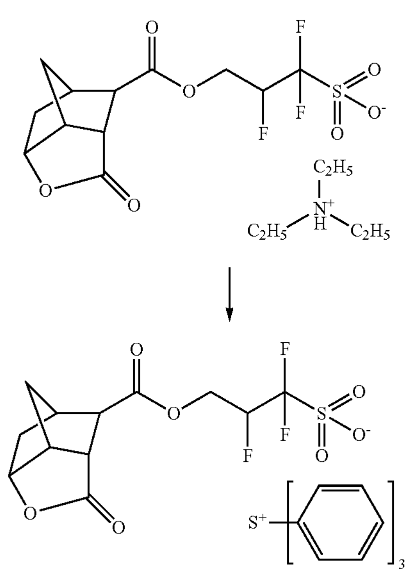 | Obtained as endo/exo isomer mixture. $^1$H-NMR and $^{19}$F-NMR (DMSO-d$_6$). [ppm]: 1.14 (t, 9H), 1.43-1.92 (m, 5H), 2.62-2.76 (m, 1H), 3.05 (q, 6H), 3.12-3.30 (m, 2H), 4.10-4.44 (m, 1H), 4.57-4.84 (m, 2H), 4.95-5.23 (m, 1H), −206.0 (m, 1F), −120.0 (m, 1F), −111.3 (m, 1F). | Obtained as endo/exo isomer mixture. $^1$H-NMR and $^{19}$F-NMR (DMSO-d$_6$). [ppm]: 1.42-1.94 (m, 5H), 2.62-2.77 (m, 1H), 3.14-3.30 (m, 2H), 4.10-4.42 (m, 1H), 4.56-4.85 (m, 2H), 4.96-5.25 (m, 1H), 7.73-7.89 (m, 15H), −205.9 (m, 1F), −119.8 (m, 1F), −111.5 (m, 1F). |

TABLE 1-continued

| Ex. | Structures | Intermediate Physical properties | Final product Physical properties |
|---|---|---|---|
| 7 | 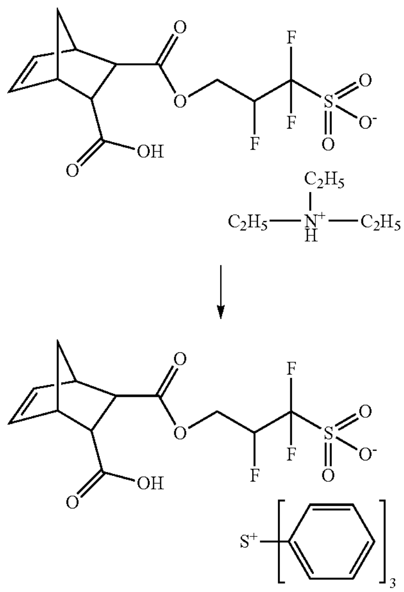 | $^1$H-NMR and $^{19}$F-NMR (CDCl$_3$). [ppm]: 1.30 (m, 1H), 1.37 (t, 9H), 1.41 (d, 1H), 3.11-3.22 (m, 8H), 3.30-3.41 (m, 2H), 4.24 (m, 1H), 4.58-4.82 (m, 2H), 5.18 (m, 1H), 6.23 (m, 2H), −204.8 (m, 1F), −116.5 (d, 1F), −114.5 (d, 1F). | $^1$H-NMR and $^{19}$F-NMR (CDCl$_3$). [ppm]: 1.30 (d, 1H), 1.42 (d, 1H), 3.12 (d, 2H), 3.28 (d, 2H), 4.28 (m, 1H), 4.69 (m, 1H), 5.05-5.45 (m, 2H), 6.15 (m, 2H), 7.65-7.79 (m, 15H), −205.0 (m, 1F), −118.6 (d, 1F), −113.1 (d, 1F). |
| 8 | 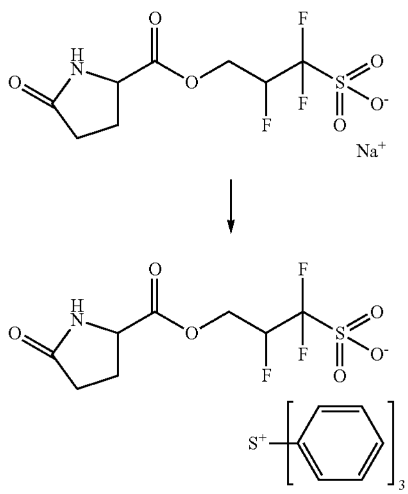 | Not islolated | $^1$H-NMR and $^{19}$F-NMR (DMSO-d$_6$). [ppm]: 1.95-2.20 (m, 3H), 2.28-2.38 (m, 1H), 4.21 (dd, 1H), 4.27-4.41 (m, 1H), 4.72 (ddd, 1H), 5.02-5.25 (m, 1H), 7.73-7.86 (m, 15H), 7.97 (br s, 1H). −206.2 (m, 1F), −119.5 (d, 1F), −111.3 (d, 1F). |
| 9 | 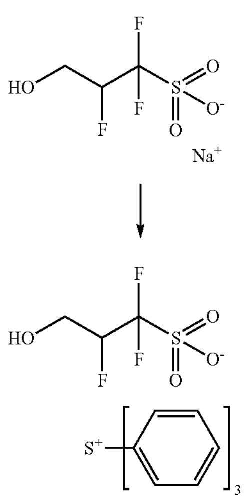 | Same to example 1.2 | $^1$H-NMR and $^{19}$F-NMR (DMSO-d$_6$). [ppm]: 3.47-3.62 (m, 1H), 4.04 (ddd, 1H), 4.70-4.92 (m, 1H), 5.10 (t, 1H), 7.75-7.90 (m, 15H), −206.0 (m, 1F), −120.2 (d, 1F), −110.9 (d, 1F). |

TABLE 1-continued
| Ex. | Structures | Intermediate Physical properties | Final product Physical properties |
|---|---|---|---|
| 10 | 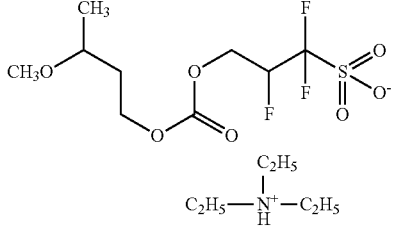 | $^1$H-NMR and $^{19}$F-NMR (DMSO-d$_6$). [ppm]: 1.06 (d, 3H), 1.73 (m, 2H), 3.21 (s, 3H), 3.42 (m, 1H), 4.19 (m, 2H), 4.26 (m, 1H), 4.71 (dd, 1H), 5.11 (m, 1H). −206.6 (m, 1F), −119.6 (d, 1F), −111.4 (d, 1F). | $^1$H-NMR and $^{19}$F-NMR (CDCl$_3$). [ppm]: 1.15 (d, 3H), 1.80 (m, 2H), 3.31 (s, 3H), 3.45 (m, 1H), 4.23 (m, 2H), 4.57 (m, 1H), 4.90 (dd, 1H), 5.30 (m, 1H), 7.67-7.81 (m, 15H), −206.8 (m, 1F), −118.9 (d, 1F), −112.6 (d, 1F). |
| 11 | 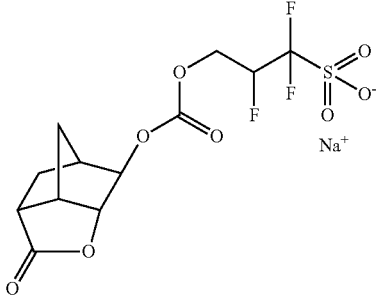 | $^{19}$F-NMR (DMSO-d$_6$). [ppm]: −206.0 (m, 1F), −120.0 (d, 1F), −110.0 (d, 1F). | $^1$H-NMR and $^{19}$F-NMR (CDCl$_3$). [ppm]: 1.60-1.74 (m, 2H), 2.01-2.10 (m, 2H), 2.55 (dd, 1H), 2.63 (s, 1H), 3.20 (s, 1H), 4.46 (s, 1H), 4.52-4.62 (m, 2H), 4.96 (dd, 1H), 5.31 (m, 1H), 7.69-7.83 (m, 15H), −207.0 (m, 1F), −119.3 (d, 1F), −112.1 (d, 1F). |

TABLE 1-continued
| Ex. | Structures | Intermediate Physical properties | Final product Physical properties |
|---|---|---|---|
| 12 | 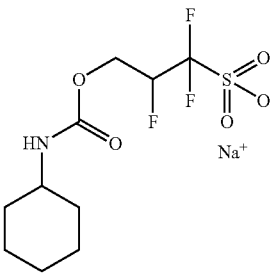 | ¹H-NMR and ¹⁹F-NMR (DMSO-$d_6$). [ppm]: 1.00-1.79 (m, 10H), 3.23 (m, 1H), 4.11 (m, 1H), 4.59 (dd, 1H), 5.01 (m, 1H), −205.2 (m, 1F), −119.8 (d, 1F), −111.7 (d, 1F). | ¹H-NMR and ¹⁹F-NMR (DMSO-$d_6$). [ppm]: 0.99-1.80 (m, 10H), 3.24 (m, 1H), 4.15 (m, 1H), 4.59 (dd, 1H), 5.01 (m, 1H), 7.28 (d, 1H), 7.74-7.88 (m, 15H), −205.3 (m, 1F), −119.8 (d, 1F), −111.7 (d, 1F). |
| | 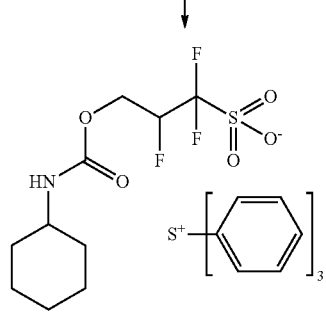 | | |
| 13 | 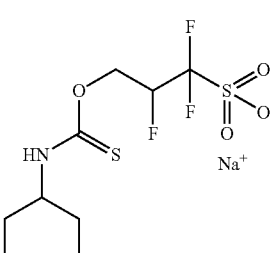 | ¹H-NMR and ¹⁹F-NMR (DMSO-$d_6$). [ppm]: 0.99-1.90 (m, 10H), 3.86 (m, 1H), 4.48 (m, 1H), 4.97 (dd, 1H), 5.15 (m, 1H), 9.21-9.36 (d, 1H), −204.1 (m, 1F), −119.6 (d, 1F), −111.6 (d, 1F). | ¹H-NMR and ¹⁹F-NMR (DMSO-$d_6$). [ppm]: 0.99-1.88 (m, 10H), 3.60 (m, 1H), 4.49 (m, 1H), 4.95 (dd, 1H), 5.15 (m, 1H), 7.73-7.88 (m, 15H), 9.21-9.36 (d, 1H), −204.1 (m, 1F), −119.6 (d, 1F), −111.7 (d, 1F). |
| | 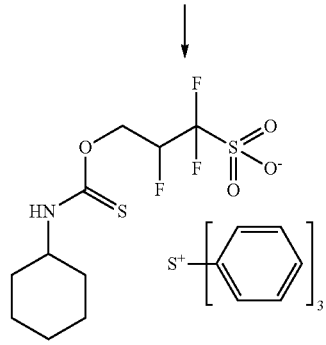 | | |

TABLE 1-continued
| Ex. | Structures | Intermediate Physical properties | Final product Physical properties |
|---|---|---|---|
| 14 | 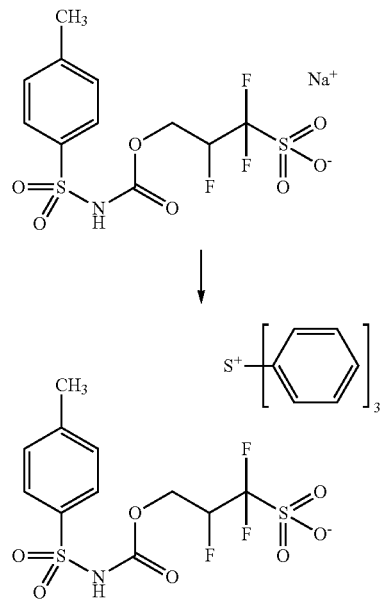 | ¹H-NMR and ¹⁹F-NMR (DMSO-$d_6$). [ppm]: 2.34 (s, 3H), 3.97 (m, 1H), 4.42 (dd, 1H), 4.91 (m, 1H), 7.28 (d, 2H), 7.67 (d, 2H), —NH— is not observed. −205.2 (m, 1F), −119.7 (d, 1F), −111.7 (d, 1F). | ¹H-NMR and ¹⁹F-NMR (CDCl$_3$). [ppm]: 2.38 (s, 3H), 4.30 (m, 1H), 4.61 (dd, 1H), 5.06 (m, 1H), 7.24 (d, 2H), 7.67-7.78 (m, 15H), 7.87 (d, 2H), —NH— is not observed. −205.5 (m, 1F), −118.0 (d, 1F), −113.0 (d, 1F). |
| 15 | 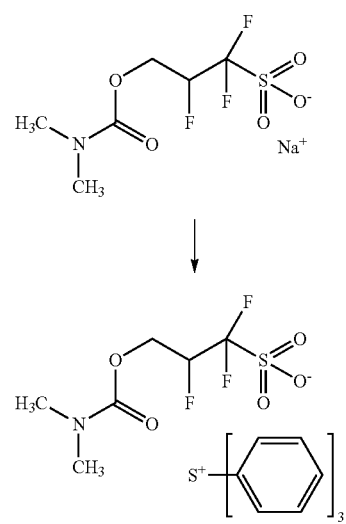 | ¹H-NMR and ¹⁹F-NMR (DMSO-$d_6$). [ppm]: 2.80 (bs, 3H), 2.84 (bs, 3H), 4.20 (m, 1H), 4.59 (dd, 1H), 5.08 (m, 1H), −206.3 (m, 1F), −119.6 (d, 1F), −111.4 (d, 1F). | ¹H-NMR and ¹⁹F-NMR (CDCl$_3$). [ppm]: 2.90 (s, 6H), 4.53 (m, 1H), 4.79 (dd, 1H), 5.29 (m, 1H), 7.67-7.79 (m, 15H), −206.3 (m, 1F), −118.2 (d, 1F), −113.2 (d, 1F). |

TABLE 1-continued
| Ex. | Structures | Intermediate Physical properties | Final product Physical properties |
|---|---|---|---|
| 16 | 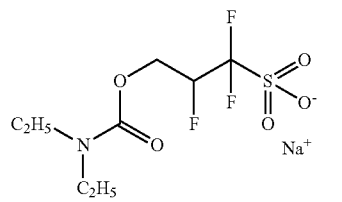 | $^1$H-NMR and $^{19}$F-NMR (DMSO-$d_6$). [ppm]: 1.02 (t, 6H), 3.19 (q, 4H), 4.21 (ddd, 1H), 4.59 (dd, 1H), 5.06 (m, 1H), −206.4 (m, 1F), −119.5 (d, 1F), −111.7 (d, 1F). | $^1$H-NMR and $^{19}$F-NMR (CDCl$_3$). [ppm]: 1.09 (t, 6H), 3.27 (q, 4H), 4.53 (ddd, 1H), 4.78 (dd, 1H), 5.32 (m, 1H), 7.67-7.79 (m, 15H), −206.2 (m, 1F), −118.0 (d, 1F), −113.6 (d, 1F). |
| 17 | 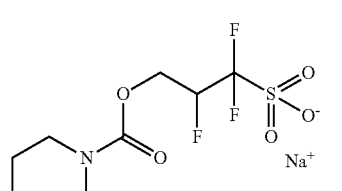 | $^1$H-NMR and $^{19}$F-NMR (DMSO-$d_6$). [ppm]: 3.35 (m, 4H), 3.54 (m, 4H), 4.23 (ddd, 1H), 4.64 (dd, 1H), 5.10 (m, 1H), −206.2 (m, 1F), −119.6 (d, 1F), −111.5 (d, 1F). | $^1$H-NMR and $^{19}$F-NMR (CDCl$_3$). [ppm]: 3.49 (m, 4H), 3.64 (m, 4H), 4.56 (ddd, 1H), 4.84 (dd, 1H), 5.30 (m, 1H), 7.68-7.79 (m, 15H), −206.8 (m, 1F), −118.8 (d, 1F), −113.5 (d, 1F). |

TABLE 1-continued
| Ex. | Structures | Intermediate Physical properties | Final product Physical properties |
|---|---|---|---|
| 18 | 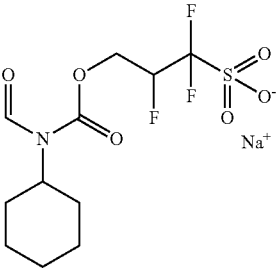 | ¹H-NMR and ¹⁹F-NMR (DMSO-d₆). [ppm]: 0.99-2.03 (m, 10H), 4.11 (m, 1H), 4.45 (ddd, 1H), 4.81 (dd, 1H), 5.27 (m, 1H), 9.10 (s, 1H), −206.7 (m, 1F), −119.4 (d, 1F), −111.1 (d, 1F). | ¹H-NMR and ¹⁹F-NMR (CDCl₃). [ppm]: 0.80-2.18 (m, 10H), 4.25 (m, 1H), 4.71 (ddd, 1H), 4.99 (dd, 1H), 5.35 (m, 1H), 7.68-7.81 (m, 15H), 9.22 (s, 1H), −207.1 (m, 1F), −119.1 (d, 1F), −112.2 (d, 1F). |
|  | 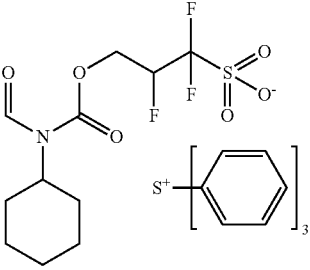 | | |
| 19 | 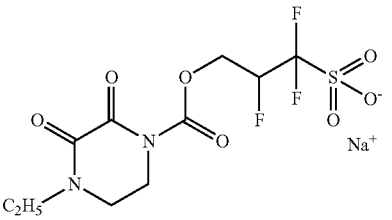 | ¹H-NMR and ¹⁹F-NMR (DMSO-d₆). [ppm]: 1.17 (t, 3H), 3.57 (m, 4H), 3.93 (m, 2H), 4.39 (ddd, 1H), 4.80 (dd, 1H), 5.17 (m, 1H), −205.9 (m, 1F), −119.7 (d, 1F), −111.4 (d, 1F). | ¹H-NMR and ¹⁹F-NMR (CDCl₃). [ppm]: 1.20 (t, 3H), 3.55 (m, 4H), 4.06 (m, 2H), 4.71 (ddd, 1H), 4.94 (dd, 1H), 5.29 (m, 1H), 7.71-7.81 (m, 15H), −206.9 (m, 1F), −119.2 (d, 1F), −111.5 (d, 1F). |
|  | 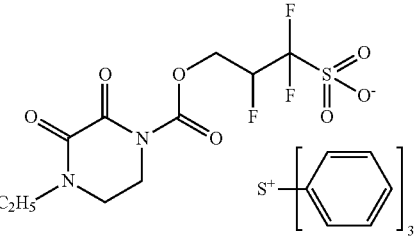 | | |

TABLE 1-continued
| Ex. | Structures | Intermediate Physical properties | Final product Physical properties |
|---|---|---|---|
| 20 | 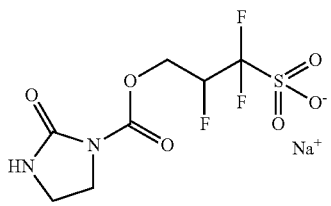 | not isolated. | $^1$H-NMR and $^{19}$F-NMR (CDCl$_3$). [ppm]: 3.45 (bs, 1H), 3.89 (m, 3H), 4.44 (m, 1H), 4.82 (dd, 1H), 5.16 (m, 1H), 7.68-7.81 (m, 15H), —NH— is not observed. −206.7 (m, 1F), −119.1 (d, 1F), −112.1 (d,1F). |
| | 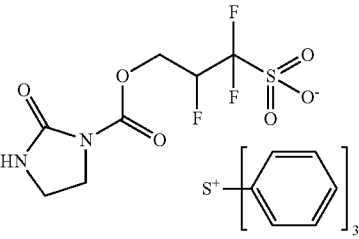 | | |
| 21 | 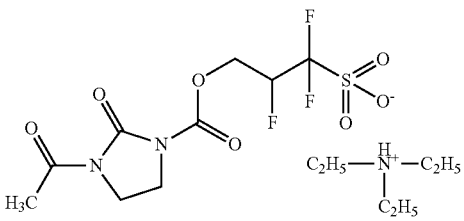 | $^1$H-NMR and $^{19}$F-NMR (DMSO-d$_6$). [ppm]: 1.15 (t, 9H), 2.37 (s, 3H), 3.03 (q, 6H), 3.70 (m, 4H), 4.39 (ddd, 1H), 4.77 (dd, 1H), 5.15 (m, 1H), −206.2 (m, 1F), −119.6 (d, 1F), −111.4 (d, 1F). | $^1$H-NMR and $^{19}$F-NMR (CDCl$_3$). [ppm]: 2.53 (s, 3H), 3.85 (m, 4H), 4.72 (ddd, 1H), 4.95 (dd, 1H), 5.35 (m, 1H), 7.72-7.81 (m, 15H), −207.3 (m, 1F), −119.1 (d, 1F), −111.9 (d, 1F). |
| | 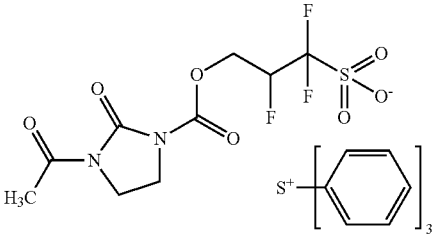 | | |

//

TABLE 1-continued

| Ex. | Structures | Intermediate Physical properties | Final product Physical properties |
|---|---|---|---|
| 22 | 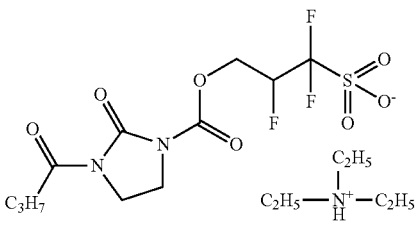 | $^1$H-NMR and $^{19}$F-NMR (DMSO-$d_6$). [ppm]: 0.89 (t, 3H), 1.19 (t, 9H), 1.56 (m, 2H), 2.78 (t, 3H), 3.04 (q, 6H), 3.73 (m, 4H), 4.40 (ddd, 1H), 4.78 (dd, 1H), 5.17 (m, 1H), −206.3 (m, 1F), −119.6 (d, 1F), −111.4 (d, 1F). | H-NMR and $^{19}$F-NMR (CDCl$_3$). [ppm]: 0.96 (t, 3H), 1.68 (m, 2H), 2.89 (t, 2H), 3.85 (m, 4H), 4.70 (ddd, 1H), 4.94 (dd, 1H), 5.34 (m, 1H), 7.70-7.83 (m, 15H), −207.1 (m, 1F), −119.1 (d, 1F), −111.9 (d, 1F). |
| | 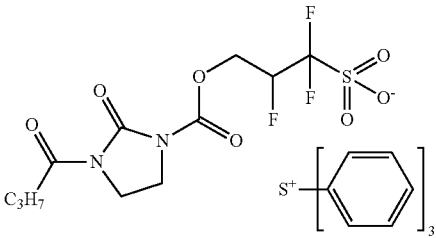 | | |
| 23 | 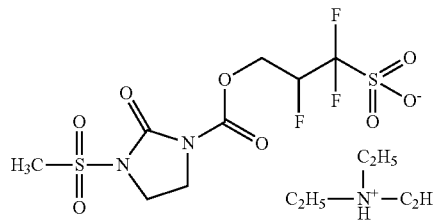 | $^1$H-NMR and $^{19}$F-NMR (DMSO-$d_6$). [ppm]: 1.17 (t, 9H), 3.03 (q, 6H) 3.21 (s, 3H), 3.64-3.88 (m, 4H), 4.39 (ddd, 1H), 4.78 (dd, 1H), 5.15 (m, 1H), −206.2 (m, 1F), −119.6 (d, 1F), −111.4 (d, 1F). | $^1$H-NMR and $^{19}$F-NMR (CDCl$_3$). [ppm]: 3.31 (s, 3H), 3.88 (t, 2H), 3.96 (t, 2H), 4.72 (ddd, 1H), 4.92 (dd, 1H), 5.31 (m, 1H), 7.68-7.81 (m, 15H), −207.3 (m, 1F), −119.2 (d, 1F), −111.7 (d, 1F). |
| | 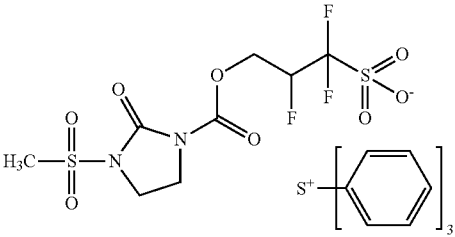 | | |

TABLE 1-continued

| Ex. | Structures | Intermediate Physical properties | Final product Physical properties |
|---|---|---|---|
| 24 | 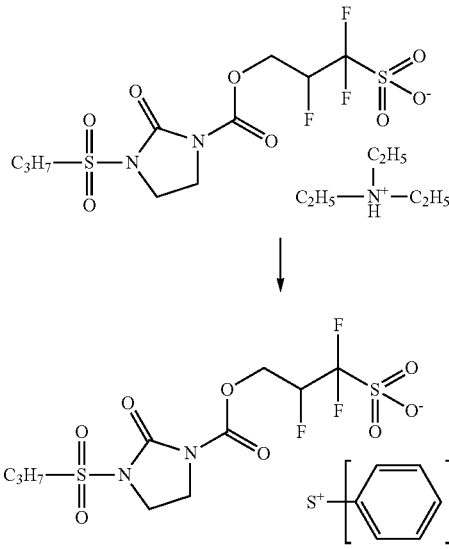 | $^1$H-NMR and $^{19}$F-NMR (DMSO-$d_6$). [ppm]: 0.97 (t, 3H), 1.18 (t, 9H), 1.75 (m, 2H), 3.04 (q, 6H), 3.44 (t, 2H), 3.77 (m, 4H), 4.37 (ddd, 1H), 4.77 (dd, 1H), 5.15 (m, 1H), −206.1 (m, 1F), −119.6 (d, 1F), −111.4 (d, 1F). | $^1$H-NMR and $^{19}$F-NMR (CDCl$_3$). [ppm]: 1.09 (t, 3H), 1.88 (m, 2H), 3.48 (t, 2H), 3.90 (m, 4H), 4.72 (ddd, 1H), 4.93 (dd, 1H), 5.33 (m, 1H), 7.70-7.84 (m, 15H), −207.3 (m, 1F), −119.2 (d, 1F), −111.7 (d, 1F). |
| 25 | 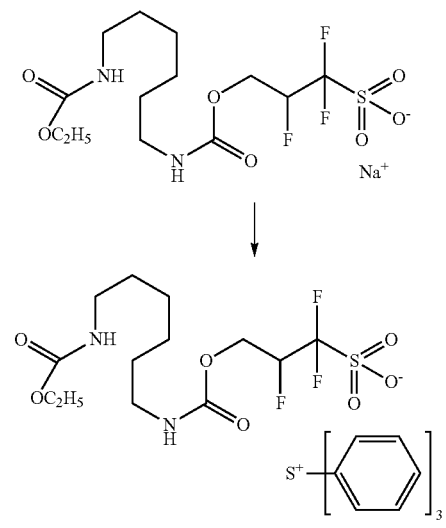 | $^1$H-NMR and $^{19}$F-NMR (DMSO-$d_6$). [ppm]: 1.12 (t, 3H), 1.21 (m, 4H), 1.36 (m, 4H), 2.93 (q, 4H), 3.93 (q, 2H), 4.12 (ddd, 1H), 4.58 (dd, 1H), 5.00 (m, 1H), 6.98-7.34 (m, 2H), −205.5 (m, 1F), −119.7 (d, 1F), −111.7 (d, 1F). | $^1$H-NMR and $^{19}$F-NMR (CDCl$_3$). [ppm]: 1.16-1.60 (m, 11H), 3.11 (q, 4H), 4.08 (q, 2H), 4.41 (m, 1H), 4.60-5.34 (m, 4H), 7.65-7.83 (m, 15H), −205.9 (m, 1F), −117.7 (d, 1F), −113.5 (d, 1F). |
| 26 | 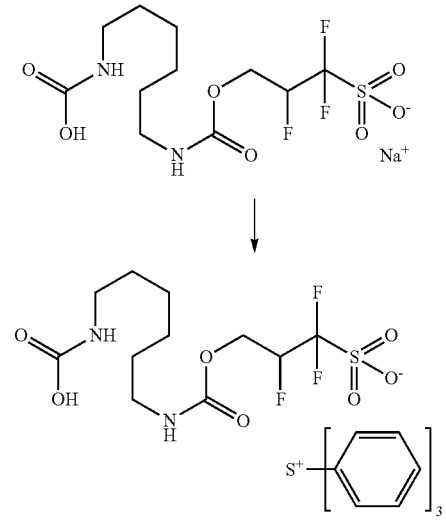 | $^1$H-NMR and $^{19}$F-NMR (DMSO-$d_6$). [ppm]: 1.20 (m, 4H), 1.32 (m, 4H), 2.93 (m, 4H), 4.12 (ddd, 1H), 4.58 (dd, 1H), 5.00 (m, 1H), 5.71 (m, 1H), 7.34 (m, 1H), −205.5 (m, 1F), −119.6 (d, 1F), −111.7 (d, 1F). | $^1$H-NMR and $^{19}$F-NMR (DMSO-$d_6$). [ppm]: 1.21 (m, 4H), 1.35 (m, 4H), 2.93 (m, 4H), 4.12 (ddd, 1H), 4.59 (dd, 1H), 5.00 (m, 1H), 5.69 (m, 1H), 7.33 (m, 1H), 7.73-7.88 (m, 15H), −205.5 (m, 1F), −119.7 (d, 1F), −111.7 (d, 1F). |

TABLE 1-continued
| Ex. | Structures | Intermediate Physical properties | Final product Physical properties |
|---|---|---|---|
| 27 | 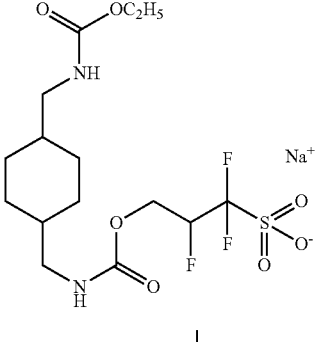 | ¹H-NMR and ¹⁹F-NMR (DMSO-d₆). [ppm]: 0.37-0.79 (m, 3H), 1.13 (t, 3H), 1.20-1.75 (m, 7H), 2.75-3.00 (m, 4H), 3.94 (q, 2H), 4.13 (m, 1H), 4.59 (dd, 1H), 5.01 (m, 1H), 7.03 (m, 1H), 7.35 (m, 1H), −205.5 (m, 1F), −119.8 (d, 1F), −111.7 (d, 1F). | ¹H-NMR and ¹⁹F-NMR (DMSO-d₆). [ppm]: 0.38-0.79 (m, 3H), 1.12 (t, 3H), 1.20-1.74 (m, 7H), 2.74-3.00 (m, 4H), 3.94 (q, 2H), 4.13 (m, 1H), 4.60 (dd, 1H), 5.02 (m, 1H), 7.05 (m, 1H), 7.35 (m, 1H), 7.74-7.88 (m, 15H), −205.8 (m, 1F), −120.2 (d, 1F), −112.1 (d, 1F). |
| 28 | 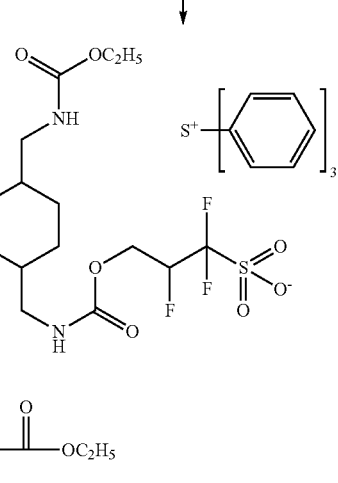 | ¹H-NMR and ¹⁹F-NMR (DMSO-d₆). [ppm]: 0.77-1.82 (m, 23H), 3.10-3.49 (m, 2H), 3.93 (q, 2H), 4.10 (m, 1H), 4.57 (ddd, 1H), 5.01 (m, 1H), 6.93 (m, 1H), 7.24 (m, 1H), −205.3 (m, 1F), −119.7 (d, 1F), −111.7 (d, 1F). | ¹H-NMR and ¹⁹F-NMR (DMSO-d₆). [ppm]: 0.77-1.83 (m, 23H), 3.09-3.49 (m, 2H), 3.95 (q, 2H), 4.11 (m, 1H), 4.60 (m, 1H), 5.01 (m, 1H), 6.94 (m, 1H), 7.25 (m, 1H), 7.74-7.88 (m, 15H), −205.6 (m, 1F), −120.2 (d, 1F), −112.1 (d, 1F). |

TABLE 1-continued

| Ex. | Structures | Intermediate Physical properties | Final product Physical properties |
|---|---|---|---|
| 30 | 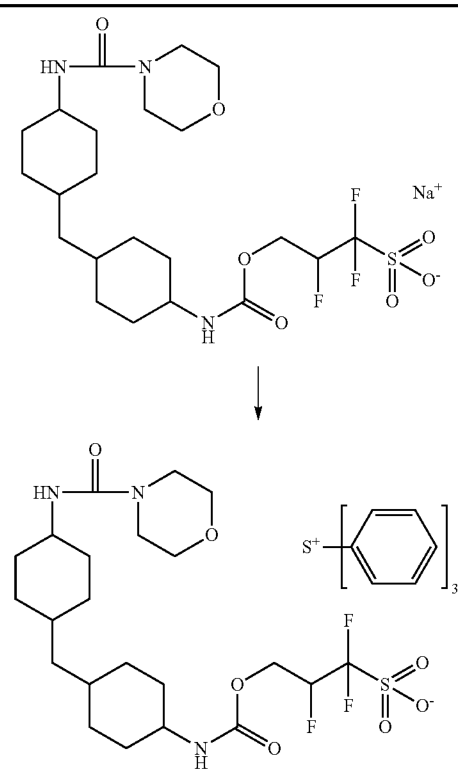 | ¹H-NMR and ¹⁹F-NMR (DMSO-$d_6$). [ppm]: 0.79-1.82 (m, 20H), 3.21 (m, 4H), 3.25-3.59 (m, 6H), 4.11 (m, 1H), 4.58 (ddd, 1H), 5.02 (m, 1H), 6.05 (m, 1H), 7.26 (m, 1H), −205.2 (m, 1F), −119.6 (d, 1F), −111.7 (d, 1F). | ¹H-NMR and ¹⁹F-NMR (DMSO-$d_6$). [ppm]: 0.77-1.82 (m, 20H), 3.10-3.59 (m, 10H), 4.12 (m, 1H), 4.60 (ddd, 1H), 5.01 (m, 1H), 6.07 (m, 1H), 7.26 (m, 1H), 7.74-7.87 (m, 15H), −205.3 (m, 1F), −119.9 (d, 1F), −111.7 (d, 1F). |
| | | ¹H-NMR and ¹⁹F-NMR (DMSO-$d_6$). [ppm]: 0.83-1.86 (m, 20H), 3.48 (m, 2H), 4.15 (m, 2H), 4.60 (m, 2H), 5.03 (m, 2H), 7.25 (m, 2H), −205.8 (m, 2F), −120.2 (d, 2F), −110.8 (d, 2F). | ¹H-NMR and ¹⁹F-NMR (CDCl$_3$). [ppm]: 0.84-2.00 (m, 20H), 3.74 (m, 2H), 4.45 (m, 2H), 4.80 (m, 2H), 5.27 (m, 2H), 7.56-7.80 (m, 32H), −206.0 (m, 2F), −118.3 (d, 2F), −113.0 (d, 2F). |

TABLE 1-continued

| Ex. | Structures | Intermediate Physical properties | Final product Physical properties |
|---|---|---|---|
| 31 | 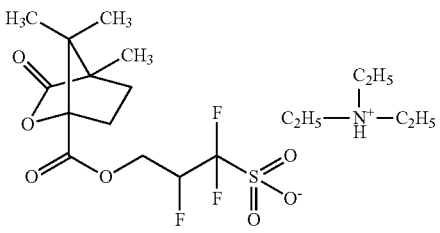 | $^1$H-NMR and $^{19}$F-NMR (DMSO-d$_6$). [ppm]: 0.82 (s, 3H), 1.00 (s, 6H), 1.16 (t, 9H), 1.54 (m, 1H), 1.90-2.03 (m, 2H), 2.39 (m, 1H), 3.08 (q, 6H), 4.52 (m, 1H), 4.77 (ddd, 1H), 5.17 (m, 1H), 8.83 (bs, 1H), −206.9 (m, 1F), −119.5 (d, 1F), −111.3 (d, 1F). | $^1$H-NMR and $^{19}$F-NMR (CDCl$_3$). [ppm]: 0.95 (s, 3H), 1.06 (s, 3H), 1.11 (s, 3H), 1.31 (s, 18H), 1.69 (m, 1H), 1.87-2.08 (m, 2H), 2.45 (m, 1H), 4.65-4.94 (m, 2H), 5.26 (m, 1H), 7.49 (d, 4H), 7.85 (d, 4H), −206.9 (m, 1F), −118.3 (d, 1F), −112.6 (d, 1F). |
| 32 | 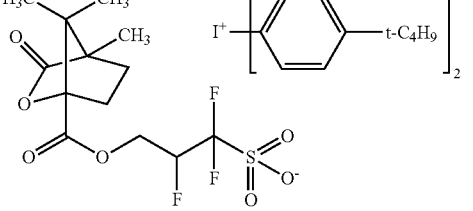 | $^1$H-NMR and $^{19}$F-NMR (CDCl$_3$). [ppm]: 0.95 (s, 3H), 1.06 (s, 3H), 1.11 (s, 3H), 1.31 (s, 18H), 1.69 (m, 1H), 1.87-2.08 (m, 2H), 2.45 (m, 1H), 4.65-4.94 (m, 2H), 5.26 (m, 1H), 7.49 (d, 4H), 7.85 (d, 4H), −206.9 (m, 1F), −118.3 (d, 1F), −112.6 (d, 1F). | $^1$H-NMR and $^{19}$F-NMR (CDCl$_3$). [ppm]: 0.96 (s, 3H), 1.07 (s, 3H), 1.11 (s, 3H), 1.35 (s, 9H), 1.68 (ddd, 1H), 1.94 (ddd, 1H), 2.04 (ddd, 1H), 2.46 (m, 1H), 2.59 (m, 4H), 3.60 (m, 2H), 4.30 (m, 2H), 4.71-4.99 (m, 2H), 5.31 (m, 1H), 7.65 (d, 2H), 7.69 (d, 2H), −206.9 (m, 1F), −118.5 (d, 1F), −112.6 (d, 1F). |

TABLE 1-continued

| Ex. | Structures | Intermediate Physical properties | Final product Physical properties |
|---|---|---|---|
| 33 | 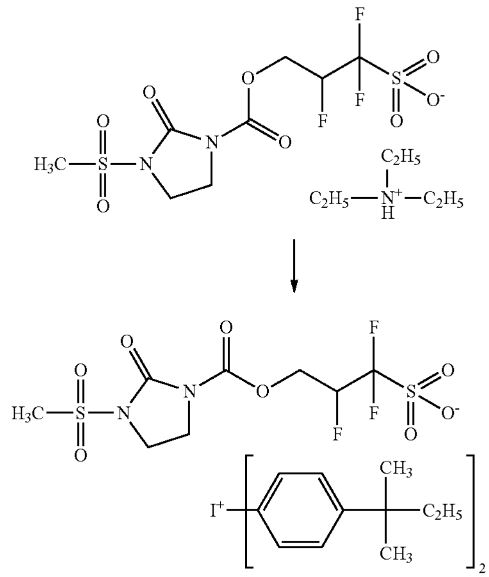 | Same to example 23 intermediate | $^1$H-NMR and $^{19}$F-NMR (DMSO-$d_6$). [ppm]: 0.56 (t, 6H), 1.20 (s, 12H), 1.58 (q, 4H), 3.31 (s, 3H), 3.72-3.86 (m, 4H), 4.32-4.45 (m, 1H), 4.78 (dd, 1H), 5.03-5.26 (m, 1H), 7.45 (d, 4H), 8.14 (d, 4H), −206.3 (m, 1F), −119.6 (d, 1F), −111.4 (d, 1F). |
| 34 | 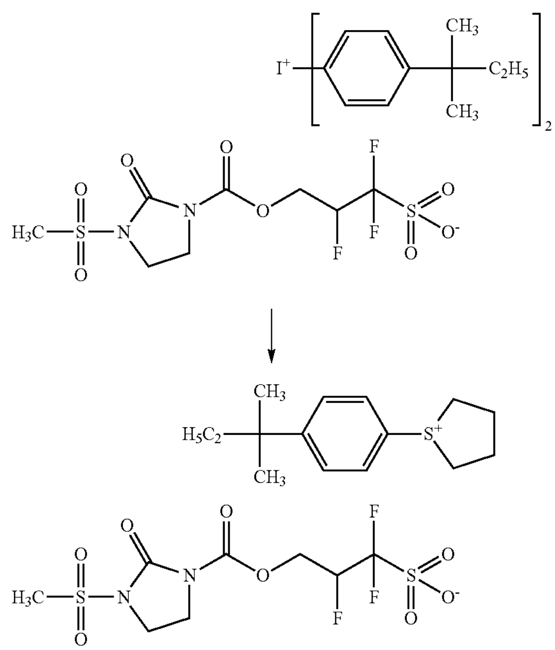 | Same to example 33 | $^1$H-NMR and $^{19}$F-NMR (DMSO-$d_6$). [ppm]: 0.60 (t, 3H), 1.25 (s, 6H), 1.63 (q, 2H), 2.20-2.38 (m, 4H), 3.31 (s, 3H), 3.67-3.93 (m, 8H), 4.33-4.45 (m, 1H), 4.78 (dd, 1H), 5.04-5.26 (m, 1H), 7.61 (d, 2H), 7.83 (d, 2H), −206.2 (m, 1F), −119.6 (d, 1F), −111.4 (d, 1F). |
| 35 | 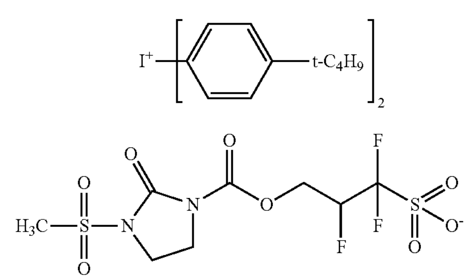 | Same to example 23 intermediate | $^1$H-NMR and $^{19}$F-NMR (DMSO-$d_6$). [ppm]: 1.22 (s, 18H), 3.32 (s, 3H), 3.71-3.86 (m, 4H), 4.33-4.46 (m, 1H), 4.79 (dd, 1H), 5.04-5.27 (m, 1H), 7.52 (d, 4H), 8.12 (d, 4H), −206.3 (m, 1F), −119.6 (d, 1F), −111.3 (d, 1F). |

TABLE 1-continued

| Ex. | Structures | Intermediate Physical properties | Final product Physical properties |
|---|---|---|---|
| 36 | 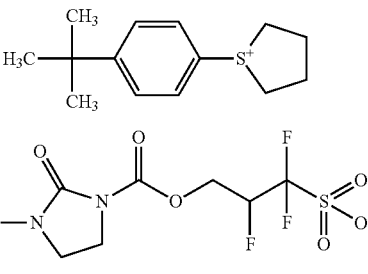 | Same to example 35 | $^1$H-NMR and $^{19}$F-NMR (DMSO-$d_6$). [ppm]: 1.27 (s, 9), 2.21-2.38 (m, 4H), 3.29 (s, 3H), 3.67-3.95 (m, 8H), 4.35-4.46 (m, 1H), 4.79 (dd, 1H), 5.05-5.28 (m, 1H), 7.67 (d, 2H), 7.83 (d, 2H), −206.2 (m, 1F), −119.5 (d, 1F), −111.4 (d, 1F). |
| 37 | 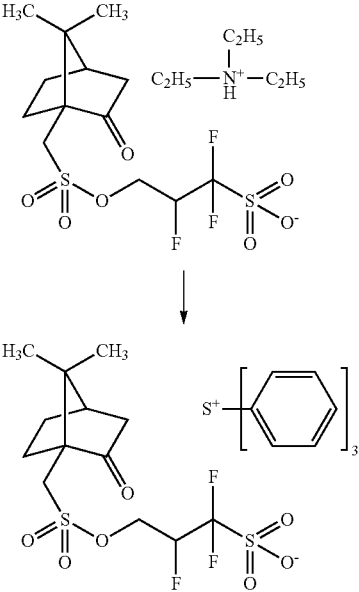 | $^1$H-NMR and $^{19}$F-NMR (DMSO-$d_6$). [ppm]: 0.79 (s, 3H), 1.00 (s, 3H), 1.17-1.12 (t, 9H), 1.41 (m, 1H), 1.54 (m, 1H), 1.97-1.88 (m, 2H), 2.05 (m, 1H), 2.36-2.19 (m, 2H), 3.05 (q, 6H), 3.54-3.38 (m, 2H), −205.9 (m, 1F), −119.9 (m, 1F), −111.3 (m, 1F). | $^1$H-NMR and $^{19}$F-NMR (CDCl$_3$). [ppm]: 0.87 (s, 3H), 1.09 (s, 3H), 1.42 (m, 1H), 1.70 (m, 1H), 1.79 (m, 1H), 2.00-2.10 (m, 2H), 2.35-2.45 (m, 2H), 3.09 (d, 1H), 3.62 (dd, 1H), 4.63 (m, 1H), 5.01 (m, 1H), 5.29 (m, 1H), 7.80-7.69 (m, 15H), −205.7 (m, 1F), −119.0 (m, 1F), −112.0 (m, 1F). |
| 38 | 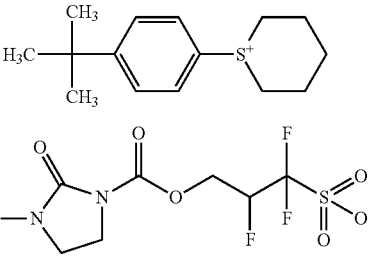 | Same to example 35 | $^1$H-NMR and $^{19}$F-NMR (DMSO-$d_6$). [ppm]: 1.30 (s, 9H), 1.58-1.80 (m, 2H), 1.82-1.94 (m, 2H), 2.10-2.20 (m, 2H), 3.32 (s, 3H), 3.70-3.84 (m, 8H), 4.33-4.46 (m, 1H), 4.78 (dd, 1H), 5.04-5.25 (m, 1H), 7.72 (d, 2H), 7.95 (d, 2H), −206.3 (m, 1F), −119.6 (d, 1F), −111.3 (d, 1F). |
| 39 | 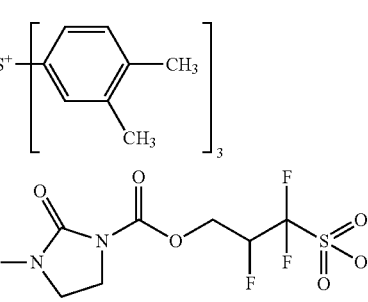 | Same to example 23 intermediate | $^1$H-NMR and $^{19}$F-NMR (DMSO-$d_6$). [ppm]: 2.28 (s, 9H), 2.32 (s, 9H), 3.31 (s, 3H), 3.73-3.84 (m, 4H), 4.33-4.45 (m, 1H), 4.78 (dd, 1H), 5.04-5.26 (m, 1H), 7.44 (d, 3H), 7.50 (d, 3H), 7.62 (s, 3H), −206.2 (m, 1F), −119.6 (d, 1F), −111.3 (d, 1F). |

TABLE 1-continued

| Ex. | Structures | Intermediate Physical properties | Final product Physical properties |
|---|---|---|---|
| 40 | 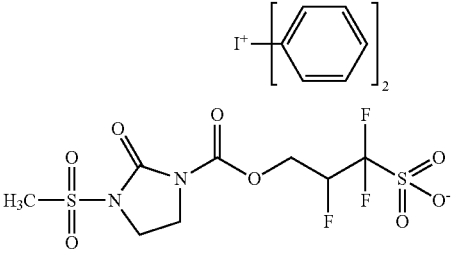 | $^1$H-NMR and $^{19}$F-NMR (DMSO-$d_6$). [ppm]: 3.31 (s, 3H), 3.73-3.87 (m, 4H), 4.35-4.46 (m, 1H), 4.80 (dd, 1H), 5.05-5.27 (m, 1H), 7.51 (t, 4H), 7.64 (t, 2H), 8.22 (d, 4H), −206.2 (m, 1F), −119.6 (d, 1F), −111.3 (d, 1F). | $^1$H-NMR and $^{19}$F-NMR (DMSO-$d_6$). [ppm]: 3.30 (s, 3H), 3.72-3.84 (m, 4H), 4.33-4.44 (m, 1H), 4.78 (dd, 1H), 5.04-5.26 (m, 1H), 7.55-7.61 (m, 4H), 7.65-7.70 (m, 1H), 7.74 (t, 2H), 7.94 (t, 2H), 8.35 (d, 2H), 8.50 (d, 2H), −206.2 (m, 1F), −119.6 (d, 1F), −111.4 (d, 1F). |
| 41 | 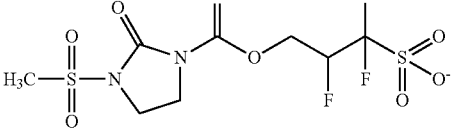 | Same to example 23 intermediate | $^1$H-NMR and $^{19}$F-NMR (DMSO-$d_6$). [ppm]: 2.26 (s, 18H), 3.31 (s, 3H), 3.70-3.86 (m, 13H), 4.33-4.46 (m, 1H), 4.78 (dd, 1H), 5.03-5.26 (m, 1H), 7.57 (s, 6H), −206.3 (m, 1F), −119.6 (d, 1F), −111.3 (d, 1F). |
| 42 | 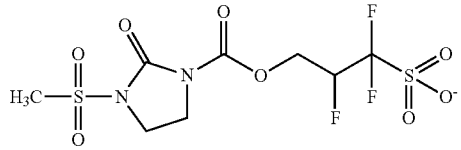 | Same to example 23 intermediate | $^1$H-NMR and $^{19}$F-NMR (CDCl$_3$). [ppm]: 1.00-1.95 (m, 60H), 2.96 (t, 6H), 3.34 (s, 3H), 3.83-3.90 (m, 2H), 3.93-4.02 (m, 2H), 4.72-5.01 (m, 2H), 5.25-5.47 (m, 1H), 7.06 (s, 6H), −207.5 (m, 1F), −118.6 (d, 1F), −111.5 (d, 1F). |

TABLE 1-continued

| Ex. | Structures | Intermediate Physical properties | Final product Physical properties |
|---|---|---|---|
| 43 | 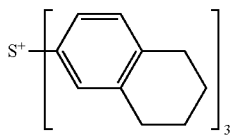 | Same to example 23 intermediate | $^1$H-NMR and $^{19}$F-NMR (DMSO-$d_6$). [ppm]: 1.67-1.80 (m, 12H), 2.72-2.85 (m, 12H), 3.31 (s, 3H), 3.74-3.85 (m, 4H), 4.33-4.46 (m, 1H), 4.78 (dd, 1H), 5.05-5.25 (m, 1H), 7.41 (s, 6H), 7.58 (s, 3H), −206.3 (m, 1F), −119.6 (d, 1F), −111.6 (d, 1F). |
| 44 | 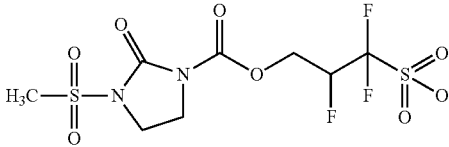 | Same to example 23 intermediate | $^1$H-NMR and $^{19}$F-NMR (CDCl$_3$). [ppm]: 2.16 (m, 4H), 3.01 (m, 8H), 3.33 (s, 3H), 3.85-3.89 (m, 2H), 3.92-4.00 (m, 2H), 4.67-4.80 (m, 1H), 4.95 (dd, 1H), 5.21-5.44 (m, 1H), 7.43 (d, 2H), 7.49-7.53 (m, 4H), 7.65-7.77 (m, 5H), −207.5 (m, 1F), −119.4 (d, 1F), −111.5 (d, 1F). |
| 45 | 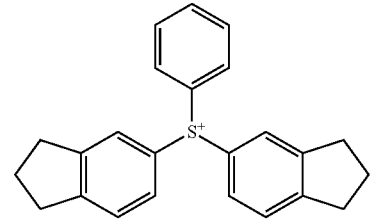 | Same to example 23 intermediate | $^1$H-NMR and $^{19}$F-NMR (DMSO-$d_6$). [ppm]: 2.57 (s, 9H), 3.31 (s, 3H), 3.72-3.83 (m, 4H), 4.32-4.43 (m, 1H), 4.79 (dd, 1H), 5.04-5.26 (m, 1H), 7.25 (d, 6H), 7.40 (d, 6H), 7.86 (d, 6H), 8.04 (d, 6H), −206.2 (m, 1F), −119.6 (d, 1F), −111.3 (d, 1F). |

TABLE 1-continued

| Ex. | Structures | Intermediate Physical properties | Final product Physical properties |
|---|---|---|---|
| 46 | 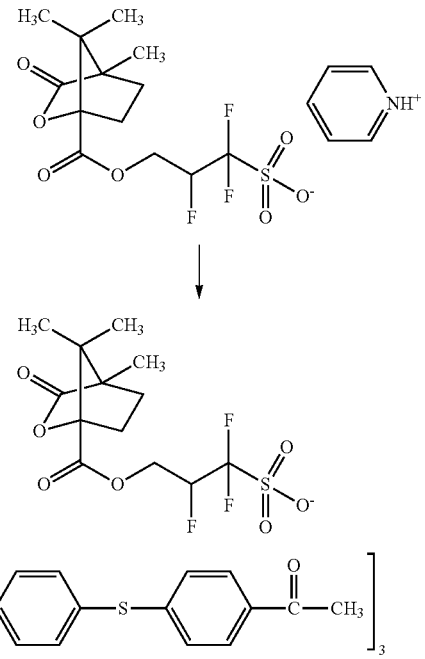 | ¹H-NMR and ¹⁹F-NMR (CDCl₃). [ppm]: 0.94 (s, 3H), 1.06 (s, 3H), 1.11 (s, 3H), 1.70 (m, 1H), 1.94 (m, 1H), 2.03 (m, 1H), 2.45 (m, 1H), 4.72 (m, 1H), 4.86 (m, 1H), 5.31 (m, 1H), 8.04 (t, 2H), 8.53 (t, 1H), 8.92 (d, 2H), −113.8 (d, 1F), −117.4 (d, 1F), −206.8 (m, 1F). | ¹H-NMR and ¹⁹F-NMR (CDCl₃). [ppm]: 0.92 (s, 3H), 1.05 (s, 3H), 1.10 (s, 3H), 1.66 (m, 1H), 1.97 (m, 2H), 2.44 (m, 1H), 2.63 (s, 9H), 4.80 (m, 2H), 5.25 (m, 1H), 7.38 (d, 6H), 7.58 (m, 12H), 7.99 (d, 6H), −112.7 (d, 1F), −119.4 (dd, 1F), −207.5 (m, 1F). |
| 47 | 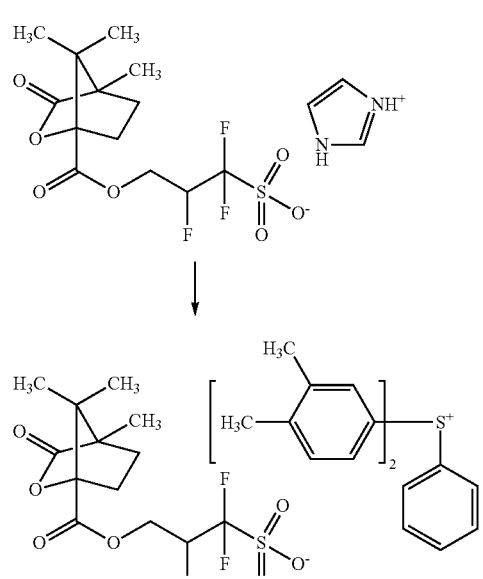 | ¹H-NMR and ¹⁹F-NMR (DMSO-d₆). [ppm]: 0.83 (s, 3H), 1.00 (s, 6H), 1.55 (m, 1H), 1.97 (m, 2H), 2.39 (m, 1H), 4.51 (m, 1H), 4.78 (m, 1H), 5.17 (m, 1H), 7.59 (s, 2H), 8.86 (s, 1H), −111.7 (d, 1F), −119.8 (d, 1F), −207.3 (m, 1F). | ¹H-NMR and ¹⁹F-NMR (CDCl₃). [ppm]: 0.94 (s, 3H), 1.06 (s, 3H), 1.10 (s, 3H), 1.67 (m, 1H), 1.95 (m, 2H), 2.45 (m, 1H), 4.55 (m, 2H), 5.26 (m, 1H), 7.35 (d, 2H), 7.44 (d, 2H), 7.49 (s, 2H), 7.69 (m, 5H), −112.5 (d, 1F), −120.3 (dd, 1F), −207.8 (m, 1F). |

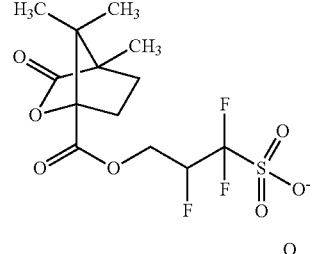

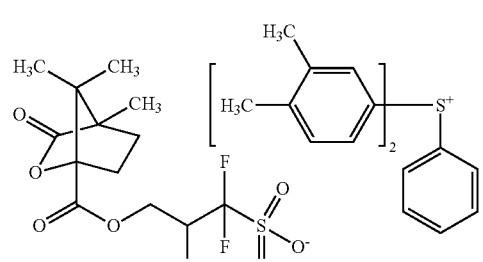

TABLE 1-continued

| Ex. | Structures | Intermediate Physical properties | Final product Physical properties |
|---|---|---|---|
| 48 | 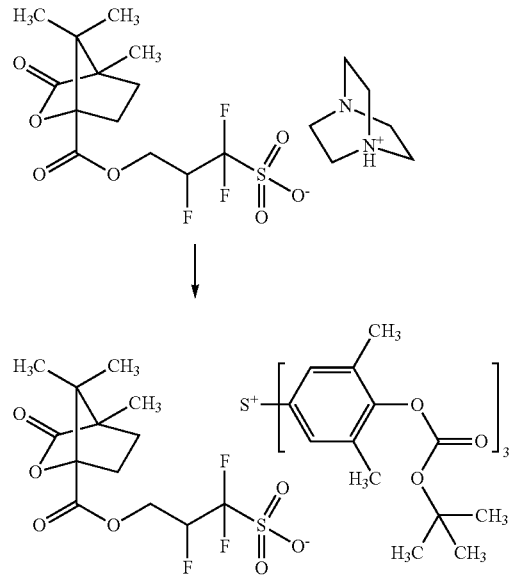 | $^1$H-NMR and $^{19}$F-NMR (CDCl$_3$). [ppm]: 0.96 (s, 3H), 1.07 (s, 3H), 1.12 (s, 3H), 1.68 (m, 1H), 1.95 (m, 1H), 2.03 (m, 1H), 2.45 (m, 1H), 3.24 (s, 12H), 4.70 (m, 1H), 4.85 (m, 1H), 5.26 (m, 1H), −113.7 (dd, 1F), −117.3 (d, 1F), −206.8 (m, 1F). | $^1$H-NMR and $^{19}$F-NMR (DMSO-d$_6$). [ppm]: 0.82 (s, 3H), 1.00 (s, 6H), 1.45-1.58 (m, 28H), 1.90-2.05 (m, 2H), 2.20 (s, 18H), 2.34-2.45 (m, 1H), 4.43-4.58 (m, 1H), 4.68-4.87 (m, 1H), 5.06-5.28 (m, 1H), 7.74 (s, 6H), −206.9 (m, 1F), −119.4 (d, 1F), −111.3 (d, 1F). |
| 49 | 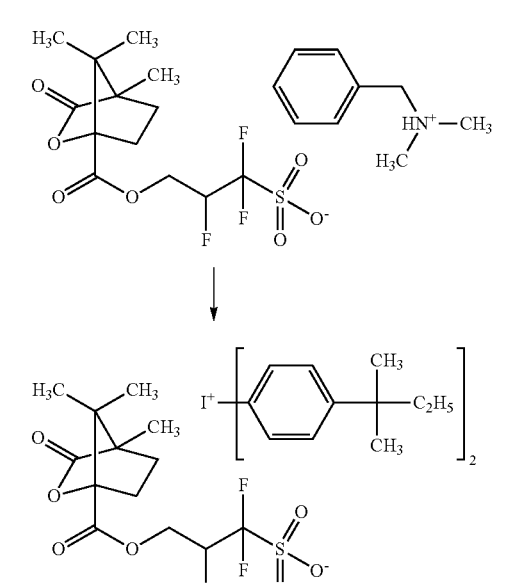 | $^1$H-NMR and $^{19}$F-NMR (CDCl$_3$). [ppm]: 0.96 (s, 3H), 1.06 (s, 3H), 1.12 (s, 3H), 1.69 (m, 1H), 1.95 (m, 1H), 2.03 (m, 1H), 2.45 (m, 1H), 2.85 (s, 6H), 4.23 (s, 2H), 4.79 (m, 2H), 5.29 (m, 1H), 7.47 (s, 5H), −113.6 (d, 1F), −117.4 (d, 1F), −206.6 (m, 1F). | $^1$H-NMR and $^{19}$F-NMR (CDCl$_3$). [ppm]: 0.66 (t, 6H), 0.94 (s, 3H), 1.05 (s, 3H), 1.11 (s, 3H), 1.27 (s, 12H), 1.65 (q, 4H), 1.68 (m, 1H), 1.94 (m, 1H), 2.04 (m, 1H), 2.45 (m, 1H), 4.74 (m, 2H), 5.20 (m, 1H), 7.42 (d, 4H), 7.90 (d, 4H), −112.6 (d, 1F), −118.3 (d, 1F), −206.8 (m, 1F). |

TABLE 1-continued

| Ex. | Structures | Intermediate Physical properties | Final product Physical properties |
|---|---|---|---|
| 50 | 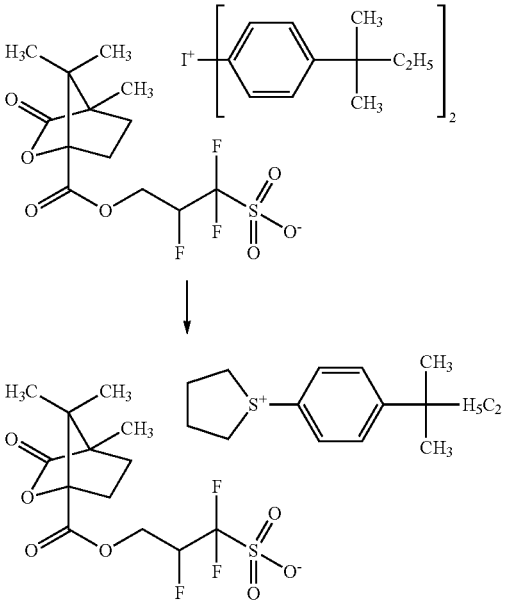 | Same to example 49 | $^1$H-NMR and $^{19}$F-NMR (CDCl$_3$). [ppm]: 0.67 (t, 3H), 0.95 (s, 3H), 1.07 (s, 3H), 1.11 (s, 3H), 1.30 (s, 6H), 1.67 (q, 2H), 1.68 (m, 1H), 1.99 (m, 2H), 2.45 (m, 1H), 2.58 (m, 4H), 3.66 (m, 2H), 4.27 (m, 2H), 4.82 (m, 2H), 5.29 (m, 1H), 7.60 (d, 2H), 7.71 (d, 2H), −112.6 (d, 1F), −118.6 (d, 1F), −206.9 (m, 1F). |
| 51 | 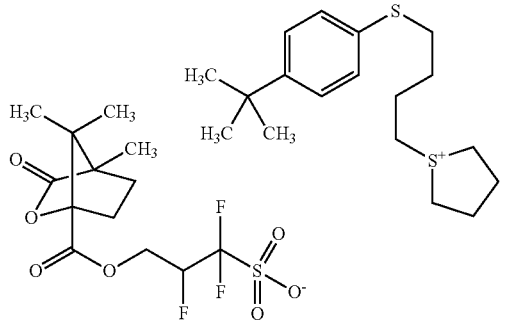 [SMILES: CC12CCC(C(=O)OCC(F)C(F)(F)S(=O)(=O)[O-])(OC1=O)C2(C)C ; CC(C)(C)c1ccc(SCCCC[S+]2CCCC2)cc1] | Same to example 31 | $^1$H-NMR (CDCl$_3$). [ppm]: 0.96 (s, 3H), 1.06 (s, 3H), 1.11 (s, 3H), 1.30 (s, 9H), 1.68 (m, 1H), 1.80-2.08 (m, 6H), 2.30-2.50 (m, 5H), 2.98 (t, 2H), 2.45 (m, 2H), 2.69 (m, 2H), 4.81 (m, 2H), 5.27 (m, 1H), 7.30 (m, 4H). |
| 52 | 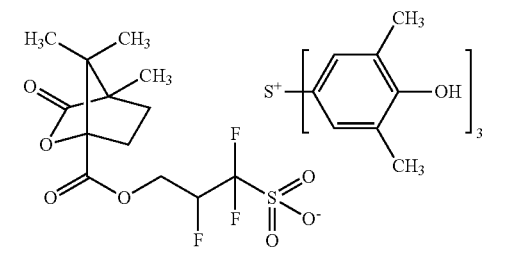 | Same to example 31 intermediate | $^1$H-NMR and $^{19}$F-NMR (DMSO-d$_6$). [ppm]: 0.82 (s, 3H), 1.01 (s, 6H), 1.50-1.59 (m, 1H), 1.88-2.03 (m, 2H), 2.18 (s, 18H), 2.32-2.44 (m, 1H), 4.43-4.59 (m, 1H), 4.70-4.86 (m, 1H), 5.05-5.28 (m, 1H), 7.37 (s, 6H), 9.68 (br s, 3H), −206.9 (m, 1F), −119.4 (d, 1F), −111.3 (d, 1F). |

TABLE 1-continued

| Ex. | Structures | Intermediate Physical properties | Final product Physical properties |
|---|---|---|---|
| 53 | 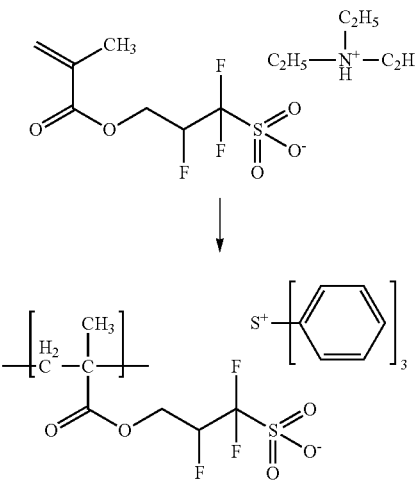 | $^1$H-NMR and $^{19}$F-NMR (CDCl$_3$). [ppm]: 1.36 (t, 9H), 1.96 (s, 3H), 3.15 (q, 6H), 4.58 (m, 1H), 4.79 (m, 1H), 5.30 (m, 1H), 5.61 (s, 1H), 6.17 (s, 1H), −114.4 (d, 1F), −117.4 (d, 1F), −205.9 (m, 1F). | Polymerized by heat during isolation and purification; $^1$H-NMR and $^{19}$F-NMR (DMSO-d$_6$). [ppm]: 0.68 (bm, 5H), 4.12 (bs, 1H), 4.51 (bs, 1H), 5.03 (bd, 1H), 7.77 (m, 15H), −112.2 (bd, 1F), −119.4 (bd, 1F), −205.8 (bs, 1F). |
| 54 | 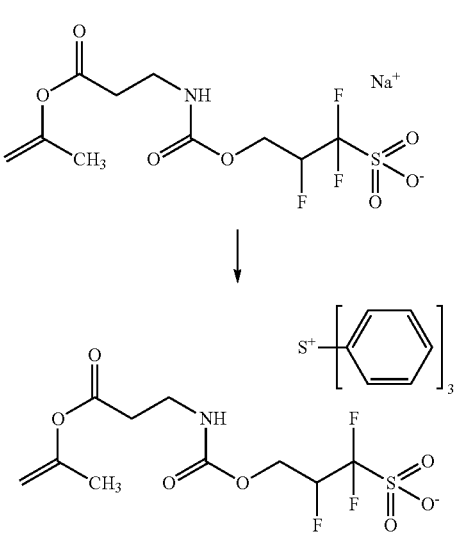 | $^1$H-NMR and $^{19}$F-NMR (DMSO-d$_6$). [ppm]: 1.84 (s, 3H), 3.27 (m, 2H), 4.04 (m, 2H), 4.14 (m, 1H), 4.65 (dd, 1H), 5.06 (m, 1H), 5.63 (s, 1H), 6.04 (s, 1H), 7.58 (m, 1H), −112.0 (d, 1F), −120.1 (d, 1F), −206.1 (m, 1F). | $^1$H-NMR and $^{19}$F-NMR (CDCl$_3$). [ppm]: 1.95 (s, 3H), 3.60 (t, 2H), 4.28 (t, 2H), 4.50 (m, 1H), 4.80 (dd, 1H), 5.12 (m, 1H), 5.57 (s, 1H), 6.12 (s, 1H), 7.74 (m, 15H), 8.24 (bs, 1H), −113.0 (d, 1F), −118.3 (d, 1F), −206.1 (m, 1F). |

TABLE 1-continued
| Ex. | Structures | Intermediate Physical properties | Final product Physical properties |
|---|---|---|---|
| 55 | 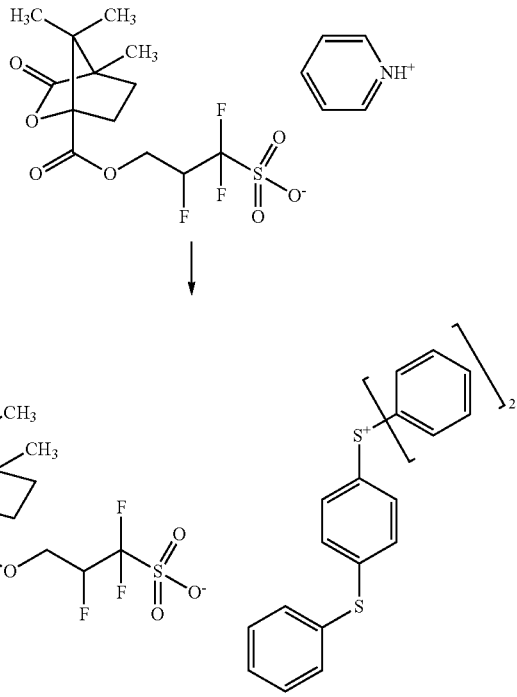 | Same to example 46 | ¹H-NMR (CDCl₃). [ppm]: 0.91 (s, 3H), 1.04 (s, 3H), 1.09 (s, 3H), 1.61-1.69 (m, 1H), 1.88-2.01 (m, 2H), 2.39-2.48 (m, 1H), 4.70-4.85 (m, 2H), 5.18-5.43 (m, 1H), 7.46 (d, 1H), 7.66-7.83 (m, 15H), 8.06, (d, 1H), 8.28 (d, 2H). |
| 56 | 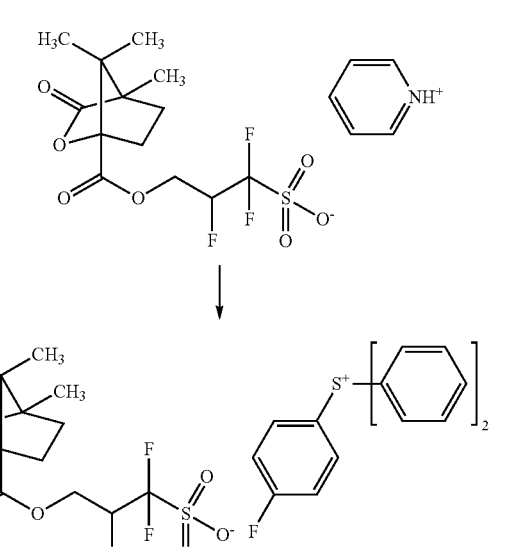 | Same to example 46 | ¹H-NMR (CDCl₃). [ppm]: 0.92 (s, 3H), 1.06 (s, 3H), 1.10 (s, 3H), 1.62-1.72 (m, 1H), 1.89-2.05 (m, 2H), 2.40-2.50 (m, 1H), 4.67-4.96 (m, 2H), 5.16-5.40 (m, 1H), 7.43 (t, 2H), 7.66-7.81 (m, 10H), 7.84-7.90, (m, 2H). |

TABLE 1-continued

| Ex. | Structures | Intermediate Physical properties | Final product Physical properties |
|---|---|---|---|
| 57 | 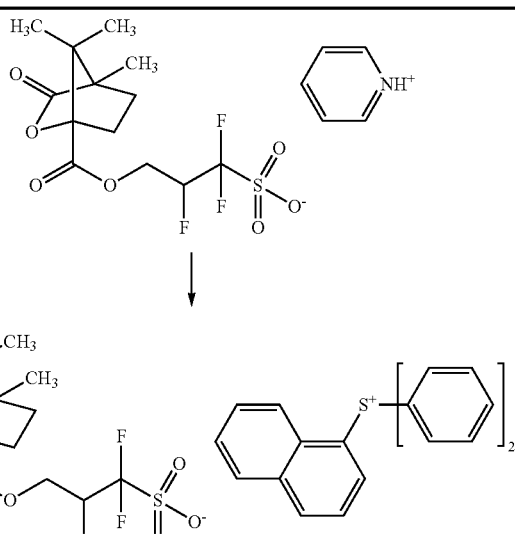 | Same to example 31 | $^1$H-NMR (CDCl$_3$). [ppm]: 0.91 (s, 3H), 1.04 (s, 3H), 1.09 (s, 3H), 1.60-1.70 (m, 1H), 1.87-2.03 (m, 2H), 2.37-2.49 (m, 1H), 4.68-4.97 (m,2H), 5.18-5.43 (m, 1H), 7.45 (d, 1H, 7.6 Hz), 7.66-7.84 (m, 13H), 8.06 (d, 1H, J = 7.6 Hz), 8.28 (d, 2H, J = 8.2 Hz). |

Example 55

Preparation of

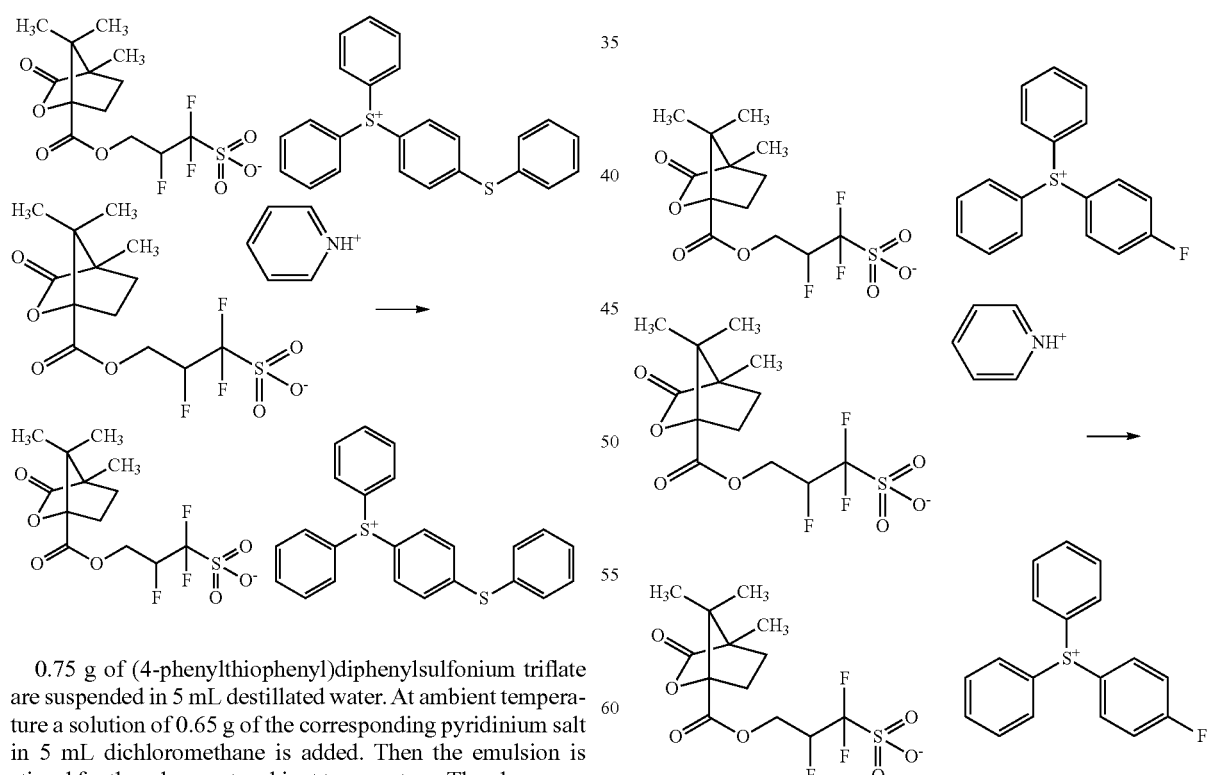

0.75 g of (4-phenylthiophenyl)diphenylsulfonium triflate are suspended in 5 mL destillated water. At ambient temperature a solution of 0.65 g of the corresponding pyridinium salt in 5 mL dichloromethane is added. Then the emulsion is stirred for three hours at ambient temperature. The phases are separated and the aqueous phase is washed twice with dichloromethane. The united organic phases are dried over sodium sulfate, filtrated and concentrated to about 3 mL. The title compound is crystallized from tert-butyl-methylether and obtained as colorless solid (1.06 g). The structure is further confirmed by $^1$H-NMR as indicated in table 1 above.

Example 56

Preparation of

The preparation method of example 55 is used exchanging (4-phenylthiophenyl)diphenylsulfonium triflate by 0.75 g of (4-fluorophenyl)diphenylsulfonium triflate. The title compound is obtained as colorless solid (0.93 g). The structure is further confirmed by H-NMR as indicated in table 1 above.

Example 57

Preparation of

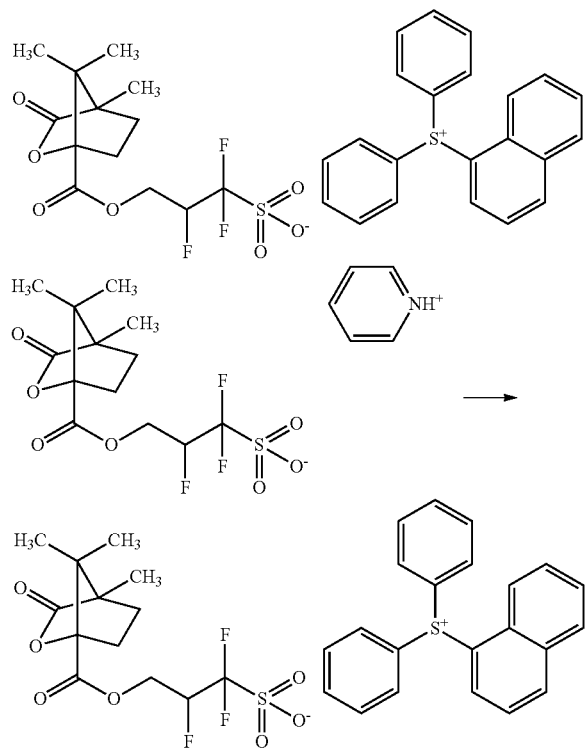

The preparation method of example 55 is followed, exchanging (4-phenylthiophenyl)diphenylsulfonium triflate by 0.75 g of 1-naphthyldiphenylsulfonium triflate. The title compound is obtained as slightly yellow solid (1.10 g). The structure is further confirmed by $^1$H-NMR as indicated in table 1 above.

APPLICATION EXAMPLES

Example A1

Photosensitivity is measured in an ArF model resist formulation with VUVES 4500 (ArF laser), Litho Tech Japan, as an exposure tool. The positive tone resist utilizes a copolymer of -butyrolactone methacrylate and 2-methyladamantyl methacrylate (54/46 mol-%, Mitsubishi Rayon Co., Ltd) having a number average molecular weight of 7600. As for solvent, propylene glycol methyl ether acetate (PGMEA) from Tokyo Kasei Kogyo Co. LTD. is employed. The exact composition of the formulation and the amount of the photoacid generator (PAG) is described in Table 2.

The resist formulations are spin-coated at 120 nm thickness on silicon wafers on which the bottom antireflection courting with ARC29A from Brewer Science is applied in advance at a thickness of 80 nm and prebaked at 120° C. for 1 min. After exposure with various exposure doses, a post exposure bake is applied at 120° C. for 1 min and the resists are then developed in NMD-3 developer from Tokyo Ohka Kogyo Co. Ltd., which is 2.38% aqueous tetramethyl ammonium hydroxide solution, for 1 min.

TABLE 2

| Binder polymer (parts) | 100 |
|---|---|
| PAG (parts) | 2 |
| Solvent (parts) | 1700 |

As a measure for photosensitivity, the "Dose to Clear" ($E_0$), which is the dose just sufficient to completely remove the resist film with 1 min development, is determined. The smaller the required dose, the more sensitive is the resist formulation. The results are collected in Table 3 and demonstrate that the compositions according to the invention are suitable for the preparation of positive tone resists.

TABLE 3

| Compound of example | $E_0$ [mJ/cm$^2$] |
|---|---|
| Example 3 | 1.8 |
| Example 9 | 2.1 |
| Example 10 | 2.1 |
| Example 15 | 1.9 |
| Example 16 | 1.9 |

Example A2

In order to determine the mobility of acid generated from PAGs, a bilayer method described in Proc. of SPIE Vol. 6923 692317 (2008) is utilised in this context. A bilayer forms a stacked layer structure of two films, which consists of an upper layer containing PAG and a PAG-free bottom layer on a silicon wafer with no intermixing between the two layers. Only in the upper layer film, the acid is uniformly distributed through the photo-decomposition process.

The PAG-free film is prepared as the bottom layer onto a four inch silicon wafer at 120 nm thickness by the same material and procedure as described in Example 1 except that no PAG is employed. In parallel, the resist formulation described in Example 1 is coated on a poly(dimethylsiloxane) substrate physically supported on a silicon wafer and prebaked at the same condition as the bottom layer to form the upper layer.

The PAG-containing upper layer prepared on a poly(dimethylsiloxane) substrate is stamped onto the PAG-free bottom film on a silicone wafer face-to-face at 120° C. for 1 min. After the stack is cooled to room temperature (at ca. 23° C.), the PDMS [poly(dimethylsiloxane)] substrate is removed. Then the bilayer is exposed by Canon PLA521-FA for 3 min photochemically to decompose all the PAG and to generate acids in the upper layer, post-exposure-baked at 110° C. for 1 min and developed as described in Example A1. The thickness loss after the process is determined, normalized with the data with TPS of (triphenylsulfonium nonafluorobutane-sulfonate) and employed as a measure for the mobility of the acid. Smaller number means lower diffusion length of the generated acid upon irradiation, namely lower acid mobility, which leads to high resolution in the resist applications. The results collected in Table 4 demonstrate that the compositions according to the invention are suitable for ArF photoresists in acid-mobility.

TABLE 4

| Compound of example | Normalised mobility |
|---|---|
| Example 4 | 0.40 |
| Example 6 | 0.30 |
| Example 7 | 0.48 |
| Example 8 | 0.21 |
| Example 11 | 0.41 |
| Example 21 | 0.40 |
| Example 22 | 0.40 |
| Example 24 | 0.34 |
| Example 28 | 0.36 |
| Example 32 | 0.41 |
| Example 34 | 0.23 |
| Example 36 | 0.25 |
| Example 38 | 0.25 |
| Example 39 | 0.26 |
| Example 40 | 0.28 |
| Example 41 | 0.28 |
| Example 43 | 0.27 |
| Example 44 | 0.29 |
| Example 45 | 0.32 |
| Example 48 | 0.35 |
| Example 52 | 0.32 |
| Reference: TPS nf | 1.00 |

Example A3

In order to determine the solubility of photoacid generator compounds of the present invention, to a weighed amount of the compound to be tested is added cyclohexanone as the solvent with stirring. Determined is the amount of cyclohexanone needed to completely dissolve the photoacid generator compound. The lower the amount of solvent, the better is the solubility of the tested compound. The results are collected in table 5.

TABLE 5

| Compound of example | Solvent needed to completely dissolve 10 g of the compound |
|---|---|
| example 55 | 25 mL |
| example 57 | 24 mL |

The invention claimed is:

1. A compound generating an acid of the formula I or II

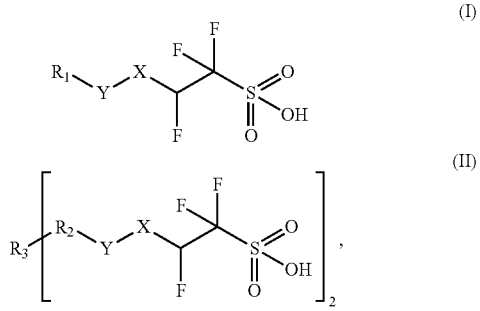

wherein
X is $CH_2$;
Y is O, O(CO), O(CO)O, O(CO)$NR_4$, O(CO)$NR_4$(CO), $OSO_2$, O(CS), or O(CS)$NR_4$; in which for each of these the oxygen atom is directly bound to X;
or is $NR_4$, S, $NR_4$(CO)O, $NR_4$(CS)O, in which the N- or S-atom is directly bound to X;

$R_1$ is hydrogen, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, $C_3$-$C_{30}$cycloalkyl, $C_3$-$C_{30}$cycloalkyl-$C_1$-$C_{18}$alkyl;
or is $C_2$-$C_{18}$alkyl which is interrupted by one or more of O, S, $NR_{14}$, CO, O(CO) or $NR_{14}$(CO);
or is $C_2$-$C_{18}$alkenyl which is interrupted by one or more of O, S, $NR_{14}$, CO, O(CO), $NR_{14}$(CO), optionally substituted phenylene, naphthylene, anthracylene, phenanthrylene, biphenylene or heteroarylene;
or is $C_3$-$C_{30}$cycloalkyl which is interrupted by one or more of O, S, $NR_{14}$, CO, O(CO) or $NR_{14}$(CO);
or is $C_3$-$C_{30}$cycloalkyl-$C_1$-$C_{18}$alkyl which is interrupted by one or more of O, S, $NR_{14}$, CO, O(CO) or $NR_{14}$(CO);
or is $C_4$-$C_{30}$cycloalkenyl which is interrupted by one or more of O, S, $NR_{14}$, CO, O(CO) or $NR_{14}$(CO);
or $R_1$ is phenyl, naphthyl, anthracyl, phenanthryl, biphenylyl, fluorenyl or heteroaryl;
or $R_1$ is $NR_{12}R_{13}$;
or $R_1$ is a monovalent $C_{17}$-$C_{50}$ hydrocarbon group of steroid structure which may contain one or more heteroatoms;
where the $C_3$-$C_{30}$cycloalkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, $C_3$-$C_{30}$cycloalkyl-$C_1$-$C_{18}$alkyl, interrupted $C_2$-$C_{18}$alkyl, interrupted $C_3$-$C_{30}$cycloalkyl, interrupted $C_3$-$C_{30}$cycloalkyl-$C_1$-$C_{18}$alkyl, interrupted $C_4$-$C_{30}$cycloalkenyl, phenyl, naphthyl, anthracyl, phenanthryl, biphenylyl, fluorenyl or heteroaryl are unsubstituted or are substituted;
$R_2$ and $R_3$ independently of each other are $C_3$-$C_{30}$cycloalkylene, $C_3$-$C_{30}$cycloalkyl-$C_1$-$C_{18}$alkylene, $C_1$-$C_{18}$alkylene, $C_1$-$C_{10}$haloalkylene, $C_2$-$C_{12}$alkenylene, $C_4$-$C_{30}$cycloalkenylene;
or independently of each other are $C_2$-$C_{18}$alkylene which is interrupted by one or more of O, S, $NR_{14}$, CO, O(CO) or $NR_{14}$(CO);
or independently of each other are $C_3$-$C_{30}$cycloalkylene which is interrupted by one or more O, S, $NR_{14}$, CO, O(CO) or $NR_{14}$(CO);
or independently of each other are $C_3$-$C_{30}$cycloalkyl-$C_1$-$C_{18}$alkylene which is interrupted by one or more of O, S, $NR_{14}$, CO, O(CO) or $NR_{14}$(CO);
or independently of each other are $C_4$-$C_{30}$cycloalkenylene which is interrupted by one or more of O, S, $NR_{14}$, CO, O(CO) or $NR_{14}$(CO);
or $R_2$ and $R_3$ independently of each other are phenylene, naphthylene, anthracylene, phenanthrylene, biphenylene or heteroarylene;
wherein the $C_3$-$C_{30}$cycloalkylene, $C_3$-$C_{30}$cycloalkyl-$C_1$-$C_{18}$alkylene, $C_1$-$C_{18}$alkylene, $C_1$-$C_{10}$haloalkylene, $C_2$-$C_{12}$alkenylene, $C_4$-$C_{30}$cycloalkenylene, interrupted $C_2$-$C_{18}$alkylene, interrupted $C_3$-$C_{30}$cycloalkylene, interrupted $C_3$-$C_{30}$cycloalkyl-$C_1$-$C_{18}$alkylene, interrupted $C_4$-$C_{30}$cycloalkenylene, phenylene, naphthylene, anthracylene, phenanthrylene, biphenylene or heteroarylene are unsubstituted or substituted;
or $R_2$ and $R_3$ independently of each other are a direct bond, provided that $R_2$ and $R_3$ are not both simultaneously a direct bond;
$R_4$ is hydrogen, $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl;
or is $C_2$-$C_{18}$alkyl which is interrupted by one or more of O, S, $NR_{14}$, CO, O(CO) or $NR_{14}$(CO);
or is $C_3$-$C_{30}$cycloalkyl which is interrupted by one or more of O, S, $NR_{14}$, CO, O(CO) or $NR_{14}$(CO);

or is $C_3$-$C_{30}$cycloalkyl-$C_1$-$C_{18}$alkyl which is interrupted by one or more of O, S, $NR_{14}$, CO, O(CO) or $NR_{14}$(CO);

or is $C_4$-$C_{30}$cycloalkenyl which is interrupted by one or more of O, S, $NR_{14}$, CO, O(CO) or $NR_{14}$(CO);

or $R_4$ is phenyl, naphthyl, anthracyl, phenanthryl, biphenyl, heteroaryl, $C_1$-$C_{18}$alkanoyl, benzoyl, $C_2$-$C_{18}$alkoxycarbonyl, phenoxycarbonyl, $C_1$-$C_{18}$alkylsulfonyl or phenylsulfonyl;

wherein the $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, interrupted $C_2$-$C_{18}$alkyl, interrupted $C_3$-$C_{30}$cycloalkyl, interrupted $C_3$-$C_{30}$cycloalkyl-$C_1$-$C_{18}$alkyl, interrupted $C_4$-$C_{30}$cycloalkenyl, phenyl, naphthyl, anthracyl, phenanthryl, biphenyl, heteroaryl, $C_1$-$C_{18}$alkanoyl, benzoyl, $C_2$-$C_{18}$alkoxycarbonyl, phenoxycarbonyl, $C_1$-$C_{18}$alkylsulfonyl or phenylsulfonyl are unsubstituted or substituted;

or $R_1$ and $R_4$, together with the nitrogen atom to which $R_4$ is attached, form a 5-, 6- or 7-membered ring which optionally is interrupted by one or more O, $NR_{14}$ or CO;

$R_{12}$ and $R_{13}$ independently of each other are hydrogen, $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl;

or independently of each other are $C_2$-$C_{18}$alkyl which is interrupted by one or more of O, S, $NR_{14}$, CO, O(CO) or $NR_{14}$(CO);

or independently of each other are $C_3$-$C_{30}$cycloalkyl which is interrupted by one or more of O, S, $NR_{14}$, CO, O(CO) or $NR_{14}$(CO);

or independently of each other are $C_3$-$C_{30}$cycloalkyl-$C_1$-$C_{18}$alkyl which is interrupted by one or more of O, S, $NR_{14}$, CO, O(CO) or $NR_{14}$(CO);

or independently of each other are $C_4$-$C_{30}$cycloalkenyl which is interrupted by one or more of O, S, $NR_{14}$, CO, O(CO) or $NR_{14}$(CO);

or $R_{12}$ and $R_{13}$ independently of each other are Ar, (CO)$R_{15}$, (CO)O$R_{15}$ or SO$_2$$R_{15}$;

wherein the $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl;

interrupted $C_2$-$C_{18}$alkyl, interrupted $C_3$-$C_{30}$cycloalkyl, interrupted $C_3$-$C_{30}$cycloalkyl-$C_1$-$C_{18}$alkyl, interrupted $C_4$-$C_{30}$cycloalkenyl or Ar are unsubstituted or substituted;

or $R_{12}$ and $R_{13}$, together with the nitrogen atom to which they are attached, form a 5-, 6- or 7-membered ring which optionally is interrupted by one or more O, $NR_{14}$ or CO;

$R_{14}$ is hydrogen, $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl;

or is $C_2$-$C_{18}$alkyl which is interrupted by one or more of O, S, CO or O(CO);

or is $C_3$-$C_{30}$cycloalkyl which is interrupted by one or more of O, S, CO or O(CO);

or is $C_3$-$C_{30}$cycloalkyl-$C_1$-$C_{18}$alkyl which is interrupted by one or more of O, S, CO or O(CO);

or is $C_4$-$C_{30}$cycloalkenyl which is interrupted by one or more O, S, CO or O(CO); or $R_{14}$ is phenyl, naphthyl, anthracyl, phenanthryl, biphenylyl, heteroaryl, $C_1$-$C_{18}$alkanoyl, benzoyl, $C_2$-$C_{18}$alkoxycarbonyl, phenoxycarbonyl, $C_1$-$C_{18}$alkylsulfonyl or phenylsulfonyl;

wherein the $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, interrupted $C_2$-$C_{18}$alkyl, interrupted $C_3$-$C_{30}$cycloalkyl, interrupted $C_3$-$C_{30}$cycloalkyl-$C_1$-$C_{18}$alkyl, $C_4$-$C_{30}$cycloalkenyl, phenyl, naphthyl, anthracyl, phenanthryl, biphenylyl, heteroaryl, $C_1$-$C_{18}$alkanoyl, benzoyl, $C_2$-$C_{18}$alkoxycarbonyl, phenoxycarbonyl, $C_1$-$C_{18}$alkylsulfonyl or phenylsulfonyl are unsubstituted or substituted;

$R_{15}$ is hydrogen, Ar, $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl;

or is $C_2$-$C_{18}$alkyl which is interrupted by one or more of O, S, $NR_{14}$, CO, O(CO) or $NR_{14}$(CO);

or is $C_3$-$C_{30}$cycloalkyl which is interrupted by one or more of O, S, $NR_{14}$, CO, O(CO) or $NR_{14}$(CO);

or is $C_3$-$C_{30}$cycloalkyl-$C_1$-$C_{18}$alkyl which is interrupted by one or more of O, S, $NR_{14}$, CO, O(CO) or $NR_{14}$(CO);

or is $C_4$-$C_{30}$cycloalkenyl which is interrupted by one or more of O, S, $NR_{14}$, CO, O(CO) or $NR_{14}$(CO);

wherein the Ar, $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, interrupted $C_2$-$C_{18}$alkyl, interrupted $C_3$-$C_{30}$cycloalkyl, interrupted $C_3$-$C_{30}$cycloalkyl-$C_1$-$C_{18}$alkyl, or interrupted $C_4$-$C_{30}$cycloalkenyl are unsubstituted or substituted; and Ar is phenyl, biphenylyl, fluorenyl, naphthyl, anthracyl, phenanthryl or heteroaryl, wherein the phenyl, biphenylyl, fluorenyl, naphthyl, anthracyl, phenanthryl or heteroaryl are unsubstituted or substituted.

2. A compound generating an acid of the formula I or II according to claim 1, which is of the formula IIIa, IIIb, IVa or IVb

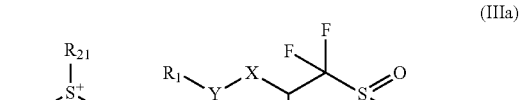

(IIIa)

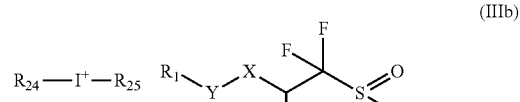

(IIIb)

(IVa)

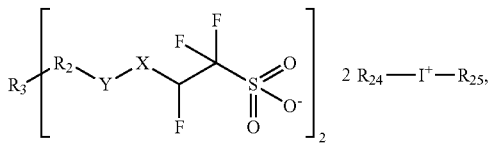

(IVb)

wherein $R_{21}$, $R_{22}$ and $R_{23}$ independently of each other are $Ar_1$, $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl;

or independently of each other are $C_2$-$C_{18}$alkyl which is interrupted by one or more of O, S, $NR_{14}$, CO, O(CO) or $NR_{14}$(CO);

or independently of each other are $C_3$-$C_{30}$cycloalkyl which is interrupted by one or more of O, S, $NR_{14}$, CO, O(CO) or $NR_{14}$(CO);

or independently of each other are $C_3$-$C_{30}$cycloalkyl-$C_1$-$C_{18}$alkyl which is interrupted by one or more of O, S, $NR_{14}$, CO, O(CO) or $NR_{14}$(CO);

or independently of each other are $C_4$-$C_{30}$cycloalkenyl which is interrupted by one or more of O, S, $NR_{14}$, CO, O(CO) or $NR_{14}$(CO);

wherein the $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, interrupted $C_2$-$C_{18}$alkyl, interrupted $C_3$-$C_{30}$cycloalkyl, interrupted $C_3$-$C_{30}$cycloalkyl-$C_1$-$C_{18}$alkyl or $C_4$-$C_{30}$cycloalkenyl are unsubstituted or are substituted by one or more Z;

or $R_{21}$ and $R_{22}$, optionally together with a direct bond, O, S, $NR_{14}$ or (CO), form a fused ring system;

or $R_{21}$ and $R_{22}$, optionally together with direct bond, $C_1$-$C_6$alkylene, O, S, $NR_{14}$ or (CO), form a 5-, 6- or 7-membered ring;

wherein all $R_{21}$, $R_{22}$ and $R_{23}$ optionally additionally are substituted by a group having a —O—C-bond or a —O—Si-bond which cleaves upon the action of an acid;

Z is $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl;

or is $C_2$-$C_{18}$alkyl which is interrupted by one or more of O, S, $NR_{14}$, CO, O(CO) or $NR_{14}$(CO);

or is $C_3$-$C_{30}$cycloalkyl which is interrupted by one or more of O, S, $NR_{14}$, CO, O(CO) or $NR_{14}$(CO);

or is $C_3$-$C_{30}$cycloalkyl-$C_1$-$C_{18}$alkyl which is interrupted by one or more of O, S, $NR_{14}$, CO, O(CO) or $NR_{14}$(CO);

or is $C_4$-$C_{30}$cycloalkenyl which is interrupted by one or more of O, S, $NR_{14}$, O(CO) or $NR_{14}$(CO);

or is $C_5$-$C_{30}$cycloalkyl-$C_1$-$C_4$alkyl, which is substituted by one or more of $NR_{14}$(CO)$OR_{11}$ or $NR_{14}$(CO)$NR_{12}R_{13}$;

or is halogen, $NO_2$, CN, Ar, (CO)$R_{15}$, (CO)$OR_{11}$, (CO)$NR_{12}R_{13}$, O(CO)$R_{15}$, O(CO)$OR_{11}$, O(CO)$NR_{12}R_{13}$, $NR_{14}$(CO)$R_{15}$, $NR_{14}$(CO)$OR_{11}$, $NR_{14}$(CO)$NR_{12}R_{13}$, $OR_{11}$, $NR_{12}R_{13}$, $SR_{14}$, $SOR_{15}$, $SO_2R_{15}$ and/or $OSO_2R_{15}$;

$R_{24}$ and $R_{25}$ independently of each other are $Ar_1$;

or $R_{24}$ and $R_{25}$, optionally together with a direct bond, O, S, $NR_{14}$ or (CO) form a fused ring;

or $R_{24}$ and $R_{25}$, optionally together with $C_1$-$C_2$alkylene, O, S, $NR_{14}$ or (CO), form a 5-, 6- or 7-membered ring;

wherein all $R_{24}$ and $R_{25}$ optionally additionally are substituted by a group having a —O—C-bond or a —O—Si-bond which cleaves upon the action of an acid;

Ar is phenyl, biphenylyl, fluorenyl, naphthyl, anthracyl, phenanthryl or heteroaryl, wherein the phenyl, biphenylyl, fluorenyl, naphthyl, anthracyl, phenanthryl or heteroaryl are unsubstituted or substituted by one or more $Z_2$;

$Ar_1$ is phenyl, biphenylyl, fluorenyl, naphthyl, anthracyl, phenanthryl or heteroaryl, wherein said phenyl, biphenylyl, fluorenyl, naphthyl, anthracyl, phenanthryl or heteroaryl are unsubstituted or are substituted by one or more Z, or are substituted by

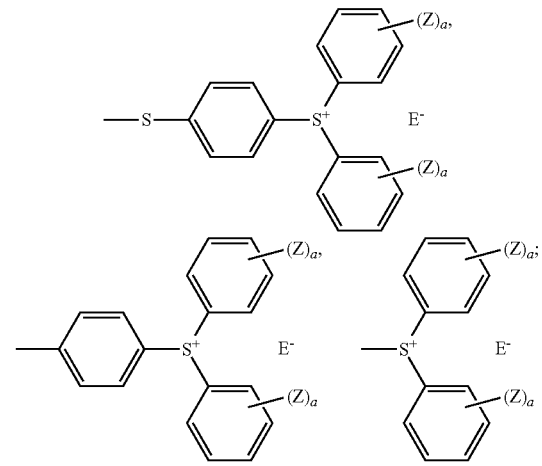

optionally the radicals Z as $C_1$-$C_{18}$alkyl, $C_2$-$C_{12}$alkenyl, (CO)$R_{15}$, (CO)$OR_{11}$, (CO)$NR_{12}R_{13}$, O(CO)$R_{15}$, O(CO)$OR_{11}$, O(CO)$NR_{12}R_{13}$, $NR_{14}$(CO)$R_{15}$, $NR_{14}$(CO)$OR_{11}$, $NR_{14}$(CO)$NR_{12}R_{13}$, $OR_{11}$, $NR_{12}R_{13}$, $SR_{14}$, $SOR_{15}$, $SO_2R_{15}$ and/or —$OSO_2R_{15}$, form 5-, 6- or 7-membered rings, via the radicals $C_1$-$C_{18}$alkyl, $C_2$-$C_{12}$alkenyl, $R_{11}$, $R_{12}$, $R_{13}$, $R_{14}$ and/or $R_{15}$, with further substituents on the phenyl, biphenylyl, fluorenyl, naphthyl, anthracyl, phenanthryl, or heteroaryl ring or with one of the carbon atoms of the phenyl, biphenylyl, fluorenyl, naphthyl, anthracyl, phenanthryl, or heteroaryl ring;

$Z_2$ is $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl;

or is $C_2$-$C_{18}$alkyl which is interrupted by one or more of O, S, $NR_{14}$, CO, O(CO) or $NR_{14}$(CO);

or is $C_3$-$C_{30}$cycloalkyl which is interrupted by one or more of O, S, $NR_{14}$, CO, O(CO) or $NR_{14}$(CO);

or is $C_3$-$C_{30}$cycloalkyl-$C_1$-$C_{18}$alkyl which is interrupted by one or more of O, S, $NR_{14}$, CO, O(CO) or $NR_{14}$(CO);

or is $C_4$-$C_{30}$cycloalkenyl which is interrupted by one or more of O, S, $NR_{14}$, O(CO) or $NR_{14}$(CO);

or is $C_5$-$C_{30}$cycloalkyl-$C_1$-$C_4$alkyl, which is substituted by one or more of $NR_{14}$(CO)$OR_{11}$ or $NR_{14}$(CO)$NR_{12}R_{13}$;

or is halogen, $NO_2$, CN, (CO)$R_{15}$, (CO)$OR_{11}$, (CO)$NR_{12}R_{13}$, O(CO)$R_{15}$, O(CO)$OR_{11}$, O(CO)$NR_{12}R_{13}$, $NR_{14}$(CO)$R_{15}$, $NR_{14}$(CO)$OR_{11}$, $NR_{14}$(CO)$NR_{12}R_{13}$, $OR_{11}$, $NR_{12}R_{13}$, $SR_{14}$, $SOR_{15}$, $SO_2R_{15}$, $OSO_2R_{15}$, phenyl, biphenylyl, fluorenyl, naphthyl, anthracyl, phenanthryl and/or heteroaryl;

optionally the radicals $Z_2$ as $C_1$-$C_{18}$alkyl, $C_2$-$C_{12}$alkenyl, (CO)$R_{15}$, (CO)$OR_{11}$, (CO)$NR_{12}R_{13}$, O(CO)$R_{15}$, O(CO)$OR_{11}$, O(CO)$NR_{12}R_{13}$, $NR_{14}$(CO)$R_{15}$, $NR_{14}$(CO)$OR_{11}$, $NR_{14}$(CO)$NR_{12}R_{13}$, $OR_{11}$, $NR_{12}R_{13}$, $SR_{14}$, $SOR_{15}$, $SO_2R_{15}$ and/or $OSO_2R_{15}$ on the phenyl, naphthyl, anthracyl, phenanthryl, biphenylyl, fluorenyl or heteroaryl; form 5-, 6- or 7-membered rings, via the radicals $C_1$-$C_{18}$alkyl, $C_2$-$C_{12}$alkenyl, $R_{11}$, $R_{12}$, $R_{13}$, $R_{14}$ and/or $R_{15}$, with further substituents on the phenyl, naphthyl, anthracyl, phenanthryl, biphenylyl, fluorenyl or heteroaryl; or with one of the carbon atoms of the phenyl, naphthyl, anthracyl, phenanthryl, biphenylyl, fluorenyl or heteroaryl;

a is 0 or 1;

E is

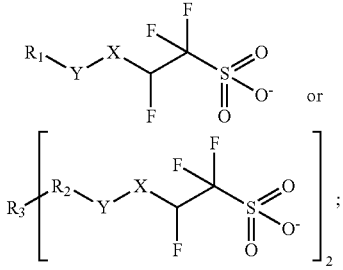

$R_{11}$ is hydrogen, $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, or is $C_2$-$C_{18}$alkyl which is interrupted by one or more of O, S, $NR_{14}$, CO, O(CO) or $NR_{14}$(CO);

or is $C_3$-$C_{30}$cycloalkyl which is interrupted by one or more of O, S, $NR_{14}$, CO, O(CO) or $NR_{14}$(CO);

or is $C_3$-$C_{30}$cycloalkyl-$C_1$-$C_{18}$alkyl which is interrupted by one or more of O, S, $NR_{14}$, CO, O(CO) or $NR_{14}$(CO);

or is $C_4$-$C_{30}$cycloalkenyl which is interrupted by one or more of O, S, $NR_{14}$, CO, O(CO) or $NR_{14}$(CO);

or $R_{11}$ is Ar, (CO)$R_{15}$, (CO)O$R_{15}$, (CO)$NR_{12}R_{13}$ or $SO_2R_{15}$;

wherein the $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, interrupted $C_2$-$C_{18}$alkyl, interrupted $C_3$-$C_{30}$cycloalkyl, interrupted $C_3$-$C_{30}$cycloalkyl-$C_1$-$C_{18}$alkyl or interrupted $C_4$-$C_{30}$cycloalkenyl are unsubstituted or substituted by one or more $Z_1$;

$Z_1$ is Ar, OH, $C_1$-$C_{18}$alkyl, $C_1$-$C_{10}$haloalkyl, phenyl-$C_1$-$C_3$-alkyl, $C_3$-$C_{30}$cycloalkyl, halogen, $NO_2$, CN, $C_1$-$C_{18}$alkoxy, phenoxy, phenoxycarbonyl, phenylthio, phenylthiocarbonyl, $NR_{12}R_{13}$, $C_1$-$C_{12}$alkylthio, $C_2$-$C_{18}$alkoxycarbonyl, $C_2$-$C_{10}$haloalkanoyl, halobenzoyl, $C_1$-$C_{18}$alkylsulfonyl, phenylsulfonyl, (4-methylphenyl)sulfonyl, $C_1$-$C_{18}$alkylsulfonyloxy, phenylsulfonyloxy, (4-methylphenyl)sulfonyloxy, $C_1$-$C_{18}$alkanoyl, $C_1$-$C_{18}$alkanoyloxy, benzoyl and/or by benzoyloxy; and $R_1$, $R_2$, $R_3$, X, Y, $R_{12}$, $R_{13}$, $R_{14}$ and $R_{15}$ are as defined in claim 1.

3. A compound generating an acid of the formula I or II according to claim 1, which is of the formula IIIc, IIId, IIIe, IVc or IVe

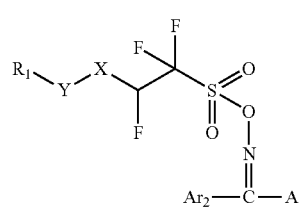

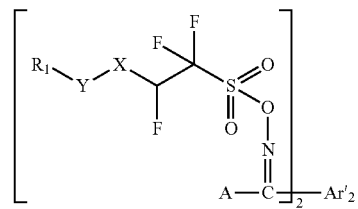

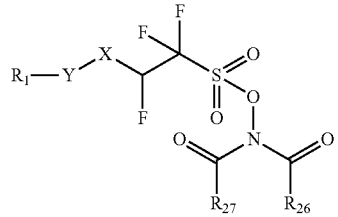

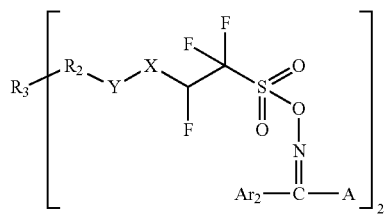

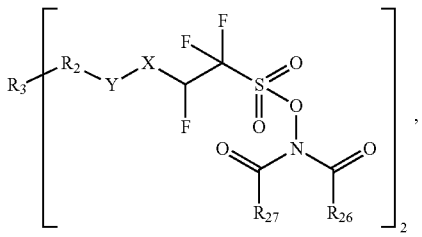

wherein

A is $C_1$-$C_{10}$haloalkyl, CN, (CO)O$R_{11}$ or $SO_2R_{15}$;

$Ar_2$ is $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl;

or is $C_2$-$C_{18}$alkyl which is interrupted by one or more of O, S, $NR_{14}$, CO, O(CO) or $NR_{14}$(CO);

or is $C_3$-$C_{30}$cycloalkyl which is interrupted by one or more of O, S, $NR_{14}$, CO, O(CO) or $NR_{14}$(CO);

or is $C_3$-$C_{30}$cycloalkyl-$C_1$-$C_{18}$alkyl which is interrupted by one or more of O, S, $NR_{14}$, CO, O(CO) or $NR_{14}$(CO);

or is $C_4$-$C_{30}$cycloalkenyl which is interrupted by one or more of O, S, $NR_{14}$, CO, O(CO) or $NR_{14}$(CO);

or $Ar_2$ is phenyl, naphthyl, anthracyl, phenanthryl, biphenylyl, fluorenyl or heteroaryl; wherein the phenyl, naphthyl, anthracyl, phenanthryl, biphenylyl, fluorenyl or heteroaryl are unsubstituted or are substituted by one or more Z;

optionally the radicals Z as $C_1$-$C_{18}$alkyl, $C_2$-$C_{12}$alkenyl, (CO)$R_{15}$, (CO)O$R_{11}$, (CO)$NR_{12}R_{13}$, O(CO)$R_{15}$, O(CO)O$R_{11}$, O(CO)$NR_{12}R_{13}$, $NR_{14}$(CO)$R_{15}$, $NR_{14}$(CO)O$R_{11}$, $NR_{14}$(CO)$NR_{12}R_{13}$, O$R_{11}$, $NR_{12}R_{13}$, $SR_{14}$, SO$R_{15}$, $SO_2R_{15}$ and/or $OSO_2R_{15}$ on the phenyl, naphthyl, anthracyl, phenanthryl, biphenylyl, fluorenyl or heteroaryl form 5-, 6- or 7-membered rings, via the radicals $C_1$-$C_{18}$alkyl, $C_2$-$C_{12}$alkenyl, $R_{11}$, $R_{12}$, $R_{13}$, $R_{14}$ and/or $R_{15}$, with further substituents on the phenyl, naphthyl, anthracyl, phenanthryl, biphenyl, fluorenyl or heteroaryl; or with one of the carbon atoms of the phenyl, naphthyl, anthracyl, phenanthryl, biphenylyl, fluorenyl or heteroaryl;

wherein all Ar$_2$ optionally additionally are substituted by a group having a —O—C-bond or a —O—Si-bond which cleaves upon the action of an acid;

Ar'$_2$ is C$_3$-C$_{30}$cycloalkylene, C$_3$-C$_{30}$cycloalkyl-C$_1$-C$_{18}$alkylene, C$_1$-C$_{18}$alkylene, C$_1$-C$_{10}$haloalkylene, C$_2$-C$_{12}$alkenylene, C$_4$-C$_{30}$cycloalkenylene;

or is C$_2$-C$_{18}$alkylene which is interrupted by one or more of O, S, NR$_{14}$, CO, O(CO) or NR$_{14}$(CO);

or is C$_3$-C$_{30}$cycloalkylene which is interrupted by one or more of O, S, NR$_{14}$, CO, O(CO) or NR$_{14}$(CO);

or is C$_3$-C$_{30}$cycloalkyl-C$_1$-C$_{18}$alkylene which is interrupted by one or more of O, S, NR$_{14}$, CO, O(CO) or NR$_{14}$(CO);

or is C$_4$-C$_{30}$cycloalkenylene which is interrupted by one or more of O, S, NR$_{14}$, CO, O(CO) or NR$_{14}$(CO);

or Ar'$_2$ is a direct bond, phenylene, naphthylene,

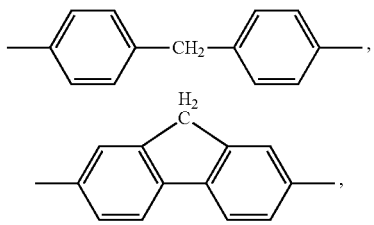

diphenylene, heteroarylene, oxydiphenylene or

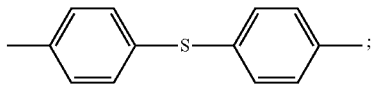

wherein the phenylene, naphthylene,

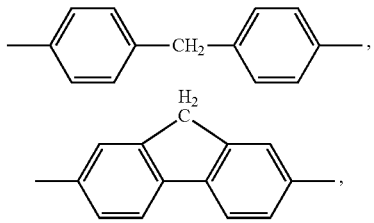

diphenylene, heteroarylene, oxydiphenylene or

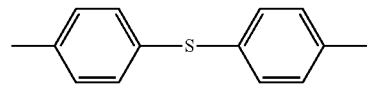

are unsubstituted or are substituted by one or more Z:

optionally the radicals Z as C$_1$-C$_{18}$alkyl, C$_2$-C$_{12}$alkenyl, (CO)R$_{15}$, (CO)OR$_{11}$, (CO)NR$_{12}$R$_{13}$, O(CO)R$_{15}$, O(CO)OR$_{11}$, O(CO)NR$_{12}$R$_{13}$, NR$_{14}$(CO)R$_{15}$, NR$_{14}$(CO)OR$_{11}$, NR$_{14}$(CO)NR$_{12}$R$_{13}$, OR$_{11}$, NR$_{12}$R$_{13}$, SR$_{14}$, SOR$_{15}$, SO$_2$R$_{15}$ and/or OSO$_2$R$_{15}$ on the phenylene, naphthylene,

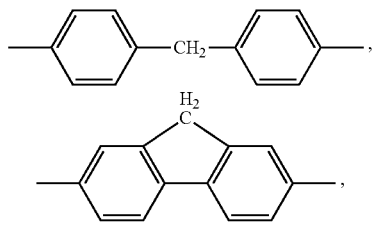

diphenylene, heteroarylene, oxydiphenylene or

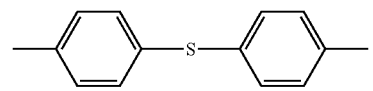

form 5-, 6- or 7-membered rings, via the radicals C$_1$-C$_{18}$alkyl, C$_2$-C$_{12}$alkenyl, R$_{11}$, R$_{12}$, R$_{13}$, R$_{14}$ and/or R$_{15}$, with further substituents on the phenylene, naphthylene,

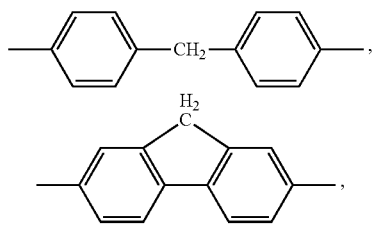

diphenylene, heteroarylene, oxydiphenylene or

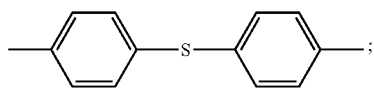

or with one of the carbon atoms of the phenylene, naphthylene,

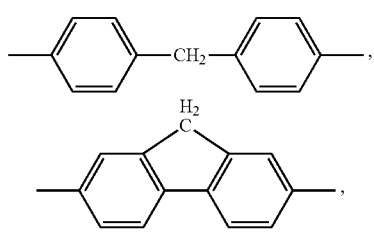

diphenylene, heteroarylene, oxydiphenylene or

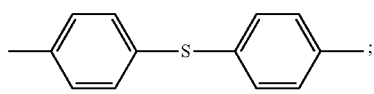

wherein all Ar'$_2$ with the exception of direct bond optionally additionally are substituted by a group having a —O—C-bond or a —O—Si-bond which cleaves upon the action of an acid;

or Ar'$_2$ is a group —Ar''$_2$-A$_1$-Y$_1$-A$_1$-Ar''$_2$—;

Ar''$_2$ is phenylene, naphthylene, anthracylene, phenanthrylene or heteroarylene, wherein the phenylene, naphthylene, anthracylene, phenanthrylene or heteroarylene are unsubstituted or are substituted by one or more Z;

optionally the radicals Z as $C_1$-$C_{18}$alkyl, $C_2$-$C_{12}$alkenyl, (CO)$R_{15}$, (CO)O$R_{11}$, (CO)N$R_{12}R_{13}$, O(CO)$R_{15}$, O(CO)O$R_{11}$, O(CO)N$R_{12}R_{13}$, N$R_{14}$(CO)$R_{15}$, N$R_{14}$(CO)O$R_{11}$, N$R_{14}$(CO)N$R_{12}R_{13}$, O$R_{11}$, N$R_{12}R_{13}$, S$R_{14}$, SO$R_{15}$, SO$_2R_{15}$ and/or OSO$_2R_{15}$ on the phenylene, naphthylene, anthracylene, phenanthrylene, or heteroarylene form 5-, 6- or 7-membered rings, via the radicals $C_1$-$C_{18}$alkyl, $C_2$-$C_{12}$alkenyl, $R_{11}$, $R_{12}$, $R_{13}$, $R_{14}$ and/or $R_{15}$, with further substituents on the phenylene, naphthylene, anthracylene, phenanthrylene, or heteroarylene or with one of the carbon atoms of the phenylene, naphthylene, anthracylene, phenanthrylene, or heteroarylene;

wherein all radicals Ar''$_2$ optionally additionally are substituted by a group having a —O—C-bond or a —O—Si-bond which cleaves upon the action of an acid;

$A_1$ is a direct bond, O, S, N$R_{14}$, CO, O(CO), S(CO), N$R_{14}$(CO), SO, SO$_2$, or OSO$_2$;

or $A_1$ is $C_1$-$C_{18}$alkylene which is unsubstituted or substituted by one or more $C_1$-$C_4$haloalkyl, halogen, O$R_{11}$ and/or S$R_{14}$, or is phenylene which is unsubstituted or substituted by one or more $C_1$-$C_{12}$alkyl, $C_1$-$C_4$haloalkyl, halogen, O$R_{11}$ and/or S$R_{14}$;

$Y_1$ is $C_1$-$C_{18}$alkylene which is unsubstituted or substituted by one or more O$R_{11}$, S$R_{14}$, halogen or phenyl; or $Y_1$ is $C_2$-$C_{18}$alkylene, which is interrupted by one or more of O, S, N$R_{14}$, CO, O(CO), S(CO), N$R_{14}$(CO), SO, SO$_2$ or OSO$_2$, and wherein the interrupted $C_2$-$C_{18}$alkylene is unsubstituted or substituted by one or more O$R_{11}$, S$R_{14}$, halogen or phenyl;

$R_{26}$ and $R_{27}$ independently of each other are $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl;

or independently of each other are $C_2$-$C_{18}$alkyl which is interrupted by one or more of O, S, N$R_{14}$, CO, O(CO) or N$R_{14}$(CO);

or independently of each other are $C_3$-$C_{30}$cycloalkyl which is interrupted by one or more of O, S, N$R_{14}$, CO, O(CO) or N$R_{14}$(CO);

or independently of each other are $C_3$-$C_{30}$cycloalkyl-$C_1$-$C_{18}$alkyl which is interrupted by one or more of O, S, N$R_{14}$, CO, O(CO) or N$R_{14}$(CO);

or independently of each other are $C_4$-$C_{30}$cycloalkenyl which is interrupted by one or more of O, S, N$R_{14}$, CO, O(CO) or N$R_{14}$(CO);

or $R_{26}$ and $R_{27}$ independently of each other are phenyl, naphthyl, anthracyl, phenanthryl, biphenylyl, fluorenyl or heteroaryl;

wherein the $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl;

interrupted $C_2$-$C_{18}$alkyl, interrupted $C_3$-$C_{30}$cycloalkyl, interrupted $C_3$-$C_{30}$cycloalkyl-$C_1$-$C_{18}$alkyl, interrupted $C_4$-$C_{30}$cycloalkenyl, phenyl, naphthyl, anthracyl, phenanthryl, biphenylyl, fluorenyl or heteroaryl are unsubstituted or are substituted by one or more Z;

or $R_{26}$ and $R_{27}$ together are 1,2-phenylene or 1,2- or 2,3- or 1,8-naphthylene or $R_{26}$ and $R_{27}$, optionally together with a direct bond, $C_1$-$C_4$alkylene, $C_3$-$C_{30}$cycloalkylene, $C_3$-$C_{30}$cycloalkyl-$C_1$-$C_{18}$alkylene, $C_1$-$C_4$haloalkylene, $C_2$-$C_4$alkenylene, $C_4$-$C_{30}$cycloalkenylene, O, S, N$R_{14}$, (CO), form a 5-, 6-, or 7-membered ring;

optionally the radicals Z as $C_1$-$C_{18}$alkyl, $C_2$-$C_{12}$alkenyl, (CO)$R_{15}$, (CO)O$R_{11}$, (CO)N$R_{12}R_{13}$, O(CO)$R_{15}$, O(CO)O$R_{11}$, O(CO)N$R_{12}R_{13}$, N$R_{14}$(CO)$R_{15}$, N$R_{14}$(CO)O$R_{11}$, N$R_{14}$(CO)N$R_{12}R_{13}$, O$R_{11}$, N$R_{12}R_{13}$, S$R_{14}$, SO$R_{15}$, SO$_2R_{15}$ and/or OSO$_2R_{15}$ on the phenyl, naphthyl, anthracyl, phenanthryl, biphenylyl, fluorenyl or heteroaryl form 5-, 6- or 7-membered rings, via the radicals $C_1$-$C_{18}$alkyl, $C_2$-$C_{12}$alkenyl, $R_{11}$, $R_{12}$, $R_{13}$, $R_{14}$ and/or $R_{15}$, with further substituents on the phenyl, naphthyl, anthracyl, phenanthryl, biphenylyl, fluorenyl or heteroaryl; or with one of the carbon atoms of the phenyl, naphthyl, anthracyl, phenanthryl, biphenylyl, fluorenyl or heteroaryl;

wherein all $R_{26}$ and $R_{27}$ optionally additionally are substituted by a group having a —O—C-bond or a —O—Si-bond which cleaves upon the action of an acid; and $R_1$, $R_2$, $R_3$, X, Y, $R_{11}$, $R_{12}$, $R_{13}$, $R_{14}$ and $R_{15}$ are as defined in claim 1 and Z is defined as $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl;

or is $C_2$-$C_{18}$alkyl which is interrupted by one or more of O, S, N$R_{14}$, CO, O(CO) or N$R_{14}$(CO);

or is $C_3$-$C_{30}$cycloalkyl which is interrupted by one or more of O, S, N$R_{14}$, CO, O(CO) or N$R_{14}$(CO);

or is $C_3$-$C_{30}$cycloalkyl-$C_1$-$C_{18}$alkyl which is interrupted by one or more of O, S, N$R_{14}$, CO, O(CO) or N$R_{14}$(CO);

or is $C_4$-$C_{30}$cycloalkenyl which is interrupted by one or more of O, S, N$R_{14}$, O(CO) or N$R_{14}$(CO);

or is $C_5$-$C_{30}$cycloalkyl-$C_1$-$C_4$alkyl, which is substituted by one or more of N$R_{14}$(CO)O$R_{11}$ or N$R_{14}$(CO)N$R_{12}R_{13}$;

or is halogen, NO$_2$, CN, Ar, (CO)$R_{15}$, (CO)O$R_{11}$, (CO)N$R_{12}R_{13}$, O(CO)$R_{15}$, O(CO)O$R_{11}$, O(CO)N$R_{12}R_{13}$, N$R_{14}$(CO)$R_{15}$, N$R_{14}$(CO)O$R_{11}$, N$R_{14}$(CO)N$R_{12}R_{13}$, O$R_{11}$, N$R_{12}R_{13}$, S$R_{14}$, SO$R_{15}$, SO$_2R_{15}$ and/or OSO$_2R_{15}$.

4. A compound generating an acid of the formula I or II according to claim 2, wherein X is CH$_2$;

Y is O, O(CO), O(CO)O, O(CO)N$R_4$, O(CO)N$R_4$(CO), OSO$_2$ or O(CS)N$R_4$; in which for each of these the oxygen atom is directly bound to X;

$R_1$ is hydrogen, $C_3$-$C_{30}$cycloalkyl, $C_3$-$C_{30}$cycloalkyl-$C_1$-$C_{18}$alkyl, $C_1$-$C_{18}$alkyl, $C_2$-$C_{12}$alkenyl or $C_4$-$C_{30}$cycloalkenyl;

or is $C_2$-$C_{18}$alkyl which is interrupted by one or more O;

or is $C_2$-$C_{18}$alkenyl which is interrupted by one or more O;

or is $C_3$-$C_{30}$cycloalkyl which is interrupted by one or more O, CO, O(CO) or N$R_{14}$(CO);

or $R_1$ is N$R_{12}R_{13}$;

or is $C_3$-$C_{30}$cycloalkyl-$C_1$-$C_{18}$alkyl which is interrupted by one or more O, CO or O(CO);

wherein the $C_1$-$C_{18}$alkyl, $C_3$-$C_{30}$cycloalkyl, $C_4$-$C_{30}$cycloalkenyl, interrupted $C_2$-$C_{18}$alkyl, interrupted $C_3$-$C_{30}$cycloalkyl, interrupted $C_3$-$C_{30}$cycloalkyl-$C_1$-$C_{18}$alkyl are unsubstituted or are substituted by one or more Z;

Z is $C_1$-$C_{18}$alkyl, $C_3$-$C_{30}$cycloalkyl, $C_3$-$C_{30}$cycloalkyl-$C_1$-$C_{18}$alkyl, halogen, (CO)O$R_{11}$, O(CO)$R_{11}$, O$R_{11}$, S$R_{14}$ or N$R_{14}$(CO)O$R_{11}$;

or is $C_5$-$C_{30}$cycloalkyl-$C_1$-$C_4$alkyl, which is substituted by one or more of N$R_{14}$(CO)O$R_{11}$ or N$R_{14}$(CO)N$R_{12}R_{13}$;

$R_2$ and $R_3$ independently of each other are $C_3$-$C_{30}$cycloalkylene or $C_1$-$C_{18}$alkylene;

$R_4$ is hydrogen;

$R_{11}$ is hydrogen, $C_1$-$C_{18}$alkyl or Ar;

$R_{12}$ and $R_{13}$ independently of each other are hydrogen, $C_3$-$C_{30}$cycloalkyl or $C_1$-$C_{18}$alkyl;

or $R_{12}$ and $R_{13}$ independently of each other are $(CO)R_{15}$ or $SO_2R_{15}$;

or $R_{12}$ and $R_{13}$, together with the nitrogen atom to which they are attached, form a 5-, 6- or 7-membered ring which optionally is interrupted by one or more O, $NR_{14}$ or CO;

$R_{14}$ is hydrogen, $C_1$-$C_{18}$alkyl, $C_1$-$C_{18}$alkanoyl, $C_1$-$C_{18}$alkylsulfonyl, phenyl, phenylsulfonyl, wherein the phenyl or $C_1$-$C_8$alkylsulfonyl are unsubstituted or substituted by one or more $Z_1$;

$R_{15}$ is hydrogen or Ar;

Ar is phenyl, which is unsubstituted or is substituted by one or more $Z_2$;

$Z_2$ is $C_1$-$C_{18}$alkyl or $(CO)R_{15}$; and $Z_1$ is Ar.

5. A compound of the formula Ia or IIa

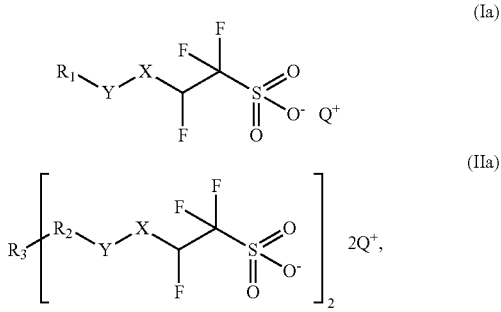

wherein $Q^+$ is a proton, lithium, sodium, potassium, cesium, magnesium, calcium, heteroaryl having one or more nitrogen atom with plus charge which is unsubstituted or substituted by one or more $(NR_{28}R_{29}R_{30}R_{31})^+$;

$R_{28}$, $R_{29}$, $R_{30}$ and $R_{31}$ independently of each other have one of the meanings of $R_{12}$ and $R_{13}$ as defined in claim 1;

or $R_{28}$, $R_{29}$, $R_{30}$, together are with a nitrogen atom to which they are attached, form a polycyclic ring which optionally is interrupted by one or more O, $NR_{14}$, CO, and/or optionally interrupted by $CR_{15}$ or N at the bridgehead; and X, Y, $R_1$, $R_2$, and $R_3$, $R_{14}$ and $R_{15}$ are as defined in claim 1.

6. A chemically amplified positive resist composition comprising as radiation sensitive acid donor (a) at least one compound generating an acid of the formula I or II according to claim 1; and a compound (c) which is insoluble or essentially insoluble in a developer and becomes soluble upon the action of the acid.

7. A chemically amplified resist composition comprising as radiation sensitive acid donor a polymer obtained by polymerizing a compound of the formula IIIa or IIIb as defined in claim 2, wherein $R_1$ as $C_2$-$C_{12}$alkenyl or interrupted $C_2$-$C_{18}$alkenyl is a polymerizable group containing at least one double bond, optionally with further monomers which comprise a polymerizable double bond.

8. A chemically amplified positive resist composition according to claim 6, which comprises additionally other additives (d).

9. A chemically amplified negative resist composition comprising as photosensitive acid donor (a), at least one compound generating an acid of the formula I or II according to claim 1; and a compound (b) which crosslinks or polymerizes upon action of the acid, wherein the coated and dried resist composition is soluble in a developer and becomes insoluble or essentially insoluble upon action of the acid.

10. A photoresist application process comprising the steps:
(1) applying to a substrate a composition according to claim 6;
(2) post apply baking the composition at temperatures between 60° C. and 160° C.;
(3) image-wise irradiating with electromagnetic radiation in the wavelength range of 10 nm to 1500 nm, or with an electron beam;
(4) optionally post exposure baking the composition at temperatures between 60° C. and 160° C.; and
(5) developing with a solvent or with an aqueous alkaline developer.

11. A composition comprising
(a) as acid donor, at least one compound of the formula Ia, IIa, according to claim 5; and
(b) a compound which cures or crosslinks upon the action of the acid.

12. A composition comprising
(a) as acid donor, at least one compound of the formula Ia, IIa, according to claim 5; and
(b) a compound which decomposes upon the action of an acid.

13. A chemically amplified resist composition comprising as radiation sensitive acid donor a polymer obtained by polymerizing a compound of the formula IIIc or IIIe as defined in claim 3, wherein $R_1$ as $C_2$-$C_{12}$alkenyl or interrupted $C_2$-$C_{18}$alkenyl is a polymerizable group containing at least one double bond, optionally with further monomers which comprise a polymerizable double bond.

14. A composition comprising
(a) as acid donor, at least one compound of the formula IIIa, IIIb, IVa and IVb according to claim 2; and
(b) a compound which cures or crosslinks upon the action of the acid.

15. A composition comprising
(a) as acid donor, at least one compound of the formula IIIc, IIId, IIIe, IVc and IVe according to claim 3; and
(b) a compound which cures or crosslinks upon the action of the acid.

16. A composition comprising
(a) as acid donor, at least one compound of the formula IIIa, IIIb, IVa and IVb according to claim 2; and
(b) a compound which decomposes upon the action of an acid.

17. A composition comprising
(a) as acid donor, at least one compound of the formula IIIc, IIId, IIIe, IVc and IVe according to claim 3; and
(b) a compound which decomposes upon the action of an acid.

* * * * *